United States Patent
Heimann et al.

(10) Patent No.: US 8,883,789 B2
(45) Date of Patent: Nov. 11, 2014

(54) PIPERAZINE DERIVATIVES AND THEIR USE AS POSITIVE ALLOSTERIC MODULATORS OF MGLUR5 RECEPTORS

(71) Applicants: Annekatrin Heimann, Biberach an der Riss (DE); Georg Dahmann, Warthausen-Birkenhard (DE); Marc Grundl, Biberach an der Riss (DE); Stephan Georg Mueller, Warthausen (DE); Bernd Wellenzohn, Friedrichshafen (DE)

(72) Inventors: Annekatrin Heimann, Biberach an der Riss (DE); Georg Dahmann, Warthausen-Birkenhard (DE); Marc Grundl, Biberach an der Riss (DE); Stephan Georg Mueller, Warthausen (DE); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 18 days.

(21) Appl. No.: 13/709,312

(22) Filed: Dec. 10, 2012

(65) Prior Publication Data

US 2013/0158042 A1    Jun. 20, 2013

(30) Foreign Application Priority Data

Dec. 14, 2011   (EP) ...................... 11193388

(51) Int. Cl.
| | | |
|---|---|---|
| A61K 31/496 | (2006.01) | |
| A61K 31/499 | (2006.01) | |
| A61K 31/506 | (2006.01) | |
| C07D 401/14 | (2006.01) | |
| C07D 403/06 | (2006.01) | |
| C07D 403/14 | (2006.01) | |
| C07D 405/14 | (2006.01) | |
| C07D 409/14 | (2006.01) | |
| C07D 413/14 | (2006.01) | |
| C07D 417/14 | (2006.01) | |
| C07D 487/04 | (2006.01) | |
| C07D 513/04 | (2006.01) | |
| C07D 471/04 | (2006.01) | |

(52) U.S. Cl.
CPC ............ *C07D 513/04* (2013.01); *C07D 403/06* (2013.01); *C07D 409/14* (2013.01); *C07D 405/14* (2013.01); *C07D 487/04* (2013.01); *C07D 413/14* (2013.01); *C07D 403/14* (2013.01); *C07D 401/14* (2013.01); *C07D 471/04* (2013.01); *C07D 417/14* (2013.01)
USPC ............ 514/252.11; 514/252.19; 514/253.06; 514/253.09; 514/254.02; 514/254.03; 514/254.05; 544/231; 544/295; 544/357; 544/362; 544/363; 544/364; 544/366; 544/367; 544/369; 544/371

(58) Field of Classification Search
None
See application file for complete search history.

(56) References Cited

U.S. PATENT DOCUMENTS

| | | |
|---|---|---|
| 6,166,008 A | 12/2000 | Johnson et al. |
| 7,582,635 B2 | 9/2009 | Sun et al. |
| 8,008,300 B2 | 8/2011 | Sun et al. |
| 8,048,890 B2 | 11/2011 | Buschmann et al. |
| 2003/0055085 A1 | 3/2003 | Wagenen et al. |
| 2004/0186111 A1 | 9/2004 | Sun et al. |
| 2005/0256130 A1 | 11/2005 | Pennell et al. |
| 2007/0154428 A1 | 7/2007 | Sato et al. |
| 2010/0004254 A1 | 1/2010 | Sun et al. |
| 2010/0216787 A1 | 8/2010 | Sato et al. |

(Continued)

FOREIGN PATENT DOCUMENTS

| | | |
|---|---|---|
| CA | 2476031 A1 | 9/2003 |
| EP | 0307145 A1 | 3/1989 |
| EP | 0919232 A1 | 6/1999 |
| WO | 9749395 | 12/1997 |
| WO | 0206288 A1 | 1/2002 |

(Continued)

OTHER PUBLICATIONS

Abstract in English for WO2011002067, Publication Date: Jan. 1, 2011.

(Continued)

*Primary Examiner* — Emily Bernhardt
(74) *Attorney, Agent, or Firm* — Michael P. Morris; Anthony P. Bottino

(57) ABSTRACT

This invention relates to compounds of formula I

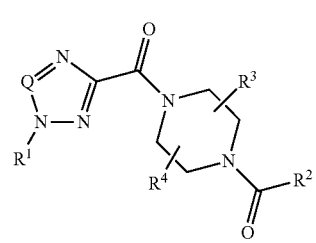

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. $R^1$, $R^2$, $R^3$, $R^4$, Q have meanings given in the description.

13 Claims, No Drawings

(56) References Cited

U.S. PATENT DOCUMENTS

| | | |
|---|---|---|
| 2012/0004217 A1 | 1/2012 | Sun et al. |
| 2012/0015954 A1 | 1/2012 | Sun et al. |
| 2013/0137688 A1 | 5/2013 | Grauert et al. |
| 2013/0143870 A1 | 6/2013 | Grauert et al. |
| 2013/0150341 A1 | 6/2013 | Grauert et al. |
| 2013/0150347 A1 | 6/2013 | Rudolf et al. |
| 2013/0150355 A1 | 6/2013 | Rudolf et al. |
| 2013/0158011 A1 | 6/2013 | Rudolf et al. |
| 2013/0158038 A1 | 6/2013 | Rudolf et al. |
| 2013/0184248 A1 | 7/2013 | Grauert et al. |

FOREIGN PATENT DOCUMENTS

| | | |
|---|---|---|
| WO | 03051833 A2 | 6/2003 |
| WO | 03053922 A2 | 7/2003 |
| WO | 03076432 A1 | 9/2003 |
| WO | 03105853 A1 | 12/2003 |
| WO | 2004058754 A1 | 7/2004 |
| WO | 2005030128 A2 | 4/2005 |
| WO | 2005056015 A1 | 6/2005 |
| WO | 2007021573 A1 | 2/2007 |
| WO | 2007087135 A2 | 8/2007 |
| WO | 2008112440 A1 | 9/2008 |
| WO | 2008145616 A1 | 12/2008 |
| WO | 2008148840 A1 | 12/2008 |
| WO | 2008156580 A1 | 12/2008 |
| WO | 2009143404 A1 | 11/2009 |
| WO | 2010124055 A1 | 10/2010 |
| WO | 2010126811 A1 | 11/2010 |
| WO | 2011002067 A1 | 1/2011 |
| WO | 2011082010 A1 | 7/2011 |

OTHER PUBLICATIONS

Adams, C.E. et al., "Chlorpromazine Versus Placebo for Schizophrenia (Review)." The Cochrane Library, 2009, pp. 1-3.

ChemCats: Accession No. 0046382561, Oct. 14, 2011.

Dorwald, F. Z. "Side Reactions in Organic Synthesis: A Guide to Successful Synthesis Design." Wiley-VCH Verlag GmbH & Co. KGaA, 2005, pp. 1-390.

European Search Report for EP 11193380.0 mailed Mar. 14, 2012.

International Search Report and Written Opinion for PCT/EP2012/075312 mailed Feb. 7, 2013.

International Search Report and Written Opinion for PCT/EP2012/075313 mailed Feb. 7, 2013.

Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.

Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.

Wermuth, Camille G. "Practice of Medicinal Chemistry, Third Edition." Elsevier Ltd., 2008, Ch. 6, 15, 18, and 20. pp. 125-335 provided.

PIPERAZINE DERIVATIVES AND THEIR USE AS POSITIVE ALLOSTERIC MODULATORS OF MGLUR5 RECEPTORS

FIELD OF THE INVENTION

This invention relates to piperazines and their use as positive allosteric modulators of mGluR5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system. Neurotransmission mediated by glutamate has been demonstrated to be critical in many physiological processes, such as synaptic plasticity, long term potentiation involved in both learning and memory as well as sensory perception (in review, Riedel et al., Behav. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Dysregulation in glutamatergic neurotransmission, for example through altered glutamate release or post-synaptic receptor activation, has been demonstrated in a variety of neurological ans well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol. Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders. mGluR5 belongs to a superfamily of currently eight identified Type III GPCRs, which are unique in that the glutamate ligand binds to a large extracellular amino-terminal protein domain. This superfamily is further divided into three groups (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization. In the CNS, mGluR5 has been demonstrated to be expressed mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders. Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state.

Positive allosteric modulators of mGluR5 have recently been identified (O'Brien et al., Mol. Pharma. 2003, 64: 731-740, Lindsley et al., J. Med. Chem. 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manor. mGluR5 positive allosteric modulators therefore represent an approach to potentiate mGluR5 signaling which in turn potentiates and normalizes the NMDA receptor hypofunction detected in neurological and psychiatric disorders.

DETAILED DESCRIPTION OF THE INVENTION

The present invention is directed to piperazine derivatives of the following formula I

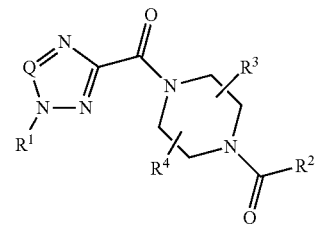

in which $R^1$ represents phenyl, pyridyl which latter two groups are optionally substituted with one to three groups selected independently of one another from halogen, cyano, nitro, amino, $C_{1-5}$alkyl, $C_{3-6}$cycloalkyl, —O—$C_{1-5}$alkyl, —N($R^5$)($R^6$), —C(O)N($R^5$)($R^6$) which latter five groups are optionally substituted with one or more fluorine atoms;

$R^2$ represents a 5-14-membered aryl, 5-14-membered heteroaryl which latter two groups are optionally substituted with 1 to 4 groups selected from —OH, halogen, cyano, 4-9-membered heterocyclyl, $C_{6-10}$aryl, 5-9 membered heteroaryl, $C_{1-5}$alkyl, —$C_{1-5}$alkyl-OH, —O—$C_{1-5}$-alkyl, —O—C$_{1-5}$alkyl-O—C$_{1-5}$-alkyl, —O—C$_{3-5}$ alkynyl, —C$_{1-5}$alkyl-O—C$_{1-5}$-alkyl, C$_{3-7}$cycloalkyl, —O—C$_{3-7}$ cycloalkyl, —O—CH$_2$—C$_{3-7}$cycloalkyl, C$_{1-5}$alkyl-CO—, —C$_{1-5}$alkyl-N(R$^5$)(R$^6$), —N(R$^5$)(R$^6$), —S(O)$_2$—C$_{1-5}$ alkyl which latter sixteen groups are optionally substituted with one or more fluorine atoms;

R$^3$ and R$^4$ independently represent hydrogen, C$_{1-3}$alkyl, —C$_{1-3}$alkyl-O—C$_{1-3}$alkyl which latter three groups are optionally substituted with one or more fluorine atoms, with the proviso that R$^3$ and R$^4$ both are not hydrogen;

or

R$^3$ and R$^4$ if both are attached to the same carbon atom, they may together with the carbon atom to which they are attached form a ring selected from the group consisting of cyclopropyl, cyclobutyl, cyclopentyl, cyclohexyl, piperidinyl, tetrahydrofuranyl, tetrahydropyranyl which latter seven groups are optionally substituted with one or more fluorine atoms;

R$^5$ and R$^6$ independently represent hydrogen, C$_{1-5}$alkyl, benzyl, —C(O)—C$_{1-5}$alkyl, —C(S)—C$_{1-5}$alkyl, —S(O)$_2$—C$_{1-5}$alkyl which latter five groups are optionally substituted with one or more fluorine atoms, or R$^5$ and R$^6$ together with the nitrogen atom to which they are attached form a 4-6-membered heterocyclyl, piperidinyl, tetrahydrofuranyl or tetrahydropyranyl ring which latter four groups are optionally substituted with one or more fluorine atoms;

Q represents CH or N;

or a salt thereof, particularly a physiologically acceptable salt thereof.

In a second embodiment, in the general formula I, R$^2$, R$^3$, R$^4$, Q have the same meaning as defined above, and R$^1$ represents phenyl optionally substituted with one to three groups selected independently of one another from halogen, cyano, nitro, amino, C$_{1-5}$alkyl, C$_{3-6}$cycloalkyl, —O—C$_{1-5}$alkyl, —N(R$^5$)(R$^6$), —C(O)N(R$^5$)(R$^6$) which latter five groups are optionally substituted with one or more fluorine atoms.

A further embodiment of the present invention comprises compounds of formula Ia

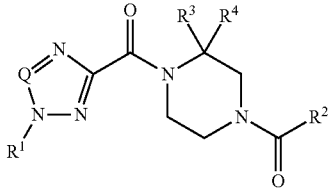

Ia in which R$^1$, R$^2$, R$^3$, R$^4$, Q have the same meaning as defined in any of the preceding embodiments;

or a salt thereof, particularly a physiologically acceptable salt thereof.

In another embodiment, in the general formula I, Ia, R$^1$, R$^3$, R$^4$, R$^5$, R$^6$, R$^7$ have the same meaning as defined in any of the preceding embodiments, and R$^1$ represents phenyl,

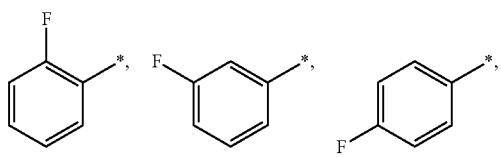

-continued

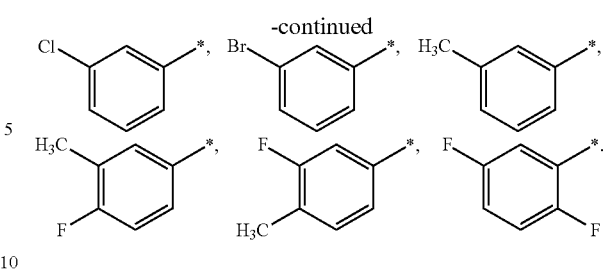

In another embodiment, in the general formula I, Ia, R$^1$, R$^2$, Q have the same meaning as defined in any of the preceding embodiments, and R$^3$ and R$^4$ independently represent hydrogen, methyl, ethyl, propyl, —CH$_2$—O—CH$_3$ which latter four groups are optionally substituted with one or more fluorine atoms with the proviso that R$^3$ and R$^4$ both are not hydrogen;

or

R$^3$ and R$^4$ if both are attached to the same carbon atom, they may together with the carbon atom to which they are attached form a ring selected from cyclopropyl, cyclobutyl, cyclopentyl which latter three groups are optionally substituted with one or more fluorine atoms.

In another embodiment, in the general formula I, Ia, R$^1$, R$^2$, R$^3$, R$^4$, Q have the same meaning as defined in any of the preceding embodiments, and R$^5$ and R$^6$ independently represent hydrogen, C$_{1-3}$alkyl, benzyl, —C(O)—C$_{1-3}$alkyl, which latter three groups are optionally substituted with one or more fluorine atoms, or R$^5$ and R$^6$ together with the nitrogen atom to which they are attached form a group selected from azetidinyl, pyrrolidinyl, piperidinyl, morpholinyl which latter four groups are optionally substituted with one or more fluorine atoms.

In another embodiment, in the general formula I, Ia, R$^1$, R$^2$, Q have the same meaning as defined in any of the preceding embodiments, and R$^3$ and R$^4$ represent methyl.

A further embodiment of the present invention comprises compounds of formula Ib

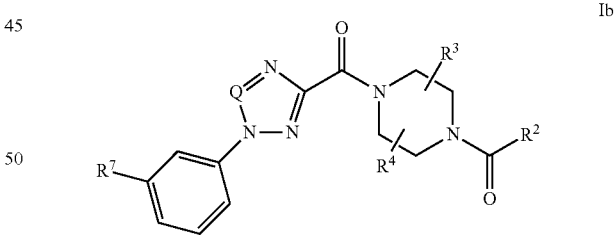

Ib in which

R$^2$, R$^3$, R$^4$, Q have the same meaning as defined in any of the preceding embodiments, and R$^7$ represents hydrogen, halogen, cyano, nitro, amino, C$_{1-5}$alkyl, C$_{3-6}$cycloalkyl, —O—C$_{1-5}$alkyl, —N(R$^5$)(R$^6$), —C(O)N(R$^5$)(R$^6$) which latter five groups are optionally substituted with one or more fluorine atoms;

R$^5$ and R$^6$ independently represent hydrogen, C$_{1-3}$alkyl, benzyl, —C(O)—C$_{1-3}$alkyl, which latter three groups are optionally substituted with one or more fluorine atoms, or R$^5$ and R$^6$ together with the nitrogen atom to which they are attached form a group selected from azetidinyl, pyrrolidinyl, piperidinyl, morpholinyl which latter four groups are optionally substituted with one or more fluorine atoms.

or a salt thereof, particularly a physiologically acceptable salt thereof.

A further embodiment of the present invention comprises compounds of formula Ic

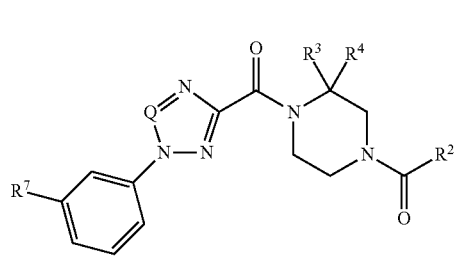

in which

R$^2$, R$^3$, R$^4$, Q have the same meaning as defined in any of the preceding embodiments, and R$^7$ represents hydrogen, halogen, cyano, nitro, amino, C$_{1-5}$alkyl, C$_{3-6}$cycloalkyl, —O—C$_{1-5}$alkyl, —N(R$^5$)(R$^6$), —C(O)N(R$^5$)(R$^6$) which latter five groups are optionally substituted with one or more fluorine atoms;

R$^5$ and R$^6$ independently represent hydrogen, C$_{1-3}$alkyl, benzyl, —C(O)—C$_{1-3}$alkyl, which latter three groups are optionally substituted with one or more fluorine atoms, or R$^5$ and R$^6$ together with the nitrogen atom to which they are attached form a group selected from azetidinyl, pyrrolidinyl, piperidinyl, morpholinyl which latter four groups are optionally substituted with one or more fluorine atoms.

or a salt thereof, particularly a physiologically acceptable salt thereof.

In another embodiment, in the general formula I, Ia, Ib, Ic, R$^2$, R$^3$, R$^4$, Q have the same meaning as defined in any of the preceding embodiments, and R$^7$ represents hydrogen, fluoro, bromo, chloro, cyano, methyl.

In another embodiment, in the general formula I, Ia, Ib, Ic, R$^1$, R$^2$, R$^3$, R$^4$, R$^7$ have the same meaning as defined in any of the preceding embodiments, and Q represents CH.

In another embodiment, in the general formula I, Ia, Ib, Ic, R$^1$, R$^2$, R$^3$, R$^4$ have the same meaning as defined in any of the preceding embodiments, and Q represents N.

In another embodiment, in the general formula I, Ia, Ib, Ic, R$^1$, R$^2$, R$^3$, R$^4$, R$^5$, R$^6$ have the same meaning as defined in any of the preceding embodiments, and R$^2$ represents phenyl, naphthyl, thiophenyl, furanyl, oxazolyl, thiazolyl, pyrazolyl, oxadiazolyl, pyridinyl, pyrimidinyl, pyrazinyl, pyridazinyl, benzofuranyl, benzothiophenyl, indolyl, aza-indolyl, benzimidazolyl, indazolyl, benzodioxolanyl, isochinolyl, benzodioxanyl, imidazo-thiazolyl, indolizine, pyrazolo-pyrimidine which latter twenty-four groups are optionally substituted with one to three groups independently selected from halogen, cyano, —NMe$_2$, acetyl, C$_{1-4}$-alkyl, —O—C$_{1-4}$-alkyl, —CH$_2$—O—C$_{1-4}$-alkyl, C$_{3-6}$cycloalkyl, —O—C$_{3-6}$cycloalkyl, phenyl, —CH$_2$—O-phenyl, 4-6-membered heterocyclyl, oxazolyl, thiazolyl, pyridyl, pyrazolyl, isoxazolyl which latter thirteen groups are optionally substituted with one or more substituents selected from fluoro, chloro, bromo, cyano, —NH—COCH$_3$, —NMe$_2$, phenyl, —O—CH$_2$-ethynyl, C$_{1-4}$-alkyl, C$_{3-6}$-cycloalkyl, —O—C$_{3-6}$cycloalkyl, —O—CH$_2$—C$_{3-6}$cycloalkyl, 4-6-membered heterocyclyl, —O—C$_{1-4}$-alkyl, —O—C$_{1-2}$alkyl-OC$_{1-2}$alkyl which latter seven groups are optionally substituted with one or more fluorine atoms.

In another embodiment, in the general formula I, Ia, Ib, Ic, R$^1$, R$^2$, R$^3$, R$^4$, R$^5$, R$^6$ have the same meaning as defined in any of the preceding embodiments, and R$^2$ represents phenyl, naphthyl, 3-isochinolyl,

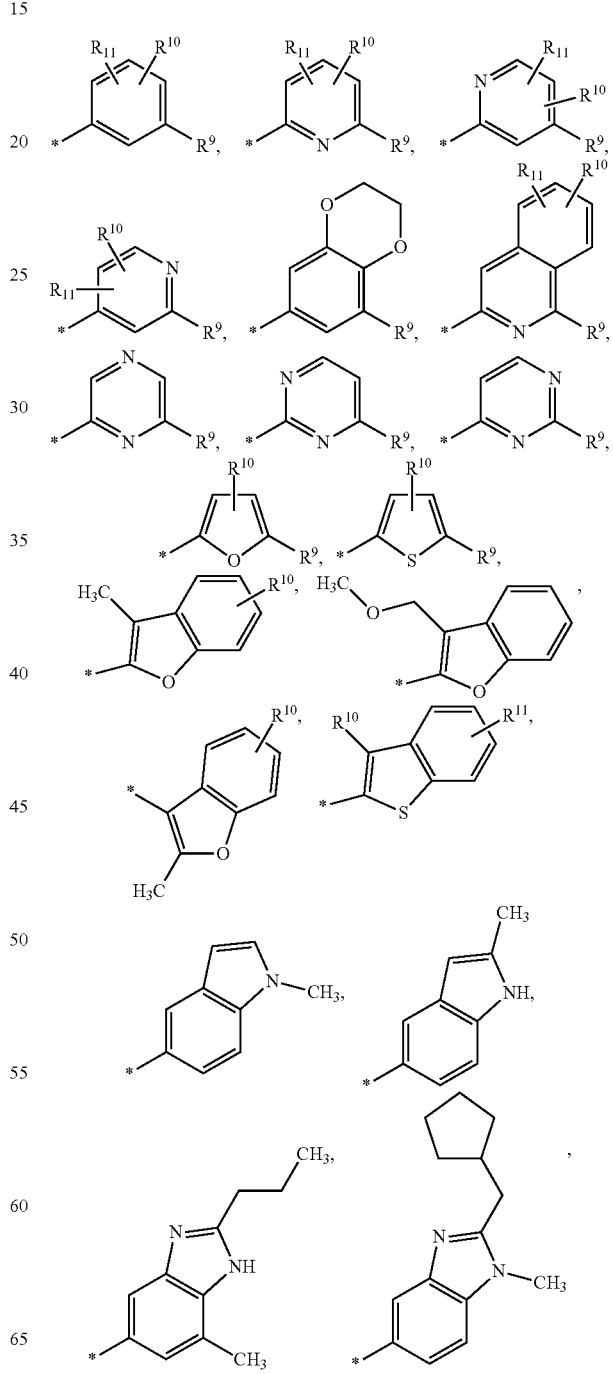

-continued

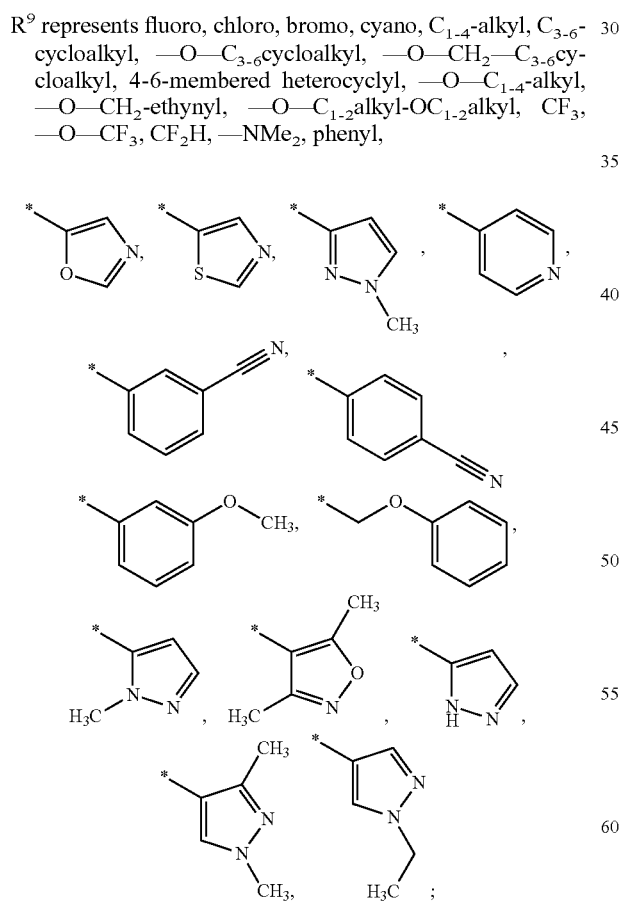

R⁹ represents fluoro, chloro, bromo, cyano, $C_{1-4}$-alkyl, $C_{3-6}$-cycloalkyl, —O—$C_{3-6}$cycloalkyl, —O—$CH_2$—$C_{3-6}$cycloalkyl, 4-6-membered heterocyclyl, —O—$C_{1-4}$-alkyl, —O—$CH_2$-ethynyl, —O—$C_{1-2}$alkyl-$OC_{1-2}$alkyl, $CF_3$, —O—$CF_3$, $CF_2H$, —$NMe_2$, phenyl,

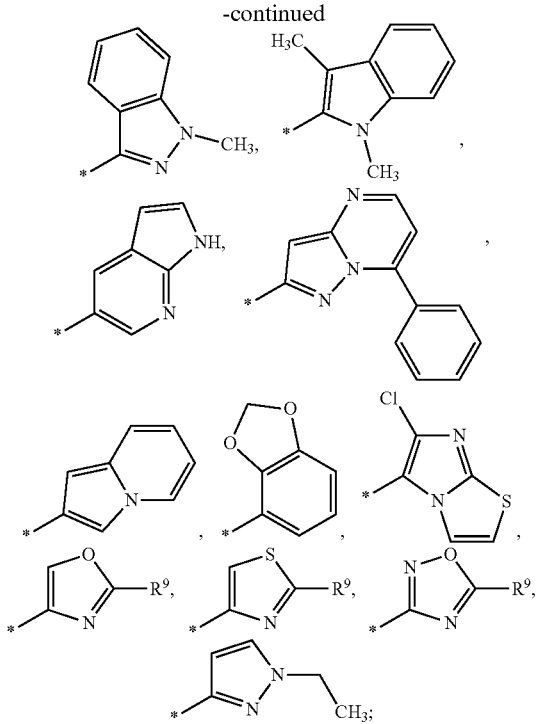

$R^{10}$, $R^{11}$ independently represents hydrogen, chloro, fluoro, methyl, ethyl, propyl, iso-propyl, $CF_3$, —$CF_2H$, —$OCH_3$, —$OCF_3$, —NH—$COCH_3$.

A further embodiment of the present invention comprises compounds of formula II

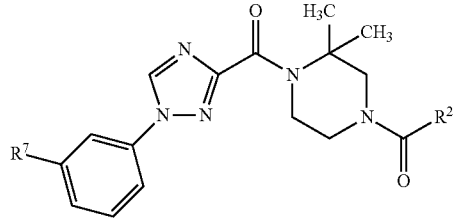

in which
$R^2$ represents phenyl, naphthyl, 3-isochinolyl,

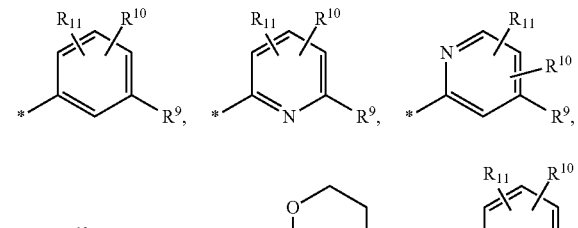

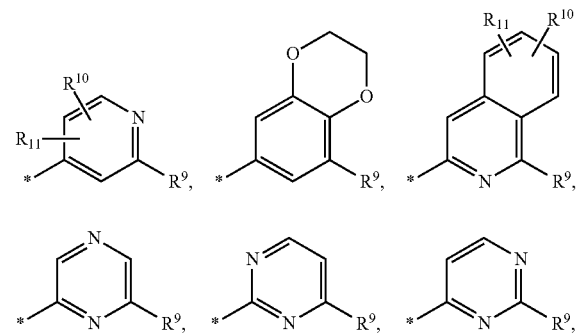

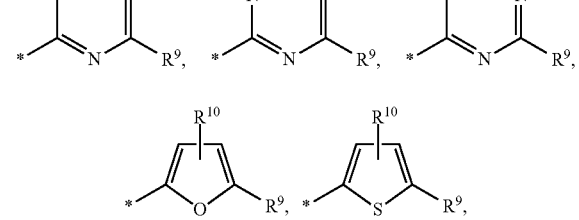

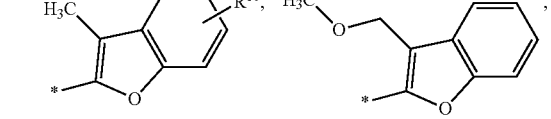

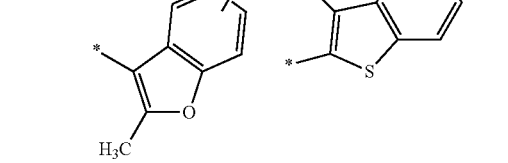

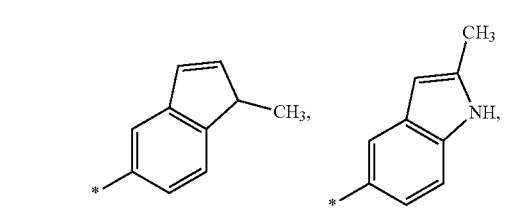

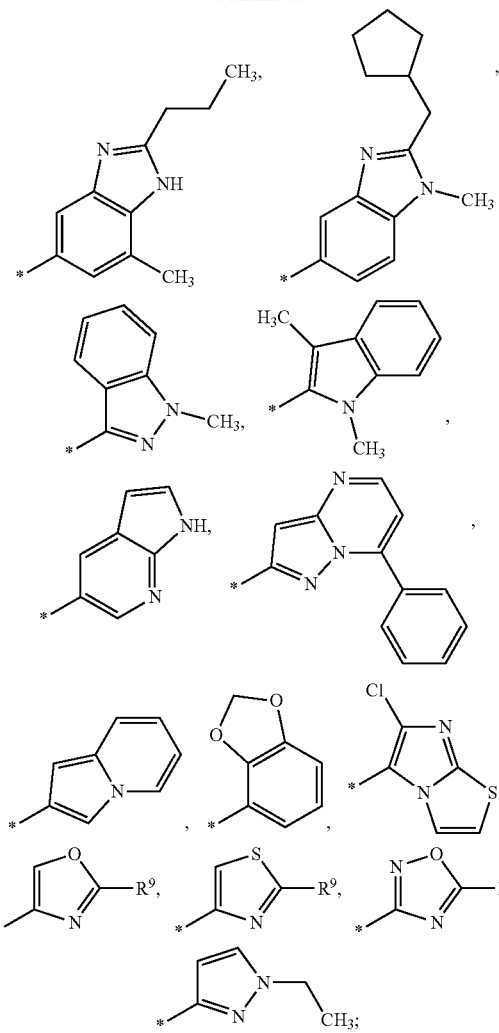

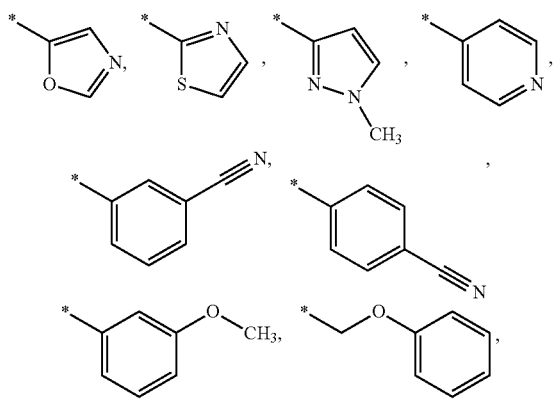

$R^7$ represents hydrogen, fluoro, bromo, chloro, cyano, methyl;

$R^9$ represents fluoro, chloro, bromo, cyano, $C_{1-4}$-alkyl, $C_{3-6}$-cycloalkyl, —O—$C_{3-6}$cycloalkyl, —O—$CH_2$—$C_{3-6}$cycloalkyl, 4-6-membered heterocyclyl, —O—$C_{1-4}$-alkyl, —O—$CH_2$-ethynyl, —O—$C_{1-2}$alkyl-O$C_{1-2}$alkyl, $CF_3$, —O—$CF_3$, $CF_2H$, —$NMe_2$, phenyl,

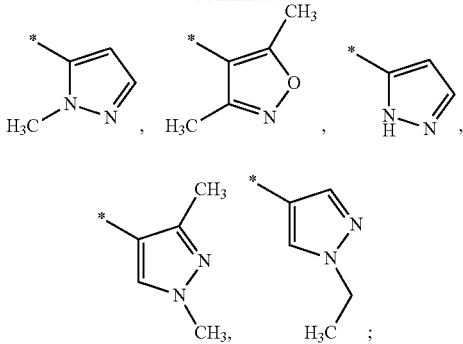

$R^{10}$, $R^{11}$ independently represents hydrogen, chloro, fluoro, methyl, ethyl, propyl, iso-propyl, $CF_3$, —$CF_2H$, —$OCH_3$, —$OCF_3$, —NH—$COCH_3$;

or a salt thereof, particularly a physiologically acceptable salt thereof.

A further embodiment of the present invention comprises compounds of formula III

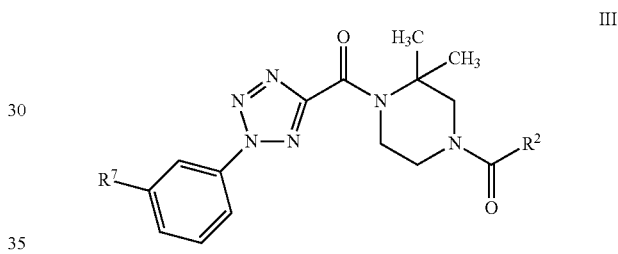

in which
$R^2$ represents phenyl, naphthyl, 3-isochinolyl,

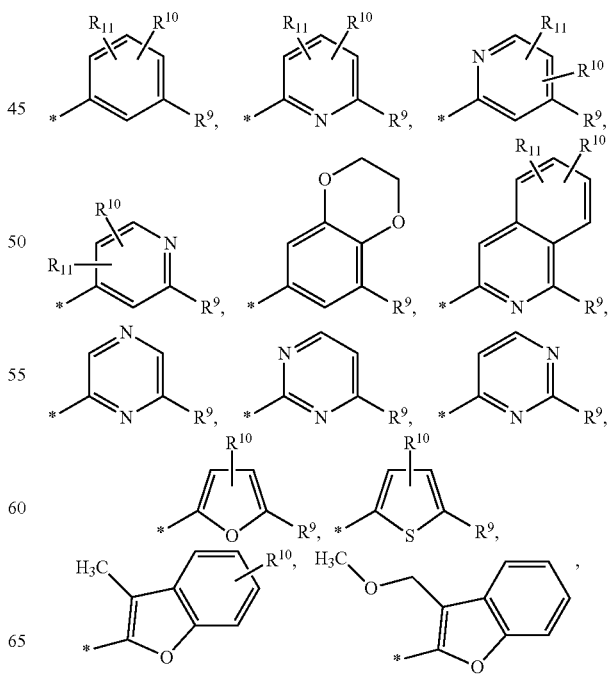

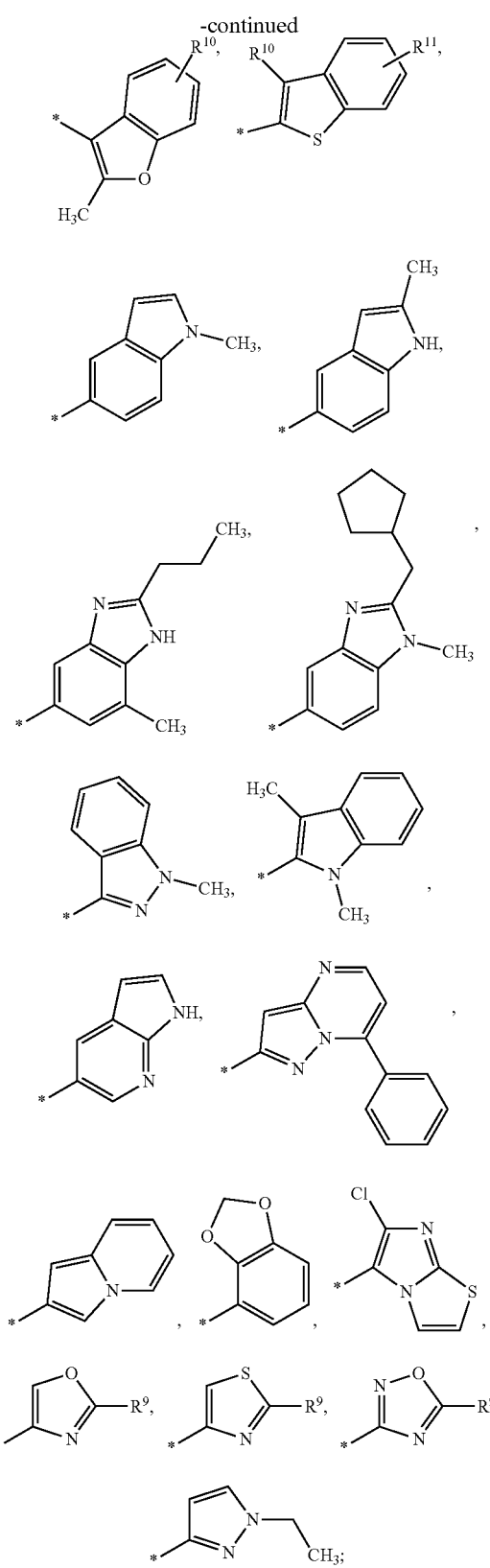

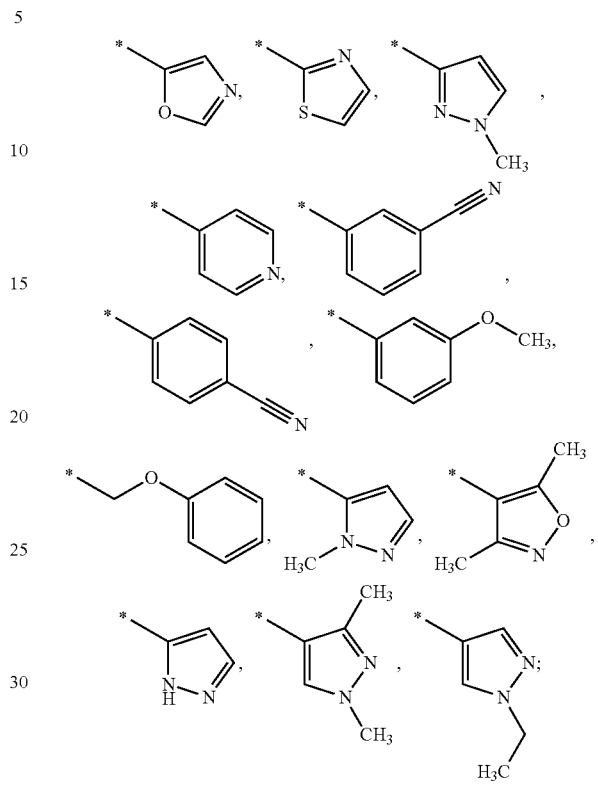

cloalkyl, 4-6-membered heterocyclyl, —O—$C_{1-4}$-alkyl, —O—$CH_2$-ethynyl, —O—$C_{1-2}$alkyl-O$C_{1-2}$alkyl, $CF_3$, —O—$CF_3$, $CF_2H$, —$NMe_2$, phenyl, $R^{10}$, $R^{11}$ independently represents hydrogen, chloro, fluoro, methyl, ethyl, propyl, iso-propyl, $CF_3$, —$CF_2H$, —$OCH_3$, —$OCF_3$, —NH—$COCH_3$;

or a salt thereof, particularly a physiologically acceptable salt thereof.

In another embodiment, in the general formula I, Ia, Ib, Ic, II, III, $R^1$, $R^3$, $R^4$, $R^5$, $R^6$, $R^7$ have the same meaning as defined in any of the preceding embodiments, and $R^2$ represents

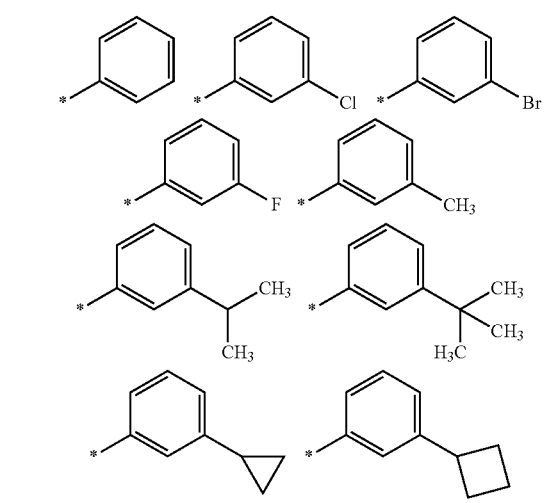

$R^7$ represents hydrogen, fluoro, bromo, chloro, cyano, methyl;

$R^9$ represents fluoro, chloro, bromo, cyano, $C_{1-4}$-alkyl, $C_{3-6}$-cycloalkyl, —O—$C_{3-6}$cycloalkyl, —O—$CH_2$—$C_{3-6}$cy- -continued
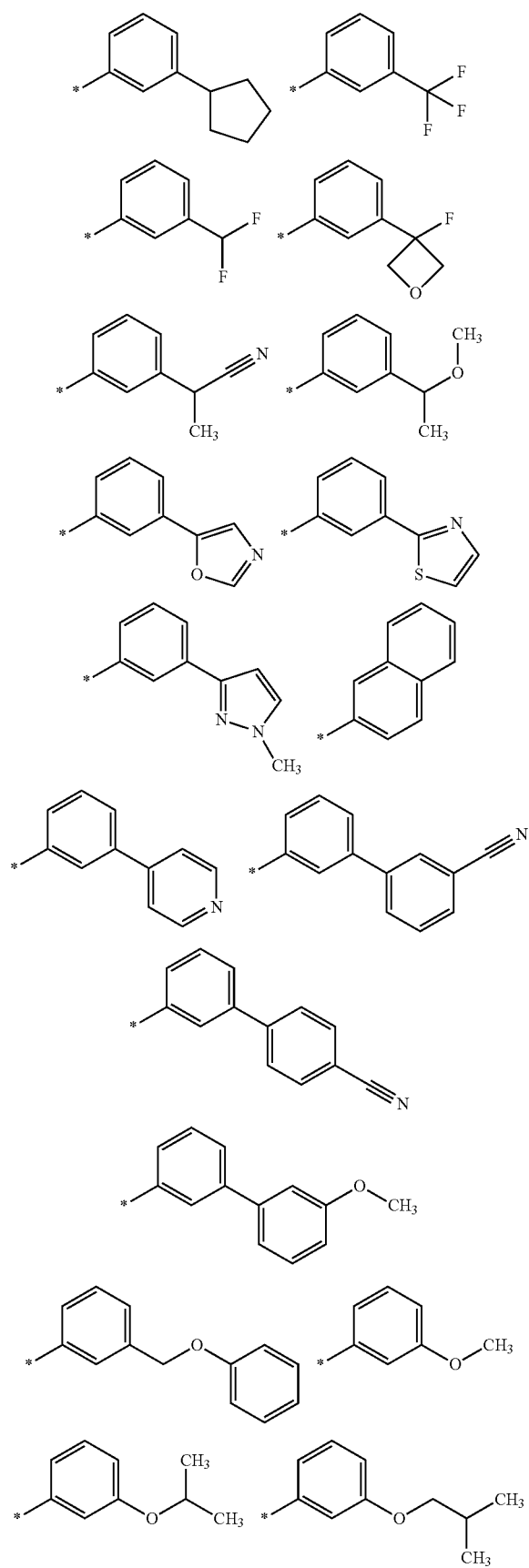
-continued
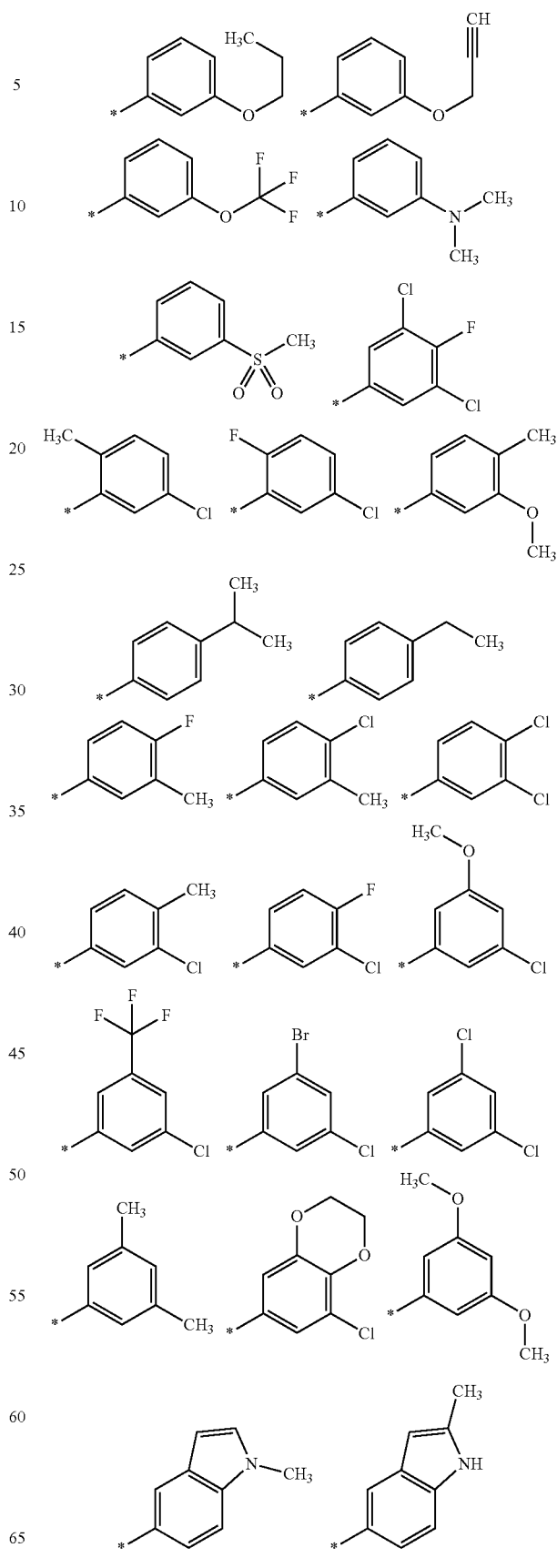

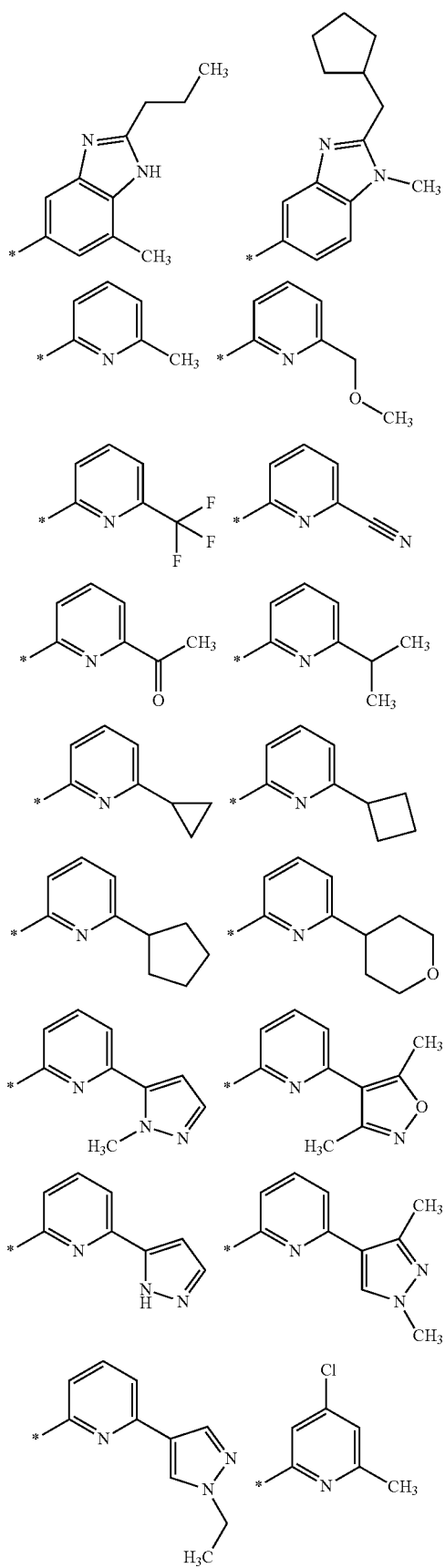
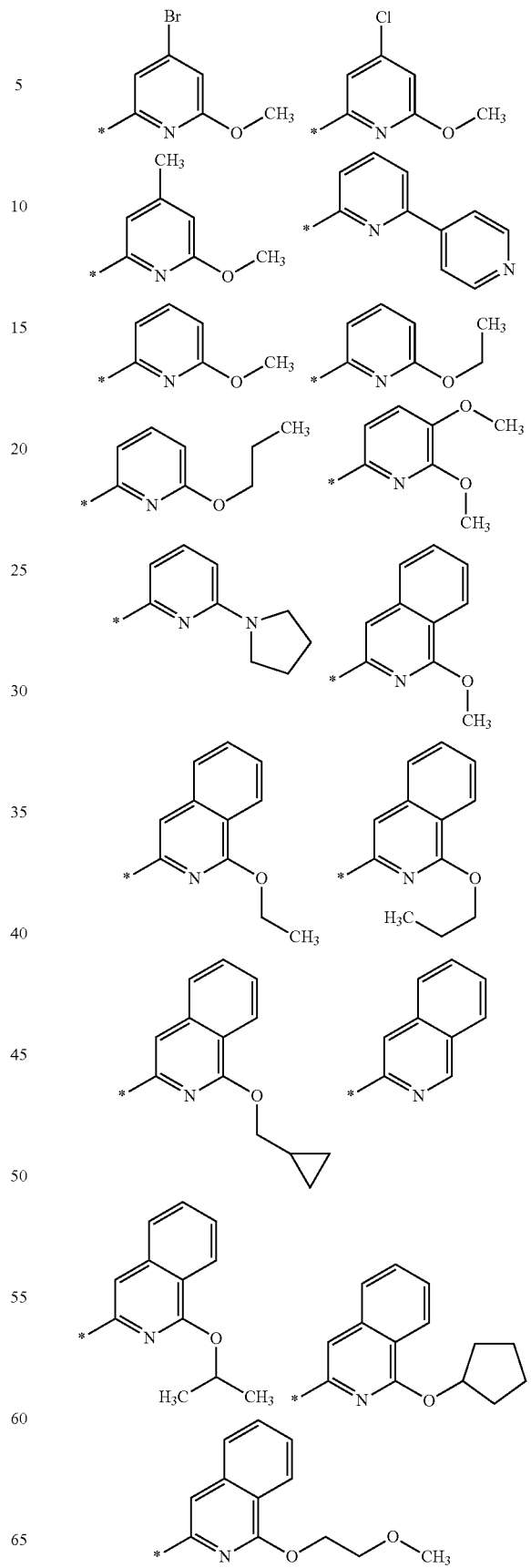

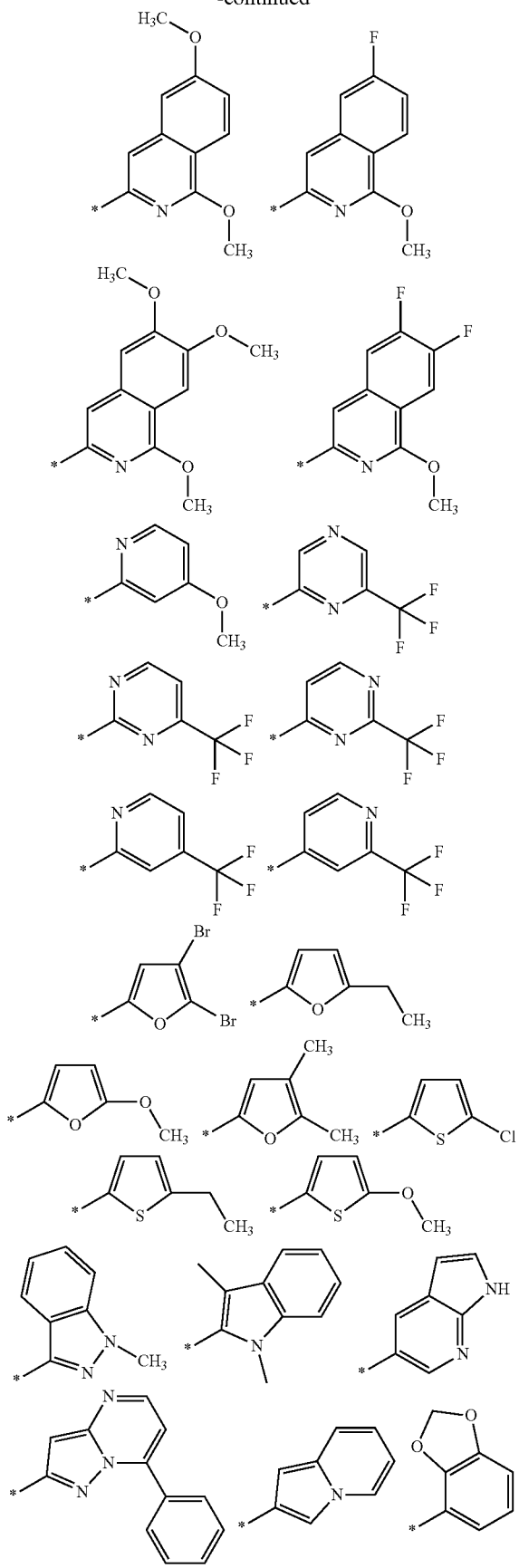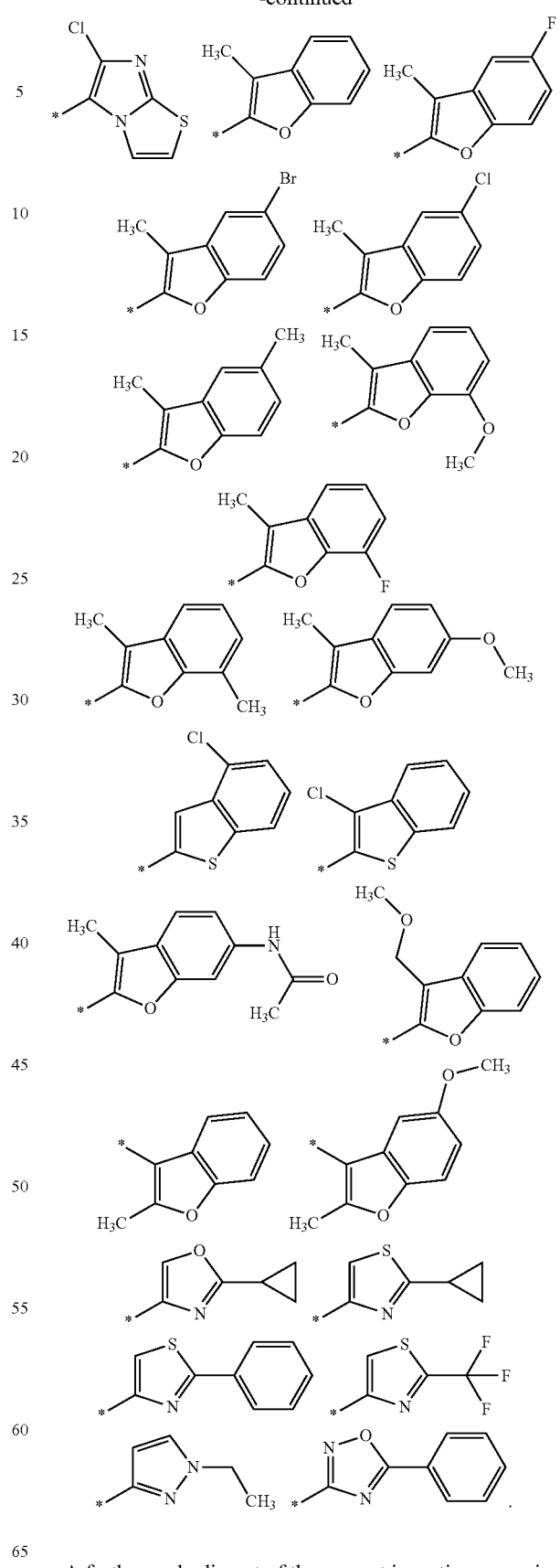
A further embodiment of the present invention comprises compounds of formulae I, Ia in which $R^1$ represents phenyl,
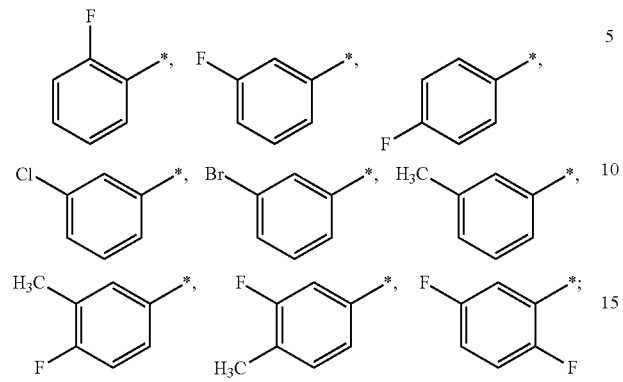
$R^2$ represents
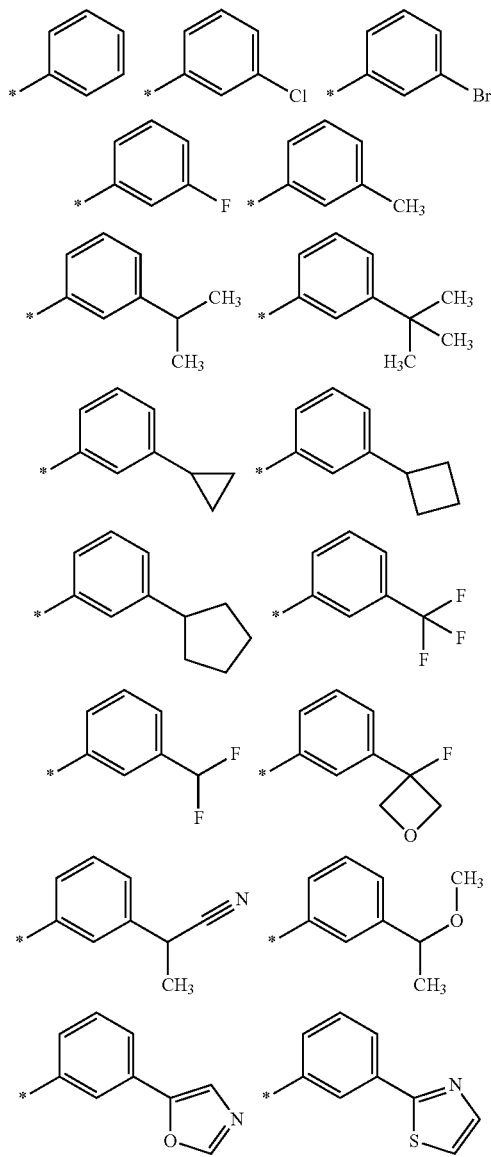
-continued
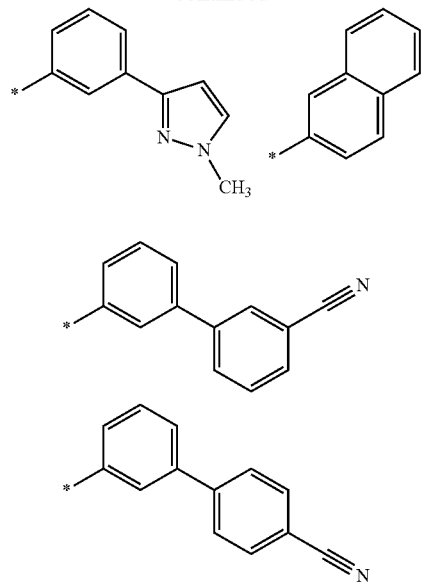
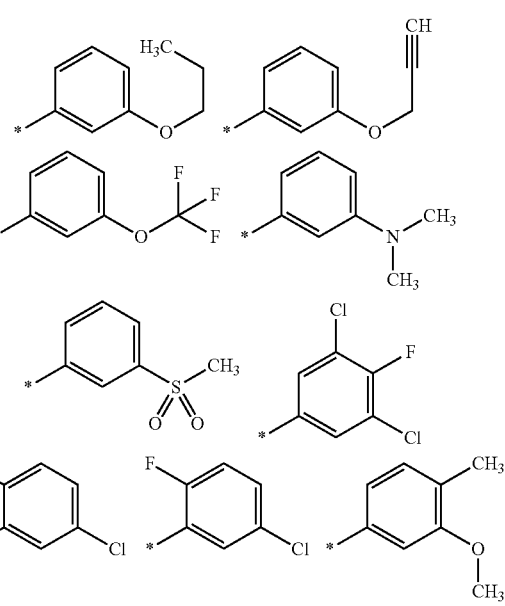

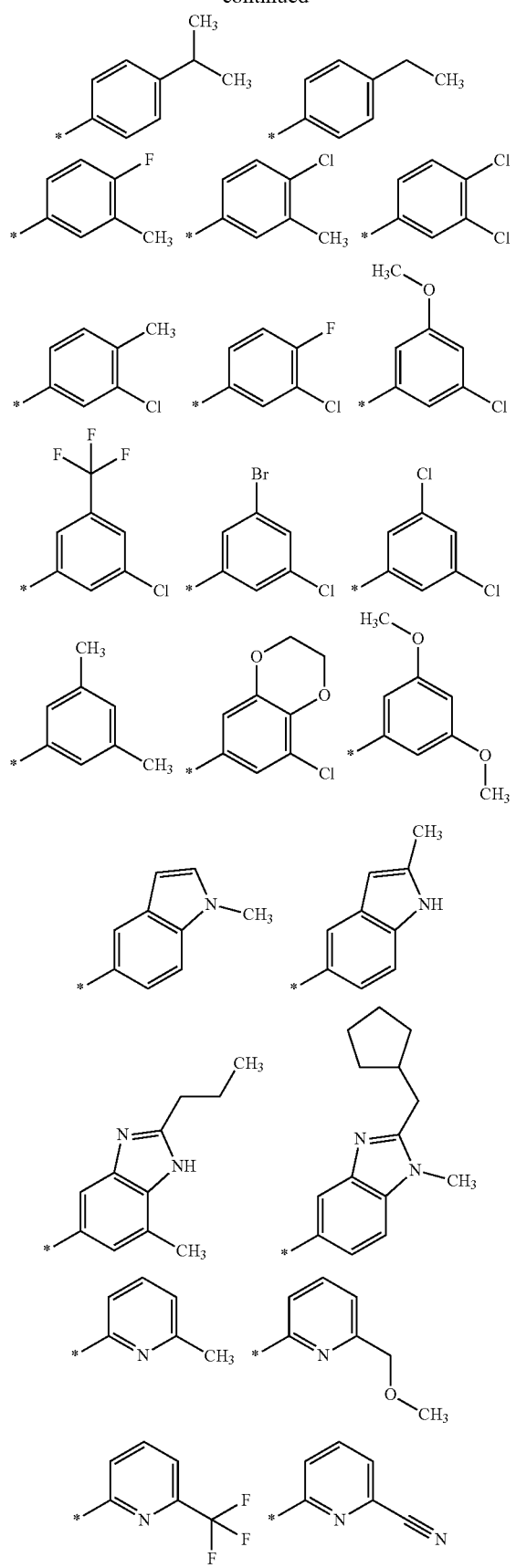
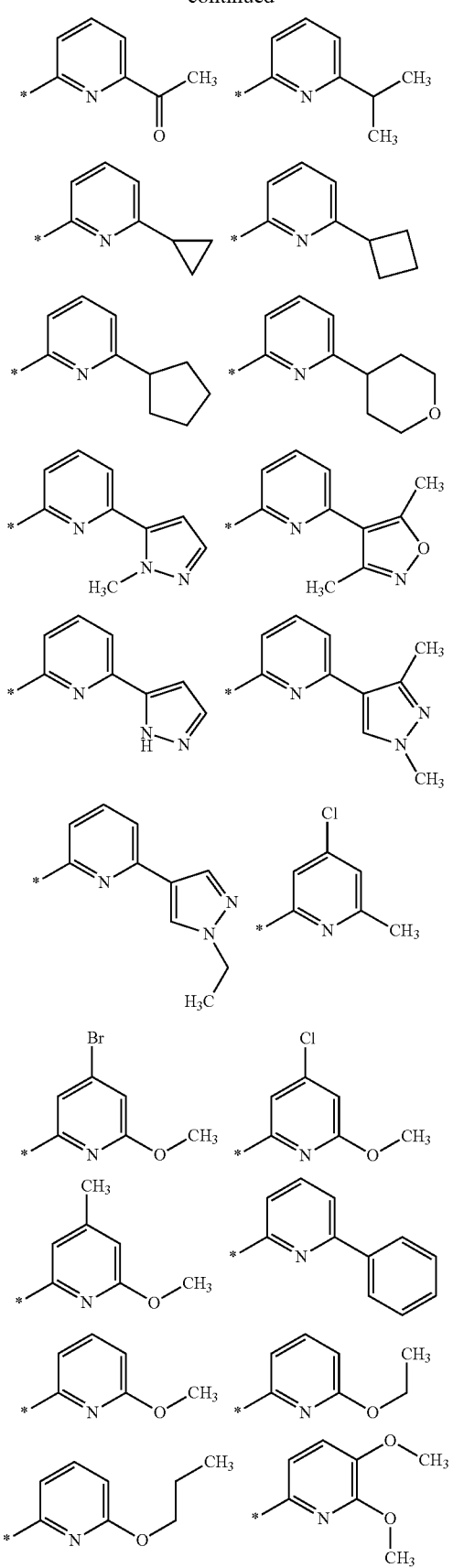

-continued
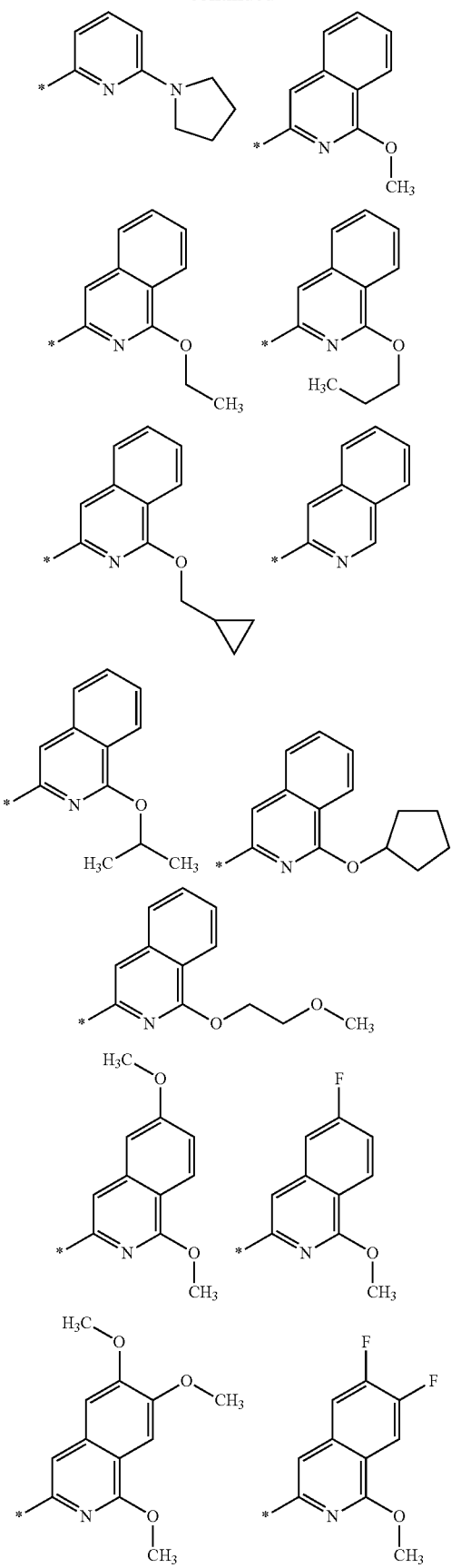
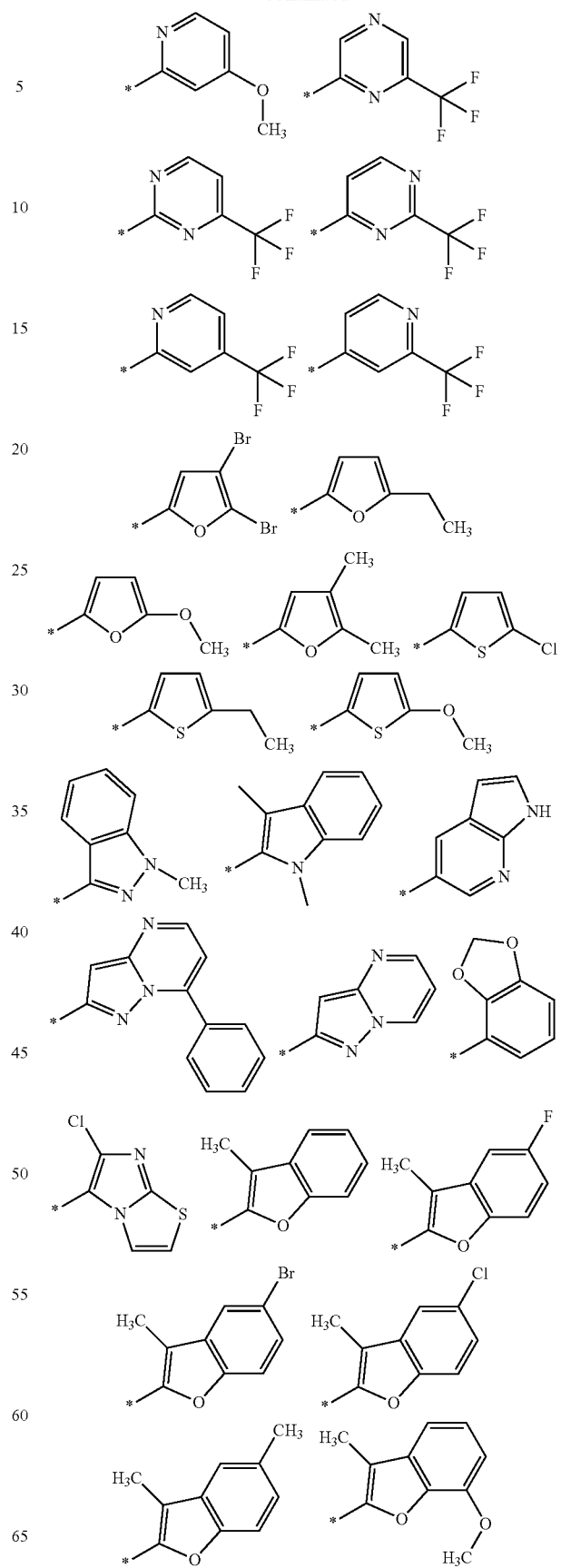

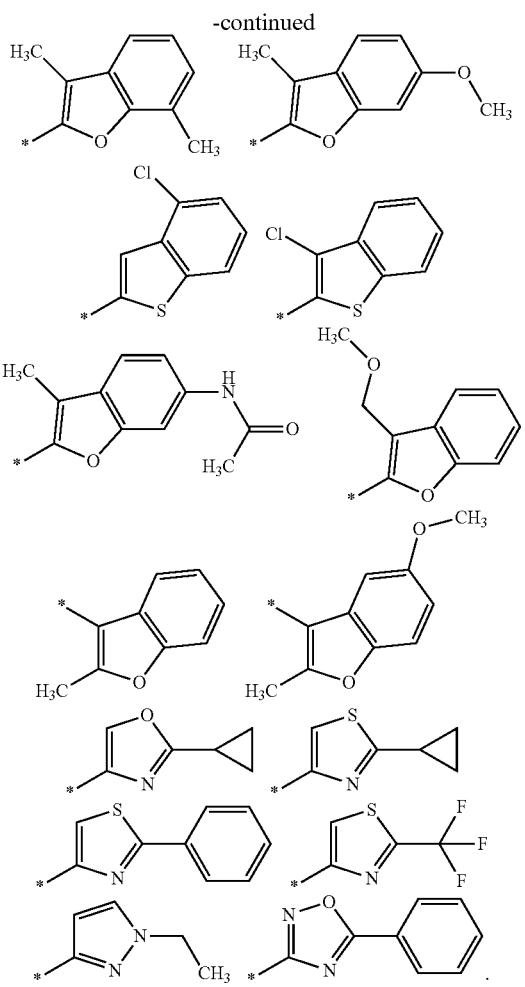

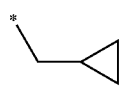

$R^3$ and $R^4$ independently represent hydrogen, methyl, ethyl, propyl, —CH$_2$—O—CH$_3$ which latter four groups are optionally substituted with one or more fluorine atoms with the proviso that $R^3$ and $R^4$ both are not hydrogen;

or $R^3$ and $R^4$ if both are attached to the same carbon atom, they may together with the carbon atom to which they are attached form a ring selected from cyclopropyl, cyclobutyl, cyclopentyl which latter three groups are optionally substituted with one or more fluorine atoms;

or a salt thereof, particularly a physiologically acceptable salt thereof.

Terms and Definitions Used

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkynyl:

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. Aryl may optionally be substituted with one or more residues such as $C_{1-4}$-alkyl, which may optionally be substituted with 0-3 fluorine radicals, cycloalkyl, hydroxy, alkoxy, aryl, halogen, cyano, nitro, amino, alkylamino or acylamino.

Heterocyclyl:

The term "heterocyclyl" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms. Heterocyclyl may optionally be substituted with one or more residues such as $C_{1-4}$-alkyl, which may optionally be substituted with 0-3 fluorine radicals, cycloalkyl, hydroxy, alkoxy, aryl, halogen, cyano, nitro, amino, alkylamino or acylamino.

Thus, the term "heterocyclyl" includes the following exemplary structures which are not depicted as radicals as each form may be attached through a covalent bond to any atom as long as appropriate valences are maintained:

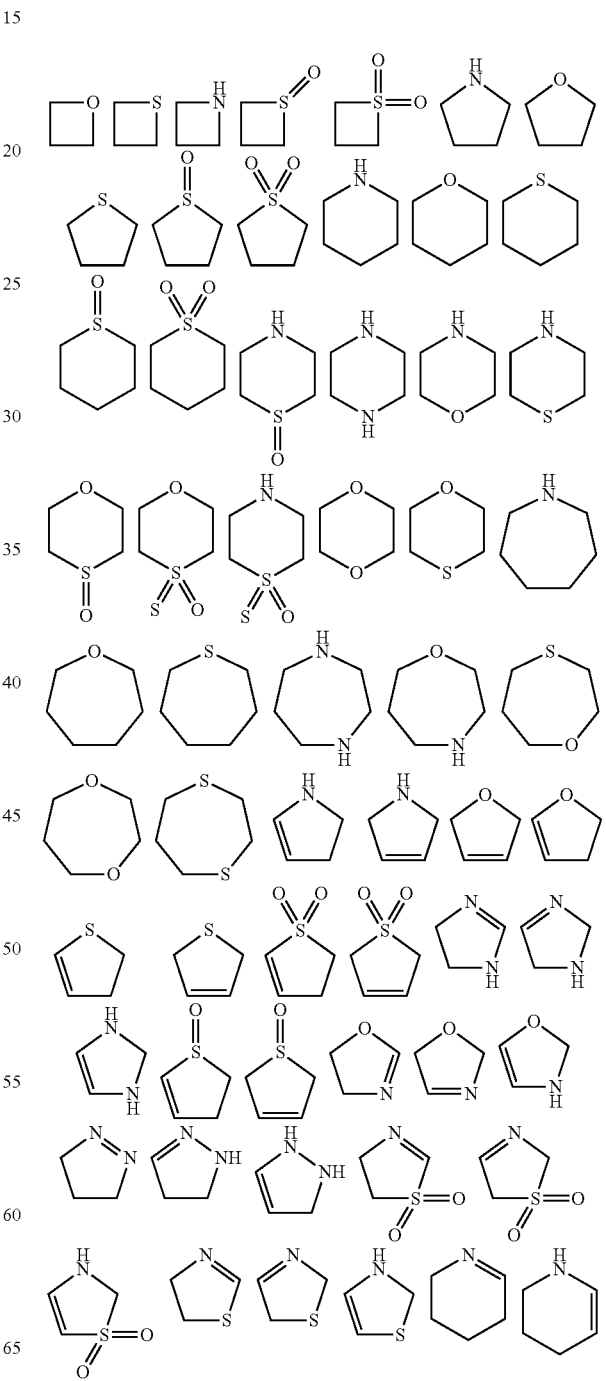

Heteroaryl:

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures which are not depicted as radicals as each form may be attached through a covalent bond to any atom as long as appropriate valences are maintained:

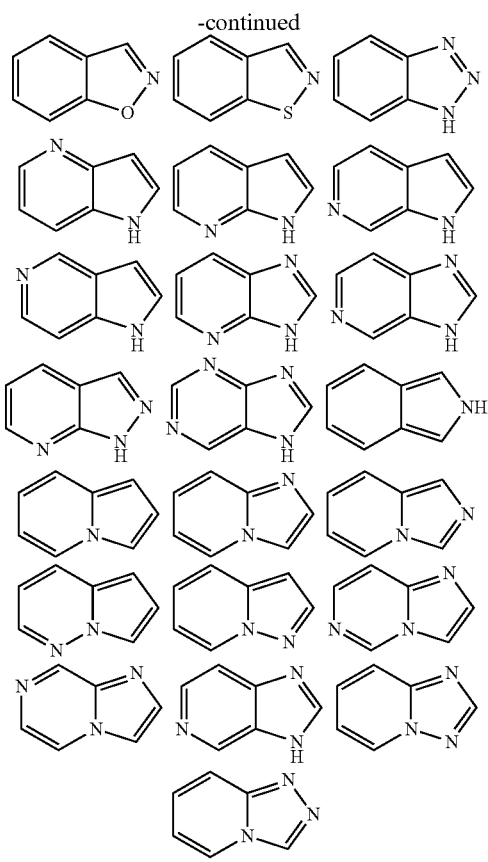

Many of the terms given above may be used repeatedly in the definition of a formula or group and in each case have one of the meanings given above, independently of one another.

General Method of Preparation

The compounds of this invention can be prepared by employing reactions as shown in the following schemes, in addition to other standard manipulations that are known in the literature, exemplified in the experimental section or clear to one skilled in the art. The starting materials which are not described herein are either commercially available or may be prepared by employing reactions described in the literature or are clear to one skilled in the art. The following examples are provided so that the invention might be more fully understood, are illustrative only, and should not be construed as limiting.

The abbreviation PG describes a "protecting group" which is introduced to a reactive group bevor a certain manipulation is carried out, and which is later removed. Exemplifications for protecting groups for reactive groups are:

for amino-alkylamino or imino groups: actyl-, trifluoracetyl-, benzoyl-, ethoxycarbonyl-, N-tert-butoxycarbonyl (BOC), N-benzyloxycarbonyl-(Cbz), benzyl-, methoxybenzyl-, 2,4-dimethoxybenzyl and for amino groups additionally the phthalyl group for amide groups: N-methoxynethyl (MOM), N-benzyloxymethyl (BOM), N-(trimethylsilyl)ethoxymethyl (SEM), N-tert-butyl-dimethylsiloxymethyl-, N-tert-butyl-dimethylsilyl (TBDMS), N-triisopropylsilyl— (TIPS), N-benzyl-, N-4-methoxybenzyl (PMB), N-triphenylmethyl— (Tr), N-tert-butoxycarbonyl (BOC), N-benzyloxycarbonyl— (Cbz), N-trimethylsilylethylsulfonyl— (SES), for hydroxy groups: methoxy-, benzyloxy-, trimethylsilyl— (TMS), acetyl-, benzoyl-, tert-butyl-, trityl-, benzyl-, or tetrahydropyranyl (THP) groups, for carboxyl groups: trimethylsilyl— (TMS), methylethyl-, tert-butyl-, benzyl-, or tetrahydropyranyl (THP) groups.

For more information on introduction and removal of protecting groups see: T. W. Greene, P. G. M. Wuts, "Protective Groups in Organic Synthesis", Wiley, 1991 and 1999 or in "Protective Groups", Kocienski P. J.; Thieme: New York, 1994.

In some cases the final product may be further modified, for example by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied in order to facilitate the reaction or to avoid unwanted reaction products. The following examples are provided so that the invention might be more fully understood. These examples are illustrative only and should not be constructed as limiting the invention in any way.

In one aspect, the compounds of formula I described in this invention, wherein $R^1$, $R^2$, $R^3$, $R^4$ and U are defined as above, can be synthesized according to the following scheme 1:

Scheme 1:

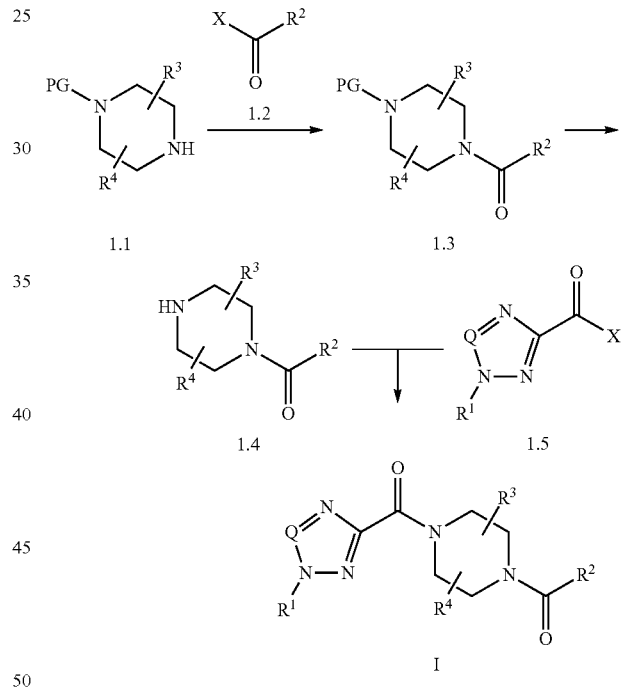

Piperazine 1.1 equipped with a suitable protecting group PG, preferably BOC or Cbz, is coupled with the carboxyclic acid (X=OH) or its acid chloride (X=Cl) 1.2 to form amide 1.3. Preferably this reaction is carried out with the carboxylic acid under in situ activation with TBTU and addition of DIPEA in an inert solvent such as DMF at RT. The protecting group is then cleaved to give piperazine 1.4 using a method described in the literature or clear to one skilled in the art. The BOC protecting group is preferably removed by treatment with TFA in an inert solvent such as DCM at RT. In the last step, piperazine 1.4 is coupled with carboxyclic acid (X=OH) or its acid chloride (X=Cl) 1.5 to form the final product I. Preferably this reaction is carried out with the carboxylic acid (X=OH) under in situ activation with TBTU and addition of DIPEA in an inert solvent such as DMF at RT or via a coupling between the acid chloride 1.5 (X=Cl) with piperazine 1.4.

Alternatively, the compounds of this invention can be synthesized according to scheme 2:

Scheme 2:

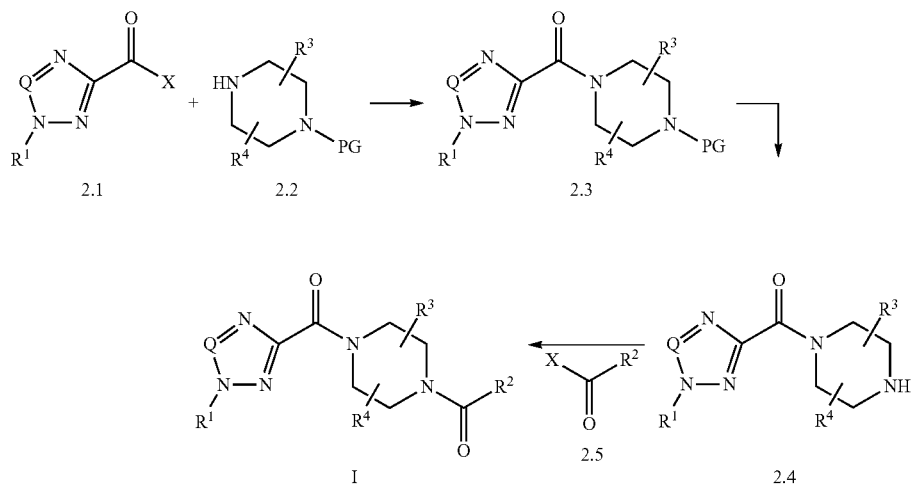

The carboxylic acid 2.1 (X=OH) or its acid chloride derivative (X=Cl) is coupled with piperidine 2.2, carrying a suitable protecting group PG, preferably BOC, to give amide 2.3. Preferably this reaction is carried out using the carboxylic acid (X=OH) under in situ activation with TBTU and addition of DIPEA in an inert solvent such as DMF at RT or via a direct coupling between the acid chloride 2.1 (X=Cl) with piperazine 2.2. The protecting group of intermediate 2.3 is then cleaved to give piperazine 1.4 using a method described in the literature or clear to one skilled in the art. The BOC protecting group is preferably removed by treatment with TFA in an inert solvent such as DCM at RT. Intermediate 2.4 may also be obtained and isolated as its trifluoracetate salt.

In the last step, intermediate 2.4 is reacted with carboxyclic acid 2.5 (X=OH) or its acid chloride (X=Cl) to form the final product I. Preferably, this reaction is carried out using the carboxylic acid (X=OH) under in situ activation with TBTU and addition of DIPEA in an inert solvent such as DMF at RT or via a coupling between the acid chloride 2.5 (X=Cl) with piperazine 2.4 under addition of a base (e.g. DIPEA) in an inert solvent such as THF.

The preparation of the required 1-aryl-1H-[1,2,4]-triazole-3-carboxylic acids, in which $R^1$ is defined as in structure I and Q is C—H can be accomplished as depicted in the following scheme:

Scheme 3:
a)

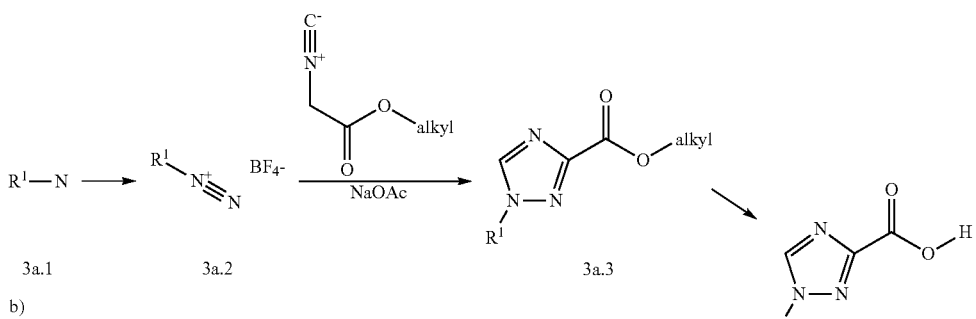

b)

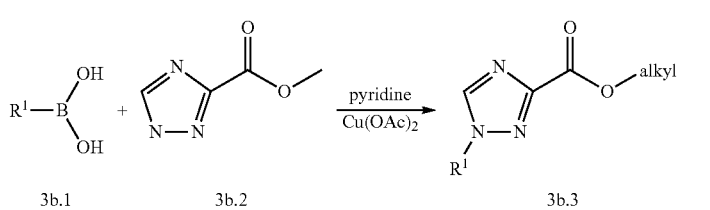

According to the synthetic route depicted in scheme 3a, 3a.1 is treated with sodium nitrate and tetrafluoroboric acid in water at low temperatures (0-5° C.) to form the diazonium salt 3a.2 which can be isolated and subsequently subjected to a cyclisation reaction with an alkyl isocyanoacetate to give 1,2,4-trazole 3a.3. This cyclisation reaction is usually carried out in a protic solvent such as methanol or ethanol, under addition of a base such as sodium acetate at temperatures between −10° C. and +5° C.

Alternatively, in a one step procedure, the diazonium species may be formed from 3a.1 and sodium nitrite in aqueous hydrochlorid acid at 0° C. and reacted in situ with a solution of the alkyl isocyanoacetate and sodium acetate in methanol to give 1,2,4-triazole 3a.3.

According to the synthetic route depicted in scheme 3b, aryl-[1,2,4]-triazole-3-carboxylic acid 3a.4 can also be synthesized by reacting an arylboronic acid 3b.1 with 1H-[1,2,4]-triazole-3-carboxylic acid alkyl ester 3b.2 under addition of copper(II) acetate and pyridine in DCM. Hydrolysis of the alkyl ester (e.g. sodium hydroxide in methanol/THF) lead to 3.4.

2-aryl-2H-tetrazole-5-carboxylic acids 4.6, in which $R^1$ is defined as in structure I and Q is N were synthesized according to the following scheme:

Scheme 5:

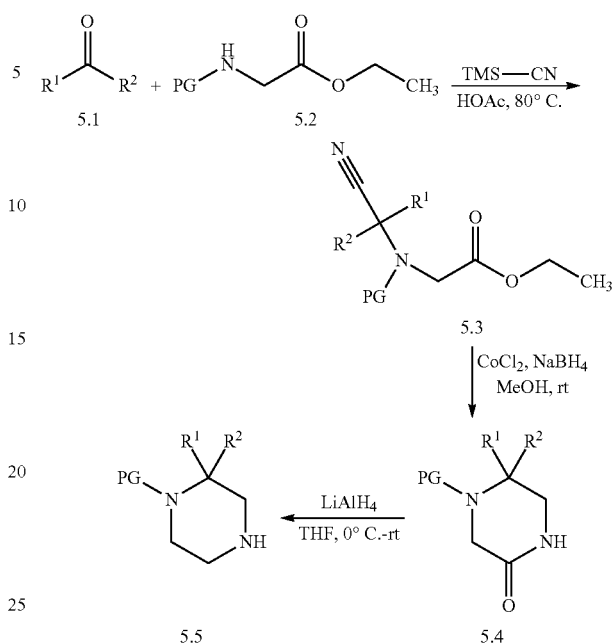

Scheme 4:

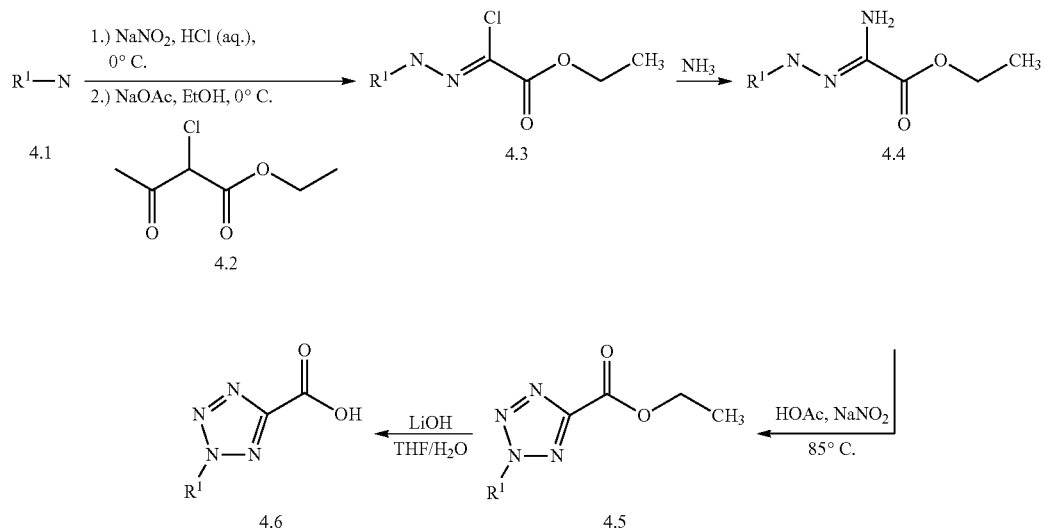

4.1 was treated with sodium nitrite in aqueous hydrochlorid acid at 0° C. to form the correspondium diazonium species which was reacted in situ with 2-chloro-3-oxo-butyric acid ethyl ester 4.2 and sodium acteate in ethanol at 0° C. to give 4.3 as an intermediate product. Treatment 4.3 with ammonia solution in tetrahydrofurane resulted in formation of 4.4. This compound was heated with acetic acid in tetrahydrofurane at 85° C. and subsequently treated with an aqueous sodium nitrite solution to give the 2-aryl-2H-tetrazole-5-carboxylic acid ethyl ester 4.5. Hydrolysis of the ester (e.g. lithium hydroxide in tetrahydrofurane/methanol/water) yielded 4.6.

The synthesis of geminal disubstituted piperazines is exemplified in scheme 5:

A ketone of structure 5.1 (with $R^1$ and $R^2$ being for example alkyl or alkoxyalkyl, optionally substituted with one to three halogen atoms) is reacted with N-protected amino-acetic acid ethyl ester 5.2 (e.g. PG equals Benzyl, . . . ) under addition of trimethylsilyl cyanide and in acetic acid at elevated temperature in a modified Strecker reaction to form 5.3. This intermediate is submitted to reductive conditions be treatment with cobalt(II)-chloride and sodium borohydride in an alcoholic solvent (e.g. methanol or ethanol) at room temperature to yield 5.4 . . . Treating 5.4 with lithium aluminium hydride in a suited solvent (e.g. THF) leads to the required piperazine 5.5.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 µg/mL tetracycline, 100 µg/mL hygromycin and 500 µg/mL geneticin. The cell culture media is exchanged for tetracycline-free cell culture media 3-7 days before the assay. One day before the assay the cell culture medium is exchanged to DMEM without glutamine and phenol red and supplemented with 10% FCS, 100 µg/mL hygromycin and 500 µg/mL geneticin. On the assay day, the medium of the subconfluent cultures is removed and the cells are detached by addition of 2.5 ml EDTA (0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 mM at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml ($1\times10^6$ cells/mL). The cells are plated onto BD BioCoat Poly-D-Lysine 384 well plates (20.000 cells/well; 20 µl/well). The lid covered plates are then incubated until use at 37° C./10% CO2. For dye loading, 20 µl of Calcium-4 assay kit solution (prepared according to the manufacturer's description in Ringer solution) are added to the cells and the plates are incubated for 80 min 37° C. and then 10 min at room temperature.

Controls, Compound Dilution and Assay Execution:

Each assay plate contained wells with "high" and "low" controls:

Low controls 1% DMSO/ringer solution+basal glutamate activation (defined as 100% CTL).

High controls 10 µM CDPPB+basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 µl of each compound solution are then transferred to the assay plate and the Ca2+ kinetic is measured to determine any intrinsic compound activity. After 5 min incubation in the FLIPR device, the second stimulation with 20 µl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50.

The EC50 of the modulation is calculated over a nonlinear regression with GraphPad Prism (Table 1).

TABLE 1

| Example | EC$_{50}$ [nM] |
|---|---|
| 1 | 39 |
| 2 | 67 |
| 3 | 86 |
| 4 | 101 |
| 5 | 131 |
| 6 | 197 |
| 7 | 50 |
| 8 | 53 |
| 9 | 53 |
| 10 | 95 |
| 11 | 19 |
| 12 | 19 |
| 13 | 22 |
| 14 | 25 |
| 15 | 30 |
| 16 | 41 |
| 17 | 45 |
| 18 | 48 |
| 19 | 51 |
| 20 | 53 |
| 21 | 62 |
| 22 | 58 |
| 23 | 58 |
| 24 | 61 |
| 25 | 62 |
| 26 | 72 |
| 27 | 80 |
| 28 | 99 |
| 29 | 109 |
| 30 | 115 |
| 31 | 160 |
| 32 | 179 |
| 33 | 203 |
| 34 | 221 |
| 35 | 350 |
| 36 | 383 |
| 37 | 388 |
| 38 | 410 |
| 39 | 419 |
| 40 | 852 |
| 41 | 200 |
| 42 | 88 |
| 43 | 80 |
| 44 | 136 |
| 45 | 54 |
| 46 | 88 |
| 47 | 184 |
| 48 | 127 |
| 49 | 222 |
| 50 | 294 |
| 51 | 102 |
| 52 | 63 |
| 53 | 77 |
| 54 | 201 |
| 55 | 64 |
| 56 | 436 |
| 57 | 120 |
| 58 | 104 |
| 59 | 1080 |
| 60 | 69 |
| 61 | 96 |
| 62 | 869 |
| 63 | 89 |
| 64 | 262 |
| 65 | 144 |
| 66 | 104 |
| 67 | 29 |
| 68 | 54 |
| 69 | 53 |
| 70 | 142 |
| 71 | 47 |
| 72 | 64 |
| 73 | 162 |
| 74 | 170 |
| 75 | 419 |
| 76 | 233 |
| 77 | 181 |
| 78 | 146 |
| 79 | 230 |
| 80 | 139 |
| 81 | 155 |

TABLE 1-continued

| Example | EC$_{50}$ [nM] |
|---|---|
| 82 | 120 |
| 83 | 64 |
| 84 | 107 |
| 85 | 109 |
| 86 | 164 |
| 87 | 105 |
| 88 | 375 |
| 89 | 168 |
| 90 | 38 |
| 91 | 113 |
| 92 | 119 |
| 93 | 242 |
| 94 | 285 |
| 96 | 25 |
| 97 | 25 |
| 98 | 32 |
| 99 | 28 |
| 100 | 29 |
| 101 | 52 |
| 102 | 49 |
| 103 | 49 |
| 104 | 50 |
| 105 | 64 |
| 106 | 89 |
| 107 | 108 |
| 108 | 112 |
| 109 | 128 |
| 110 | 142 |
| 111 | 215 |
| 112 | 770 |
| 113 | 76 |
| 114 | 233 |
| 115 | 158 |
| 116 | 388 |
| 117 | 208 |
| 118 | 50 |
| 119 | 695 |
| 120 | 43 |
| 121 | 123 |
| 122 | 213 |
| 123 | 254 |
| 124 | 145 |
| 125 | 83 |
| 126 | 91 |
| 127 | 296 |
| 129 | 88 |
| 130 | 31 |
| 131 | 1870 |
| 132 | 1810 |
| 133 | 1110 |
| 134 | 21 |
| 135 | 47 |
| 136 | 52 |
| 137 | 69 |
| 138 | 136 |
| 139 | 314 |
| 140 | 661 |
| 141 | 487 |
| 142 | 122 |
| 143 | 589 |
| 144 | 23 |
| 145 | 120 |
| 146 | 2170 |
| 147 | 613 |
| 148 | 113 |
| 149 | 353 |
| 151 | 16 |
| 152 | 291 |
| 153 | 101 |
| 154 | 157 |
| 155 | 134 |
| 156 | 232 |
| 157 | 364 |
| 158 | 441 |
| 159 | 693 |
| 160 | 207 |
| 161 | 316 |

TABLE 1-continued

| Example | EC$_{50}$ [nM] |
|---|---|
| 162 | 475 |
| 163 | 1511 |
| 164 | 19 |
| 165 | 25 |
| 166 | 15 |
| 167 | 15 |
| 168 | 15 |
| 169 | 27 |
| 170 | 37 |
| 171 | 56 |
| 172 | 26 |
| 173 | 19 |
| 174 | 221 |
| 175 | 104 |
| 176 | 366 |
| 177 | 37 |
| 179 | 153 |
| 180 | 16 |
| 181 | 19 |
| 182 | 28 |
| 183 | 49 |
| 184 | 33 |
| 185 | 36 |
| 186 | 39 |
| 187 | 24 |
| 188 | 33 |
| 189 | 36 |
| 190 | 57 |
| 191 | 64 |
| 192 | 159 |
| 193 | 173 |
| 194 | 491 |
| 195 | 1000 |
| 196 | 156 |
| 197 | 149 |
| 198 | 123 |
| 199 | 69 |
| 200 | 132 |
| 201 | 102 |
| 202 | 65 |
| 203 | 62 |
| 204 | 129 |
| 205 | 42 |
| 206 | 188 |
| 207 | 34 |
| 208 | 125 |
| 210 | 314 |
| 211 | 264 |
| 212 | 568 |
| 213 | 817 |
| 214 | 428 |
| 215 | 534 |
| 216 | 612 |
| 217 | 1535 |
| 218 | 422 |
| 219 | 356 |
| 220 | 799 |
| 221 | 174 |
| 222 | 294 |
| 223 | 330 |
| 224 | 369 |
| 225 | 498 |
| 226 | 600 |
| 227 | 954 |
| 228 | 404 |
| 229 | 512 |
| 230 | 570 |
| 231 | 1778 |
| 232 | 1163 |
| 233 | 476 |
| 234 | 301 |
| 235 | 314 |
| 236 | 1618 |
| 237 | 174 |
| 238 | 317 |
| 239 | 326 |
| 240 | 350 |

TABLE 1-continued

| Example | EC$_{50}$ [nM] |
|---|---|
| 241 | 987 |
| 242 | 114 |
| 243 | 365 |
| 244 | 216 |
| 245 | 357 |
| 246 | 230 |
| 247 | 373 |
| 248 | 169 |
| 249 | 198 |
| 250 | 371 |
| 251 | 886 |
| 252 | 278 |
| 253 | 336 |
| 254 | 157 |
| 255 | 152 |
| 256 | 205 |
| 257 | 1103 |
| 258 | 172 |
| 259 | 231 |
| 260 | 153 |
| 261 | 168 |
| 262 | 193 |
| 263 | 251 |
| 264 | 891 |
| 265 | 194 |
| 266 | 538 |
| 267 | 558 |
| 268 | 327 |
| 269 | 447 |
| 270 | 677 |
| 271 | 621 |
| 272 | 350 |
| 273 | 1319 |
| 274 | 810 |
| 275 | 170 |
| 276 | 264 |
| 277 | 507 |
| 278 | 929 |
| 279 | 530 |
| 280 | 476 |
| 281 | 1496 |
| 282 | 597 |
| 283 | 233 |
| 284 | 858 |
| 285 | 746 |
| 286 | 1331 |
| 287 | 242 |
| 288 | 372 |
| 289 | 487 |
| 290 | 272 |
| 291 | 47 |
| 292 | 1210 |
| 293 | 361 |
| 294 | 1077 |
| 295 | 95 |
| 296 | 269 |
| 297 | 411 |
| 298 | 619 |
| 299 | 376 |
| 300 | 154 |
| 301 | 162 |
| 302 | 166 |
| 303 | 215 |
| 304 | 845 |
| 305 | 503 |
| 306 | 445 |
| 307 | 754 |
| 308 | 367 |
| 309 | 145 |
| 310 | 802 |
| 311 | 577 |
| 312 | 182 |
| 313 | 931 |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia. Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula Ito a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole. Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.).

It is preferred that the active compounds of the invention be administered either three or fewer times, more preferably once or twice daily.

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

Abbreviations

AcOH acetic acid
AN acetonitrile
BOC tert-butyloxycarbonyl conc. concentrated
DCM dichloromethane
DIPEA N,N-diisopropylethylamin
DMF N,N-dimethylformamide
DMSO dimethyl sulfoxide
dppf 1,1'-bis(diphenyl-phosphino)ferrocene
EI electron ionisation
ESI electrospray ionisation
EtOAc ethyl acetate
EtOH ethanol
HATU (2-(7-aza-1H-benzotriazole-1-yl)-1,1,3,3-tetramethyluronium hexafluorophosphate)
HCl hydrochloric acid
HCOOH formic acid
HPLC high performance liquid chromatography
HPLC-MS HPLC coupled with mass spectrometry
i.vac. under vacuum
MeOH methanol
MS mass spectrometry
MW molecular weight
NaOH sodium hydroxide
$NH_4OH$ ammonium hydroxide (30% ammonia in water)
PE petroleum ether
$R_f$ retention value (from thin layer chromatography)
RT room temperature
$R_t$ retention time (from HPLC)
TBTU (2-(1H-benzotriazole-1-yl)-1,1,3,3-tetramethyluronium tetrafluoroborate)
THF tetrahydrofurane
TEA triethyl amine
TFA trifluoracetic acid
THF tetrahydrofurane HPLC Purification Methods:

Method 1
Column: XBridge C18, 4.6×30 mm, 3.5 μm (Waters)
Solvent A: water with 0.1% TFA, solvent B: methanol with 0.1% TFA
Flow: 4 mL/min, temperature: 60° C.
Gradient:

| time [min] | % solvent A | % solvent B |
|---|---|---|
| 0.0 | 95 | 5 |
| 0.15 | 95 | 5 |
| 1.70 | 0 | 100 |
| 2.25 | 0 | 100 |

Method 2
Column: StableBond C18, 3×30 mm, 1.8 μm (Agilent)
Solvent A: water with 0.1% TFA, solvent B: acetonitrile
Flow: 2.2 mL/min, temperature: 60° C.
Gradient:

| time [min] | % solvent A | % solvent B |
|---|---|---|
| 0.0 | 95 | 5 |
| 0.05 | 95 | 5 |
| 1.40 | 0 | 100 |
| 1.80 | 0 | 100 |

Method 3
Column: Sunfire C18, 3×30 mm, 2.5 μm (Waters)
Solvent A: water with 0.1% TFA, solvent B: methanol
Flow 2.2 mL/min, temperature: 60° C.
Gradient:

| time [min] | % solvent A | % solvent B |
|---|---|---|
| 0.0 | 95 | 5 |
| 0.05 | 95 | 5 |
| 1.40 | 0 | 100 |
| 1.80 | 0 | 100 |

Method 4
Column: XBridge C18, 3×30 mm, 2.5 μm (Waters)
Solvent A: water with 0.1% TFA, solvent B: methanol
Flow: 2.2 mL/min, temperature: 60° C.
Gradient:

| time [min] | % solvent A | % solvent B |
|---|---|---|
| 0.0 | 95 | 5 |
| 0.05 | 95 | 5 |
| 1.40 | 0 | 100 |
| 1.80 | 0 | 100 |

Method 5
Column: StableBond C18, 3×30 mm, 1.8 μm (Waters)
Solvent A: water with 0.1% TFA, solvent B: methanol
Flow: 2.2 mL/min, temperature: 60° C.
Gradient:

| time [min] | % solvent A | % solvent B |
|---|---|---|
| 0.0 | 95 | 5 |
| 0.05 | 95 | 5 |
| 1.40 | 0 | 100 |
| 1.80 | 0 | 100 |

Method 6
Column: XBridge C18, 3×30 mm, 2.5 μm (Waters)
Solvent A: water with 0.1% TFA, solvent B: methanol
Flow: 2.2 mL/min, temperature: 60° C.
Gradient:

| time [min] | % solvent A | % solvent B |
|---|---|---|
| 0.0 | 95 | 5 |
| 0.05 | 95 | 5 |
| 1.40 | 0 | 100 |
| 1.80 | 0 | 100 |

Method 8
Column: StableBond C18, 3×30 mm, 1.8 μm (Zorbax)
Solvent A: water with 0.1% HCOOH, solvent B: acetonitril with 0.1% HCOOH
Flow: 1.6 mL/min, temperature: RT
Gradient:

| time [min] | % solvent A | % solvent B |
|---|---|---|
| 0.00 | 95 | 5 |
| 0.10 | 95 | 5 |
| 1.75 | 5 | 95 |
| 1.90 | 5 | 95 |
| 1.95 | 95 | 5 |
| 2.00 | 95 | 5 |

Method 9
Column: XBridge C18, 3×30 mm, 2.5 μm (Waters)
Solvent A: water with 0.1% TFA, solvent B: methanol
Flow: 2.2 mL/min, temperature: 60° C.
Gradient:

| time [min] | % solvent A | % solvent B |
|---|---|---|
| 0.00 | 95 | 5 |
| 0.05 | 95 | 5 |
| 1.4 | 5 | 95 |
| 1.8 | 5 | 95 |

Method 11
Column: XBridge C18, 3×30 mm, 2.5 μm (Waters)
Solvent A: water with 0.1% NH$_4$OH, solvent B: methanol
Temperature: 60° C.
Gradient:

| time [min] | % solvent A | % solvent B | Flow [mL/min] |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Method 12
Column: Sunfire C18, 4.6×50 mm, 3.5 μm
Solvent A: water with 0.1% TFA, solvent B: methanol
Flow: 2.0 mL/min, Temperature: 60° C.
Gradient:

| time [min] | % solvent A | % solvent B |
|---|---|---|
| 0.0 | 80 | 20 |
| 1.70 | 0 | 100 |
| 2.50 | 0 | 100 |
| 2.60 | 80 | 20 |

Method 13
Column: Symmetry C18, 4.6×75 mm, 3.5 μm
Solvent A: water with 0.01M % ammonium acetate, solvent B: acetonitrile
Flow: 1 mL/min, temperature: 25° C.
Gradient:

| time [min] | % solvent A | % solvent B |
|---|---|---|
| 0.0 | 90 | 10 |
| 1 | 90 | 10 |
| 3 | 55 | 45 |
| 4 | 55 | 45 |
| 8 | 10 | 90 |
| 12 | 10 | 90 |
| 12.1 | 90 | 10 |

Method 14
Column: XBridge C18, 4.6×150 mm, 3.5 μm
Solvent A: water with 0.05% TFA, solvent B: acetonitrile
Flow: 1 mL/min, temperature: 25° C.
Gradient:

| time [min] | % solvent A | % solvent B |
|---|---|---|
| 0.0 | 70 | 30 |
| 8 | 10 | 90 |
| 15 | 10 | 90 |
| 15.1 | 70 | 30 |

Method 15
Column: XBridge C18, 4.6×150 mm, 5 μm
Solvent A: water with 0.01M % ammonium acetate, solvent B: acetonitrile
Flow: 1 mL/min, temperature: 25° C.
Gradient:

| time [min] | % solvent A | % solvent B |
|---|---|---|
| 0.0 | 70 | 30 |
| 8 | 10 | 90 |
| 15 | 10 | 90 |
| 15.1 | 70 | 30 |

Method 16
Column: Symmetry C18, 4.6×75 mm, 3.5 μm
Solvent A: water with 0.01M % ammonium acetate, solvent B: acetonitrile
Flow: 1 mL/min, temperature: 25° C.
Gradient:

| time [min] | % solvent A | % solvent B |
|---|---|---|
| 0.0 | 70 | 30 |
| 5 | 10 | 90 |
| 12 | 10 | 90 |
| 12.1 | 90 | 10 |

Method 19
Column: XBridge C18, 2.1×50 mm, 1.7 μm (Waters)
Solvent A: water with 0.032% NH₄OH, solvent B: acetonitrile
Flow: 1.3 mL/min, Temperature: 60° C.
Gradient:

| time [min] | % solvent A | % solvent B |
|---|---|---|
| 0.00 | 95 | 5 |
| 0.30 | 70 | 30 |
| 0.70 | 0 | 100 |
| 0.80 | 0 | 100 |
| 0.90 | 95 | 5 |

Method 22
Column: Sunfire C18, 3×30 mm, 2.5 μm (Waters)
Solvent A: water with 0.1% TFA, solvent B: MeOH
Temperature: 60° C.
Gradient:

| time [min] | % solvent A | % solvent B | Flow [mL/min] |
|---|---|---|---|
| 0.0 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Method 23
Column: XBridge C18, 3×30 mm, 2.5 μm (Waters)
Solvent A: water with 0.1% TFA, solvent B: MeOH with 0.1% TFA
Temperature: 60° C.
Gradient:

| time [min] | % solvent A | % solvent B | Flow [mL/min] |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.65 | 0 | 100 | 2.9 |

Method 24
Column: Waters XBridge C18, 3.0×30 mm, 2.5 μm
Solvent A: water with 0.2% NH₄OH, solvent B: methanol
Flow: 1.3 mL/min, Temperature: 40° C.
Gradient:

| time [min] | % solvent A | % solvent B |
|---|---|---|
| 0.0 | 95 | 5 |
| 0.20 | 95 | 5 |
| 2.20 | 5 | 95 |
| 2.30 | 5 | 95 |
| 2.40 | 0 | 100 |
| 2.60 | 95 | 100 |

Method 25
Column: Microsorb 100 C18, 4.6×30 mm, 3 μm (Varian)
Solvent A: water with 0.13% TFA, solvent B: acetonitrile
Flow: 3.5 mL/min, Temperature: RT
Gradient:

| time [min] | % solvent A | % solvent B |
|---|---|---|
| 0.0 | 95 | 5 |
| 0.18 | 95 | 5 |
| 2.00 | 2 | 98 |
| 2.20 | 2 | 98 |
| 2.30 | 95 | 5 |
| 2.50 | 95 | 5 |

Method 26
Column: XBridge C18, 4.6×30 mm, 3.5 μm (Waters)
Solvent A: water with 0.1% NH₄OH, solvent B: methanol
Flow: 4 mL/min, temperature: 60° C.
Gradient:

| time [min] | % solvent A | % solvent B |
|---|---|---|
| 0.0 | 95 | 5 |
| 0.15 | 95 | 5 |
| 1.70 | 0 | 100 |
| 2.25 | 0 | 100 |

Preparation of Intermediates:

Intermediate 1: (2,2-Dimethyl-piperazin-1-yl)-(1-phenyl-1H-[1,2,4]triazol-3-yl)-methanone 1.1: 1-Phenyl-1H-[1,2,4]triazole-3-carboxylic acid

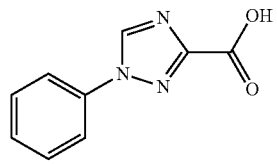 [SMILES: O=C(O)c1ncn(-c2ccccc2)n1]

Method A (According to K. Matsumoto et al., Synthesis 1975, 609-610):

A solution of 741 mg (10.7 mmol) sodium nitrite in water was added dropwise to a solution of 1.00 g (10.7 mmol) aniline in 4 M hydrochloric acid at 0° C. The resulting mixture was stirred at 0° C. for 15 min. In a separate flask, a solution of 1.21 g (10.7 mmol) ethyl isocyanoacetate in 10 mL ethanol was added to a solution of 4.40 g (53.7 mmol) sodium acetate in 10 mL water. Under cooling with ice/acetone, the diazonium salt mixture was added dropwise to the isocyanoacetate mixture. After complete conversion (30 min), ethanol was removed by distillation, EtOAc was added, and the organic phase was washed with water. The combined organic phases were dried over sodium sulfate, filtered and concentrated in vacuo. 15 mL ethanol and 15 mL 1 M lithium hydroxide solution were added to the remainder and the mixture was stirred at RT for 12 h. 4M aqueous HCl was added, the precipitating product was filtered, washed with water and dried.
yield: 550 mg (26%)
ESI-MS: m/z=190 (M+H)⁺
R_f(HPLC): 0.82 min (method 8)

Method B:

A suspension of 10.0 mL (110 mmol) aniline in 30 mL tetrafluoroboric acid (48% in water) was diluted with 30 mL water and cooled to 0° C. A solution 7.56 g (110 mmol) sodium nitrite in 10 mL water was added and the resulting mixture was stirred at 0° C. for 1 h. The precipitate was filtered off, washed with diethyl ether and dried to give 14.2 g (64%) of the diazonium tetrafluoroborate.

8.09 mL (74.0 mmol) ethyl isocyanoacetate was suspended in 50 mL EtOH and added to a solution of 20.0 g (244 mmol) sodium acetate in 50 mL water. The mixture was cooled with ice/acetone. 14.2 g (74.0 mmol) of the diazonium tetrafluoroborate were added to the cooled mixture in small portions. The cooling was removed and the reaction was allowed to come to RT and stirred for 1.5 h. EtOH was removed by distillation and the product was extracted with DCM. The combined organic phases were dried over sodium sulfate, filtered and concentrated in vacuo. The crude material was suspended in 40 mL MeOH/water=1/1. 10 mL of a 50% aqueous sodium hydroxide solution was added and stirring continued for 48 h. MeOH was removed by distillation, the remaining slurry was treated with 25 mL conc. hydrochlorid acid under ice cooling. The precipitate was filtered off, washed with water, triturated with diethyl ether and dried.

yield: 7.70 g (55%)

ESI-MS: m/z=190 (M+H)$^+$ $R_t$(HPLC): 0.82 min (Method 8)

Method C (According to P. Y. S. Lam et al., Tetrahedron Lett. 1998 (30), 2941-2944):

To a mixture of 7.52 g (61.7 mmol) phenylboronic acid and 8.00 g (61.7 mmol) methyl 1,2,4-triazole-3-carboxylate in 200 mL DCM was added 15.0 mL (186 mmol) pyridine followed by 11.2 g (61.7 mmol) copper (II) acetate. The reaction mixture was stirred at RT for 3 days, and then filtered over celite. The filtrate was washed with 1M aqueous KHSO$_4$ solution and saturated aqueous bicarbonate solution. The organic layer was dried over sodium sulfate and concentrated in vacuo to give 6.4 g solid. This crude material was taken up in 30 mL THF and treated with 20 mL 4M aqueous NaOH solution at RT. At complete conversion the THF was removed by distillation, ice water was added and the mixture was acidified with 4 M aqueous HCl solution. The precipitated was filtered off, washed with water and dried.

yield: 4.33 g (33%)

ESI-MS: m/z=190 (M+H)$^+$ $R_t$(HPLC): 0.66 min (method 5)

Intermediate 2:
1-m-Tolyl-1H-[1,2,4]-triazole-3-carboxylic acid

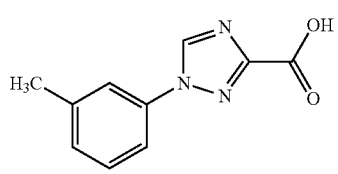

Method A (According to K. Matsumoto et al., Synthesis 1975, 609-610):

A solution of 1.61 g (23.3 mmol) sodium nitrite in water was added dropwise to a solution of 2.50 g (23.3 mmol) m-toluidine in 4 M hydrochloric acid at 0° C. The resulting mixture was stirred at 0° C. for 15 min, before a solution of 9.57 g (117 mmol) sodium acetate in 10 mL water was added, followed by addition of 2.55 mL (23.3 mmol) ethyl isocyanate and 50 mL EtOH. The resulting mixture was stirred for 2 h. The solvent was removed by distillation and the residue taken up in MeOH/water. 1 M lithium hydroxide solution was added and the mixture was stirred at RT. When saponification was complete, MeOH was removed by distillation and the product was precipitated with conc. HCl, filtered and washed with water. The crude product was purified by trituration with diethyl ether.

yield: 1.44 g (27%)

ESI-MS: m/z=204 (M+H)$^+$ $R_t$(HPLC): 0.99 min (method 8)

Method B (According to P. Y. S. Lam et al., Tetrahedron Lett. 1998 (30), 2941-2944):

A suspension of 5.00 mL (49.2 mmol) m-toluidine in 20 mL tetrafluoroboric acid (48% in water) was diluted with 20 mL water and cooled to 0° C. A solution of 3.20 g (46.3 mmol) sodium nitrite in 10 mL water was added slowly and the resulting mixture was stirred at RT for 1 h. The precipitate was filtered off, washed with diethyl ether and dried to give 6.00 g (63%) of the diazonium tetrafluoroborate.

A mixture of 3.30 mL (30.2 mmol) ethyl isocyanoacetate in 40 mL EtOH was added to a solution of 10.0 g (122 mmol) sodium acetate in 50 mL water. The mixture was cooled with ice/acetone. 6.00 g (29.1 mmol) of the diazonium tetrafluoroborate were added to the cooled mixture in small portions. The cooling was removed and the reaction was allowed to come to RT and stirred over night. EtOH was removed by distillation and the product was extracted with DCM. The combined organic phases were dried over sodium sulfate, filtered and concentrated in vacuo. The crude material was taken up in 40 mL MeOH. 15 mL aqueous sodium hydroxide solution (4M) was added and stirring continued for 3 h. The reaction mixture was acidified with conc. hydrochlorid acid. The organic solvent was removed by distillation and the precipitating product collected by filtration, washed with water and diethyl ether and dried.

yield: 2.70 g (27%)

ESI-MS: m/z=204 (M+H)$^+$ $R_t$(HPLC): 0.99 min (method 8)

Intermediate 3: 1-(3-Bromo-phenyl)-1H-[1,2,4]-triazole-3-carboxylic acid

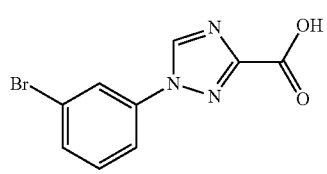

This intermediate was prepared from 3-bromoaniline in three steps according to the preparation of 1-m-tolyl-1H-[1,2,4]-triazole-3-carboxylic acid (Method B).

ESI-MS: m/z=268 (M+H)$^+$ $R_t$(HPLC): 1.00 min (method 8)

Intermediate 4: 1-(3-Chloro-phenyl)-1H-[1,2,4]-triazole-3-carboxylic acid (Prepared according to P. Y. S. Lam et al., Tetrahedron Lett. 1998 (30), 2941-2944)

4.1: 1-(3-Chloro-phenyl)-1H-[1,2,4]-triazole-3-carboxylic acid methyl ester

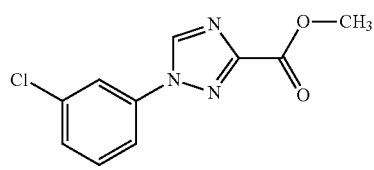 [SMILES: COC(=O)c1ncn(-c2cccc(Cl)c2)n1]

To a mixture of 12.1 g (77.1 mmol) 3-chlorophenylboronic acid and 10.0 g (77.1 mmol) methyl 1,2,4-triazole-3-carboxylate in 200 mL DCM was added 19.0 mL (235 mmol) pyridine followed by 14.0 g (77.1 mmol) copper (II) acetate. The reaction mixture was stirred at RT for 3 days, and then filtered over celite. The filtrate was washed with 1M aqueous $KHSO_4$ solution and saturated aqueous bicarbonate solution. The organic layer was dried over sodium sulfate, concentrated in vacuo and dried.

yield: 14.8 g (62.3%); ESI-MS: m/z=238 (M+H)$^+$; $R_t$(HPLC): 1.01 min (method 5)

4.2: 1-(3-Chloro-phenyl)-1H-[1,2,4]-triazole-3-carboxylic acid

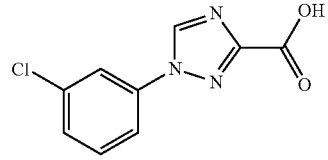 [SMILES: O=C(O)c1ncn(-c2cccc(Cl)c2)n1]

14.8 g (62.3 mmol) 1-(3-chloro-phenyl)-1H-[1,2,4]-triazole-3-carboxylic acid methyl ester was taken up in 70 mL THF and treated with 40 mL 4M aqueous NaOH solution at RT for 12 h. The reaction mixture was diluted with water, THF was removed by distillation, ice water was added and the mixture was acidified with 4 M aqueous HCl solution. The precipitated was filtered off, washed with water and triturated with diethyl ether.

yield: 10.4 g (90%)
ESI-MS: m/z=224 (M+H)$^+$
$R_t$(HPLC): 0.85 min (method 5)

Intermediate 6: 1-(3-Fluoro-phenyl)-1H-[1,2,4]-triazole-3-carboxylic acid

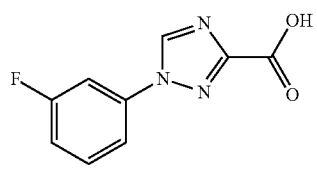

This intermediate was prepared from 3-fluorophenylboronic acid and methyl 1,2,4-triazole-3-carboxylate in two steps according to the preparation of 1-(3-chloro-phenyl)-1H-[1,2,4]-triazole-3-carboxylic acid.
ESI-MS: m/z=208 (M+H)$^+$
$R_t$(HPLC): 0.82 min (method 8)

Intermediate 5: 1-(2-Fluoro-phenyl)-1H-[1,2,4]-triazole-3-carboxylic acid

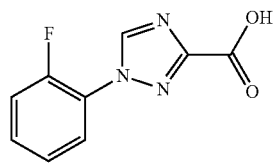 [SMILES: O=C(O)c1ncn(-c2ccccc2F)n1]

This intermediate was prepared from 2-fluorophenylboronic acid and methyl 1,2,4-triazole-3-carboxylate in two steps according to the preparation of 1-(3-chloro-phenyl)-1H-[1,2,4]-triazole-3-carboxylic acid.
ESI-MS: m/z=208 (M+H)$^+$
$R_t$(HPLC): 0.87 min (method 8)

Intermediate 6: 1-(2,5-Difluoro-phenyl)-1H-[1,2,4]-triazole-3-carboxylic acid

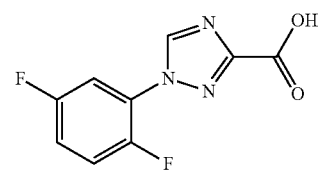 [SMILES: O=C(O)c1ncn(-c2cc(F)ccc2F)n1]

This intermediate was prepared from 2,5-difluorophenylboronic acid and methyl 1,2,4-triazole-3-carboxylate in two steps according to the preparation of 1-(3-chloro-phenyl)-1H-[1,2,4]-triazole-3-carboxylic acid.
ESI-MS: m/z=226 (M+H)$^+$
$R_t$(HPLC): 0.67 min (method 6)

Intermediate 7: 1-(3-Fluoro-4-methyl-phenyl)-1H-[1,2,4]-triazole-3-carboxylic acid

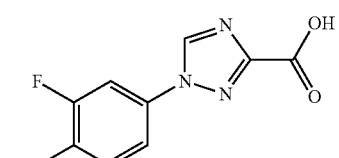

This intermediate was prepared from 3-fluoro-4-methylphenylboronic acid and methyl 1,2,4-triazole-3-carboxylate in two steps according to the preparation of 1-(3-chloro-phenyl)-1H-[1,2,4]-triazole-3-carboxylic acid.
ESI-MS: m/z=222 (M+H)$^+$
$R_t$(HPLC): 1.10 min (method 9)

Intermediate 8: 1-(4-Fluoro-3-methyl-phenyl)-1H-[1,2,4]-triazole-3-carboxylic acid

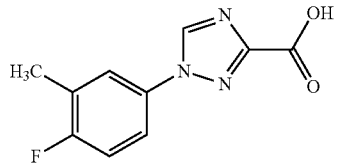 [SMILES: Cc1cc(-n2cnc(C(=O)O)n2)ccc1F]

This intermediate was prepared from 4-fluoro-3-methylphenylboronic acid and methyl 1,2,4-triazole-3-carboxylate in two steps according to the preparation of 1-(3-chlorophenyl)-1H-[1,2,4]-triazole-3-carboxylic acid.
ESI-MS: m/z=222 (M+H)$^+$
R$_t$(HPLC): 0.85 min (method 6)

Intermediate 9: 2,2-Dimethyl-piperazine-1-carboxylic acid benzyl ester trifluoroacetate

9.1: 2,2-Dimethyl-piperazine-1,4-dicarboxylic acid 1-benzyl ester 4-tert-butyl ester

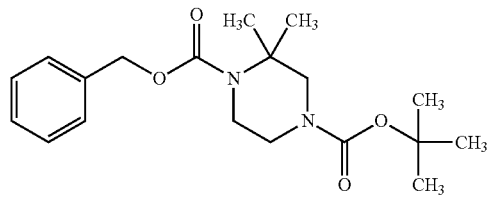 [SMILES: CC(C)(C)OC(=O)N1CCN(C(=O)OCc2ccccc2)C(C)(C)C1]

To a solution of 18.5 g (82.0 mmol) 3,3-dimethyl-piperazine-1-carboxylic acid tert-butyl ester in 150 mL DCM at RT was added 30.0 mL (174 mmol) DIPEA. The mixture was cooled with ice and a solution of 14.0 mL (93.2 mmol) benzyl chloroformate in 60 mL DCM was added dropwise. The reaction mixture was stirred at RT over night and quenched with saturated aqueous sodium bicarbonate solution. The product was extracted with DCM. The organic layers were combined, dried over sodium sulfate and concentrated in vacuo.
Yield: 23.0 g (81%)
ESI-MS: m/z=249 (M-BOC+H)$^+$
R$_t$(HPLC): 1.60 min (method 1)

9.2: 2,2-Dimethyl-piperazine-1-carboxylic acid benzyl ester trifluoroacetate

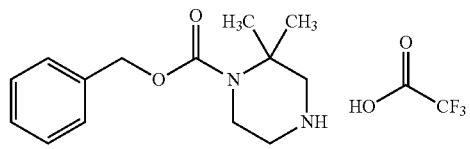 [SMILES: CC1(C)CNCCN1C(=O)OCc1ccccc1 ; O=C(O)C(F)(F)F]

A mixture of 23.0 g (66.1 mmol) 2,2-dimethyl-piperazine-1,4-dicarboxylic acid 1-benzyl ester 4-tert-butyl ester in 200 mL DCM was treated with 34.5 mL (448 mmol) TFA. The reaction mixture was stirred at RT over night and concentrated in vacuo. The residue was triturated with diethyl ether. The solid was filtered, washed with diethyl ether and dried.
Yield: 25.0 g (quantitative)
ESI-MS: m/z=249 (M+H)$^+$
R$_t$(HPLC): 0.86 min (method 5)

Intermediate 10.a and 10.b: (6-Cyclopropyl-pyridin-2-yl)-(3,3-dimethyl-piperazin-1-yl)-methanone trifluoroacetate and (3,3-Dimethyl-piperazin-1-yl)-(6-isopropyl-pyridin-2-yl)-methanone trifluoroacetate

10.1: 4-(6-Cyclopropyl-pyridine-2-carbonyl)-2,2-dimethyl-piperazine-1-carboxylic acid benzyl ester

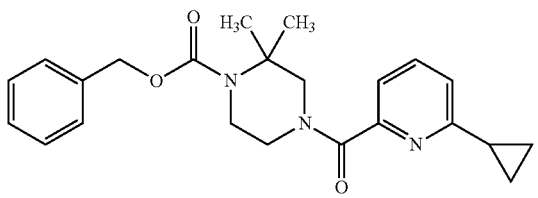 [SMILES: CC1(C)CN(C(=O)c2cccc(C3CC3)n2)CCN1C(=O)OCc1ccccc1]

200 mg (1.23 mmol) 6-cyclopropyl-pyridine-2-carboxylic acid was stirred with 450 mg (1.40 mmol) TBTU and 500 µL (2.91 mmol) DIPEA in 5.0 mL DMF at RT. After 10 min, 440 mg (1.23 mmol) 2,2-dimethyl-piperazine-1-carboxylic acid benzyl ester trifluoroacetate was added and the reaction mixture was stirred at RT over night. Water was added and the product was extracted with EtOAc. The organic layers were dried over sodium sulfate and concentrated in vacuo.
Yield: 0.480 g (quantitative)
ESI-MS: m/z=394 (M+H)$^+$
R$_t$(HPLC): 1.27 min (method 6)

10.2.a and 10.2.b: (6-Cyclopropyl-pyridin-2-yl)-(3,3-dimethyl-piperazin-1-yl)-methanone and (3,3-Dimethyl-piperazin-1-yl)-(6-isopropyl-pyridin-2-yl)-methanone

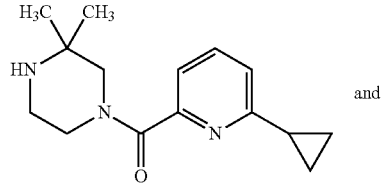

Intermediate 12.a and

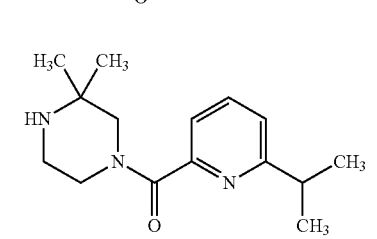

Intermediate 12.b

A mixture of 480 mg (1.22 mmol) 4-(6-cyclopropyl-pyridine-2-carbonyl)-2,2-dimethyl-piperazine-1-carboxylic acid benzyl ester and 50 mg palladium on carbon in 15.0 mL methanol was hydrogenated at RT for 5 h. The catalyst was removed by filtration and the solvent was evaporated in vacuo to give 310 mg of a colourless oil containing intermediate 12.2.a and intermediate 12.2.b in a 70:30 mixture.

Intermediate 10.2.a

ESI-MS: m/z=260 (M+H)$^+$
R$_t$(HPLC): 0.67 min (method 6)

Intermediate 10.2.b

ESI-MS: m/z=262 (M+H)$^+$
R$_t$(HPLC): 0.72 min (method 6)

10.3.a and 10.3.b: 4-(6-Cyclopropyl-pyridine-2-carbonyl)-2,2-dimethyl-piperazine-1-carboxylic acid tert-butyl ester and 4-(6-Isopropyl-pyridine-2-carbonyl)-2,2-dimethyl-piperazine-1-carboxylic acid tert-butyl ester Intermediate 10.3.a

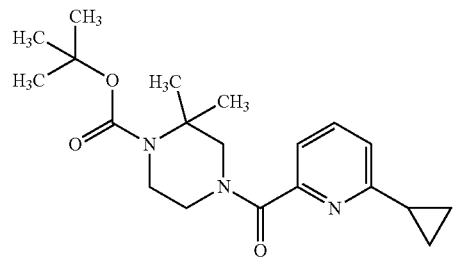

and

Intermediate 10.3.b

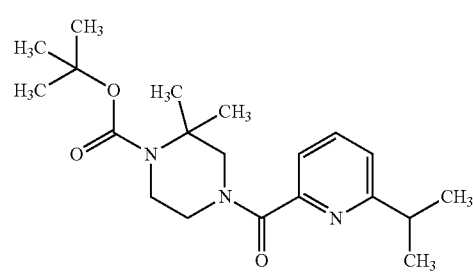

To a mixture of 310 mg intermediate 10.2.a and intermediate 10.2.b (70:30) in 10 mL THF were added 300 mg (1.38 mmol) di-tert-butyl dicarbonate. The resulting mixture was stirred at RT for 12 h. The solvent was removed by distillation. The resulting residue was purified by flash chromatography (DCM/EtOAc=3/2).

Intermediate 10.3.a

Yield: 200 mg (92%, purity 70%)
ESI-MS: m/z=360 (M+H)$^+$
R$_t$(HPLC): 1.31 min (method 5)

Intermediate 10.3.b

Yield: 70.0 mg (75%, purity 70%)
ESI-MS: m/z=362 (M+H)$^+$
R$_t$(HPLC): 1.32 min (method 5)

10.4.a: (6-Cyclopropyl-pyridin-2-yl)-(3,3-dimethyl-piperazin-1-yl)-methanone trifluoroacetate

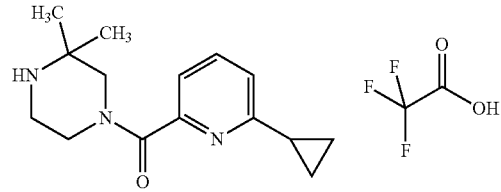 [SMILES: CC1(C)CN(C(=O)c2cccc(C3CC3)n2)CCN1 ; O=C(O)C(F)(F)F]

To a mixture of 190 mg (0.529 mmol) 4-(6-cyclopropyl-pyridine-2-carbonyl)-2,2-dimethyl-piperazine-1-carboxylic acid tert-butyl ester was added 500 μl (6.48 mmol) TFA. The resulting mixture was stirred at RT for 3.5 h. The solvent was evaporated.

Yield: 200 mg (96%)
ESI-MS: m/z=260 (M+H)$^+$
R$_t$(HPLC): 0.70 min (method 5)

10.4.b: (3,3-Dimethyl-piperazin-1-yl)-(6-isopropyl-pyridin-2-yl)-methanone trifluoroacetate

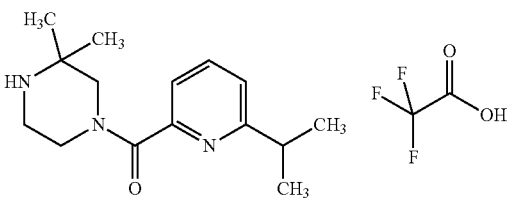 [SMILES: CC(C)c1cccc(C(=O)N2CCNC(C)(C)C2)n1 ; O=C(O)C(F)(F)F]

To a mixture of 55.0 mg (0.152 mmol) 4-(6-isopropyl-pyridine-2-carbonyl)-2,2-dimethyl-piperazine-1-carboxylic acid tert-butyl ester was added 100 μl (1.30 mmol) TFA. The resulting mixture was stirred at RT for 12 h. The solvent was evaporated.

Yield: 55.0 mg (96%)
ESI-MS: m/z=262 (M+H)$^+$
R$_t$(HPLC): 0.76 min (method 5)

Intermediate 11: (3,3-Dimethyl-piperazin-1yl)-(6-methoxy-pyridin-2-yl)methanone 11.1: 4-(6-Methoxy-pyridine-2-carbonyl)-2,2-dimethyl-piperazine-1-carboxylic acid benzyl ester

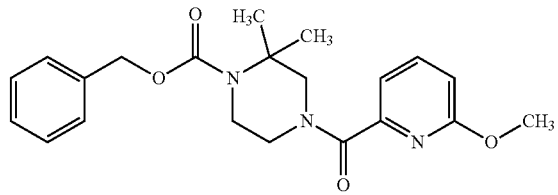 [SMILES: COc1cccc(C(=O)N2CCN(C(=O)OCc3ccccc3)C(C)(C)C2)n1]

510 mg (3.31 mmol) 6-methoxy-2-pyridinecarboxylic acid was stirred with 1.17 g (3.31 mmol) TBTU and 1.50 mL (8.72 mmol) DIPEA in 10 mL DCM at RT. After 10 min, 1.20 g (3.31 mmol) 2,2-dimethyl-piperazine-1-carboxylic acid benzyl ester trifluoroacetate was added and the reaction mixture was stirred at RT for 2 h. Then the reaction mixture was washed with saturated aqueous NaHCO$_3$ solution. The combined organic phases were dried over sodium sulfate, filtered and concentrated in vacuo. The crude material was purified by flash chromatography (PE/EtOAc=9/1→1/2).

Yield: 1.10 g (87%)

ESI-MS: m/z=384 (M+H)$^+$

R$_t$(HPLC): 1.07 min (method 3)

11.2: (3,3-Dimethyl-piperazin-1yl)-(6-methoxy-pyridin-2-yl)-methanone

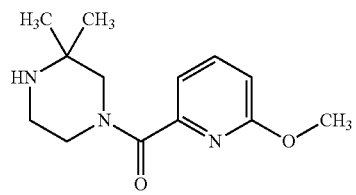 [SMILES: COc1cccc(C(=O)N2CCNC(C)(C)C2)n1]

A mixture of 1.10 g (2.87 mmol) 4-(6-methoxy-pyridine-2-carbonyl)-2,2-dimethyl-piperazine-1-carboxylic acid benzyl ester and 100 mg palladium on carbon in 20 mL methanol was hydrogenated at RT for 12 h at 3 bar. The catalyst was removed by filtration and the solvent was evaporated in vacuo.

Yield: 660 mg (92%)

ESI-MS: m/z=250 (M+H)$^+$

R$_t$(HPLC): 0.55 min (method 23)

Intermediate 12: (3,3-Dimethyl-piperazin-1-yl)-(1-methoxy-isoquinolin-3-yl)-methanone trifluoroacetate

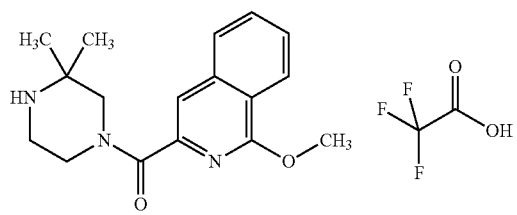 [SMILES: COc1nc(C(=O)N2CCNC(C)(C)C2)cc2ccccc12 ; O=C(O)C(F)(F)F]

This intermediate was prepared from 1-methoxy-isoquinoline-3-carboxylic acid in two steps according to the preparation of (3,3-dimethyl-piperazin-1yl)-(6-methoxy-pyridin-2-yl)-methanone.

ESI-MS: m/z=300 (M+H)$^+$

R$_t$(HPLC): 0.91 min (method 2)

Intermediate 13: (3-Chloro-phenyl)-(3,3-dimethyl-piperazin-1-yl)-methanone trifluoroacetate 13.1: 4-(3-Chloro-benzoyl)-2,2-dimethyl-piperazine-1-carboxylic acid benzyl ester

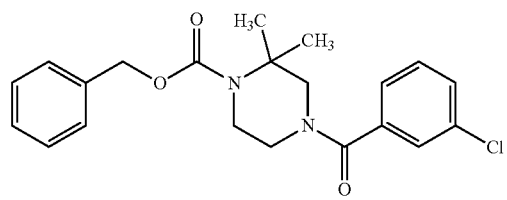 [SMILES: CC1(C)CN(C(=O)c2cccc(Cl)c2)CCN1C(=O)OCc1ccccc1]

To a solution of 3.00 g (8.28 mmol) 2,2-dimethyl-piperazine-1-carboxylic acid benzyl ester trifluoroacetate in 50 mL EtOAc was added 3.50 mL (20.3 mmol) DIPEA followed by 1.07 mL (8.28 mmol) 3-chloro-benzoyl chloride dropwise at RT. The reaction mixture was stirred at RT for 1 h. Then the suspension was washed with water. The combined organic phases were dried over sodium sulfate, filtered and concentrated in vacuo.

Yield: 3.20 g (99%)

ESI-MS: m/z=387 (M+H)$^+$

R$_t$(HPLC): 1.32 min (method 5)

13.2: (3-Chloro-phenyl)-(3,3-dimethyl-piperazin-1-yl)-methanone trifluoroacetate

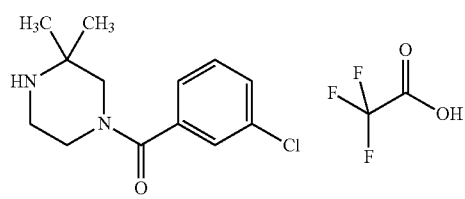 [SMILES: CC1(C)CN(C(=O)c2cccc(Cl)c2)CCN1 ; O=C(O)C(F)(F)F]

To a solution of 1.93 g (4.99 mmol) 4-(3-chloro-benzoyl)-2,2-dimethyl-piperazine-1-carboxylic acid benzyl ester in 10 mL glacial acetic acid was added 2.81 mL (25.0 mmol) hydrobromid acid. The reaction mixture was stirred at RT for the weekend. The solvent was evaporated, diluted with aqueous potassium carbonate solution and extracted with EtOAc. The combined organic phases were dried over sodium sulfate, filtered and concentrated in vacuo. The resulting residue was diluted in DCM. TFA was added and the solvent was evaporated. The resulting residue was triturated with diethyl ether, the precipitate was filtered off, washed with diethyl ether and dried.

Yield: 1.60 g (87%)

ESI-MS: m/z=253 (M+H)$^+$

R$_t$(HPLC): 0.69 min (method 5)

Intermediate 14: (1-Cyclopropyl-isoquinolin-3-yl)- (3,3-dimethyl-piperazin-1-yl)-methanone trifluoroacetate

14.1: 1-Cyclopropyl-isoquinoline-3-carboxylic acid methyl ester

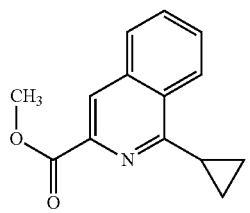 [SMILES: COC(=O)c1cc2ccccc2c(C2CC2)n1]

A mixture of 481 mg (2.17 mmol) 1-chloro-isoquinoline-3-carboxylic acid methyl ester, 235 mg (2.74 mmol) cyclopropylboronic acid, 100 mg (0.137 mmol) 1,1'-bis(diphenylphosphino)ferrocenedichloropalladium(II) and 950 mg (4.47 mmol) potassium phosphate in 20 mL dioxane was stirred at 110° C. for 12 h. The mixture was diluted with EtOAc, filtered over Celite and activated carbon and concentrated in vacuo. The crude material was purified by flash chromatography (PE/EtOAc=3/1).
yield: 370 mg (75%)
ESI-MS: m/z=228 (M+H)$^+$
R$_t$(HPLC): 1.15 min (method 5)

14.2: 1-Cyclopropyl-isoquinoline-3-carboxylic acid

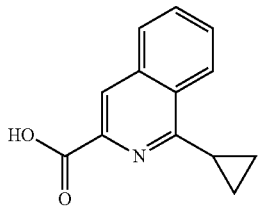 [SMILES: O=C(O)c1cc2ccccc2c(C2CC2)n1]

350 mg (1.54 mmol) 1-cyclopropyl-isoquinoline-3-carboxylic acid methyl ester was dissolved in 10 mL MeOH and treated with 2.50 mL 4 M aqueous NaOH solution at RT for 12 h. The solvent was removed by distillation, the residue taken up in water, acidified with 4 M aqueous hydrochlorid acid and extracted with EtOAc. The combined organic phases were dried over sodium sulfate, filtered and concentrated in vacuo.
yield: 250 mg (76%)
ESI-MS: m/z=214 (M+H)$^+$
R$_t$(HPLC): 0.77 min (method 5)

14.3: 3-(1-Cyclopropyl-isoquinoline-3-carbonyl)-2,2-dimethyl-piperazine-1-carboxylic acid benzyl ester

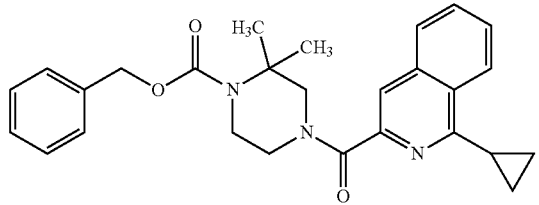 [SMILES: CC1(C)CN(C(=O)c2cc3ccccc3c(C3CC3)n2)CCN1C(=O)OCc1ccccc1]

230 mg (1.08 mmol) 1-cyclopropyl-isoquinoline-3-carboxylic acid and 391 mg (1.08 mmol) 2,2-dimethyl-piperazine-1-carboxylic acid benzyl ester trifluoroacetate was stirred with 385 mg (1.20 mmol) TBTU and 640 µL (3.70 mmol) DIPEA in 3 mL DMF at RT for 1 h. The mixture was worked up by adding water, followed by extraction with EtOAc. Then the reaction mixture was washed with saturated aqueous NaHCO$_3$ solution. The combined organic phases were dried over sodium sulfate, filtered and concentrated in vacuo. Yield: 600 mg (99%), purity: 80%; ESI-MS: m/z=444 (M+H)$^+$; R$_t$(HPLC): 1.42 min (method 5)

14.4: (1-Cyclopropyl-isoquinolin-3-yl)-(3,3-dimethyl-piperazin-1-yl)-methanone trifluoroacetate

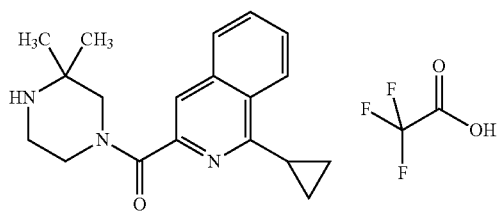 [SMILES: CC1(C)CN(C(=O)c2cc3ccccc3c(C3CC3)n2)CCN1 ; O=C(O)C(F)(F)F]

To a solution of 0.600 g (1.08 mmol, purity: 80%) 4-(1-cyclopropyl-isoquinoline-3-carbonyl)-2,2-dimethyl-piperazine-1-carboxylic acid benzyl ester in 5.0 mL glacial acetic acid was added 500 µL (4.45 mmol) hydrobromid acid. The reaction mixture was stirred at RT for 12 h. 500 µL (4.45 mmol) hydrobromid acid were added and the mixture was stirred at 40° C. for 2 h. The solvent was evaporated, the residue taken up in water, alkalized with 4 N aqueous NaOH solution and extracted with EtOAc.

The combined organic phases were dried over sodium sulfate, filtered and concentrated in vacuo. The resulting residue was taken up in DCM and treated with 0.5 mL TFA. The solvent was evaporated and the resulting residue was crystallized from diethyl ether and dried.
Yield: 420 mg (92%)
ESI-MS: m/z=310 (M+H)$^+$
R$_t$(HPLC): 0.94 min (method 5)

Intermediate 15: 2-(3-Chloro-phenyl)-2H-tetrazole-5-carboxylic acid (Prepared according to WO2010/123451 p. 28, step A, B, C)

15.1: Ethyl 2-chloro-2-(2-(3-chlorophenyl)hydrazono)acetate

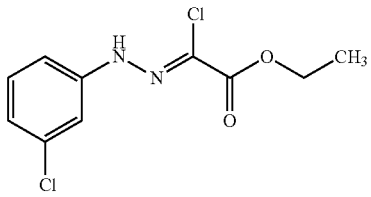 [SMILES: CCOC(=O)/C(Cl)=N/Nc1cccc(Cl)c1]

12.2 g (149 mmol) sodium acetate trihydrate was added to a solution of 15.5 g (94.1 mmol) ethyl 2-chloroacetoacetate in 300 mL ethanol. The solution was cooled to 0° C. A parallel reaction consisted of the addition of an ice-cold aqueous solution of 6.49 g (94.1 mmol) sodium nitrite in 30 mL water to a solution of 10.0 g (78.4 mol) 3-chloro-phenylamine in 75 mL 6N aqueous HCl. The cold solution of phenyldiazonium chloride was then added to the ester mixture at 0° C. and stirred for 3 h at 0° C. The resulting mixture was diluted with water and ice and stirred for 2 h at 0° C. The precipitate was filtered off, washed with water, dried and used without further purification for the next synthesis step (yield: 13.0 g (64%)).

15.2: N'-(3-chlorophenyl)-2-ethoxyacetohydrazonamide

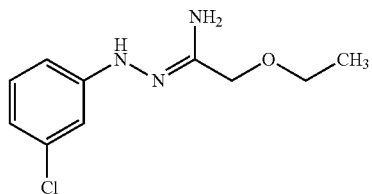

45.0 mL (60.2 mmol) aqueous ammonia solution (25%) was added over 20 minutes to a solution of 15.0 g (57.4 mmol) ethyl 2-chloro-2-(2-(3-chlorophenyl)hydrazono)acetate in 75 mL THF and stirred for 1 h. The resulting mixture was diluted and extracted with hexane and EtOAc (1:1 mixture). The organic layer was washed with brine, dried over sodium sulfate, filtered, concentrated and used without further purification for the next synthesis step (yield: 12.0 g (92%)).

15.3: 2-(3-Chloro-phenyl)-2H-tetrazole-5-carboxylic acid ethyl ester

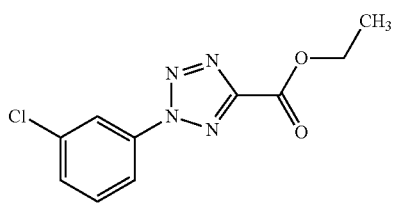 [SMILES: CCOC(=O)c1nnn(-c2cccc(Cl)c2)n1]

12.0 mL (210 mmol) acetic acid was added to a solution of 12.0 g (52.7 mmol) N'-(3-chloro-phenyl)-2-ethoxyacetohydrazonamide in 120 mL THF. The mixture was heated to 85° C. and a solution of 4.36 g (63.2 mmol) sodium nitrite in 12 mL water was added over 4 h. After stirring for 1 h at 85° C., the mixture was cooled to RT. The solvent was evaporated. The residue was dissolved in EtOAc and extracted with aqueous sodium bicarbonate. The organic layer was washed with brine, dried over sodium sulfate, filtered and concentrated. The resulting residue was purified by column chromatography eluted with hexane/EtOAc (90:10).

yield: 9.00 g (68%)
ESI-MS: m/z=253 (M+H)$^+$
R$_t$(HPLC): 6.93 min (method 15)

15.4: 2-(3-Chloro-phenyl)-2H-tetrazole-5-carboxylic acid

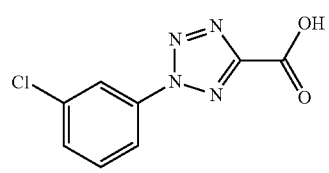 [SMILES: O=C(O)c1nnn(-c2cccc(Cl)c2)n1]

7.00 g (27.7 mmol) 2-(3-chloro-phenyl)-2H-tetrazole-5-carboxylic acid ethyl ester was dissolved in 50 mL THF and 50 mL water and treated with 2.33 g (55.4 mmol) LiOH at RT for 14 h. The reaction mixture was concentrated and acidified with 1 M aqueous hydrochlorid acid. The precipitate was filtered off, washed with water and dried.

yield: 5.50 g (88%)
ESI-MS: m/z=223 (M−H)$^-$
R$_t$(HPLC): 4.68 min (method 14)

Intermediate 16: 2-(3-Fluoro-phenyl)-2H-tetrazole-5-carboxylic acid

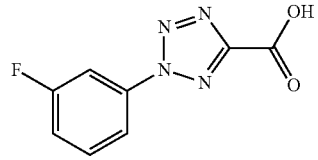 [SMILES: O=C(O)c1nnn(-c2cccc(F)c2)n1]

This intermediate was prepared from 3-fluoro-phenylamine in four steps according to the preparation of 2-(3-chloro-phenyl)-2H-tetrazole-5-carboxylic acid.
ESI-MS: m/z=209 (M+H)$^+$
R$_t$(HPLC): 3.31 min (method 16)

Intermediate 17: 2-(2-Fluoro-phenyl)-2H-tetrazole-5-carboxylic acid

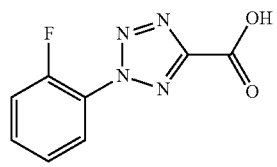 [SMILES: O=C(O)c1nnn(-c2ccccc2F)n1]

This intermediate was prepared from 2-fluoro-phenylamine in four steps according to the preparation of 2-(3-chloro-phenyl)-2H-tetrazole-5-carboxylic acid.
ESI-MS: m/z=209 (M+H)$^+$
R$_t$(HPLC): 2.73 min (method 13)

Intermediate 18: 2-(4-Fluoro-phenyl)-2H-tetrazole-5-carboxylic acid

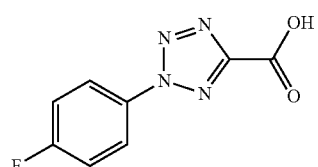

This intermediate was prepared from 4-fluoro-phenylamine in four steps according to the preparation of 2-(3-chloro-phenyl)-2H-tetrazole-5-carboxylic acid.
ESI-MS: m/z=209 (M+H)$^+$
R$_t$(HPLC): 3.33 min (method 13)

Intermediate 19: 2-m-Tolyl-2H-tetrazole-5-carboxylic acid

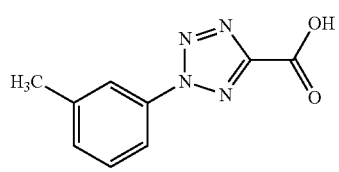

This intermediate was prepared from m-tolylamine in four steps according to the preparation of 2-(3-chlorophenyl)-2H-tetrazole-5-carboxylic acid.
ESI-MS: m/z=205 (M+H)$^+$
R$_t$(HPLC): 1.01 min (method 8)

Intermediate 20: 1-Cyclopropylmethyl-1H-[1,2,4]triazole-3-carboxylic acid

20.1: 3,3-Dimethyl-4-(1-phenyl-1H-[1,2,4]triazole-3-carbonyl)-piperazine-1-carboxylic acid tert-butyl ester

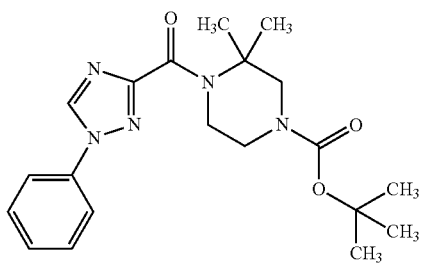 [SMILES: CC(C)(C)OC(=O)N1CCN(C(=O)c2ncn(-c3ccccc3)n2)C(C)(C)C1]

A mixture of 420 mg (2.22 mmol) 1-phenyl-1H-[1,2,4]-triazole-3-carboxylic acid, 500 mg (2.22 mmol) 3,3-dimethyl-piperazine-1-carboxylic acid tert-butyl ester, 750 mg (2.22 mmol) TBTU and 500 µL (2.91 mmol) DIPEA in 5 mL DMF was stirred at RT for 2 h.

The reaction mixture was poured into ice water. The precipitate was filtered off, taken up in EtOAc, dried over sodium sulfate, filtered and concentrated in vacuo.

yield: 850 mg (99%)
ESI-MS: m/z=386 (M+H)⁻
$R_t$(HPLC): 1.20 min (method 23)

20.2: (2,2-Dimethyl-piperazin-1-yl)-(1-phenyl-1-H-[1,2,4]-triazol-3-yl)-methanone trifluoroacetate

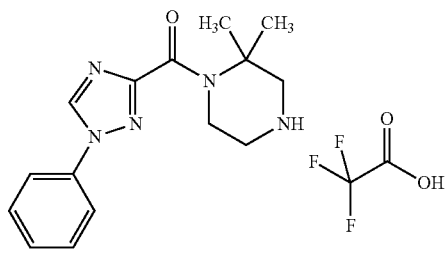

To a stirred solution of 4.10 g (10.6 mmol) 3,3-dimethyl-4-(1-phenyl-1H-[1,2,4]-triazole-3-carbonyl)-piperazine-1-carboxylic acid tert-butyl ester in 20 mL DCM was added 7.00 mL (90.7 mmol) TFA and the resulting mixture was stirred at RT for 4 h. The solvent was evaporated. The residue was triturated with diethyl ether and DCM. The precipitate was filtered off, washed with diethyl ether and dried.

yield: 3.63 g (85%)
ESI-MS: m/z=286 (M+H)⁻
$R_t$(HPLC): 0.67 min (method 5)

Intermediate 21: [1-(3-Chloro-phenyl)-1H-[1,2,4]-triazol-3-yl]-(2,2-dimethyl-piperazin-1-yl)methanone trifluoroacetate

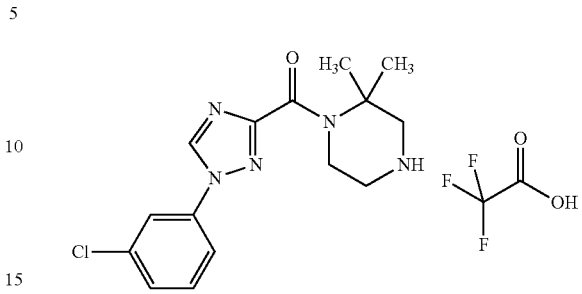

This intermediate was prepared from 1-(3-chloro-phenyl)-1H-[1,2,4]-triazole-3-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]triazol-3-yl)-methanone trifluoroacetate and purified using HPLC.
ESI-MS: m/z=320 (M+H)⁺
$R_t$(HPLC): 0.79 min (method 23)

Intermediate 22: (2,2-Dimethyl-piperazin-1-yl)-(1-m-tolyl-1H-[1,2,4]-triazol-3-yl)-methanone trifluoroacetate

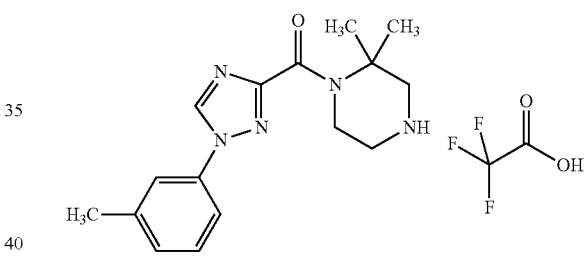

This intermediate was prepared from 1-m-tolyl-1H-[1,2,4]-triazole-3-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.
ESI-MS: m/z=300 (M+H)⁺
$R_t$(HPLC): 0.82 min (method 4)

Intermediate 23: (2,2-Dimethyl-piperazin-1-yl)-[1-(3-fluoro-4-methyl-phenyl)-1H-[1,2,4]triazol-3-yl)-methanone trifluoroacetate

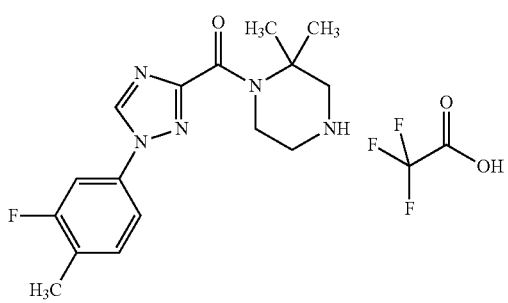

This intermediate was prepared from 1-(3-fluoro-4-methyl-phenyl)-1H-[1,2,4]-triazole-3-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.

ESI-MS: m/z=318 (M+H)$^+$ $R_t$(HPLC): 0.63 min (method 6)

Intermediate 24: (2,2-Dimethyl-piperazin-1-yl)-[1-(4-fluoro-3-methyl-phenyl)-1H-[1,2,4]-triazol-3-yl)-methanone trifluoroacetate

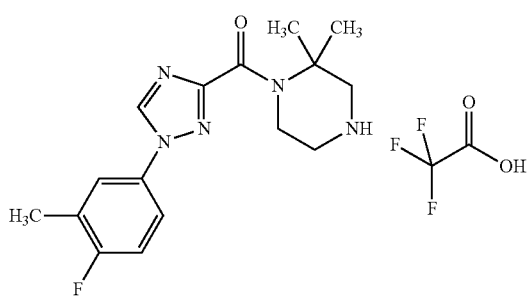

This intermediate was prepared from 1-(4-fluoro-3-methyl-phenyl)-1H-[1,2,4]triazole-3-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.

ESI-MS: m/z=318 (M+H)$^+$ $R_t$(HPLC): 0.79 min (method 6)

Intermediate 25: (2,2-Dimethyl-piperazin-1-yl)-(2-phenyl-2H-tetrazol-5-yl)-methanone trifluoroacetate

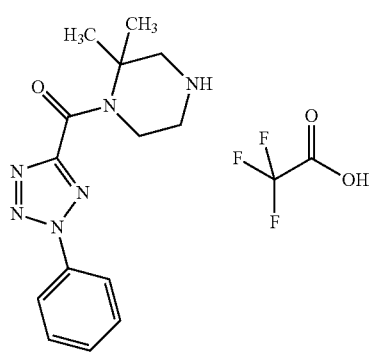 [SMILES: CC1(C)CNCCN1C(=O)c1nnn(-c2ccccc2)n1 ; O=C(O)C(F)(F)F]

This intermediate was prepared from 2-phenyl-2H-tetrazole-5-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.

ESI-MS: m/z=287 (M+H)$^+$ $R_t$(HPLC): 0.79 min (method 5)

Intermediate 26: (2,2-Dimethyl-piperazin-1-yl)-[2-(3-fluoro-phenyl)-2H-tetrazol-5-yl]-methanone trifluoroacetate

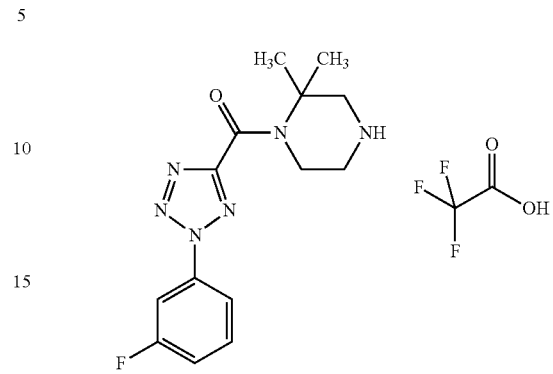

This intermediate was prepared from 2-(3-fluoro-phenyl)-2H-tetrazole-5-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.

ESI-MS: m/z=305 (M+H)$^+$ $R_t$(HPLC): 0.83 min (method 5)

Intermediate 27: [2-(3-Chloro-phenyl)-2H-tetrazol-5-yl]-(2,2-dimethyl-piperazin-1-yl)methanone trifluoroacetate

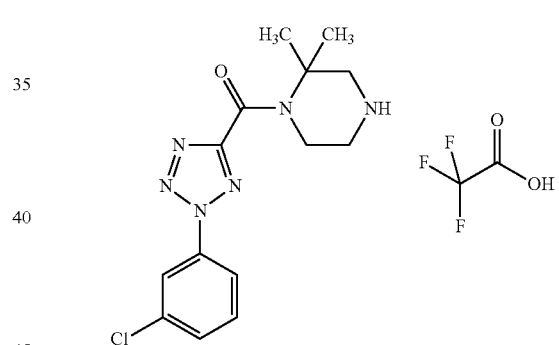

This intermediate was prepared from 2-(3-chloro-phenyl)-2H-tetrazole-5-carboxylic acid and 3,3-dimethyl-piperazine-1-carboxylic acid tert-butyl ester in two steps according to the preparation of (2,2-dimethyl-piperazin-1-yl)-(1-phenyl-1-H-[1,2,4]-triazol-3-yl)-methanone trifluoroacetate.

ESI-MS: m/z=321 (M+H)$^+$ $R_t$(HPLC): 0.92 min (method 5)

Intermediate 28: (2,2-Dimethyl-piperazin-1yl)-[1-(3-fluoro-phenyl)-1H-[1,2,4]triazol-3yl]-methanone

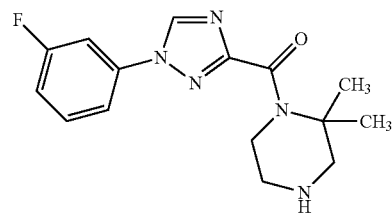 [SMILES: CC1(C)CNCCN1C(=O)c1ncn(-c2cccc(F)c2)n1]

A mixture of 460 mg (2.22 mmol) 1-(3-fluoro-phenyl)-1H-[1,2,4]-triazole-3-carboxylic acid and 330 μL (2.49 mmol) 1-chloro-N,N,2-trimethylpropylamine in 10 mL THF was stirred at RT for 30 min, 500 mg (2.22 mmol) 3,3-dimethyl-piperazine-1-carboxylic acid tert-butyl ester and 620 μL (4.45 mmol) TEA were added and the mixture was stirred at RT for 1 h. The solvent was removed by distillation and the residue was purified by HPLC.

yield: 205 mg (30%)
ESI-MS: m/z=304 (M+H)$^+$
$R_t$(HPLC): 1.24 min (method 3)

Intermediate 29:
6-Cyclopropyl-pyridine-2-carboxylic acid 29.1: 6-Cyclopropyl-pyridine-2-carboxylic acid ethyl ester

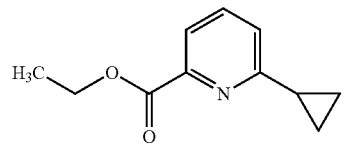

To a mixture of 2.90 g (12.6 mmol) 6-bromo-pyridine-2-carboxylic acid ethyl ester in 25 mL toluene was added 3.00 g (29.7 mmol) cyclopropylboronic acid and 5.50 g (25.9 mmol) potassium phosphate followed by 700 mg (0.957 mmol) 1,1'-bis(diphenylphosphino)-ferrocenedichloropalladium(II). The reaction mixture was stirred at 100° C. for 8 h. 1.00 g (9.90 mmol) of cyclopropylboronic acid and 1.50 g (7.07 mmol) of potassium phosphate were added and the mixture was stirred at 100° C. for 5 h. The reaction mixture was filtered through Celite, and washed with DCM and the solvent was evaporated in vacuo. The crude material was purified by flash chromatography (PE/EtOAc=4/1→2/1).

yield: 1.00 g (41%)
ESI-MS: m/z=192 (M+H)$^+$
$R_t$(HPLC): 1.15 min (method 1)

29.2: 6-Cyclopropyl-pyridine-2-carboxylic acid

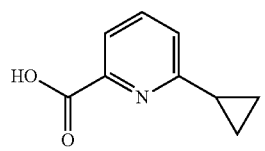 [SMILES: O=C(O)c1cccc(C2CC2)n1]

1.00 g (5.23 mmol) 6-cyclopropyl-pyridine-2-carboxylic acid ethyl ester was suspended in 10 mL THF and treated with 350 mg (14.6 mmol) LiOH and 5 mL water at RT for 2.5 h. The reaction mixture was acidified with 4 M aqueous hydrochlorid acid and extracted with EtOAc. The combined organic phases were dried over sodium sulfate, filtered and concentrated in vacuo.

yield: 510 mg (60%); ESI-MS: m/z=164 (M+H)$^+$; $R_t$(HPLC): 0.30 min (method 6)

Intermediate 30: 6-Cyclopentyl-benzoic acid 30.1: 6-Cyclopentyl-benzoic acid ethyl ester

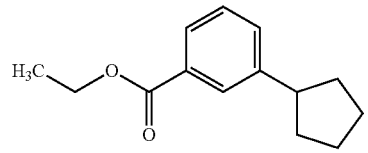 [SMILES: CCOC(=O)c1cccc(C2CCCC2)c1]

To 1.00 mL (6.24 mmol) ethyl 3-bromobenzoate was added 13.0 mL (6.50 mmol) 0.5 M cyclopentylzinc bromide solution in THF followed by 100 mg (0.137 mmol) 1,1'-bis(diphenylphosphino)ferrocenedichloropalladium(II) under argon atmosphere. The reaction mixture was stirred at 85° C. for 1.5 h, then diluted with water and stirred at RT for 12 h. The suspension was extracted with EtOAc. The combined organic phases were dried over sodium sulfate, filtered and concentrated in vacuo. The crude material was filtered through Alox (EtOAC) and concentrated in vacuo.

yield: 1.10 g (81%)
ESI-MS: m/z=219 (M+H)$^+$
$R_t$(HPLC): 1.73 min (method 7)

30.2: 6-Cyclopentyl-benzoic acid

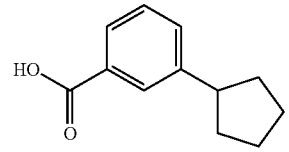

0.200 g (8.35 mmol) lithium hydroxide and 15 mL water were added to a solution of 1.10 g (5.04 mmol) 6-cyclopentyl-benzoic acid ethyl ester in 20 mL THF at RT, and the resulting mixture was stirred over night. 5.00 mL (20.0 mmol) 4 M aqueous NaOH solution were added and stirring was continued at 50° C. for 5 h. THF was removed by distillation. The residue was acidified with 4 M aqueous hydrochlorid and the precipitate was filtered off, washed with water and dried.

yield: 890 mg (93%)
ESI-MS: m/z=191 (M+H)$^+$
$R_t$(HPLC): 1.29 min (method 5)

Intermediate 31: 3-Cyclobutyl-benzoic acid

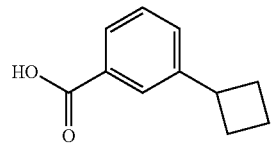 [SMILES: O=C(O)c1cccc(C2CCC2)c1]

This intermediate was prepared from ethyl 3-bromobenzoate and cyclobutylzinc bromide in two steps according to the preparation of 6-cyclopentyl-benzoic acid.

ESI-MS: m/z=177 (M+H)$^+$
$R_t$(HPLC): 1.44 min (method 5)

Intermediate 32: 6-Cyclobutyl-pyridine-2-carboxylic acid

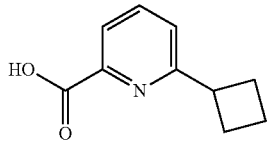 [SMILES: O=C(O)c1cccc(C2CCC2)n1]

This intermediate was prepared from ethyl-6-bromo-2-pyridinecarboxylate and cyclobutylzinc bromide in two steps according to the preparation of 6-cyclopentyl-benzoic acid.
ESI-MS: m/z=178 (M+H)+
R$_t$(HPLC): 0.53 min (method 5)

Intermediate 33: 3-(3-Fluoro-oxetan-3-yl)-benzoic acid

33.1: 3-(3-Iodo-phenyl)-oxetan-3-ol

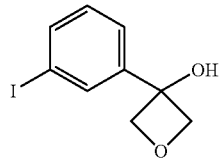 [SMILES: OC1(c2cccc(I)c2)COC1]

2.55 mL (6.37 mmol) n-butyl lithium (2.5 M in THF) was added dropwise to a mixture of 2.00 g (6.06 mmol) 1,3-diiodobenzene in 40 mL THF under argon atmosphere at −70° C. The resulting mixture was stirred for 15 min 476 μL (7.28 mmol) 3-oxetanone was added and the mixture was stirred over night at RT. The mixture was worked up by adding saturated NH$_4$Cl solution followed by extraction with EtOAc. The combined organic phases were dried over magnesium sulfate, filtered and concentrated in vacuo. The crude material was purified by HPLC.
yield: 660 mg (39%)
ESI-MS: m/z=275 (M−H)−
R$_t$(HPLC): 0.99 min (method 5)

33.2: 3-Fluoro-3-(3-iodo-phenyl)-oxetane

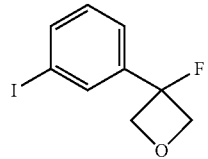 [SMILES: FC1(c2cccc(I)c2)COC1]

To a solution of 500 mg (1.81 mmol) 3-(3-iodo-phenyl)-oxetan-3-ol in 10.6 mL DCM was added 1.17 mL (2.72 mmol) [bis(2-methoxyethyl)amino]sulfur trifluoride at RT under argon atmosphere. The resulting mixture was stirred for 1 h. The mixture was worked up by adding saturated NH$_4$Cl solution. Phases were separated. The combined organic phases were dried over magnesium sulfate, filtered and concentrated in vacuo. The crude material was purified by flash chromatography (PE/EtOAc=9/1).
yield: 360 mg (71%)
ESI-MS: m/z=278 (M+)
R$_t$(HPLC): 1.19 min (method 5)

33.3: 3-(3-Fluoro-oxetan-3-yl)-benzoic acid methyl ester

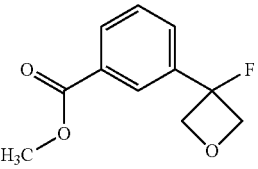

A mixture of 360 mg (1.30 mmol) 3-fluoro-3-(3-iodo-phenyl)-oxetane, 35.8 mg (64.7 μmol) 1,1′-bis-(diphenylphosphino)-ferrocene, 14.5 mg (64.7 μmol) palladium(II) acetate, 360 μL (2.59 mmol) TEA in 5 mL MeOH and 2 mL DMF was stirred under an carbon monoxide atmosphere at 5 bar and 50° C. for 24 h. The reaction mixture was filtered, the solvent was evaporated and the residue was purified by HPLC.
yield: 200 mg (73%)
ESI-MS: m/z=211 (M+H)+
R$_t$(HPLC): 1.02 min (method 5)

33.4: 3-(3-Fluoro-oxetan-3-yl)-benzoic acid

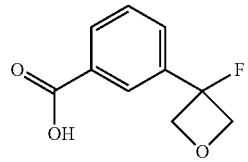 [SMILES: O=C(O)c1cccc(C2(F)COC2)c1]

200 mg (0.951 mmol) 3-(3-fluoro-oxetan-3-yl)-benzoic acid methyl ester was dissolved in 10 mL MeOH and treated with 0.40 mL 4 M aqueous NaOH solution at RT over the weekend. 0.20 mL 4 M aqueous NaOH solution was added and the mixture was stirred at 50° C. for 2 h. The reaction mixture was concentrated, acidified with 4 M aqueous hydrochlorid acid and stirred for 30 min at 0° C. The precipitate was filtered off, washed with water and dried.
yield: 150 mg (80%)
ESI-MS: m/z=195 (M−H)−
R$_t$(HPLC): 0.86 min (method 5)

Intermediate 34: 6-Methoxymethyl-pyridine-2-carboxylic acid

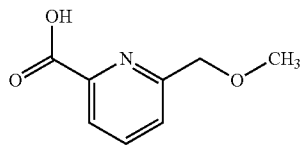

To a stirred solution of 300 mg (1.96 mmol) 6-hydroxymethyl-pyridine-2-carboxylic acid in 20 mL THF was added 188 mg (4.31 mmol) NaH in mineral oil (55%) at 0° C. After gas formation ceased, 310 μL (4.90 mmol) methyl iodide was added dropwise, then the mixture was stirred for 1 h at 0° C. and for 1 h at RT. The reaction mixture was diluted with EtOAc, extracted with water, washed with brine, dried over sodium sulfate, filtered and concentrated in vacuo.
yield: 190 mg (58%)
ESI-MS: m/z=168 (M+H)+
R$_t$(HPLC): 0.38 min (method 6)

Intermediate 35: 4-Chloro-6-methoxy-pyridine-2-carboxylic acid

35.1: 2-Chloro-6-methoxy-pyridin-4-ylamine

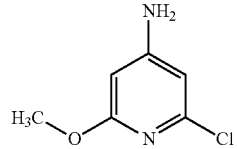

To a solution of 1.84 g (44.0 mmol) sodium in 40 mL MeOH was added 6.72 g (40.0 mmol) 2,6-dichloro-pyridin-4-ylamine. The reaction mixture was stirred at 150° C. for 30 min under microwave irradiation. The solvent was evaporated and ice water was added. The precipitate was filtered off, washed with water and dried.
yield: 5.00 g (79%); ESI-MS: m/z=159 (M+H)$^+$; $R_t$(HPLC): 0.41 min (method 5)

35.2: 4-Amino-6-methoxy-pyridine-2-carboxylic acid methyl ester

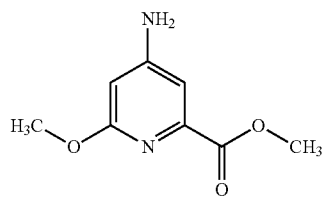

A mixture of 3.10 g (19.5 mmol) 2-chloro-6-methoxy-pyridin-4-ylamine, 410 mg (0.550 mmol) 1,1'-bis(diphenylphosphino)ferrocenedichloropalladium(II) and 5.62 mL (40.0 mmol) TEA in 60 mL MeOH was stirred at 100° C. for 6 h under carbon monoxide atmosphere. The solvent was evaporated. The resulting residue was purified by flash chromatography (PE/EtOAc=3/1).
yield: 1.20 g (34%); ESI-MS: m/z=183 (M+H)$^+$; $R_t$(HPLC): 0.40 min (method 5)

35.3: 4-Chloro-6-methoxy-pyridine-2-carboxylic acid methyl ester

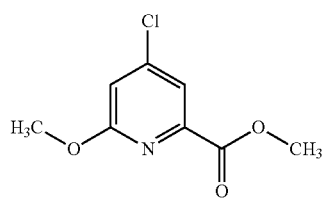

To a mixture of 1.25 mL (10.5 mmol) tert-butyl nitrite and 1.42 g (10.5 mmol) copper(II)chloride in 40 mL acetonitrile was added a solution of 1.20 g (6.59 mmol) 4-amino-6-methoxy-pyridine-2-carboxylic acid methyl ester in 10 mL acetonitrile dropwise at 40° C. This mixture was stirred at 80° C. for 1 h, then poured into ice water, acidified with 4 M aqueous HCl and extracted with EtOAc. The combined organic phases were dried over sodium sulfate, filtered and concentrated in vacuo. The crude material was purified by flash chromatography (PE/EtOAc=3/1→2/1).
yield: 650 mg (49%)
ESI-MS: m/z=202 (M+H)$^+$
$R_t$(HPLC): 1.12 min (method 5)

35.4: 4-Chloro-6-methoxy-pyridine-2-carboxylic acid

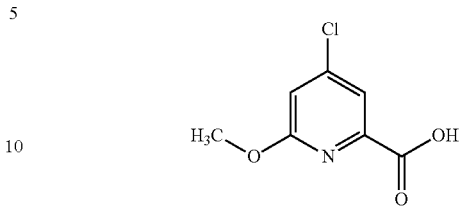

630 mg (3.13 mmol) 4-chloro-6-methoxy-pyridine-2-carboxylic acid methyl ester was dissolved in 20 mL MeOH and treated with 2.34 mL 4 M aqueous NaOH solution at RT for 12 h. The reaction mixture was acidified with 4 M aqueous HCl. The solvent was removed by distillation and the residue taken up in water. The precipitate was filtered off, washed with water and dried.
yield: 540 mg (92%)
ESI-MS: m/z=188 (M+H)$^+$
$R_t$(HPLC): 0.96 min (method 5)

Intermediate 36: 4-Bromo-6-methoxy-pyridine-2-carboxylic acid

36.1: 2-Chloro-6-methoxy-pyridin-4-ylamine

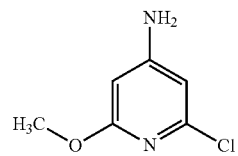

To a solution of 1.84 g (44.0 mmol) sodium in 40 mL MeOH was added 6.72 g (40.0 mmol) 2,6-dichloro-pyridin-4-ylamine. The reaction mixture was stirred at 150° C. for 30 min under microwave irradiation. The solvent was evaporated and ice water was added. The precipitate was filtered off, washed with water and dried.
yield: 5.00 g (79%)
ESI-MS: m/z=159 (M+H)$^+$
$R_t$(HPLC): 0.41 min (method 5)

36.2: 4-Amino-6-methoxy-pyridine-2-carboxylic acid methyl ester

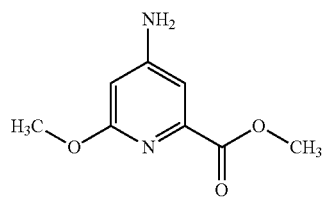

A mixture of 3.10 g (19.5 mmol) 2-chloro-6-methoxy-pyridin-4-ylamine, 410 mg (0.550 mmol) 1,1'-bis(diphenylphosphino)ferrocenedichloropalladium(II) and 5.62 mL (40.0 mmol) TEA in 60 mL MeOH was stirred at 100° C. for 6 h under carbon monoxide atmosphere. The solvent was evaporated. The resulting residue was purified by flash chromatography (PE/EtOAc=3/1).
yield: 1.20 g (34%)
ESI-MS: m/z=183 (M+H)$^+$
$R_t$(HPLC): 0.40 min (method 5)

36.3: 4-Bromo-6-methoxy-pyridine-2-carboxylic acid methyl ester

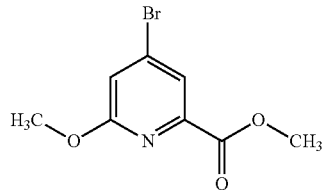

To a mixture of 3.47 mL (29.3 mmol) tert-butyl nitrite and 6.60 g (29.3 mmol) copper(II)bromide in 120 mL acetonitrile was added a solution of 3.33 g (18.3 mmol) 4-amino-6-methoxy-pyridine-2-carboxylic acid methyl ester in 30 mL acetonitrile dropwise at 40° C. This mixture was stirred at 80° C. for 1 h, then poured into ice water. The precipitate was filtered off, washed with water and dried. The crude material was purified by flash chromatography (PE/EtOAc=4/1→3/1).

yield: 2.50 g (56%)
ESI-MS: m/z=246 (M+H)$^+$

36.4: 4-Bromo-6-methoxy-pyridine-2-carboxylic acid

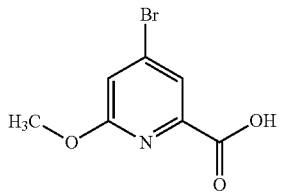

246 mg (1.00 mmol) 4-bromo-6-methoxy-pyridine-2-carboxylic acid methyl ester was dissolved in 5 mL MeOH and treated with 2.50 mL 4 M aqueous NaOH solution at RT for 12 h. The solvent was removed by distillation. the residue was taken up in water and acidified with 4 M aqueous hydrochlorid acid. The precipitate was filtered off, washed with water and dried.

yield: 45.0 mg (19%)
ESI-MS: m/z=232 (M+H)$^+$
$R_t$(HPLC): 1.00 min (method 5)

Intermediate 37: 1,6-Dimethoxy-isoquinoline-3-carboxylic acid

37.1: 3-Chloro-1,6-dimethoxy-isoquinoline

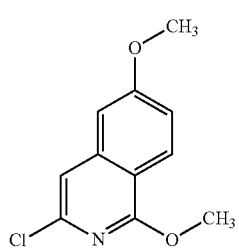

To a solution of 158 mg (3.79 mmol) sodium in 40 mL MeOH was added 843 mg (3.79 mmol) 1,3-dichloro-6-fluoro-isoquinoline. The reaction mixture was stirred at 150° C. for 30 min under microwave irradiation and then diluted with ice water. The precipitate was filtered off, washed with water and dried.

yield: 840 mg (98%)
ESI-MS: m/z=224 (M+)
$R_t$(HPLC): 1.34 min (method 5)

37.2: 1,6-Dimethoxy-isoquinoline-3-carboxylic acid methyl ester

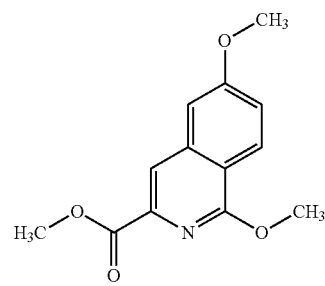

A mixture of 840 mg (3.72 mmol) 3-chloro-1,6-dimethoxy-isoquinoline, 82.1 mg (0.110 mmol) 1,1'-bis(diphenylphosphino)ferrocenedichloropalladium(II) and 1.05 mL (7.46 mmol) TEA in 40 mL MeOH was stirred at 100° C. for 12 h under carbon monoxide atmosphere. The solvent was evaporated. The resulting residue was stirred with diethyl ether. The precipitate was filtered off and purified by flash chromatography (PE/EtOAc=2/1).

yield: 550 mg (60%)
ESI-MS: m/z=248 (M+H)$^+$
$R_t$(HPLC): 1.23 min (method 5)

37.3: 1,6-Dimethoxy-isoquinoline-3-carboxylic acid

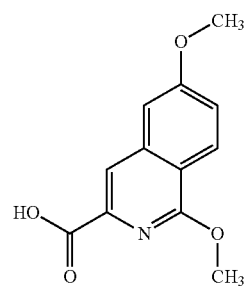

500 mg (2.02 mmol) 1,6-dimethoxy-isoquinoline-3-carboxylic acid methyl ester was dissolved in 20 mL MeOH and treated with 2.50 mL 4 M aqueous NaOH solution at RT for 12 h. The solvent was removed by distillation, the residue taken up in water and acidified with 4 M aqueous hydrochlorid acid. The precipitate was filtered off, washed with water and purified by HPLC.

yield: 460 mg (98%)
ESI-MS: m/z=234 (M+H)$^+$
$R_t$(HPLC): 1.11 min (method 5)

Intermediate 38:
6-Fluoro-1-methoxy-isoquinoline-3-carboxylic acid 38.1: 3-Chloro-6-fluoro-1-methoxy-isoquinoline

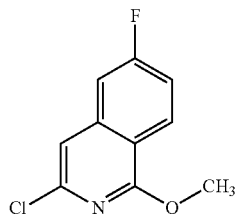

To a solution of 125 mg (3.00 mmol) sodium in 40 mL MeOH was added 668 mg (3.00 mmol) 1,3-dichloro-6-fluoro-isoquinoline. The reaction mixture was stirred at 70° C. for 30 min. The solvent was removed by distillation and the residue diluted with ice water. The precipitate was filtered off, washed with water and dried.
yield: 620 mg (98%)
ESI-MS: m/z=211 (M+)
$R_t$(HPLC): 1.35 min (method 5)

38.2: 6-Fluoro-1-methoxy-isoquinoline-3-carboxylic acid methyl ester

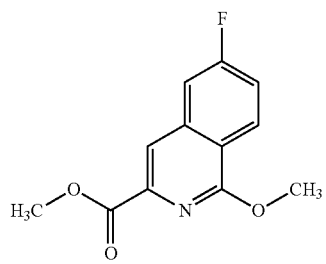

A mixture of 620 mg (2.93 mmol) 3-chloro-6-fluoro-1-methoxy-isoquinoline, 64.2 mg (86.0 µmol) 1,1'-bis(diphenylphosphino)ferrocenedichloropalladium(II) and 820 µL (5.86 mmol) TEA in 40 mL MeOH was stirred at 100° C. for 12 h under carbon monoxide atmosphere. The solvent was evaporated. The resulting residue was stirred with diethyl ether. The precipitate was filtered off, washed with diethyl ether and dried.
yield: 690 mg (99%)
ESI-MS: m/z=236 (M+H)+
$R_t$(HPLC): 1.23 min (method 5)

38.3: 6-Fluoro-1-methoxy-isoquinoline-3-carboxylic acid

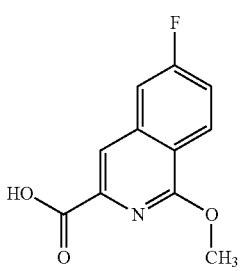 [SMILES: COc1nc(C(=O)O)cc2cc(F)ccc12]

690 mg (2.93 mmol) 6-fluoro-1-methoxy-isoquinoline-3-carboxylic acid methyl ester was dissolved in 20 mL MeOH and treated with 3.75 mL 4 M aqueous NaOH solution at RT for 3 h. The solvent was removed by distillation, the residue taken up in water and acidified with 4 M aqueous hydrochlorid acid. The precipitate was filtered off, washed with water and purified by HPLC.
yield: 50.0 mg (8%)
ESI-MS: m/z=222 (M+H)+
$R_t$(HPLC): 1.10 min (method 5)

Intermediate 39:
1,6,7-Trimethoxy-isoquinoline-3-carboxylic acid

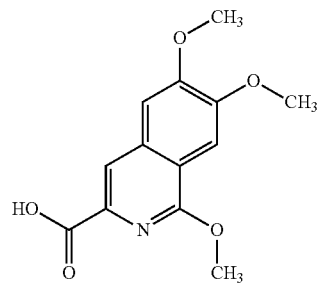 [SMILES: COc1cc2cc(C(=O)O)nc(OC)c2cc1OC]

This intermediate was prepared from 1,3-dichloro-6,7-dimethoxy-isoquinoline in three steps according to the preparation of 1,6-dimethoxy-isoquinoline-3-carboxylic acid.
ESI-MS: m/z=264 (M+H)+
$R_t$(HPLC): 1.02 min (method 5)

Intermediate 40: 3-(1-Methoxy-ethyl)-benzoic acid 40.1: 1-Bromo-3-(1-methoxy-ethyl)-benzene

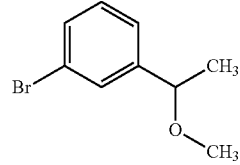

To a stirred and ice-cooled mixture of 1.09 g (27.4 mmol) NaH (60% in mineral oil) in 20 mL dry DMF was added a solution of 5.00 g (24.9 mmol) 1-(3-bromo-phenyl)-ethanol in 10 mL dry DMF under argon atmosphere. The mixture was stirred for 30 min at 0° C. 1.70 mL (27.4 mmol) methyl iodide was added and stirring was continued for 4 h at RT. The mixture was worked up by adding water, followed by extraction with EtOAc. The combined organic phases were dried over sodium sulfate, filtered and concentrated in vacuo. The crude material was purified by flash chromatography (Cyc/EtOAc=9/1).
yield: 2.60 g (49%)
ESI-MS: m/z=214 (M+)

40.2: 3-(1-Methoxy-ethyl)-benzoic acid methyl ester

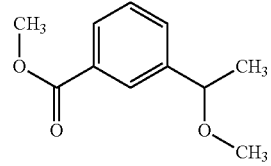

A mixture of 2.60 g (12.1 mmol) 1-bromo-3-(1-methoxy-ethyl)-benzene, 919 mg (1.26 mmol) 1,1'-bis(diphenylphosphino)ferrocenedichloropalladium(II) and 3.43 mL (24.6 mmol) TEA in 50 mL MeOH and 20 mL DMF was stirred at 80° C. for 12 h under carbon monoxide atmosphere. The solvent was evaporated. The residue was taken up in water and extracted with EtOAc. The combined organic phases were dried over magnesium sulfate, filtered and concentrated in vacuo. The crude material was purified by flash chromatography (Cyc/EtOAc=8/2).
yield: 1.31 g (56%)
ESI-MS: m/z=195 (M+H)+
$R_t$(HPLC): 1.29 min (method 1)

40.3: 3-(1-Methoxy-ethyl)-benzoic acid

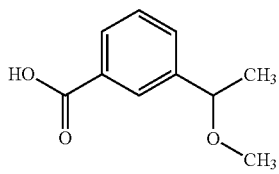

1.30 g (6.69 mmol) 3-(1-methoxy-ethyl)-benzoic acid methyl ester was dissolved in 20 mL MeOH and treated with 3.35 mL 4 M aqueous NaOH solution at RT for 5 h. The solvent was removed by distillation, the residue taken up in water and acidified with 4 M aqueous hydrochlorid acid. The precipitate was filtered off, washed with water and dried.
yield: 1.14 g (95%)
ESI-MS: m/z=179 (M−H)−
$R_t$(HPLC): 1.14 min (method 1)

Intermediate 42:
5-Bromo-methyl-benzofuran-3-carboxylic acid 41.1: 1,4-Dibromo-2-iodo-benzene

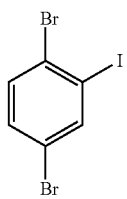

To a stirred mixture of 2.50 g (9.96 mmol) 2,5-dibromoaniline in 7 mL conc. sulfuric acid and 20 mL water, was added a solution of 1.00 g (14.5 mmol) sodium nitrite in 10 mL water dropwise at 0° C. and the mixture was stirred at this temperature for 1.25 h. A solution of 2.15 g (13.0 mmol) potassium iodide in 20 mL water was added dropwise under ice cooling. The ice bath was removed and the reaction mixture was heated to 65° C. for 30 min. After cooling to RT, the mixture was worked up by adding aqueous sodium thiosulfate solution, followed by extraction with PE/EtOAc. The combined organic phases were washed with aqueous sodium thiosulfate solution and saturated aqueous sodium bicarbonate solution, dried over sodium sulfate, filtered and concentrated in vacuo. The crude material was purified by flash chromatography (PE/EtOAc=100→96/4).
yield: 1.8 g (47%); ESI-MS: m/z=360 (M+); $R_t$(HPLC): 1.69 min (method 1)

41.2: 5-Bromo-2-methyl-benzofuran-3-carboxylic acid methyl ester

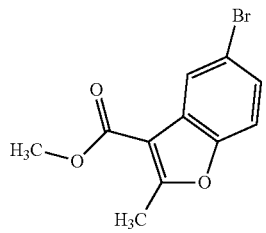

To a stirred mixture of 100 mg (0.525 mmol) copper(I) iodide and 1.90 g (13.7 mmol) potassium carbonate in 10 mL THF was added 1.75 g (4.84 mmol) 1,4-dibromo-2-iodo-benzene and 520 μL methyl acetoacetate under argon atmosphere. Then the mixture was stirred at 100° C. for 5 h under reflux. The reaction mixture was diluted with EtOAc and extracted with water. The combined organic phases were dried over sodium sulfate, filtered and concentrated in vacuo. The crude material was purified by flash chromatography (PE/EtOAc=9/1).
yield: 350 mg (27%)
$R_t$(HPLC): 1.63 min (method 1)

41.3: 5-Bromo-methyl-benzofuran-3-carboxylic acid

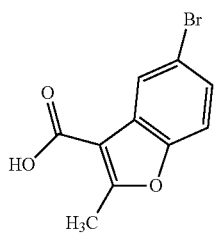

350 mg (1.30 mmol) 5-bromo-2-methyl-benzofuran-3-carboxylic acid methyl ester was dissolved in 10 mL THF and treated with 5.0 mL 1 M aqueous LiOH solution at 60° C. for 12 h. The reaction mixture was acidified with 1 M aqueous hydrochlorid acid. The precipitate was filtered off, washed with water and dried.
yield: 200 mg (54%), purity: 90%
ESI-MS: m/z=253 (M−H)−
$R_t$(HPLC): 0.58 min (method 4)

Intermediate 42:
5-Fluoro-methyl-benzofuran-3-carboxylic acid

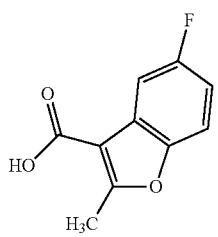

This intermediate was prepared from 1-bromo-4-fluoro-2-iodo-benzene in two steps according to the preparation of 5-bromo-methyl-benzofuran-3-carboxylic acid (from 1,4-dibromo-2-iodo-benzene).
ESI-MS: m/z=195 (M+H)+
$R_t$(HPLC): 1.12 min (method 6)

Intermediate 43: 2-Cyclopentylmethyl-1-methyl-1H-benzoimidazole-5-carboxylic acid 43.1: 3-(2-Cyclopentyl-acetylamino)-4-methylamino-benzoic acid methyl ester

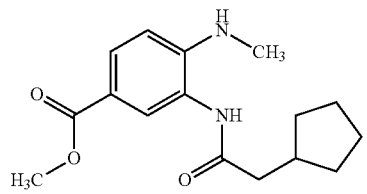 [SMILES: CNc1ccc(C(=O)OC)cc1NC(=O)CC1CCCC1]

650 mg (5.07 mmol) cyclopentyl-acetic acid was stirred with 1.80 g (5.61 mmol) TBTU and 2.00 mL (14.4 mmol) TEA in 50 mL DMF at RT. After 30 min, 900 mg (5.00 mmol) 3-amino-4-methylamino-benzoic acid methyl ester was added and the mixture was stirred at RT for 3 h and at 50° C. for 12 h. The solvent was removed by distillation. The residue was taken up in aqueous potassium carbonate solution and water and extracted with EtOAc. The combined organic extracts were washed with water and saturated brine, dried over sodium sulfate, filtered and concentrated in vacuo.
yield: 1.10 g (76%)
ESI-MS: m/z=291 (M+H)$^+$
R$_f$(TLC): 0.23 (DCM/MeOH=19:1)

43.2: 2-Cyclopentylmethyl-1-methyl-1H-benzoimidazole-5-carboxylic acid methyl ester

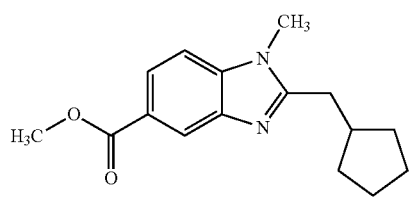 [SMILES: COC(=O)c1ccc2c(c1)nc(CC1CCCC1)n2C]

A mixture of 1.00 g (3.44 mmol) 3-(2-cyclopentyl-acetylamino)-4-methylamino-benzoic acid methyl ester in 20 mL glacial acetic acid was stirred under reflux for 1 h. The solvent was evaporated. The resulting residue was taken up in water and extracted with EtOAc. The combined organic phases were washed with water and saturated brine, dried over sodium sulfate, filtered and concentrated in vacuo.
yield: 790 mg (84%)
ESI-MS: m/z=273 (M+H)$^+$
R$_f$(TLC): 0.70 (DCM/MeOH=50:1)

43.3: 2-Cyclopentylmethyl-1-methyl-1H-benzoimidazole-5-carboxylic acid

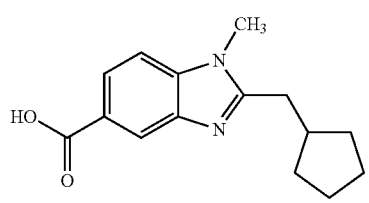 [SMILES: Cn1c(CC2CCCC2)nc2cc(C(=O)O)ccc21]

A mixture of 780 mg (2.86 mmol) 2-cyclopentylmethyl-1-methyl-1H-benzoimidazole-5-carboxylic acid methyl ester, 1.00 g (25.0 mmol) NaOH in 30 mL MeOH and 10 mL water was stirred at RT for 18 h. The solvent was removed by distillation, the residue taken up in water and neutralized with aqueous hydrochlorid acid. The precipitate was filtered off, washed with water and dried.
yield: 650 mg (88%)
ESI-MS: m/z=259 (M+H)$^+$
R$_f$(TLC): 0.59 (DCM/MeOH=9:1)

Intermediate 44: 2-(2,6-Difluoro-phenylamino)-1-methyl-1H-benzoimidazole-5-carboxylic acid 44.1: 2-(2,6-Difluoro-phenylamino)-1-methyl-1H-benzoimidazole-5-carboxylic acid ethyl ester

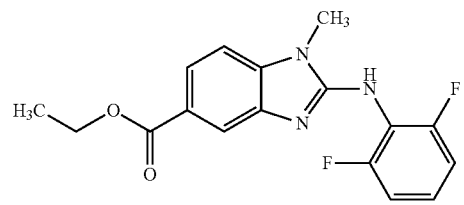 [SMILES: CCOC(=O)c1ccc2c(c1)nc(Nc1c(F)cccc1F)n2C]

A mixture of 2.00 g (10.3 mmol) 3-amino-4-methylamino-benzoic acid methyl ester and 1.76 g (10.3 mmol) 2,6-difluorophenyl isothiocyanate in 50 mL acetonitrile and 10 mL DMF was stirred at RT for 12 h. 1.80 g (14.3 mmol) N,N'-diisopropylcarbodiimide was added and the mixture was stirred at 80° C. for 5 h. The solvent was removed by distillation. The residue was taken up in EtOAc. The precipitate was filtered off and washed with EtOAc and diethyl ether. The residue was taken up in acetonitrile. The precipitate was filtered off, washed with acetonitrile and diethyl ether and dried.
yield: 2.20 g (64%)
ESI-MS: m/z=332 (M+H)$^+$
R$_f$(TLC): 0.30 (DCM/MeOH=19:1)

Intermediate 45: [4-(6-Bromo-pyridine-2-carbonyl)-2,2-dimethyl-piperazin-1-yl]-[1-(3-chloro-phenyl)-1H-[1,2,4]triazol-3-yl]-methanone

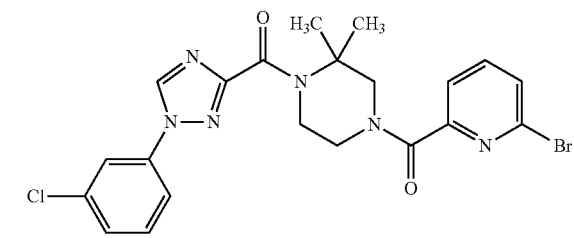 [SMILES: CC1(C)CN(C(=O)c2cccc(Br)n2)CCN1C(=O)c1ncn(-c2cccc(Cl)c2)n1]

To a solution of 394 mg (1.94 mmol) 6-bromo-pyridine-2-carboxylic acid in 30 mL THF was added 369 mg (2.28 mmol) 1,1'-carbonyldiimidazole. After stiffing at 60° C. for 4 h, 520 mg (1.63 mmol) [1-(3-chloro-phenyl)-1H-[1,2,4]triazol-3-yl]-(2,2-dimethyl-piperazin-1-yl)-methanone was added. The resulting mixture was stirred at 50° C. for 12 h. The solvent was evaporated. The residue was taken up in DMF and purified by HPLC.
yield: 700 mg (85%)
ESI-MS: m/z=503 (M+H)$^+$
R$_t$(HPLC): 1.42 min (method 22)

Intermediate 46: [1-(3-Chloro-phenyl)-1H-[1,2,4]triazol-3-yl]-{4-[6-(3,6-dihydro-2H-pyran-4-yl)-pyridine-2-carbonyl]-2,2-dimethyl-piperazin-1-yl}-methanone

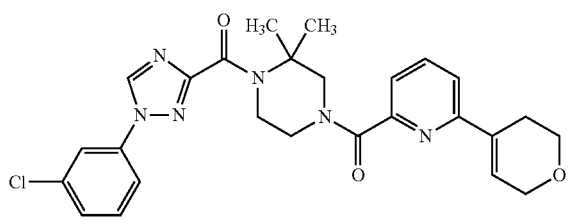 [SMILES: CC1(C)CN(C(=O)c2cccc(C3=CCOCC3)n2)CCN1C(=O)c1ncn(-c2cccc(Cl)c2)n1]

A mixture of 500 mg (0.10 mmol) [4-(6-bromo-pyridine-2-carbonyl)-2,2-dimethyl-piperazin-1-yl]-[1-(3-chloro-phenyl)-1H-[1,2,4]triazol-3-yl]-methanone, 28 mg (0.13 mmol) 3,6-dihydro-2H-pyran-4-boronic acid pinacol ester, 16 mg (0.020 mmol) [1,1'-bis(diphenylphosphino)-ferrocene]dichloropalladium(II) complex with DCM (1:1) and 0.10 mL 5M aqueous potassium carbonate solution in 1.0 mL dioxane and 0.50 mL MeOH was stirred at 140° C. for 15 min under microwave irradiation. The reaction mixture was filtered through Alox (alkaline) and purified by HPLC.
yield: 16.8 mg (33%)
ESI-MS: m/z=507 (M+H)+
$R_t$(HPLC): 1.20 min (method 11)

Intermediate 47: [1-(3-Chloro-phenyl)-1H-[1,2,4]triazol-3-yl]-[4-(6-cyclopent-1-enyl-pyridine-2-carbonyl]-2,2-dimethyl-piperazin-1-yl]-methanone

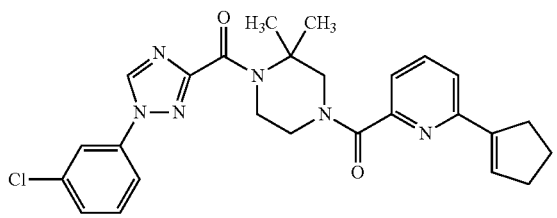 [SMILES: CC1(C)CN(C(=O)c2cccc(C3=CCCC3)n2)CCN1C(=O)c1ncn(-c2cccc(Cl)c2)n1]

This intermediate was prepared from [4-(6-bromo-pyridine-2-carbonyl)-2,2-dimethyl-piperazin-1-yl]-[1-(3-chloro-phenyl)-1H-[1,2,4]triazol-3-yl]-methanone and cyclopenten-1-ylboronic acid ester according to the preparation of [1-(3-chloro-phenyl)-1H-[1,2,4]triazol-3-yl]-[4-[6-(3,6-dihydro-2H-pyran-4-yl)-pyridine-2-carbonyl]-2,2-dimethyl-piperazin-1-yl]-methanone.
yield: 15.0 mg (31%); ESI-MS: m/z=490 (M–H)+; $R_t$(HPLC): 1.55 min (method 22)

Intermediate 48: [4-(4-Amino-3-methylamino-benzoyl)-2,2-dimethyl-piperazin-1-yl]-(1-phenyl-1H-[1,2,4]triazol-3-yl)-methanone 48.1: [2,2-Dimethyl-4-(3-methylamino-4-nitro-benzoyl)-piperazin-1-yl]-(1-phenyl-1H-[1,2,4]-triazol-3-yl)-methanone

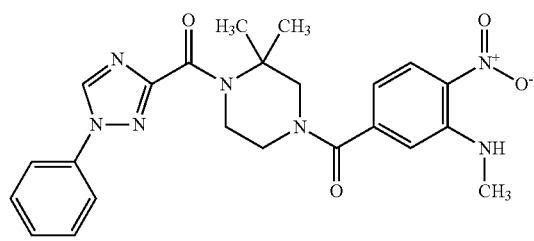 [SMILES: CNc1cc(C(=O)N2CCN(C(=O)c3ncn(-c4ccccc4)n3)C(C)(C)C2)ccc1[N+](=O)[O-]]

A mixture of 399 mg (1.00 mmol) (2,2-dimethyl-piperazin-1-yl)-(1-phenyl-1-H-[1,2,4]triazol-3-yl)-methanone trifluoroacetate, 196 mg (1.00 mmol) 3-methylamino-4-nitro-benzoic acid, 353 mg (1.10 mmol) TBTU and 600 µL (3.50 mmol) DIPEA in 1.00 mL DMF was stirred at RT for 1 h. The reaction mixture was poured into ice water. The precipitate was filtered off, washed with water and dried.

yield: 445 mg (96%)
ESI-MS: m/z=464 (M+H)+
$R_t$(HPLC): 1.10 min (method 5)

48.2: [4-(4-Amino-3-methylamino-benzoyl)-2,2-dimethyl-piperazin-1-yl]-(1-phenyl-1H-[1,2,4]-triazol-3-yl)-methanone

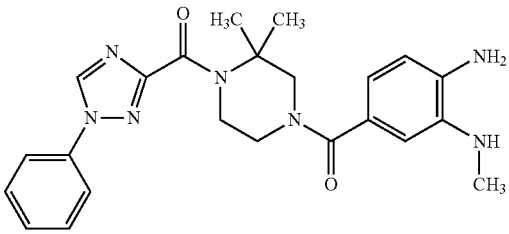 [SMILES: CNc1cc(C(=O)N2CCN(C(=O)c3ncn(-c4ccccc4)n3)C(C)(C)C2)ccc1N]

A mixture of 445 mg (0.960 mmol) [2,2-dimethyl-4-(3-methylamino-4-nitro-benzoyl)-piperazin-1-yl]-(1-phenyl-1H-[1,2,4]-triazol-3-yl)-methanone and 300 mg Raney nickel in 50 mL MeOH was hydrogenated at RT for 7.5 h. The catalyst was removed by filtration and the solvent was evaporated in vacuo.
yield: 440 mg (99%)
ESI-MS: m/z=434 (M+H)+
$R_t$(HPLC): 1.27 min (method 5)

Intermediate 49: 6-Methoxy-pyridine-2-carbonyl chloride

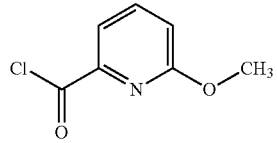

To a mixture of 5.00 g (32.7 mmol) 6-methoxy-pyridine-2-carboxylic acid in 100 mL DCM was added 40.8 mL (81.6 mmol) 2 M oxalyl chloride solution in DCM and stirred at 40° C. for 2 h. The solvent was removed by distillation.
Yield: 5.60 g (100%)
ESI-MS: m/z=168 (M+H)+ (methyl ester)
$R_t$(HPLC): 1.04 min (method 8) (methyl ester)

Intermediate 50:
(S)-2-Propyl-piperazine-1-carboxylic acid tert-butyl ester 50.1:
(S)-4-Benzyl-2-propyl-piperazine-1-carboxylicacid tert-butyl ester

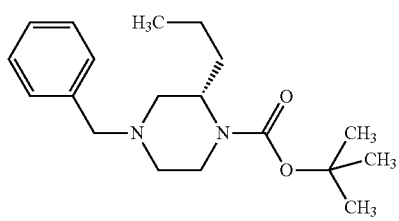 [SMILES: CCC[C@H]1CN(Cc2ccccc2)CCN1C(=O)OC(C)(C)C]

To a solution of 1.00 g (4.58 mmol) (S)-1-benzyl-3-propylpiperazine in 20 mL DCM was added 1.00 g (4.58 mmol) di-tert-butyl dicarbonate and 1.00 mL (5.81 mmol) DIPEA. The reaction mixture was stirred at RT for 2 h. Then the reaction mixture was washed with saturated aqueous NaHCO3 solution. The combined organic phases were washed with water, dried over sodium sulfate, filtered and concentrated in vacuo.
Yield: 1.50 g (93%), purity: 90%
ESI-MS: m/z=319 (M+H)+
$R_t$(HPLC): 1.15 min (method 8)

50.2: (S)-2-Propyl-piperazine-1-carboxylic acid tert-butyl ester

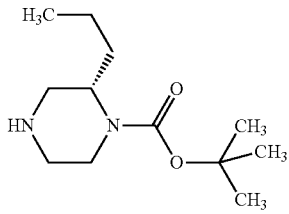 [SMILES: CCC[C@H]1CNCCN1C(=O)OC(C)(C)C]

A mixture of 1.50 g (4.24 mmol; purity: 90%) (S)-4-benzyl-2-propyl-piperazine-1-carboxylic acid tert-butyl ester and 150 mg palladium on carbon in 30 mL methanol was hydrogenated at RT for 6 h at 3 bar. The catalyst was removed by filtration and the solvent was evaporated in vacuo.
Yield: 1.00 g (88%), purity: 85%; ESI-MS: m/z=229 (M+H)$^+$; R$_t$(HPLC): 0.94 min (method 8)

Intermediate 51: (3-Methyl-piperazin-1-yl)-(1-m-tolyl-1H-[1,2,4]triazol-3-yl)-methanone

51.1: 2-Methyl-4-(1-m-tolyl-1H-[1,2,4]triazole-3-carbonyl)-piperazine-1-carboxylic acid tert-butyl ester

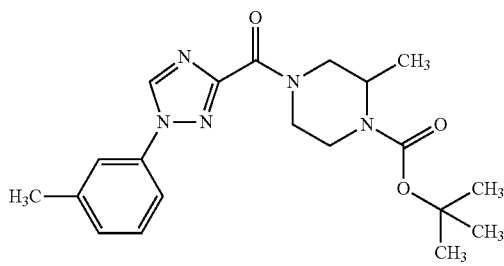 [SMILES: Cc1cccc(-n2cnc(C(=O)N3CCN(C(=O)OC(C)(C)C)C(C)C3)n2)c1]

2.00 g (9.84 mmol) 1-m-tolyl-1H-[1,2,4]-triazole-3-carboxylic acid was stirred with 3.30 g (10.3 mmol) TBTU and 2.50 mL (14.6 mmol) DIPEA in 30 mL DCM at RT. After 10 min, 2.05 g (9.84 mmol) 2-methyl-piperazine-1-carboxylic acid tert-butyl ester was added and the reaction mixture was stirred at RT for 12 h. The solvent was removed by distillation. The residue was taken up in water and extracted with EtOAc. The combined organic phases were dried over sodium sulfate, filtered and concentrated in vacuo. The crude material was purified by flash chromatography (EtOAc).
Yield: 4.00 g (95%), purity: 90%
ESI-MS: m/z=386 (M+H)$^+$
R$_t$(HPLC): 1.48 min (method 8)

51.2: (3-Methyl-piperazin-1-yl)-(1-m-tolyl-1H-[1,2,4]-triazol-3-yl)-methanone

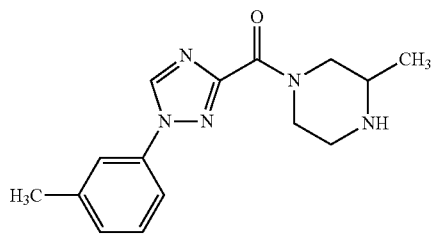

A mixture of 4.00 g (9.33 mmol; purity: 90%) 2-methyl-4-(1-m-tolyl-1H-[1,2,4]-triazole-3-carbonyl)-piperazine-1-carboxylic acid tert-butyl ester and 5.00 mL (64.9 mmol) TFA in 20 mL DCM was stirred at RT for 12 h. The reaction mixture was extracted with 4 M aqueous NaOH solution. The combined organic phases were dried over sodium sulfate, filtered and concentrated in vacuo. The crude material was purified by HPLC.
Yield: 1.54 g (55%)
ESI-MS: m/z=286 (M+H)$^+$
R$_t$(HPLC): 0.79 min (method 8)
By using the same synthesis strategy as for (3-methyl-piperazin-1-yl)-(1-m-tolyl-1H-[1,2,4]-triazol-3-yl)-methanone the following compounds were prepared in two steps:

| In # | product name | product structure | R$_t$ [min]/ HPLC method | ESI-MS m/z |
|---|---|---|---|---|
| 52 | [1-(3-chloro-phenyl)-1H-[1,2,4]triazol-3-yl]-(3-methyl-piperazin-1-yl)-methanone | | 0.79/8 | 306 (M + H)$^+$ |
| 53 | [1-(3-chloro-phenyl)-1H-[1,2,4]triazol-3-yl]-((R)-3-methyl-piperazin-1-yl)-methanone | | 0.83/8 | 306 (M + H)$^+$ |

-continued

| In # | product name | product structure | R$_t$ [min]/ HPLC method | ESI- MS m/z |
|---|---|---|---|---|
| 54 | ((R)-3-methyl-piperazin-1-yl)-(1-m-tolyl-1H-[1,2,4]triazol-3-yl)-methanone | | 0.78/8 | 286 (M + H)$^+$ |
| 55 | [1-(3-chloro-phenyl)-1H-[1,2,4]triazol-3-yl]-((S)-3-methyl-piperazin-1-yl)-methanone | | 0.81/8 | 306 (M + H)$^+$ |
| 56 | ((S)-3-methyl-piperazin-1-yl)-(1-m-tolyl-1H-[1,2,4]triazol-3-yl)-methanone | | 0.75/8 | 286 (M + H)$^+$ |
| 57 | [1-(3-fluoro-phenyl)-1H-[1,2,4]triazol-3-yl]-((S)-3-methyl-piperazin-1-yl)-methanone | | 0.69/8 | 290 (M + H)$^+$ |
| 58 | [1-(3-fluoro-phenyl)-1H-[1,2,4]triazol-3-yl]-((S)-3-propyl-piperazin-1-yl)-methanone | | 0.86/8 | 318 (M + H)$^+$ |
| 59 | [1-(3-fluoro-phenyl)-1H-[1,2,4]triazol-3-yl]-(2-methyl-piperazin-1-yl)-methanone | | 0.72/8 | 290 (M + H)$^+$ |

-continued

| In # | product name | product structure | R$_t$ [min]/ HPLC method | ESI-MS m/z |
|---|---|---|---|---|
| 60 | (6-methoxy-pyridin-2-yl)-((S)-3-methyl-piperazin-1-yl)-methanone | | 0.41/8 | 236 (M + H)$^+$ |
| 61 | (6-methoxy-pyridin-2-yl)-((R)-3-methyl-piperazin-1-yl)-methanone | | 0.34/8 | 236 (M + H)$^+$ |
| 62 | (4,7-diaza-spiro[2.5]oct-7-yl)-(6-methoxy-pyridin-2-yl)-methanone | | 1.15/24 | 248 (M + H)$^+$ |
| 63 | (3-chloro-phenyl)-(6,9-diaza-spiro[4.5]dec-9-yl)-methanone trifluoroacetate | | 0.83/5 | 279 (M + H)$^+$ |
| 64 | (4,5-dibromo-furan-2-yl)-(2-ethyl-piperazin-1-yl)-methanone | | 0.85/8 | 365 (M + H)$^+$ |
| 65 | (4,7-diaza-spiro[2.5]oct-7-yl)-(4,5-dibromo-furan-2-yl)-methanone trifluoroacetate | | 1.05/10 | 363 (M + H)$^+$ |

Intermediate 66: (3R*,5S*)-3,5-Dimethyl-piperazin-1-yl)-(1-m-tolyl-1H-[1,2,4]triazol-3-yl)-methanone

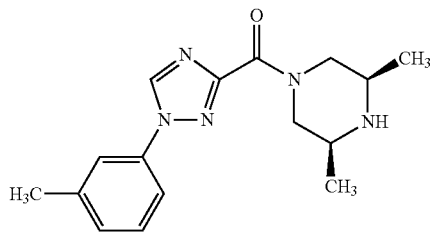

A mixture of 610 mg (3.00 mmol) 1-m-tolyl-1H-[1,2,4]-triazole-3-carboxylic acid, 350 mg (3.00 mmol) cis-2,6-dimethyl-piperazine, 1.06 g (3.30 mmol) TBTU and 770 µL (4.50 mmol) DIPEA in 5.0 mL DMF was stirred with at RT for 12 h. The reaction mixture was poured into ice water and extracted with EtOAc. The combined organic phases were washed with saturated NaHCO$_3$ solution, dried over sodium sulfate, filtered and concentrated in vacuo.

Yield: 520 mg (58%)
ESI-MS: m/z=300 (M+H)$^+$
R$_t$(HPLC): 0.80 min (method 8)

By using the same synthesis strategy as for (3R*,5S*)-3,5-dimethyl-piperazin-1-yl)-(1-m-tolyl-1H-[1,2,4]-triazol-3-yl)-methanone the following compounds were prepared:

Intermediate 70: 2-Methyl-piperazin-1-yl)-(1-phenyl-1H-[1,2,4]-triazol-3-yl)-methanone 70.1: 1-Phenyl-1H-[1,2,4]-triazole-3-carbonyl chloride

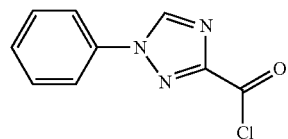 [SMILES: O=C(Cl)c1ncn(-c2ccccc2)n1]

To a mixture of 2.00 g (10.5 mmol) 1-phenyl-1H-[1,2,4]-triazole-3-carboxylic acid in 20 mL DCM was added 10.0 mL (137 mmol) thionyl chloride and 1 drop of DMF. The reaction mixture was stirred at 40° C. for 1 h. The solvent was removed by distillation. Yield: 2.20 g (100%); ESI-MS: m/z=204 (M+H)$^+$ (methyl ester); R$_t$(HPLC): 1.04 min (method 8) (methyl ester)

| # | product name | product structure | R$_t$ [min]/ HPLC method | ESI-MS m/z |
|---|---|---|---|---|
| 67 | (3S*,5R*)-3,5-dimethyl-piperazin-1-yl)-(6-methoxy-pyridin-2-yl)-methanone | | 0.51/3 | 250 (M + H)$^+$ |
| 68 | (5,8-diaza-spiro[3.5]non-8-yl)-(6-methoxy-pyridin-2-yl)-methanone | | 0.87/4 | 262 (M + H)$^+$ |
| 69 | (5,8-diaza-spiro[3.5]non-8-yl)-(4,5-dibromo-furan-2-yl)-methanone | | 1.13/4 | 377 (M + H)$^+$ |

70.2: 3-Methyl-4-(1-phenyl-1H-[1,2,4]-triazole-3-carbonyl)-piperazine-1-carboxylic acid tert-butyl ester

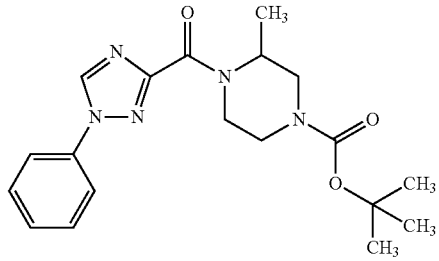 [SMILES: CC1CN(C(=O)OC(C)(C)C)CCN1C(=O)c1ncn(-c2ccccc2)n1]

To a mixture of 2.19 g (10.5 mmol) 3-methyl-piperazine-1-carboxylic acid tert-butyl ester and 2.50 mL (14.6 mmol) DIPEA in 15 mL DCM was added a solution of 2.18 g (10.5 mmol) 1-phenyl-1H-[1,2,4]-triazole-3-carbonyl chloride in 15 mL DCM. The reaction mixture was stirred at RT for 3 days, then washed with water. The combined organic phases were dried over sodium sulfate, filtered and concentrated in vacuo.

Yield: 3.90 g (100%)
ESI-MS: m/z=372 (M+H)$^+$
$R_t$(HPLC): 1.38 min (method 8)

71.3: (2-Methyl-piperazin-1-yl)-(1-phenyl-1H-[1,2,4]-triazol-3-yl)-methanone

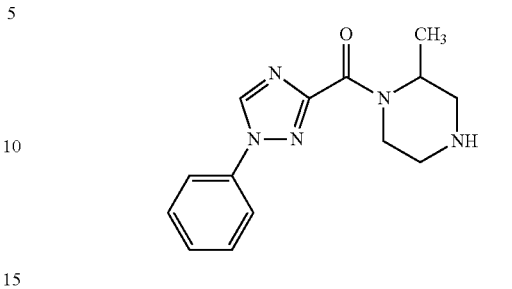

A mixture of 3.90 g (10.5 mmol) 3-methyl-4-(1-phenyl-1H-[1,2,4]-triazole-3-carbonyl)-piperazine-1-carboxylic acid tert-butyl ester and 5.00 mL (64.9 mmol) TFA in 20 mL DCM was stirred at 40° C. for 2 h and at RT for 12 h. The solvent was removed by distillation. The crude material was purified by HPLC.

Yield: 1.60 g (53%)
ESI-MS: m/z=272 (M+H)$^+$
$R_t$(HPLC): 0.71 min (method 8)

By using the same synthesis strategy as for (2-methyl-piperazin-1-yl)-(1-phenyl-1H-[1,2,4]-triazol-3-yl)-methanone the following compounds were prepared in three steps:

| # | product name | product structure | $R_t$ [min]/ HPLC method | ESI-MS m/z |
|---|---|---|---|---|
| 72 | [1-(3-chloro-phenyl)-1H-[1,2,4]triazol-3-yl]-(2-methyl-piperazin-1-yl)-methanone | | 0.82/8 | 306 (M + H)$^+$ |
| 73 | (2-methyl-piperazin-1-yl)-(1-m-tolyl-1H-[1,2,4]triazol-3-yl)-methanone | | 0.79/8 | 286 (M + H)$^+$ |
| 74 | [1-(3-fluoro-phenyl)-1H-[1,2,4]triazol-3-yl]-(3-methyl-piperazin-1-yl)-methanone | | 0.70/8 | 290 (M + H)$^+$ |

By using the same synthesis strategy as for (2-methyl-piperazin-1-yl)-(1-phenyl-1H-[1,2,4]-triazol-3-yl)-methanone the following compounds were prepared from 6-methoxy-pyridine-2-carbonyl chloride and the respective BOC-protected piperazine in three steps:

| # | product name | product structure | R$_t$ [min]/ HPLC method | ESI-MS m/z |
|---|---|---|---|---|
| 75 | (6-methoxy-pyridin-2-yl)-(2-methyl-piperazin-1-yl)-methanone | | 0.34/8. | 236 (M + H)$^+$ |
| 76 | (2-ethyl-piperazin-1-yl)-(6-methoxy-pyridin-2-yl)-methanone | | 0.53/8 | 250 (M + H)$^+$ |
| 77 | (6-methoxy-pyridin-2-yl)-(3-methyl-piperazin-1-yl)-methanone | | 0.38/8 | 236 (M + H)$^+$ |

By using the same synthesis strategy as for (2-methyl-piperazin-1-yl)-(1-phenyl-1H-[1,2,4]-triazol-3-yl)-methanone the following compounds were prepared from 3-chloro-benzoyl chloride and the respective BOC-protected piperazine in three steps:

| # | product name | product structure | R$_t$ [min]/ HPLC method | ESI-MS m/z |
|---|---|---|---|---|
| 78 | (3-chloro-phenyl)-(1,4-diaza-spiro[5.5]undec-4-yl)-methanone trifluoroacetate | | 0.88/5 | 293 (M + H)$^+$ |
| 79 | (3-chloro-phenyl)-(3,3-diethyl-piperazin-1-yl)-methanone trifluoroacetate | | 0.84/5 | 281 (M + H)$^+$ |

Intermediate 80: (2,2-Dimethyl-piperazin-1-yl)-(6-methoxy-pyridin-2-yl)-methanone trifluoroacetate

80.1: 4-(6-Methoxy-pyridine-2-carbonyl)-3,3-dimethyl-piperazine-1-carboxylic acid tert-butyl ester

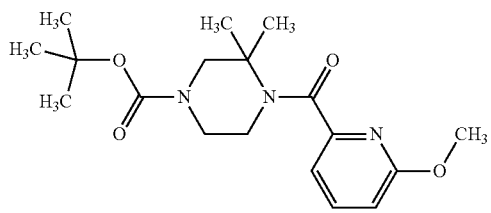 [SMILES: COc1cccc(C(=O)N2CCN(C(=O)OC(C)(C)C)CC2(C)C)n1]

A mixture of 410 mg (2.28 mmol) 6-methoxy-2-pyridinecarboxylic acid and 400 μL (3.02 mmol) 1-chloro-N,N,2-trimethylpropenylamine in 10 mL THF was stirred at RT. After 1.5 h, 600 mg (2.66 mmol) 3,3-dimethyl-piperazine-1-carboxylic acid tert-butyl ester and 1.00 mL (5.81 mmol) DIPEA was added and the reaction mixture was stirred at RT for 30 min. The reaction mixture was diluted with saturated NaHCO$_3$ solution and extracted with EtOAc. The combined organic phases were dried over sodium sulfate, filtered and concentrated in vacuo. The crude material was purified by flash chromatography (PE/EtOAc=1/1).
Yield: 780 mg (84%)
ESI-MS: m/z=350 (M+H)$^+$
R$_t$(HPLC): 1.23 min (method 3)

80.2: (2,2-Dimethyl-piperazin-1-yl)-(6-methoxy-pyridin-2-yl)-methanone trifluoroacetate

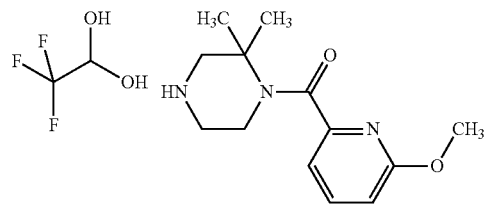

A mixture of 780 mg (2.23 mmol) 4-(6-methoxy-pyridine-2-carbonyl)-3,3-dimethyl-piperazine-1-carboxylic acid tert-butyl ester and 2.00 mL (25.9 mmol) TFA in 10 mL DCM was stirred at RT for 12 h. The solvent was evaporated and the residue triturated with diethyl ether. The precipitate was filtered off, washed with diethyl ether and dried.
Yield: 600 mg (74%)
ESI-MS: m/z=250 (M+H)$^+$
R$_t$(HPLC): 0.66 min (method 4)

Intermediate 81: (3-Methoxymethyl-3-methyl-piperazin-1-yl)-(6-methoxy-pyridin-2-yl)-methanone

81.1: [Benzyl-(1-cyano-2-methoxy-1-methyl-ethyl)-amino]-acetic acid ethyl ester

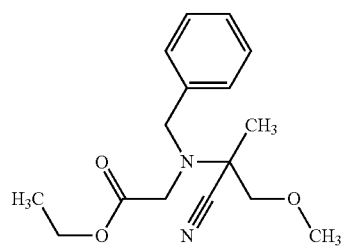 [SMILES: CCOC(=O)CN(Cc1ccccc1)C(C)(C#N)COC]

To a mixture of 500 μL (5.43 mmol) methoxyacetone and 1.05 g (5.43 mmol) N-benzylglycine ethyl ester in 2.0 mL acetic acid was added 780 μl (6.18 mmol) trimethylsilyl cyanide dropwise. The resulting mixture was stirred at 80° C. for 30 min and then poured into ice water. The water was decanted and the oily residue was triturated with DIPE. The precipitate was filtered off and the solvent was washed with saturated aqueous NaHCO$_3$ solution, dried over sodium sulfate, filtered and concentrated in vacuo.
Yield: 550 mg (33%)
ESI-MS: m/z=291 (M+H)$^+$
R$_t$(HPLC): 1.21 min (method 4)

81.2: 4-Benzyl-5-methoxymethyl-5-methyl-piperazin-2-one

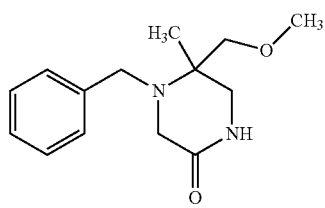 [SMILES: COCC1(C)CNC(=O)CN1Cc1ccccc1]

To a solution of 545 mg (1.78 mmol) [benzyl-(1-cyano-2-methoxy-1-methyl-ethyl)-amino]-acetic acid ethyl ester in 10 mL MeOH was added 460 mg (3.57 mmol) cobalt(II) chloride. The mixture was cooled with ice and 270 mg (7.13 mmol) sodium borohydride was added. The resulting mixture was stirred at RT for 1 h. The reaction mixture was diluted with a small amount of water, acidified with acetic acid and stirred for 30 min. The organic solvent was removed by distillation; the residue was alkalized with 4 N aqueous NaOH solution and filtered through Celite. The solvent was extracted with EtOAc. The combined organic phases were dried over sodium sulfate, filtered and concentrated in vacuo.
Yield: 240 mg (54%)
ESI-MS: m/z=249 (M+H)$^+$
R$_t$(HPLC): 1.04 min (method 4)

81.3: 1-Benzyl-2-methoxymethyl-2-methyl-piperazine

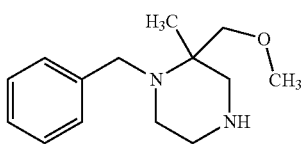 [SMILES: COCC1(C)CNCCN1Cc1ccccc1]

A mixture of 130 mg (0.524 mmol) 4-benzyl-5-methoxymethyl-5-methyl-piperazin-2-one in 5 mL THF was cooled with ice and 780 μL (0.780 mmol) 1M lithium aluminum hydride solution in THF was added dropwise under argon atmosphere. The resultant mixture was stirred 3 h under ice-bath cooling and 2.5 h at Rt. Then the mixture was quenched with saturated aqueous Na$_2$SO$_4$ solution, stirred for 1 h, filtered through Celite, washed with EtOAc and concentrated in vacuo.
Yield: 125 mg (97%)
ESI-MS: m/z=235 (M+H)$^+$
R$_t$(HPLC): 1.04 min (method 4)

81.4: (4-Benzyl-3-methoxymethyl-3-methyl-piperazin-1-yl)-(6-methoxy-pyridin-2-yl)-methanone

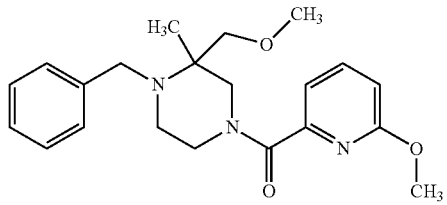 [SMILES: COCC1(C)CN(C(=O)c2cccc(OC)n2)CCN1Cc1ccccc1]

A mixture of 77.6 mg (507 μmol) 6-methoxy-2-pyridinecarboxylic acid, 125 mg (507 μmol) 1-benzyl-2-methoxymethyl-2-methyl-piperazine, 177 mg (551 μmol) TBTU and 100 μL (581 μmol) DIPEA in 1.5 mL DMF was stirred at RT for 2 h. The reaction mixture was poured into ice water and extracted with EtOAc. The combined organic phases were dried over sodium sulfate, filtered and concentrated in vacuo.
Yield: 170 mg (82%), purity: 90%
ESI-MS: m/z=370 (M+H)+
R$_t$(HPLC): 1.48 min (method 1)

81.5: (3-Methoxymethyl-3-methyl-piperazin-1-yl)-(6-methoxy-pyridin-2-yl)-methanone

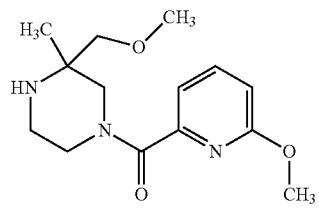

A mixture of 170 mg (414 μmol, purity: 90%) (4-benzyl-3-methoxymethyl-3-methyl-piperazin-1-yl)-(6-methoxy-pyridin-2-yl)-methanone and 20 mg palladium on carbon in 10 mL methanol was hydrogenated at 50° C. for 12 h at 50 psi. The catalyst was removed by filtration and the solvent was evaporated in vacuo.
Yield: 100 mg (86%)
ESI-MS: m/z=280 (M+H)+
R$_t$(HPLC): 1.46 min (method 24)

PREPARATION OF EXAMPLES

Example 1

[4-(5-Bromo-2-methyl-benzofuran-3-carbonyl)-2,2-dimethyl-piperazin-1-yl]-[1-(3-fluoro-phenyl)-1H-[1,2,4]triazol-3yl]-methanone

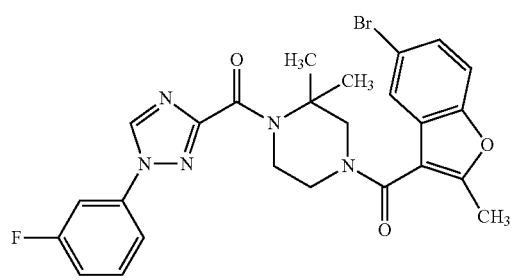 [SMILES: Cc1oc2ccc(Br)cc2c1C(=O)N1CCN(C(=O)c2ncn(-c3cccc(F)c3)n2)C(C)(C)C1]

A mixture of 50 mg (0.12 mmol) (2,2-dimethyl-piperazin-1yl)-[1-(3-fluoro-phenyl)-1H-[1,2,4]triazol-3yl]-methanone, 31 mg (0.12 mmol) 5-bromo-methyl-benzofuran-3-carboxylic acid, 40 mg (0.13 mmol) TBTU and 0.10 mL (0.58 mmol) DIPEA in 1.5 mL DMF was stirred at RT for 12 h. The precipitate was filtered off and the filtrate was purified by HPLC.
yield: 45.0 mg (70%)
ESI-MS: m/z=540 (M+H)+
R$_t$(HPLC): 1.55 min (method 1)

By using the same synthesis strategy as for [4-(5-bromo-2-methyl-benzofuran-3-carbonyl)-2,2-dimethyl-piperazin-1-yl]-[1-(3-fluoro-phenyl)-1H-[1,2,4]triazol-3yl]-methanone the following compounds were prepared:

| Ex # | carboxylic acid | product | R$_t$ [min] HPLC/method | ESI-MS m/z | yield |
|---|---|---|---|---|---|
| 2 | 5-fluoro-methyl-benzofuran-3-carboxylic acid | ![structure] | 1.47/1 | 480 (M + H)+ | 48 mg (84 %) |
| 3 | 8-chloro-2,3-dihydro-benzo[1,4]dioxine-6-carboxylic acid | ![structure] | 1.17/5 | 500 (M + H)+ | 77 mg (76 %) |

-continued

| Ex # | carboxylic acid | product | R$_t$ [min] HPLC/ method | ESI-MS m/z | yield |
|---|---|---|---|---|---|
| 4 | 6-methoxy-pyridine-2-carboxylic acid | | 1.12/3 | 439 (M + H)$^+$ | 8 mg (8 %) |
| 5 | 2-methyl-benzofuran-3-carboxylic acid | | 1.23/5 | 462 (M + H)$^+$ | 61 mg (69 %) |
| 6 | 1,3-dimethyl-1H-indole-2-carboxylic acid | | 1.51/1 | 475 (M + H)$^+$ | 45 mg (79 %) |

Example 7

[4-(6-Methoxy-pyridine-2-carbonyl)-2,2-dimethyl-piperazin-1-yl]-[1-m-tolyl-1H-[1,2,4]triazol-3yl]-methanone

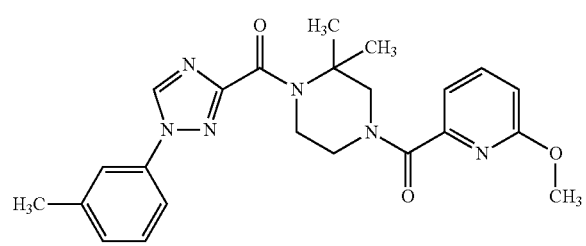

A mixture of 83 mg (0.20 mmol) (2,2-dimethyl-piperazin-1-yl)-(1-m-tolyl-1H-[1,2,4]triazol-3-yl)-methanone trifluoroacetate, 32 mg (0.20 mmol) 6-methoxy-pyridine-2-carboxylic acid, 71 mg (0.22 mmol) TBTU and 85 μL (0.50 mmol) DIPEA in 1.0 mL DMF was stirred at RT for 2 h. The reaction mixture was purified by HPLC.

yield: 44.0 mg (51%)

ESI-MS: m/z=435 (M+H)$^+$

R$_t$(HPLC): 1.02 min (method 4)

By using the same synthesis strategy as for [4-(6-methoxy-pyridine-2-carbonyl)-2,2-dimethyl-piperazin-1-yl]-[1-m-tolyl-1H-[1,2,4]triazol-3yl]-methanone the following compounds were prepared:

| Ex # | carboxylic acid | product | R$_t$ [min]/ HPLC method | ESI-MS m/z | yield |
|---|---|---|---|---|---|
| 8 | 4,5-dibromo-furan-2-carboxylic acid | 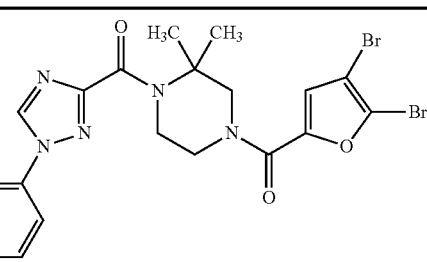 | 1.18/4 | 550 (M + H)$^+$ | 62 mg (56%) |
| 9 | 8-chloro-2,3-dihydro-benzo-[1,4]dioxine-6-carboxylic acid | 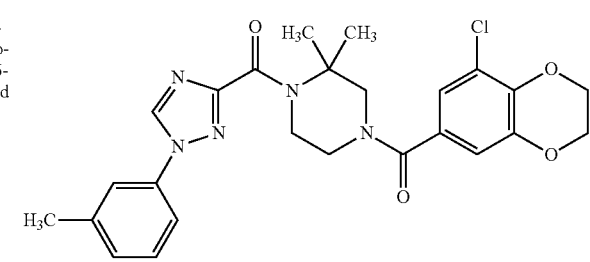 | 1.06/4 | 496 (M + H)$^+$ | 63 mg (64%) |
| 10 | 2-methyl-benzofuran-3-carboxylic acid | 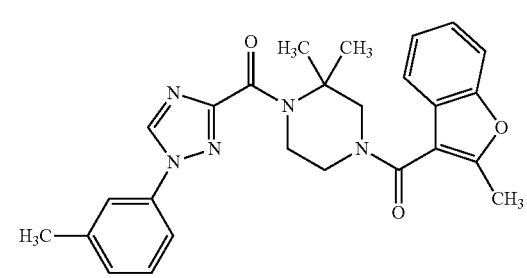 [SMILES: Cc1cccc(-n2cnc(C(=O)N3CCN(C(=O)c4c(C)oc5ccccc45)CC3(C)C)n2)c1] | 1.27/3 | 458 (M + H)$^+$ | 43 mg (37%) |

Example 11

[1-(3-Chloro-phenyl)-1H-[1,2,4]-triazol-3-yl]-[4-(3-isopropyl-benzoyl)-2,2-dimethyl-piperazin-1-yl]methanone

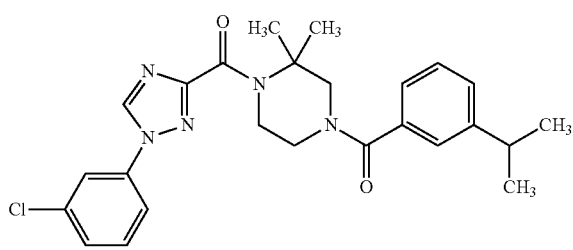

A mixture of 40 mg (92 µmol) [1-(3-chloro-phenyl)-1H-[1,2,4]-triazol-3-yl]-(2,2-dimethyl-piperazin-1-yl)-methanone trifluoroacetate, 15 mg (91 µmol) 3-isopropyl-benzoic acid, 32 mg (0.10 mmol) TBTU and 50 µL (0.29 mmol) DIPEA in 1.0 mL DMF was stirred at RT for 3 h. The reaction mixture was purified by HPLC.

yield: 25 mg (58%)

ESI-MS: m/z=466 (M+H)$^+$

R$_t$(HPLC): 1.34 min (method 5)

By using the same synthesis strategy as for [1-(3-chloro-phenyl)-1H-[1,2,4]triazol-3-yl]-[4-(3-isopropyl-benzoyl)-2,2-dimethyl-piperazin-1-yl]methanone the following compounds were prepared:

| Ex # | carboxylic acid | product | R_t [min]/ HPLC method | ESI-MS m/z | yield |
|---|---|---|---|---|---|
| 12 | 4-bromo-6-methoxy-pyridine-2-carboxylic acid | | 1.32/5 | 533 (M + H)+ | 25 mg (68%) |
| 13 | 6-trifluoromethyl-pyridine-2-carboxylic acid | | 1.25/5 | 493 (M + H)+ | 30 mg (66%) |
| 14 | 3-trifluoromethyl-benzoic acid | | 1.28/5 | 492 (M + H)+ | 35 mg (77%) |
| 15 | 3-bromo-benzoic acid | | 1.27/5 | 502 (M + H)+ | 19 mg (76%) |
| 16 | 6-cyclo-propyl-pyridine-2-carboxylic acid | | 1.21/6 | 465 (M + H)+ | 50 mg (58%) |
| 17 | 4-chloro-6-methoxy-pyridine-2-carboxylic acid | | 1.31/5 | 489 (M + H)+ | 26 mg (66%) |

-continued

| Ex # | carboxylic acid | product | $R_t$ [min]/ HPLC method | ESI-MS m/z | yield |
|---|---|---|---|---|---|
| 18 | 6-methoxy-pyridine-2-carboxylic acid | | 1.04/4 | 455 (M + H)+ | 57 mg (63%) |
| 19 | 8-chloro-2,3-dihydro-benzo[1,4]dioxine-6-carboxylic acid | | 1.08/4 | 516 (M + H)+ | 70 mg (68%) |
| 20 | 3-propoxy-benzoic acid | | 1.32/5 | 482 (M + H)+ | 13 mg (28%) |
| 21 | 6-fluoro-1-methoxy-iso-quinoline-3-carboxylic acid | | 1.35/5 | 523 (M + H)+ | 39 mg (75%) |
| 22 | 6-methoxy-4-methyl-pyridine-2-carboxylic acid | | 1.24/5 | 469 (M + H)+ | 22 mg (68%) |

-continued
| Ex # | carboxylic acid | product | R_t [min]/ HPLC method | ESI-MS m/z | yield |
|---|---|---|---|---|---|
| 23 | 3-(3-fluoro-oxetan-3yl)-benzoic acid | 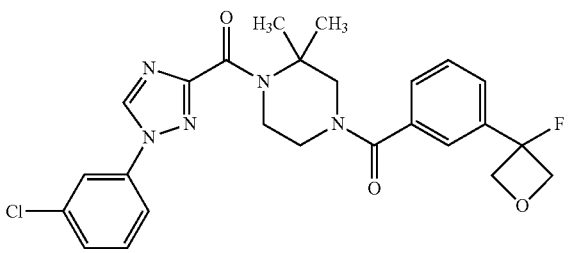 [SMILES: CC1(C)CN(C(=O)c2cccc(C3(F)COC3)c2)CCN1C(=O)c1ncn(-c2cccc(Cl)c2)n1] | 1.19/5 | 498 (M + H)+ | 30 mg (62%) |
| 24 | naphthalene-2-carboxylic acid | 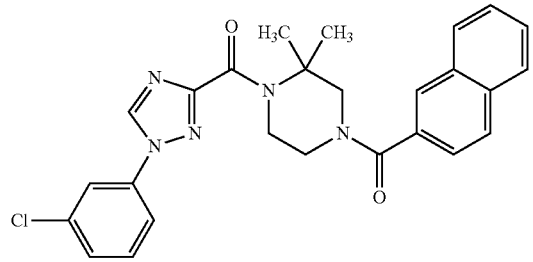 [SMILES: CC1(C)CN(C(=O)c2ccc3ccccc3c2)CCN1C(=O)c1ncn(-c2cccc(Cl)c2)n1] | 1.30/5 | 474 (M + H)+ | 33 mg (70%) |
| 25 | 4,5-dibromo-furan-2-carboxylic acid | 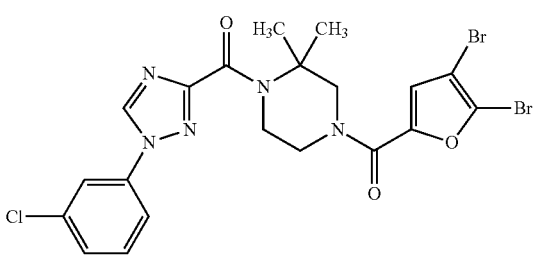 [SMILES: CC1(C)CN(C(=O)c2cc(Br)c(Br)o2)CCN1C(=O)c1ncn(-c2cccc(Cl)c2)n1] | 1.19/4 | 570 (M + H)+ | 76 mg (66%) |
| 26 | 3-thiazol-2-yl-benzoic acid | 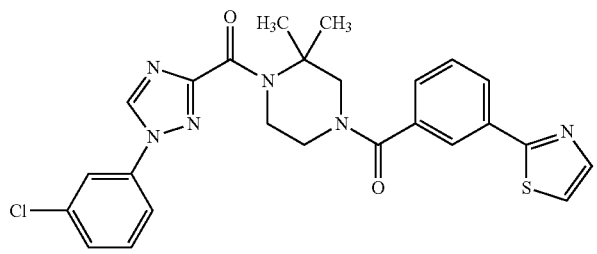 [SMILES: CC1(C)CN(C(=O)c2cccc(-c3nccs3)c2)CCN1C(=O)c1ncn(-c2cccc(Cl)c2)n1] | 1.23/5 | 507 (M + H)+ | 30 mg (64%) |
| 27 | 3,4-dichloro-benzoic acid | 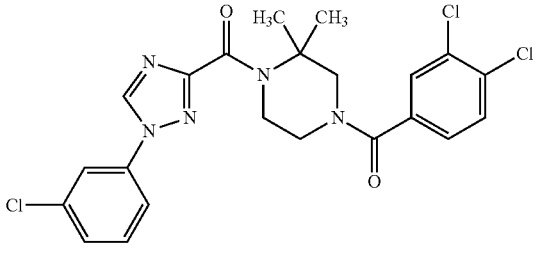 | 1.32/5 | 492 (M + H)+ | 16 mg (65%) |
| 28 | 3-oxazol-5-yl-benzoic acid | 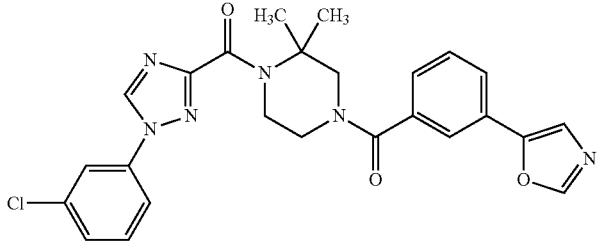 [SMILES: CC1(C)CN(C(=O)c2cccc(-c3cnco3)c2)CCN1C(=O)c1ncn(-c2cccc(Cl)c2)n1] | 1.18/5 | 491 (M + H)+ | 29 mg (61%) |

-continued
| Ex # | carboxylic acid | product | R_t [min]/ HPLC method | ESI-MS m/z | yield |
|---|---|---|---|---|---|
| 29 | 3-chloro-5-trifluoromethyl-benzoic acid | 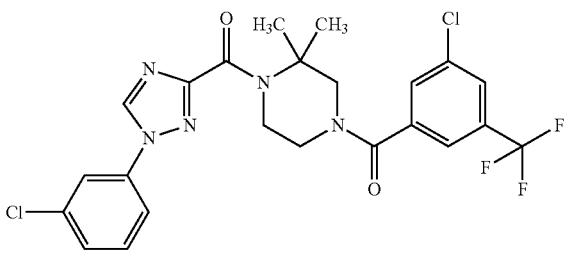 [SMILES: CC1(C)CN(C(=O)c2cc(Cl)cc(C(F)(F)F)c2)CCN1C(=O)c1ncn(-c2cccc(Cl)c2)n1] | 1.35/5 | 526 (M + H)+ | 19 mg (72%) |
| 30 | 3-pyridin-4-yl-benzoic acid | 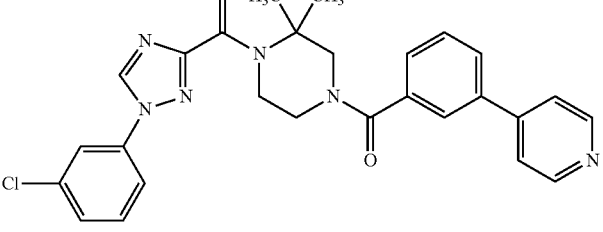 | 0.99/5 | 501 (M + H)+ | 38 mg (74%) |
| 31 | 1,6-di-methoxy-isoquinoline-3-car-boxylic acid | 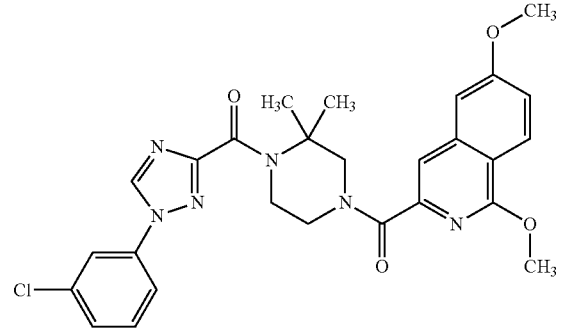 [SMILES: COc1ccc2c(OC)nc(C(=O)N3CCN(C(=O)c4ncn(-c5cccc(Cl)c5)n4)C(C)(C)C3)cc2c1] | 1.37/5 | 535 (M + H)+ | 37 mg (69%) |
| 32 | 1,6,7-tri-methoxy-iso-quinoline-3-carboxylic acid | 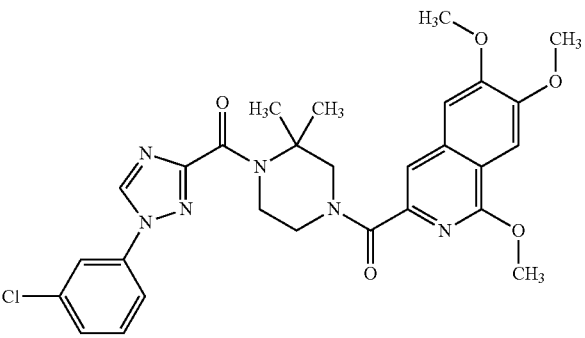 [SMILES: COc1cc2cc(C(=O)N3CCN(C(=O)c4ncn(-c5cccc(Cl)c5)n4)C(C)(C)C3)nc(OC)c2cc1OC] | 1.31/5 | 565 (M + H)+ | 33 mg (58%) |
| 33 | 6-cyano-pyridine-2-carboxylic acid | 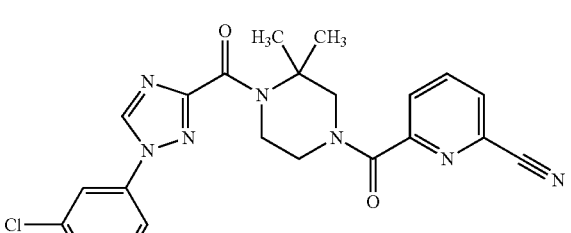 | 1.11/5 | 450 (M + H)+ | 27 mg (62%) |

-continued

| Ex # | carboxylic acid | product | R_t [min]/ HPLC method | ESI-MS m/z | yield |
|---|---|---|---|---|---|
| 34 | 1-(2-methoxyethoxy)-isoquinoline-3-carboxylic acid | | 1.60/7 | 549 (M + H)+ | 25 mg (57%) |
| 35 | isoquinoline-3-carboxylic acid | | 1.21/5 | 475 (M + H)+ | 17 mg (72%) |
| 36 | 4-chloro-6-methoxy-pyridine-2-carboxylic acid | | 1.25/5 | 473 (M + H)+ | 28 mg (61%) |
| 37 | 3-trifluoromethoxy-benzoic acid | | 1.23/5 | 508 (M + H)+ | 28 mg (60%) |
| 38 | 6-methoxy-methyl-pyridine-2-carboxylic acid | | 1.15/5 | 469 (M + H)+ | 20 mg (38%) |

-continued

| Ex # | carboxylic acid | product | R*t* [min]/ HPLC method | ESI-MS m/z | yield |
|---|---|---|---|---|---|
| 39 | 6-methyl-pyridine-2-carboxylic acid | | 1.13/5 | 439 (M + H)⁺ | 28 mg (69%) |
| 40 | 4-methoxy-pyridine-2-carboxylic acid | | 1.07/5 | 455 (M + H)⁺ | 35 mg (83%) |
| 41 | 5-fluoro-3-methyl-benzofuran-2-carboxylic acid | | 1.93/12 | 496 (M + H)⁺ | |
| 42 | 1-methoxy-isoquinoline-3-carboxylic acid | | 1.91/12 | 505 (M + H)⁺ | |
| 43 | 3-methoxy-benzoic acid | | 1.78/12 | 454 (M + H)⁺ | |
| 44 | 3-dimethyl-amino-benzoic acid | | 1.70/12 | 467 (M + H)⁺ | |

| Ex # | carboxylic acid | product | R$_t$ [min]/ HPLC method | ESI-MS m/z | yield |
|---|---|---|---|---|---|
| 45 | 3-methyl-benzofuran-2-carboxylic acid | | 1.94/12 | 478 (M + H)$^+$ | |
| 46 | 3-methoxy-4-methyl-benzoic acid | | 1.88/12 | 468 (M + H)$^+$ | |
| 47 | 6-methoxy-3-methyl-benzofuran-2-carboxylic acid | | 1.97/12 | 508 (M + H)$^+$ | |
| 48 | benzo[1,3]-dioxole-4-carboxylic acid | | 1.75/12 | 468 (M + H)$^+$ | |
| 49 | 6-trifluoro-methyl-pyrazine-2-carboxylic acid | | 1.24/5 | 494 (M + H)$^+$ | 21 mg (85%) |

| Ex # | carboxylic acid | product | R_t [min]/ HPLC method | ESI-MS m/z | yield |
|---|---|---|---|---|---|
| 50 | 3,5-dimethyl-benzofuran-2-carboxylic acid | 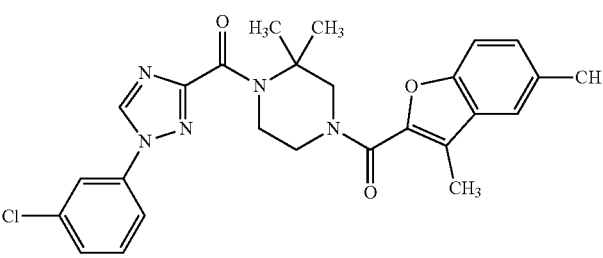 [SMILES: Cc1ccc2oc(C(=O)N3CCN(C(=O)c4ncn(-c5cccc(Cl)c5)n4)C(C)(C)C3)c(C)c2c1] | 2.03/12 | 492 (M + H)+ | |
| 51 | 6-pyrrolidin-1-yl-pyridine-2-carboxylic acid | 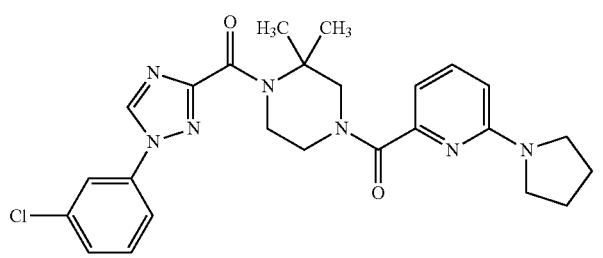 | 1.65/12 | 494 (M + H)+ | |
| 52 | 6-acetyl-pyridine-2-carboxylic acid | 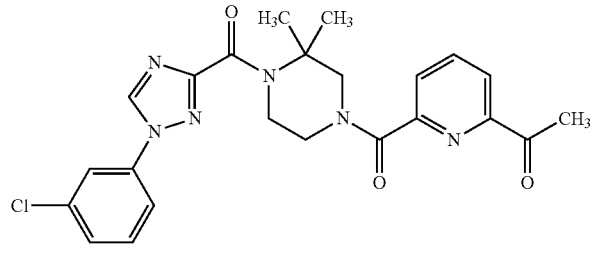 [SMILES: CC(=O)c1cccc(C(=O)N2CCN(C(=O)c3ncn(-c4cccc(Cl)c4)n3)C(C)(C)C2)n1] | 1.72/12 | 467 (M + H)+ | |
| 53 | 7-fluoro-3-methyl-benzo-furan-2-carboxylic acid | 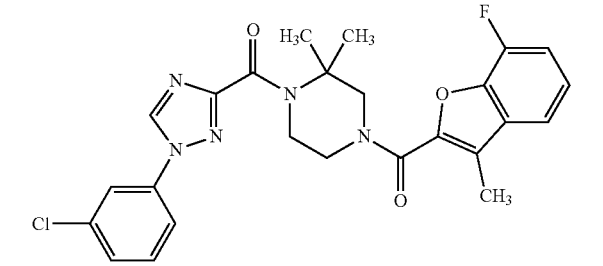 [SMILES: Cc1c(C(=O)N2CCN(C(=O)c3ncn(-c4cccc(Cl)c4)n3)C(C)(C)C2)oc2c(F)cccc12] | 1.99/12 | 496 (M + H)+ | |
| 54 | 2-phenyl-thiazole-4-carboxylic acid | 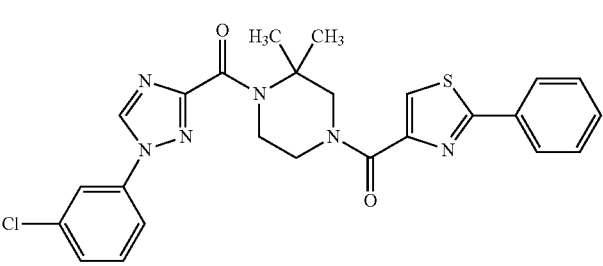 [SMILES: CC1(C)CN(C(=O)c2csc(-c3ccccc3)n2)CCN1C(=O)c1ncn(-c2cccc(Cl)c2)n1] | 1.87/12 | 507 (M + H)+ | |

-continued

| Ex # | carboxylic acid | product | R_t [min]/ HPLC method | ESI-MS m/z | yield |
|---|---|---|---|---|---|
| 55 | 3'-cyano-biphenyl-3-carboxylic acid | | 1.75/12 | 525 (M + H)+ | |
| 56 | 1-ethyl-1H-pyrazole-3-carboxylic acid | | 1.60/12 | 442 (M + H)+ | |
| 57 | 5-chloro-2-methyl-benzoic acid | | 1.79/12 | 472 (M + H)+ | |
| 58 | indolizine-2-carboxylic acid | | 1.70/12 | 463 (M + H)+ | |
| 59 | 1H-pyrrolo[2,3-b]pyridine-5-carboxylic acid | | 1.54/12 | 464 (M + H)+ | |

-continued

| Ex # | carboxylic acid | product | R$_t$ [min]/ HPLC method | ESI-MS m/z | yield |
|---|---|---|---|---|---|
| 60 | 5-ethyl-furan-2-carboxylic acid | | 1.75/12 | 442 (M + H)$^+$ | |
| 61 | 4-isopropyl-benzoic acid | | 1.84/12 | 466 (M + H)$^+$ | |
| 62 | 6-ethoxy-pyridine-2-carboxylic acid | | 1.76/12 | 469 (M + H)$^+$ | |
| 63 | 6-chloro-imidazo-[2,1-2]-thia-zole-5-carboxylic acid | | 1.66/12 | 504 (M + H)$^+$ | |
| 64 | 4-fluoro-3-methyl-benzoic acid | | 1.75/12 | 456 (M + H)$^+$ | |
| 65 | 4-chloro-3-methyl-benzoic acid | | 1.83/12 | 472 (M + H)$^+$ | |

-continued

| Ex # | carboxylic acid | product | R$_t$ [min]/ HPLC method | ESI-MS m/z | yield |
|---|---|---|---|---|---|
| 66 | 3,7-di-methyl-benzo-furan-2-carboxylic acid | | 1.96/12 | 492 (M + H)⁺ | |
| 67 | 7-phenyl-pyrazolo-[1,5-a]-pyrimidine-2-carboxylic acid | | 1.77/12 | 541 (M + H)⁺ | |
| 68 | 7-methoxy-3-methyl-benzo-furan-2-carboxylic acid | | 1.89/12 | 508 (M + H)⁺ | |
| 79 | 3'-methoxy-biphenyl-3-carboxylic acid | | 1.86/12 | 530 (M + H)⁺ | |
| 70 | 3,5-dimethyl-benzoic acid | | 1.81/12 | 452 (M + H)⁺ | |

-continued

| Ex # | carboxylic acid | product | R_t [min]/ HPLC method | ESI-MS m/z | yield |
|---|---|---|---|---|---|
| 71 | 3-chloro-4-methyl-benzoic acid | | 1.52/22 | 494 (M + Na)+ | |
| 72 | 3-prop-2-ynyloxy-benzoic acid | | 1.67/12 | 478 (M + H)+ | |
| 73 | 5-chloro-2-fluoro-benzoic acid | | 1.74/12 | 476 (M + H)+ | |
| 74 | 3-phenoxy-methyl-benzoic acid | | 1.86/12 | 530 (M + H)+ | |
| 75 | 3-(cyano-methyl-methyl)-benzoic acid | | 1.59/12 | 477 (M + H)+ | |
| 76 | 5-methoxy-thiophene-2-carboxylic acid | | 1.68/12 | 460 (M + H)+ | |

-continued
| Ex # | carboxylic acid | product | $R_t$ [min]/ HPLC method | ESI-MS m/z | yield |
|---|---|---|---|---|---|
| 77 | 1-methyl-1H-indazole-3-carboxylic acid | 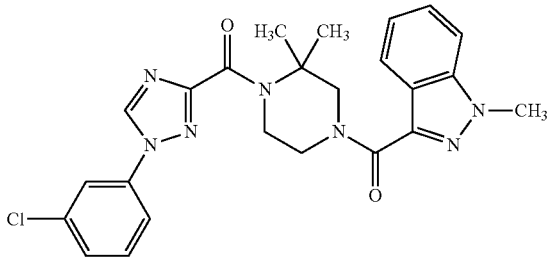 [SMILES: Cn1nc(C(=O)N2CCN(C(=O)c3ncn(-c4cccc(Cl)c4)n3)C(C)(C)C2)c2ccccc21] | 1.75/12 | 478 (M + H)+ | |
| 78 | 4'-cyano-biphenyl-3-carboxylic acid | 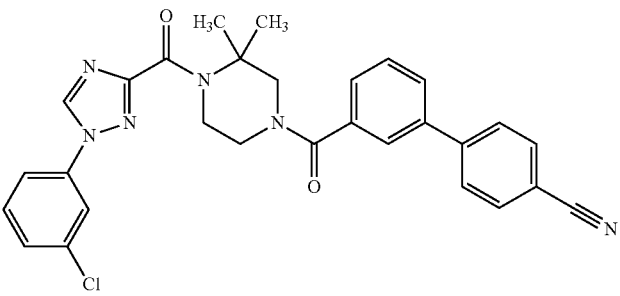 [SMILES: CC1(C)CN(C(=O)c2cccc(-c3ccc(C#N)cc3)c2)CCN1C(=O)c1ncn(-c2cccc(Cl)c2)n1] | 1.74/12 | 525 (M + H)+ | |
| 79 | 5,6-dimethoxy-pyridine-2-carboxylic acid | 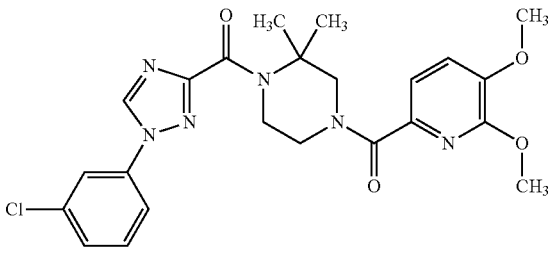 [SMILES: COc1ccc(C(=O)N2CCN(C(=O)c3ncn(-c4cccc(Cl)c4)n3)C(C)(C)C2)nc1OC] | 1.65/12 | 485 (M + H)+ | |
| 80 | 2-methyl-1H-indole-5-carboxylic acid | 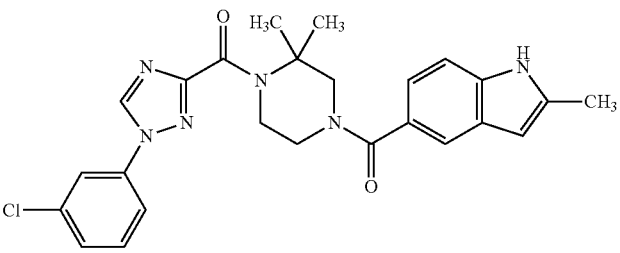 [SMILES: Cc1cc2cc(C(=O)N3CCN(C(=O)c4ncn(-c5cccc(Cl)c5)n4)C(C)(C)C3)ccc2[nH]1] | 1.68/12 | 477 (M + H)+ | |
| 81 | 4-ethyl-benzoic acid | 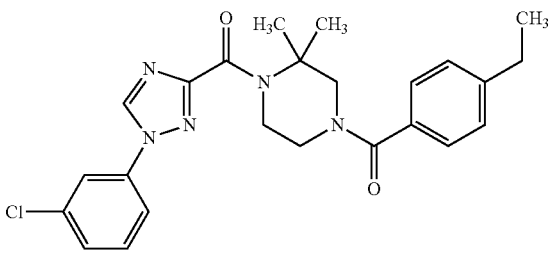 [SMILES: CCc1ccc(C(=O)N2CCN(C(=O)c3ncn(-c4cccc(Cl)c4)n3)C(C)(C)C2)cc1] | 1.80/12 | 452 (M + H)+ | |

-continued

| Ex # | carboxylic acid | product | R_t [min]/ HPLC method | ESI-MS m/z | yield |
|---|---|---|---|---|---|
| 82 | 1-methyl-1H-indole-5-carboxylic acid | | 1.69/12 | 477 (M + H)+ | |
| 83 | 5-ethyl-thiophene-2-carboxylic acid | | 1.79/12 | 458 (M + H)+ | |
| 84 | 4-trifluoro-methyl-pyrimidine-2-carboxylic acid | | 1.17/5 | 494 (M + H)+ | 20 mg (81%) |
| 85 | 1-cyclo-pro-pyl-methoxy-isoquinoline-3-carboxylic acid | | 1.43/5 | 545 (M + H)+ | 15 mg (60%) |
| 86 | [2,4']bi-pyridinyl-6-carboxylic acid | | 0.97/5 | 502 (M + H)+ | 21 mg (91%) |

-continued

| Ex # | carboxylic acid | product | $R_t$ [min]/ HPLC method | ESI-MS m/z | yield |
|---|---|---|---|---|---|
| 87 | 1-propoxy-isoquinoline-3-carboxylic acid | 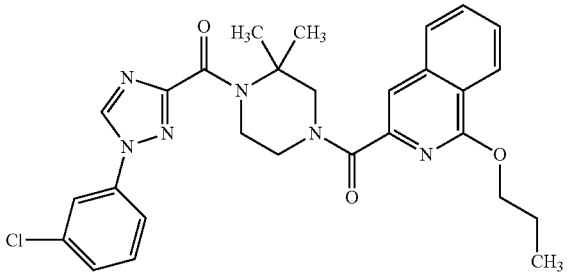 [SMILES: CCCOc1nc(C(=O)N2CCN(C(=O)c3ncn(-c4cccc(Cl)c4)n3)C(C)(C)C2)cc2ccccc12] | 1.43/5 | 533 (M + H)+ | 15 mg (61%) |
| 88 | 2-trifluoro-methyl-isonicotinic acid | 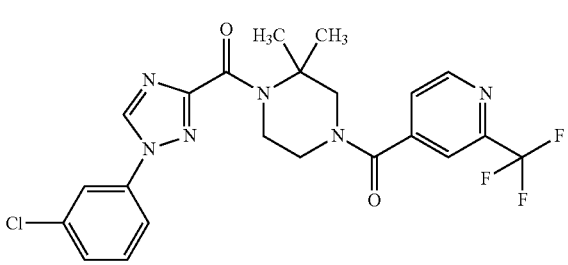 | 1.20/5 | 493 (M + H)+ | 36 mg (73%) |
| 89 | 4-trifluoro-methyl-pyridine-2-carboxylic acid | 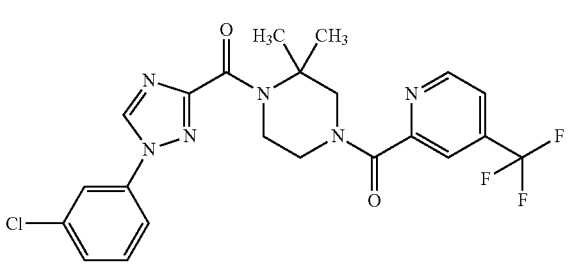 [SMILES: CC1(C)CN(C(=O)c2cc(C(F)(F)F)ccn2)CCN1C(=O)c1ncn(-c2cccc(Cl)c2)n1] | 1.24/5 | 493 (M + H)+ | 35 mg (71%) |

Example 90

[1-(3-Chloro-phenyl)-1H-[1,2,4]triazol-3-yl]-{4-[6-(3,5-dimethyl-isoxazol-4-yl)-pyridine-2-carbonyl]-2,2-dimethyl-piperazin-1-yl]-methanone

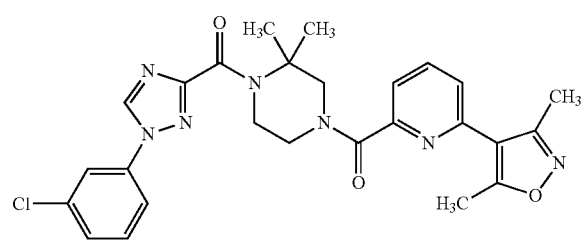 [SMILES: Cc1noc(C)c1-c1cccc(C(=O)N2CCN(C(=O)c3ncn(-c4cccc(Cl)c4)n3)C(C)(C)C2)n1]

A mixture of 50 mg (0.010 mmol) [4-(6-bromo-pyridine-2-carbonyl)-2,2-dimethyl-piperazin-1-yl]-[1-(3-chlorophenyl)-1H-[1,2,4]triazol-3-yl]-methanone, 18 mg (0.013 mmol) 3,5-dimethyl-4-isoxazolylboronic acid, 16 mg (0.020 mmol) [1,1'-bis(diphenylphosphino)-ferrocene]dichloropalladium(II) complex with DCM (1:1) and 0.010 mL 5M aqueous potassium carbonate solution in 1.0 mL dioxane and 0.50 mL MeOH was stirred at 140° C. for 15 min under microwave irradiation. The reaction mixture was filtered over Alox (alkaline) and purified by HPLC.

yield: 9.1 mg (18%)

ESI-MS: m/z=520 (M+H)+

$R_t$(HPLC): 1.17 min (method 11)

By using the same synthesis strategy as for [1-(3-chlorophenyl)-1H-[1,2,4]triazol-3-yl]-[4-[6-(3,5-dimethyl-isoxazol-4-yl)-pyridine-2-carbonyl]-2,2-dimethyl-piperazin-1-yl]methanone the following compounds were prepared:

| | boronic acid (ester) | product | R_t [min]/ HPLC method | ESI-MS m/z | yield |
|---|---|---|---|---|---|
| 91 | 1-methyl-1H-pyrazole-5-boronic acid pinacol ester | | 1.14/11 | 505 (M + H)+ | 11 mg (22%) |
| 92 | 1-ethyl-1H-pyrazole-4-boronic acid pinacol ester | | 1.17/11 | 519 (M + H)+ | 12 mg (23%) |
| 93 | 1,3-dimethyl-1H-pyrazole-4-boronic acid pinacol ester | | 1.16/11 | 519 (M + H)+ | 9 mg (17%) |
| 94 | 5-(5,5-di-methyl-1,3,2-dioxaborinan-2-yl)-1H-pyrazol | | 1.12/11 | 491 (M + H)+ | 4 mg (9%) |

Example 96

[4-(3-Isopropyl-benzoyl)-2,2-dimethyl-piperazin-1-yl]-(1-phenyl-1H-[1,2,4]triazol-3-yl)-methanone

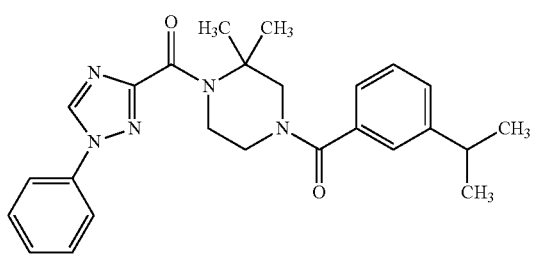 [SMILES: CC(C)c1cccc(C(=O)N2CCN(C(=O)c3ncn(-c4ccccc4)n3)C(C)(C)C2)c1]

A mixture of 49 mg (0.12 mmol) (2,2-dimethyl-piperazin-1-yl)-(1-phenyl-1-H-[1,2,4]-triazol-3-yl)-methanone trifluoroacetate, 20 mg (0.12 mmol) 3-isopropyl-benzoic acid, 43 mg (0.13 mmol) TBTU and 50 μL (0.29 mmol) DIPEA in 1.0 mL DMF was stirred at RT for three days. The reaction mixture was purified using HPLC.

yield: 35.0 mg (67%)

ESI-MS: m/z=432 (M+H)+

R_t(HPLC): 1.27 min (method 5)

By using the same synthesis strategy as for [4-(3-isopropyl-benzoyl)-2,2-dimethyl-piperazin-1-yl](1-phenyl-1H-[1,2,4]triazol-3-yl)-methanone the following compounds were prepared:

| Ex # | carboxylic acid | product | R$_t$ [min]/ HPLC method | ESI-MS m/z | yield |
|---|---|---|---|---|---|
| 97 | 1-methoxy-isoquinoline-3-carboxylic acid | | 1.03/2 | 471 (M + H)$^+$ | 35 mg (35%) |
| 98 | 3-trifluoro-methyl-benzoic acid | | 1.20/5 | 458 (M + H)$^+$ | 33 mg (69%) |
| 99 | 1-propoxy-isoquinoline-3-carboxylic acid | | 1.39/5 | 499 (M + H)$^+$ | 32 mg (73%) |
| 100 | 5-bromo-methyl-benzofuran-3-carboxylic acid | | 1.52/1 | 522 (M + H)$^+$ | 8 mg (12%) |
| 101 | 6-trifluoro-methyl-pyridine-2-carboxylic acid | | 1.17/5 | 459 (M + H)$^+$ | 30 mg (63%) |

-continued

| Ex # | carboxylic acid | product | R_t [min]/ HPLC method | ESI-MS m/z | yield |
|---|---|---|---|---|---|
| 102 | 5-fluoro-methyl-benzo-furan-3-carboxylic acid | | 1.44/1 | 462 (M + H)+ | 15 mg (26%) |
| 103 | 1-cyclopropyl-methoxy-isoquinoline-3-carboxylic acid | | 1.38/5 | 511 (M + H)+ | 30 mg (67%) |
| 104 | 8-chloro-2,3-dihydro-benzo[1,4]-dioxine-6-carboxylic acid | | 0.93/2 | 482 (M + H)+ | 41 mg (40%) |
| 105 | 4,5-dibromo-furan-2-carboxylic acid | | 1.02/2 | 536 (M + H)+ | 39 mg (36%) |
| 106 | 2-methyl-benzofuran-3-carboxylic acid | | 1.21/2 | 444 (M + H)+ | 33 mg (35%) |

-continued

| Ex # | carboxylic acid | product | R_t [min]/ HPLC method | ESI-MS m/z | yield |
|---|---|---|---|---|---|
| 107 | 3-methoxy-methyl-benzo-furan-2-carboxylic acid | | 1.21/6 | 474 (M + H)+ | 15 mg (25%) |
| 108 | 5-fluoro-3-methyl-benzo-furan-2-carboxylic acid | | 1.84/12 | 462 (M + H)+ | |
| 109 | 6-methoxy-pyridine-2-carboxylic acid | | 0.88/2 | 421 (M + H)+ | 38 mg (38%) |
| 110 | 1,3-di-methyl-1H-indole-2-carboxylic acid | | 1.48/1 | 457 (M + H)+ | 20 mg (35%) |
| 111 | [2,4']bipyridinyl-6-carboxylic acid | | 0.83/5 | 468 (M + H)+ | 39 mg (95%) |
| 112 | benzoic acid | | 1.10/5 | 390 (M + H)+ | 30 mg (77%) |

-continued

| Ex # | carboxylic acid | product | R_t [min]/ HPLC method | ESI-MS m/z | yield |
|---|---|---|---|---|---|
| 113 | 3,5-dimethyl-benzoic acid | | 1.23/5 | 418 (M + H)+ | 31 mg (74%) |
| 114 | 3-fluoro-benzoic acid | | 1.11/5 | 408 (M + H)+ | 27 mg (66%) |
| 115 | 1-cyclo-pentyloxy-isoquinoline-3-carboxylic acid | | 1.43/5 | 525 (M + H)+ | 32 mg (70%) |
| 116 | 3-(1-methoxy-ethyl)-benzoic acid | | 1.15/5 | 448 (M + H)+ | 33 mg (74%) |
| 117 | 3-methyl-benzoic acid | | 1.16/5 | 404 (M + H)+ | 36 mg (89%) |
| 118 | 1-iso-propoxyiso-quinoline-3-carboxylic acid | | 1.37/5 | 499 (M + H)+ | 35 mg (80%) |

-continued
| Ex # | carboxylic acid | product | R<sub>t</sub> [min]/ HPLC method | ESI-MS m/z | yield |
|---|---|---|---|---|---|
| 119 | 5-methoxy-thiophene-2-carboxylic acid | 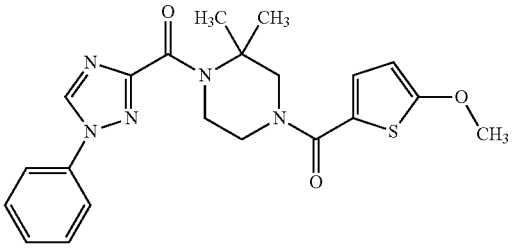 | 1.13/5 | 426 (M + H)⁺ | 29 mg (68%) |
| 120 | 1-ethoxy-isoquinoline-3-carboxylic acid | 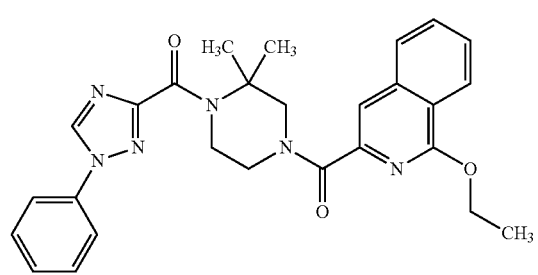 [SMILES: CCOc1nc(C(=O)N2CCN(C(=O)c3ncn(-c4ccccc4)n3)C(C)(C)C2)cc2ccccc12] | 1.34/5 | 485 (M + H)⁺ | 35 mg (82%) |
| 121 | 3-chloro-5-methoxy-benzoic acid | 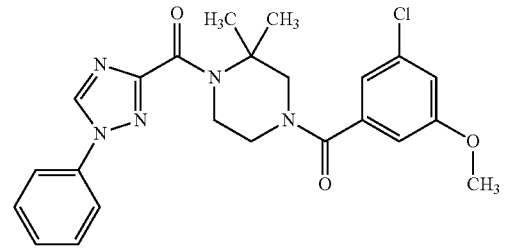 [SMILES: COc1cccc(C(=O)N2CCN(C(=O)c3ncn(-c4ccccc4)n3)C(C)(C)C2)c1] | 1.22/5 | 454 (M + H)⁺ | 16 mg (35%) |
| 122 | 3-methoxy-benzoic acid | 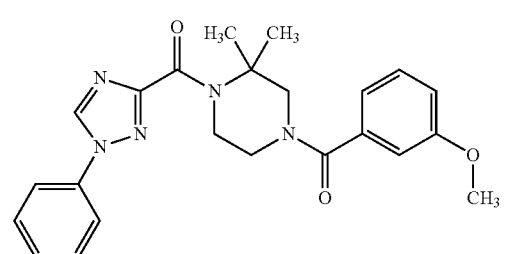 | 1.12/5 | 420 (M + H)⁺ | 30 mg (63%) |
| 123 | 1-methyl-1H-indazole-3-carboxylic acid | 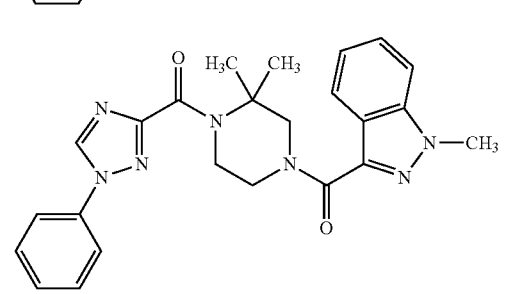 | 1.19/5 | 444 (M + H)⁺ | 38 mg (76%) |
| 124 | 6-acetyl-pyridine-2-carboxylic acid | 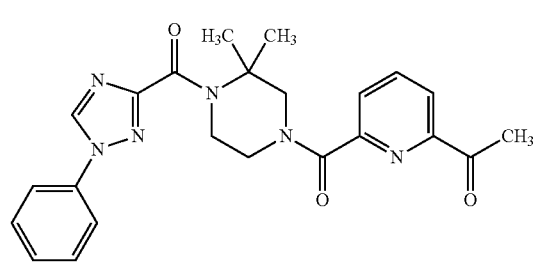 [SMILES: CC(=O)c1cccc(C(=O)N2CCN(C(=O)c3ncn(-c4ccccc4)n3)C(C)(C)C2)n1] | 1.06/5 | 433 (M + H)⁺ | 25 mg (51%) |

-continued

| Ex # | carboxylic acid | product | R$_t$ [min]/ HPLC method | ESI-MS m/z | yield |
|---|---|---|---|---|---|
| 125 | 3-bromo-5-chloro-benzoic acid | | 1.29/5 | 502 (M + H)$^+$ | 31 mg (55%) |
| 126 | 3-isopropoxy-benzoic acid | | 1.22/5 | 448 (M + H)$^+$ | 37 mg (73%) |
| 127 | 3-oxazol-5-yl-benzoic acid | | 1.09/5 | 457 (M + H)$^+$ | 35 mg (68%) |
| 129 | 3-isobutoxy-benzoic acid | | 1.31/5 | 462 (M + H)$^+$ | 28 mg (54%) |
| 130 | 3-tert-butyl-benzoic acid | | 1.31/5 | 446 (M + H)$^+$ | 37 mg (74%) |
| 131 | 3-methane-sulfonyl-benzoic acid | | 0.95/5 | 468 (M + H)$^+$ | 41 mg (78%) |

-continued

| Ex # | carboxylic acid | product | R$_t$ [min]/ HPLC method | ESI-MS m/z | yield |
|---|---|---|---|---|---|
| 132 | 5-methoxy-furan-2-carboxylic acid | | 1.08/5 | 410 (M + H)$^+$ | 13 mg (28%) |
| 133 | 5-acetyl-amino-3-methyl-benzofuran-2-carboxylic acid | | 1.11/5 | 501 (M + H)$^+$ | 32 mg (64%) |
| 134 | 3-methyl-benzofuran-2-carboxylic acid | | 1.28/5 | 444 (M + H)$^+$ | 22 mg (50%) |
| 135 | 3-difluoro-methyl-benzoic acid | | 1.35/7 | 440 (M + H)$^+$ | 31 mg (56%) |
| 136 | 3-cyclo-propyl-benzoic acid | | 1.23/5 | 430 (M + H)$^+$ | 34 mg (70%) |
| 137 | 6-cyclo-butyl-pyridine-2-carboxylic acid | | 1.49/7 | 445 (M + H)$^+$ | 35 mg (70%) |

-continued

| Ex # | carboxylic acid | product | R_t [min]/ HPLC method | ESI-MS m/z | yield |
|---|---|---|---|---|---|
| 138 | 1-methyl-1H-indole-5-carboxylic acid | | 1.26/5 | 443 (M + H)+ | 35 mg (79%) |
| 139 | 5-phenyl-[1,2,4]oxadiazole-3-carboxylic acid | | 1.23/5 | 458 (M + H)+ | 27 mg (52%) |
| 140 | 2-cyclopropyl-oxazole-4-carboxylic acid | | 1.13/5 | 421 (M + H)+ | 26 mg (62%) |
| 141 | 2-cyclopropyl-thiazole-4-carboxylic acid | | 1.41/5 | 437 (M + H)+ | 30 mg (69%) |
| 142 | 2-methyl-1H-indole-5-carboxylic acid | | 1.28/5 | 443 (M + H)+ | 33 mg (77%) |
| 143 | 2-trifluoromethyl-pyrimidine-4-carboxylic acid | | 1.31/5 | 460 (M + H)+ | 26 mg (57%) |

-continued
| Ex # | carboxylic acid | product | R$_t$ [min]/ HPLC method | ESI-MS m/z | yield |
|---|---|---|---|---|---|
| 144 | 3-cyclo-pentyl-benzoic acid | 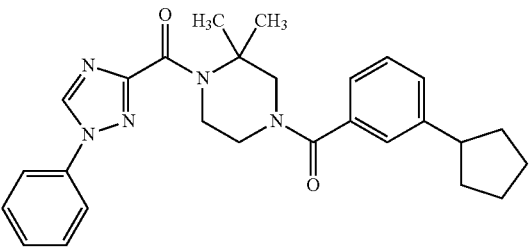 [SMILES: CC1(C)CN(C(=O)c2cccc(C3CCCC3)c2)CCN1C(=O)c1ncn(-c2ccccc2)n1] | 1.49/5 | 458 (M + H)$^+$ | 33 mg (72%) |
| 145 | 3-chloro-5-trifluoro-methyl-benzoic acid | 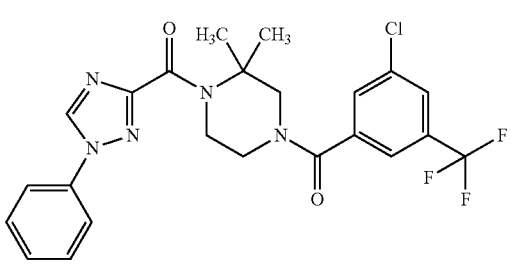 [SMILES: CC1(C)CN(C(=O)c2cc(Cl)cc(C(F)(F)F)c2)CCN1C(=O)c1ncn(-c2ccccc2)n1] | 1.43/5 | 492 (M + H)$^+$ | 44 mg (89%) |
| 146 | 7-methyl-2-propyl-1H-benzo-imidazole-5-car-boxylic acid | 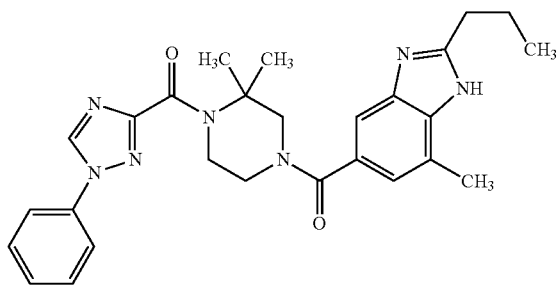 [SMILES: CCCc1nc2cc(C(=O)N3CCN(C(=O)c4ncn(-c5ccccc5)n4)C(C)(C)C3)cc(C)c2[nH]1] | 0.96/5 | 486 (M + H)$^+$ | 34 mg (70%) |
| 147 | 4-trifluoro-methyl-pyr-imidine-2-carboxylic acid | 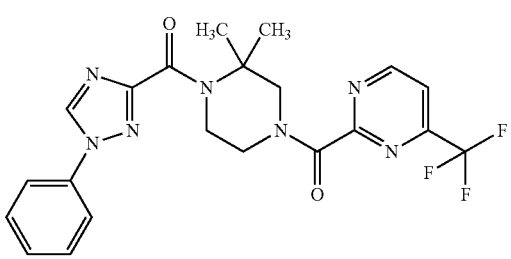 [SMILES: CC1(C)CN(C(=O)c2nccc(C(F)(F)F)n2)CCN1C(=O)c1ncn(-c2ccccc2)n1] | 1.02/5 | 460 (M + H)$^+$ | 31 mg (67%) |
| 148 | 6,7-difluoro-1-methoxy-isoquinoline-3-car-boxylic acid | 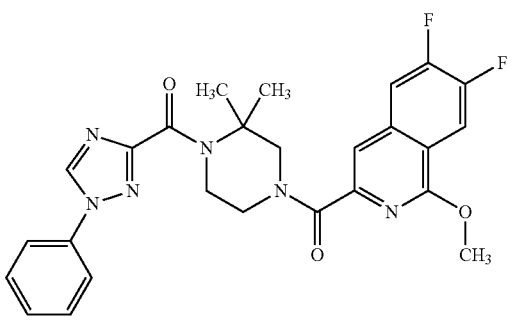 [SMILES: COc1nc(C(=O)N2CCN(C(=O)c3ncn(-c4ccccc4)n3)C(C)(C)C2)cc2cc(F)c(F)cc12] | 1.32/5 | 507 (M + H)$^+$ | 34 mg (67%) |

-continued

| Ex # | carboxylic acid | product | R_t [min]/ HPLC method | ESI-MS m/z | yield |
|---|---|---|---|---|---|
| 149 | 3-chloro-4-fluoro-benzoic acid | | 1.19/5 | 442 $(M+H)^+$ | 38 mg (86%) |
| 151 | 3-cyclo-butyl-benzoic acid | | 1.31/5 | 444 $(M+H)^+$ | 26 mg (59%) |
| 152 | 2-trifluoro-methyl-thia-zole-4-car-boxylic acid | | 1.20/5 | 465 $(M+H)^+$ | 34 mg (73%) |
| 153 | 3,5-dichloro-benzoic acid | | 1.27/5 | 458 $(M+H)^+$ | 34 mg (74%) |
| 154 | 5-chloro-2-methyl-benzoic acid | | 1.21/5 | 438 $(M+H)^+$ | 34 mg (78%) |
| 155 | 5-chloro-2-fluoro-benzoic acid | | 1.17/5 | 442 $(M+H)^+$ | 36 mg (81%) |

| Ex # | carboxylic acid | product | R$_t$ [min]/ HPLC method | ESI-MS m/z | yield |
|---|---|---|---|---|---|
| 156 | 3,5-dichloro-4-fluoro-benzoic acid | | 1.28/5 | 476 (M + H)$^+$ | 26 mg (54%) |

Example 157

[4-(8-Chloro-2,3-dihydro-benzo[1,4]dioxine-6-carbonyl)-2,2-dimethyl-piperazin-1-yl]-[1-(3-fluoro-4-methyl-phenyl)-1H-[1,2,4]triazol-3-yl]-methanone

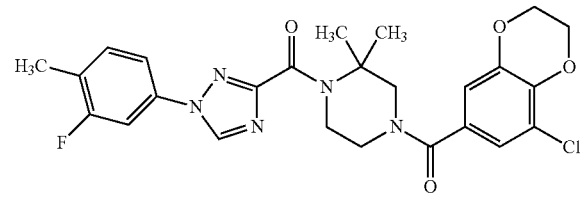 [SMILES: Cc1ccc(-n2cnc(C(=O)N3CCN(C(=O)c4cc(Cl)c5c(c4)OCCO5)CC3(C)C)n2)cc1F]

A mixture of 80 mg (0.19 mmol) (2,2-dimethyl-piperazin-1-yl)-[1-(3-fluoro-4-methyl-phenyl)-1H-[1,2,4]triazol-3-yl)-methanone trifluoroacetate, 40 mg (0.19 mmol) 8-chloro-2,3-dihydro-benzo[1,4]dioxine-6-carboxylic acid, 70 mg (0.22 mmol) TBTU and 100 µL (0.58 mmol) DIPEA in 1.5 mL DMF was stirred at RT for 12 h. The reaction mixture was purified by HPLC.

yield: 20.0 mg (21%)

ESI-MS: m/z=514 (M+H)$^+$

R$_t$(HPLC): 1.20 min (method 6)

By using the same synthesis strategy as for [4-(8-chloro-2,3-dihydro-benzo[1,4]dioxine-6-carbonyl)-2,2-dimethyl-piperazin-1-yl]-[1-(3-fluoro-4-methyl-phenyl)-1H-[1,2,4]triazol-3-yl]-methanone the following compounds were prepared:

| Ex # | carboxylic acid | product | R$_t$ [min]/ HPLC method | ESI-MS m/z | yield |
|---|---|---|---|---|---|
| 158 | 1-methoxy-isoquinoline-3-carboxylic acid | | 1.31/6 | 503 (M + H)$^+$ | 50 mg (54%) |
| 159 | 6-methoxy-pyridine-2-carboxylic acid | | 1.17/6 | 453 (M + H)$^+$ | 40 mg (48%) |

Example 160

[1-(4-Fluoro-3-methyl-phenyl)-1H-[1,2,4]triazol-3-yl]-[4-(1-methoxy-isoquinoline-3-carbonyl)-2,2-dimethyl-piperazin-1-yl]-methanone

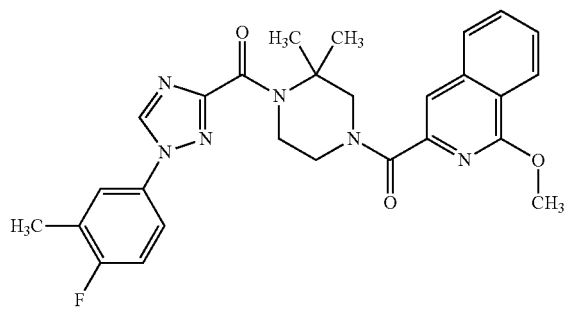 [SMILES: COc1nc(C(=O)N2CCN(C(=O)c3ncn(-c4ccc(F)c(C)c4)n3)C(C)(C)C2)cc2ccccc12]

A mixture of 80 mg (0.19 mmol) (2,2-dimethyl-piperazin-1-yl)-[1-(4-fluoro-3-methyl-phenyl)-1H-[1,2,4]-triazol-3-yl)-methanone trifluoroacetate, 38 mg (0.19 mmol) 1-methoxy-isoquinoline-3-carboxylic acid, 65 mg (0.20 mmol) TBTU and 100 µL (0.58 mmol) DIPEA in 1.5 mL DMF was stirred at RT for 12 h. The reaction mixture was purified by HPLC.

yield: 59 mg (63%)

ESI-MS: m/z=503 (M+H)$^+$

R$_t$(HPLC): 1.30 min (method 6)

By using the same synthesis strategy as for [1-(4-fluoro-3-methyl-phenyl)-1H-[1,2,4]triazol-3-yl]-[4-(1-methoxy-isoquinoline-3-carbonyl)-2,2-dimethyl-piperazin-1-yl]-methanone the following compounds were prepared:

| Ex # | carboxylic acid | product | R$_t$ [min]/ HPLC method | ESI-MS m/z | yield |
|---|---|---|---|---|---|
| 161 | 6-methoxy-pyridine-2-carboxylic acid | | 1.16/ 6 | 453 (M + H)$^+$ | 42 mg (48%) |
| 162 | 8-chloro-2,3-dihydro-benzo[1,4]di-oxine-6-carboxylic acid | | 1.20/ 6 | 514 (M + H)$^+$ | 49 mg (49%) |
| 163 | 2-methyl-benzofuran-3-carboxylic acid | | 1.25/ 6 | 476 (M + H)$^+$ | 56 mg (60%) |

Example 164

[4-(8-Chloro-2,3-dihydro-benzol-[1,4]dioxine-6-carbonyl)-2,2-dimethyl-piperazin-1-yl]-(2-phenyl-2H-tetrazol-5-yl)-methanone

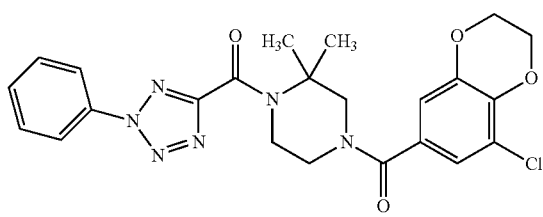 [SMILES: CC1(C)CN(C(=O)c2cc(Cl)c3c(c2)OCCO3)CCN1C(=O)c1nnn(-c2ccccc2)n1]

A mixture of 60 mg (0.15 mmol) (2,2-dimethyl-piperazin-1-yl)-(2-phenyl-2H-tetrazol-5-yl)-methanone trifluoroacetate, 32 mg (0.15 mmol) 8-chloro-2,3-dihydro-benzol-[1,4]-dioxine-6-carboxylic acid, 53 mg (0.17 mmol) TBTU and 90 µL (0.52 mmol) DIPEA in 1.0 mL DMF was stirred at RT for 2 h. The reaction mixture was purified by HPLC.

yield: 40 mg (55%)
ESI-MS: m/z=483 (M+H)$^+$
$R_t$(HPLC): 1.24 min (method 5)

By using the same synthesis strategy as for [4-(8-chloro-2,3-dihydro-benzol-[1,4]dioxine-6-carbonyl)-2,2-dimethyl-piperazin-1-yl]-(2-phenyl-2H-tetrazol-5-yl)-methanone the following compounds were prepared:

| Ex # | carboxylic acid | product | $R_t$ [min]/ HPLC method | ESI-MS m/z | yield |
|---|---|---|---|---|---|
| 165 | 4-chloro-6-methoxy-pyridine-2-carboxylic acid | | 1.31/ 5 | 456 (M + H)$^+$ | 39 mg (86%) |
| 166 | 3-trifluoromethyl-benzoic acid | | 1.27/ 5 | 459 (M + H)$^+$ | 25 mg (73%) |
| 167 | 3-isopropyl-benzoic acid | | 1.33/ 5 | 433 (M + H)$^+$ | 25 mg (77%) |
| 168 | 6-trifluoromethyl-pyridine-2-carboxylic acid | | 1.25/ 5 | 460 (M + H)$^+$ | 20 mg (58%) |

Example 169

[4-(4-Chloro-6-methoxy-pyridine-2-carbonyl)-2,2-dimethyl-piperazin-1-yl]-[2-(3-fluoro-phenyl)-2H-tetrazol-5-yl]-methanone

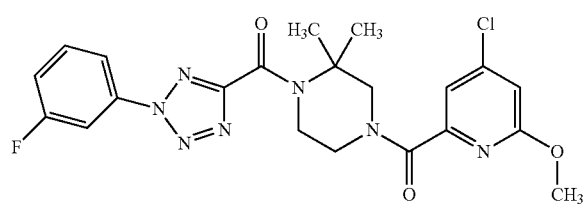 [SMILES: COc1cc(Cl)cc(C(=O)N2CCN(C(=O)c3nnn(-c4cccc(F)c4)n3)C(C)(C)C2)n1]

A mixture of 42 mg (0.10 mmol) (2,2-dimethyl-piperazin-1-yl)$_{42}$-(3-fluoro-phenyl)-2H-tetrazol-5-yl]-methanone trifluoroacetate, 19 mg (0.10 mmol) 4-chloro-6-methoxy-pyridine-2-carboxylic acid, 35 mg (0.11 mmol) TBTU and 59 µL (0.35 mmol) DIPEA in 1.0 mL DMF was stirred at RT for 2 h. The reaction mixture was purified by HPLC.

yield: 34 mg (72%)
ESI-MS: m/z=474 (M+H)$^+$
R$_t$(HPLC): 1.32 min (method 5)

By using the same synthesis strategy as for [4-(4-chloro-6-methoxy-pyridine-2-carbonyl)-2,2-dimethyl-piperazin-1-yl]-[2-(3-fluoro-phenyl)-2H-tetrazol-5-yl]-methanone the following compound was prepared:

| Ex # | carboxylic acid | product | R$_t$ [min]/ HPLC method | ESI-MS m/z | yield |
|---|---|---|---|---|---|
| 170 | 8-chloro-2,3-dihydrobenzo-[1,4]dioxine 6-carboxylic acid | (structure) | 1.25/ 5 | 501 (M + H)$^+$ | 38 mg (51%) |

Example 171

[4-(8-Chloro-2,3-dihydro-benzo[1,4]dioxine-6-carbonyl)-2,2-dimethyl-piperazin-1-yl]-[2-(3-chloro-phenyl)-2H-tetrazol-5-yl]-methanone

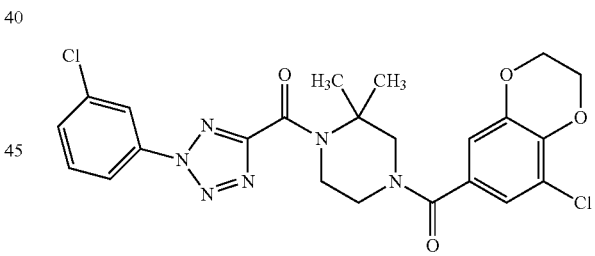

A mixture of 65 mg (0.15 mmol) [2-(3-chloro-phenyl)-2H-tetrazol-5-yl]-(2,2-dimethyl-piperazin-1-yl)-methanone trifluoroacetate, 32 mg (0.15 mmol) 8-chloro-2,3-dihydro-benzo[1,4]dioxine-6-carboxylic acid, 53.0 mg (0.165 mmol) TBTU and 90 µL (0.53 mmol) DIPEA in 1.0 mL DMF was stirred at RT for 2 h. The reaction mixture was purified by HPLC.

yield: 37 mg (48%)
ESI-MS: m/z=517 (M+H)$^+$
R$_t$(HPLC): 1.30 min (method 5)

By using the same synthesis strategy as for [4-(8-chloro-2,3-dihydro-benzo[1,4]dioxine-6-carbonyl)-2,2-dimethyl-piperazin-1-yl]-[2-(3-chloro-phenyl)-2H-tetrazol-5-yl]-methanone the following compound was prepared:

| Ex # | carboxylic acid | product | $R_t$ [min]/ HPLC method | ESI-MS m/z | yield |
|---|---|---|---|---|---|
| 172 | 4-chloro-6-methoxy-pyridine-2-carboxylic acid | 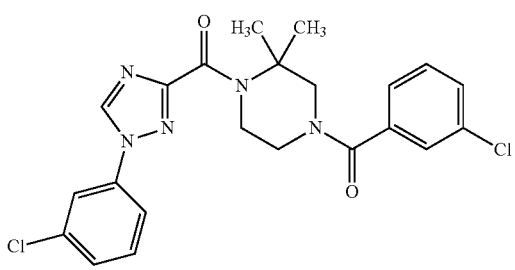 | 1.37/ 5 | 490 (M + H)⁺ | 39 mg (80%) |

Example 173

[4-(3-Chloro-benzoyl)-2,2-dimethyl-piperazin-1-yl]-[1-(3-chloro-phenyl)-1H-[1,2,4]triazol-3-yl]-methanone To a solution of 43 mg (0.10 mmol) [1-(3-chloro-phenyl)-1H-[1,2,4]triazol-3-yl]-(2,2-dimethyl-piperazin-1-yl)-methanone trifluoroacetate and 43 µL (0.25 mmol) DIPEA in 1.0 mL DMF was added 13 µL (0.10 mmol) 3-chloro-benzoyl chloride. The reaction mixture was stirred at RT for 30 min and purified by HPLC.

yield: 25 mg (55%)

ESI-MS: m/z=458 (M+H)⁺

$R_t$(HPLC): 1.25 min (method 5)

Example 174

[4-(4,5-Dimethyl-furan-2-carbonyl)-2,2-dimethyl-piperazin-1-yl]-[1-(3-fluoro-phenyl)-1H-[1,2,4]triazol-3-yl]-methanone A mixture of 18 mg (0.13 mmol) 4,5-dimethyl-furan-2-carboxylic acid and 20 µL (0.15 mmol) 1-chloro-N,N,2-trimethylpropenylamine in 2.0 mL THF was stirred at RT for 30 min A suspension of 40 mg (0.13 mmol) (2,2-dimethyl-piperazin-1yl)-[1-(3-fluoro-phenyl)-1H-[1,2,4]triazol-3yl]-methanone and 0.10 mL (0.58 mmol) DIPEA in 1.0 mL DMF was added. The reaction mixture was stirred at RT for 2 h and purified by HPLC.

yield: 28 mg (50%)

ESI-MS: m/z=426 (M+H)⁺

$R_t$(HPLC): 1.18 min (method 3)

By using the same synthesis strategy as for [4-(4,5-dimethyl-furan-2-carbonyl)-2,2-dimethyl-piperazin-1-yl]-[1-(3-fluoro-phenyl)-1H-[1,2,4]triazol-3-yl]-methanone the following compound was prepared:

| Ex # | carboxylic acid | product | $R_t$ [min]/ HPLC method | ESI-MS m/z | yield |
|---|---|---|---|---|---|
| 175 | 4,5-dibromo-furan-2-carboxylic acid | 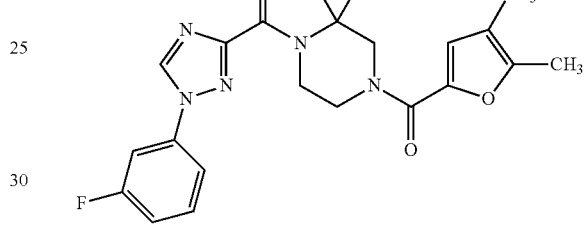 | 1.26/ 3 | 554 (M + H)⁺ | 18 mg (39%) |

Example 176

[1-(3-Chloro-phenyl)-1H-[1,2,4]-triazol-3-yl]-{2,2-dimethyl-4-[6-(tetrahydro-pyran-4-yl)-pyridine-2-carbonyl]-piperazin-1-yl}-methanone

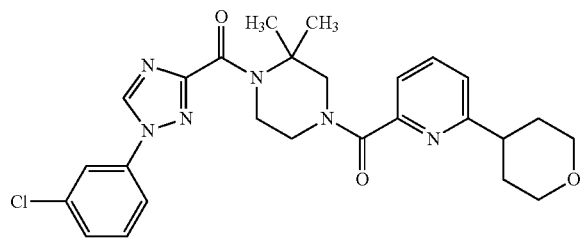 [SMILES: CC1(C)CN(C(=O)c2cccc(C3CCOCC3)n2)CCN1C(=O)c1ncn(-c2cccc(Cl)c2)n1]

A mixture of 17 mg (34 µmol) [1-(3-chloro-phenyl)-1H-[1,2,4]-triazol-3-yl]-{4-[6-(3,6-dihydro-2H-pyran-4-yl)-pyridine-2-carbonyl]-2,2-dimethyl-piperazin-1-yl}-methanone and 4 mg palladium on carbon in 5.0 mL EtOAc was hydrogenated at RT for 4 days. The catalyst was removed by filtration and the solvent was evaporated in vacuo. The resulting residue was purified by HPLC.

yield: 13 mg (77%)

ESI-MS: m/z=509 (M+H)$^+$

R$_t$(HPLC): 1.24 min (method 22)

Example 177

[1-(3-Chloro-phenyl)-1H-[1,2,4]-triazol-3-yl]-[4-(6-cyclopentyl-pyridine-2-carbonyl)-2,2-dimethyl-piperazin-1-yl]-methanone

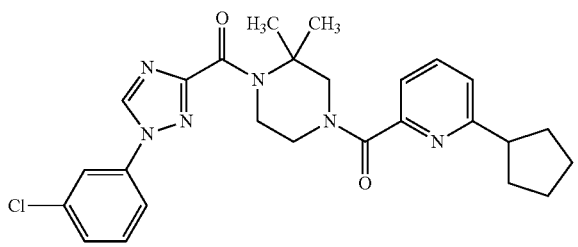

A mixture of 15 mg (31 µmol) [1-(3-chloro-phenyl)-1H-[1,2,4]-triazol-3-yl]-[4-(6-cyclopent-1-enyl-pyridine-2-carbonyl]-2,2-dimethyl-piperazin-1-yl]-methanone and 4 mg palladium on carbon in 5.0 mL EtOAc was hydrogenated at RT for 3.5 h. The catalyst was removed by filtration and the solvent was evaporated in vacuo. The resulting residue was purified by HPLC.

yield: 12 mg (80%)

ESI-MS: m/z=493 (M+H)$^+$

R$_t$(HPLC): 1.56 min (method 22)

Example 179

[4-(2-cyclopentylmethyl-3-methyl-3H-benzoimidazole-5-carbonyl)-2,2-dimethyl-piperazin-1-yl]-(1-phenyl-1H-[1,2,4]-triazol-3-yl)-methanone

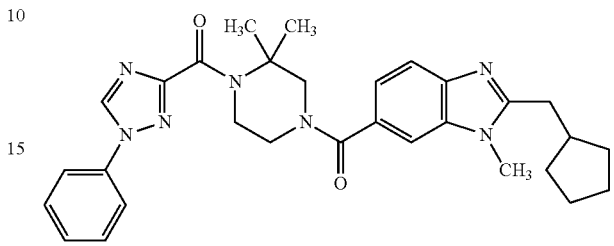

A mixture of 123 mg (0.284 mmol) [4-(4-amino-3-methylamino-benzoyl)-2,2-dimethyl-piperazin-1-yl]-(1-phenyl-1H-[1,2,4]-triazol-3-yl)-methanone and 500 µL (3.99 mmol) cyclopentylacetic acid was stirred at 200° C. for 30 min. The reaction mixture was diluted with DMF and purified by HPLC.

yield: 22 mg (15%)

ESI-MS: m/z=526 (M+H)$^+$

R$_t$(HPLC): 1.02 min (method 5)

Example 180

[4-(6-Cyclopropyl-pyridine-2-carbonyl)-2,2-dimethyl-piperazin-1-yl]-(2-phenyl-2H-tetrazol-5-yl)-methanone

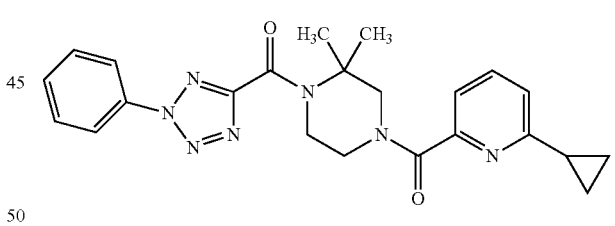

A mixture of 30 mg (80 µmol) (6-cyclopropyl-pyridin-2-yl)-(3,3-dimethyl-piperazin-1-yl)-methanone trifluoroacetate, 15.3 mg (80.3 µmol) 2-phenyl-2H-tetrazole-5-carboxylic acid, 30 mg (94 µmol) TBTU and 50 µL (0.29 mmol) DIPEA in 1.0 mL DMF was stirred at RT for 2 h. The reaction mixture was purified by HPLC.

yield: 12 mg (33%)

ESI-MS: m/z=432 (M+H)$^+$

R$_t$(HPLC): 1.25 min (method 5)

By using the same synthesis strategy as for [4-(6-cyclopropyl-pyridine-2-carbonyl)-2,2-dimethyl-piperazin-1-yl]-(2-phenyl-2H-tetrazol-5-yl)-methanone the following compounds were prepared:

| Ex # | carboxylic acid | product | R_t [min]/ HPLC method | ESI-MS m/z | yield |
|---|---|---|---|---|---|
| 181 | 1-m-tolyl-1H-[1,2,4]triazol-3-carboxylic acid | | 1.24/ 5 | 445 (M + H)+ | 25 mg (66%) |
| 182 | 2-(3-chlorophenyl)-2H-tetrazole-5-carboxylic acid | | 1.32/ 5 | 466 (M + H)+ | 12 mg (29%) |
| 183 | 1-phenyl-1H-[1,2,4]-triazole-3-carboxylic acid | | 1.17/ 5 | 431 (M + H)+ | 25 mg (72%) |
| 184 | 1-(3-fluorophenyl)-1H-[1,2,4]-triazole-3-carboxylic acid | | 1.20/ 5 | 449 (M + H)+ | 26 mg (69%) |
| 185 | 2-(3-fluorophenyl)-2H-tetrazole-5-carboxylic acid | | 1.27/ 5 | 450 (M + H)+ | 10 mg (25%) |

Example 186

[4-(3-Chloro-benzoyl)-2,2-dimethyl-piperazin-1-yl]-(1-phenyl-1H-[1,2,4]-triazol-3-yl)-methanone

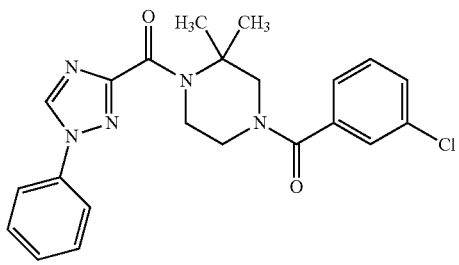 [SMILES: CC1(C)CN(C(=O)c2cccc(Cl)c2)CCN1C(=O)c1ncn(-c2ccccc2)n1]

60 μL (0.35 mmol) DIPEA were added to a mixture of 19 mg (0.10 mmol) 1-phenyl-1H-[1,2,4]triazole-3-carboxylic acid, 37 mg (0.10 mmol) (3-chloro-phenyl)-(3,3-dimethyl-piperazin-1-yl)-methanone trifluoroacetate and 35 mg (0.10 mmol) TBTU in 1.0 mL DMF at RT. The mixture was stirred at RT for 1 h and subsequently purified using HPLC.

yield: 35 mg (83%)

ESI-MS: m/z=424 (M+H)$^+$

R$_t$(HPLC): 1.18 min (method 5)

By using the same synthesis strategy as for [4-(3-chloro-benzoyl)-2,2-dimethyl-piperazin-1-yl]-(1-phenyl-1H-[1,2,4]-triazol-3-yl)-methanone the following compounds were prepared:

| Ex # | carboxylic acid | product | R$_t$ [min]/ HPLC method | ESI-MS m/z | yield |
|---|---|---|---|---|---|
| 187 | 2-phenyl-2H-tetrazole-5-carboxylic acid | | 1.24/ 5 | 425 (M + H)$^+$ | 25 mg (59%) |
| 188 | 1-m-tolyl-1H-[1,2,4]-triazol-3-carboxylic acid | | 1.24/ 5 | 438 (M + H)$^+$ | 38 mg (80%) |
| 189 | 2-m-tolyl-2H-tetrazole-5-carboxylic acid | | 1.31/ 5 | 439 (M + H)$^+$ | 24 mg (50%) |
| 190 | 1-(3-fluoro-phenyl)-1H-[1,2,4]-triazole-3-carboxylic acid | | 1.20/ 5 | 442 (M + H)$^+$ | 40 mg (83%) |

-continued

| Ex # | carboxylic acid | product | $R_t$ [min]/ HPLC method | ESI- MS m/z | yield |
|---|---|---|---|---|---|
| 191 | 2-(3-chloro-phenyl)-2H-tetrazole-5-carboxylic acid | | 1.31/ 5 | 459 (M + H)+ | 24 mg (52%) |
| 192 | 2-(3-fluoro-phenyl)-2H-tetrazole-5-carboxylic acid | | 0.48/ 17 | 443 (M + H)+ | |
| 193 | 2-(4-fluoro-phenyl)-2H-tetrazole-5-carboxylic acid | | 0.48/ 17 | 443 (M + H)+ | |
| 194 | 1-(2-fluoro-phenyl)-1H-[1,2,4]-triazole-3-carboxylic acid | | 1.17/ 5 | 442 (M + H)+ | 27 mg (56%) |
| 195 | 1-(2,5-di-fluorophenyl)-1H-[1,2,4]-triazole-3-carboxylic acid | | 1.19/ 5 | 460 (M + H)+ | 28 mg (56%) |
| 196 | 2-(2-fluoro-phenyl)-2H-tetrazole-5-carboxylic acid | | 1.22/ 5 | 443 (M + H)+ | 21 mg (43%) |

Example 197

[1-(2,5-Difluoro-phenyl)-1H-[1,2,4]triazol-3-yl]-[4-(6-methoxy-pyridine-2-carbonyl)-2,2-dimethyl-piperazin-1-yl]-methanone

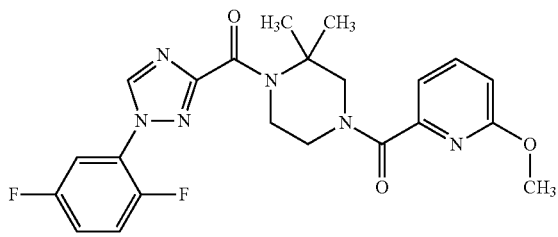 [SMILES: COc1cccc(C(=O)N2CCN(C(=O)c3ncn(-c4cc(F)ccc4F)n3)C(C)(C)C2)n1]

A mixture of 25 mg (0.10 mmol) (3,3-dimethyl-piperazin-1yl)-(6-methoxy-pyridin-2-yl)-methanone, 23 mg (0.10 mmol) 1-(2,5-difluoro-phenyl)-1H-[1,2,4]-triazole-3-carboxylic acid, 35 mg (0.10 mmol) TBTU and 100 µL (0.61 mmol) DIPEA in 1.0 mL DMF was stirred at RT over night. The reaction mixture was purified by HPLC.

yield: 30 mg (66%)

ESI-MS: m/z=457 (M+H)$^+$ $R_t$(HPLC): 1.10 min (method 6)

By using the same synthesis strategy as for [1-(2,5-difluoro-phenyl)-1H-[1,2,4]-triazol-3-yl]-[4-(6-methoxy-pyridine-2-carbonyl)-2,2-dimethyl-piperazin-1-yl]-methanone the following compounds were prepared:

| | carboxylic acid | product | $R_t$ [min]/ HPLC method | ESI-MS m/z |
|---|---|---|---|---|
| 198 | 2-m-tolyl-2H-tetrazole-5-carboxylic acid | | 1.81/ 12 | 436 (M + H)$^+$ |
| 199 | 2-(3-chloro-phenyl)-2H-tetrazole-5-carboxylic acid | | 1.69/ 12 | 456 (M + H)$^+$ |
| 200 | 2-(4-fluoro-phenyl)-2H-tetrazole-5-carboxylic acid | | 1.74/ 12 | 440 (M + H)$^+$ |
| 201 | 2-(2-fluoro-phenyl)-2H-tetrazole-5-carboxylic acid | | 1.67/ 12 | 440 (M + H)$^+$ |
| 202 | 2-(3-fluoro-phenyl)-2H-tetrazole-5-carboxylic acid | | 1.76/ 12 | 440 (M + H)$^+$ |

According to the preparation of [4-(3-chloro-benzoyl)-2,2-dimethyl-piperazin-1-yl]-(1-phenyl-1H-[1,2,4]-triazol-3-yl)-methanone the following compounds were prepared from 0.10 mmol (1-cyclopropyl-isoquinolin-3-yl)-(3,3-dimethyl-piperazin-1-yl)-methanone trifluoro acetate and 0.10 mmol of the appropriate carboxylic acid as depicted in the following table:

DIPEA in 1.5 mL DMF was stirred at RT over the weekend. The reaction mixture was purified by HPLC.

yield: 10.0 mg (16%)
ESI-MS: m/z=433 (M+H)+
$R_t$(HPLC): 1.19 min (method 5)

| Ex # | carboxylic acid | product | $R_t$ [min]/ HPLC method | ESI-MS m/z | yield |
|---|---|---|---|---|---|
| 203 | 1-phenyl-1H-[1,2,4]-triazole-3-carboxylic acid | | 1.30/ 5 | 481 (M + H)+ | 33 mg (69%) |
| 204 | 1-(3-chloro-phenyl)-1H-[1,2,4]-triazole-3-carboxylic acid | | 1.36/ 5 | 515 (M + H)+ | 38 mg (74%) |
| 205 | 2-phenyl-2H-tetrazole-5-carboxylic acid | | 1.36/ 5 | 482 (M + H)+ | 42 mg (87%) |

Example 206

[4-(6-isopropyl-pyridine-2-carbonyl)-2,2-dimethyl-piperazin-1-yl]-(1-phenyl-1H-[1,2,4]triazol-3-yl)-methanone

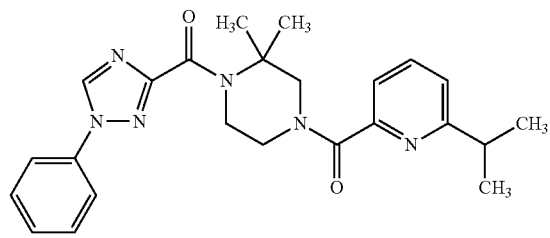 [SMILES: CC(C)c1cccc(C(=O)N2CCN(C(=O)c3ncn(-c4ccccc4)n3)C(C)(C)C2)n1]

A mixture of 55 mg (0.15 mmol) (3,3-dimethyl-piperazin-1-yl)-(6-isopropyl-pyridin-2-yl)-methanone trifluoroacetate, 28 mg (0.15 mmol) 1-phenyl-1H-[1,2,4]-triazole-3-carboxylic acid, 52 mg (0.16 mmol) TBTU and 0.10 mL (0.61 mmol)

Example 207

[2-(3-Fluoro-phenyl)-2H-tetrazol-5-yl]-[4-(1-methoxy-isoquinoline-3-carbonyl)-2,2-dimethyl-piperazin-1-yl]-methanone

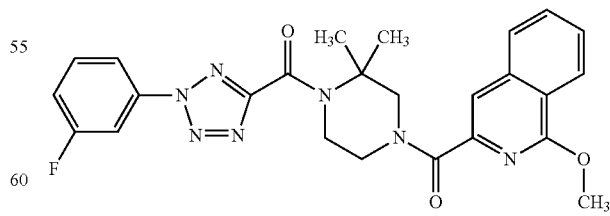

A mixture of 21 mg (0.10 mmol) 2-(3-fluoro-phenyl)-2H-tetrazole-5-carboxylic acid, 32 mg (0.10 mmol) TBTU and 18 µL (0.11 mmol) DIPEA in 0.5 mL DMF was stirred for 10 min A solution of 30 mg (0.10 mmol) (3,3-dimethyl-piperazin-1-yl)-(1-methoxy-isoquinolin-3-yl)-methanone and 18 µL (0.11 mmol) DIPEA in 0.5 mL DMF was added. The resulting mixture was stirred at RT for 5 h and purified by HPLC.

ESI-MS: m/z=490 (M+H)$^+$
$R_t$(HPLC): 1.93 min (method 12)

By using the same synthesis strategy as for [2-(3-fluoro-phenyl)-2H-tetrazol-5-yl]-[4-(1-methoxy-isoquinoline-3-carbonyl)-2,2-dimethyl-piperazin-1-yl]-methanone the following compounds were prepared:

| Ex # | carboxylic acid | Product | $R_t$ [min]/ HPLC method | ESI-MS m/z |
|---|---|---|---|---|
| 208 | 2-(3-chloro-phenyl)-2H-tetrazole-5-carboxylic acid | 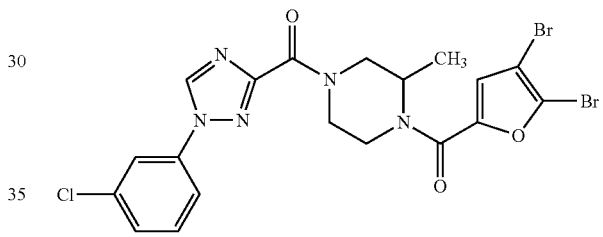 | 1.99/ 12 | 506 (M + H)$^+$ |

Example 210

[1-(3-Chloro-phenyl)-1H-[1,2,4]triazol-3-yl]-[4-(4,5-dibromo-furan-2-carbonyl)-3-methyl-piperazin-1-yl]-methanone A mixture of 115 mg (0.376 mmol) [1-(3-chloro-phenyl)-1H-[1,2,4]triazol-3-yl]-(3-methyl-piperazin-1-yl)-methanone, 113 mg (0.420 mmol) 4,5-dibromo-2-furoic acid, 135 mg (0.420 mmol) TBTU and 103 µL (0.606 mmol) DIPEA in 2.0 mL DMF was stirred at RT for 12 h. The reaction mixture was purified by HPLC.
yield: 120 mg (57%)
ESI-MS: m/z=556 (M+H)$^+$
$R_t$(HPLC): 1.50 min (method 8)

By using the same synthesis strategy as for [1-(3-chloro-phenyl)-1H-[1,2,4]triazol-3-yl]-[4-(4,5-dibromo-furan-2-carbonyl)-3-methyl-piperazin-1-yl]-methanone the following compounds were prepared:

| Ex # | carboxylic acid | product | $R_t$ [min]/ HPLC method | ESI-MS m/z | yield |
|---|---|---|---|---|---|
| 211 | 6-methoxy-pyridine-2-carboxylic acid | | 1.30/ 8 | 441 (M + H)$^+$ | 120 mg (77%) |

-continued

| Ex # | carboxylic acid | product | R$_t$ [min]/ HPLC method | ESI-MS m/z | yield |
|---|---|---|---|---|---|
| 212 | 5-fluoro-3-methyl-benzofuran-2-carboxylic acid | | 1.54/ 8 | 482 (M + H)$^+$ | 138 mg (76%) |
| 213 | 6-methoxy-3-methyl-benzofuran-2-carboxylic acid | | 1.78/ 17 | 494 (M + H)$^+$ | |
| 214 | benzofuran-2-carboxylic acid | | 1.69/ 17 | 450 (M + H)$^+$ | |
| 215 | 2-methyl-benzofuran-3-carboxylic acid | | 1.71/ 17 | 465 (M + H)$^+$ | |
| 216 | 3-isobutoxy-benzoic acid | | 1.82/ 17 | 482 (M + H)$^+$ | |

| Ex # | carboxylic acid | product | R_t [min]/ HPLC method | ESI-MS m/z | yield |
|---|---|---|---|---|---|
| 217 | 3-methoxy-methyl-benzofuran-2 carboxylic acid | | 1.74/ 17 | 494 (M + H)+ | |
| 218 | 3-thiazol-2-yl-benzoic acid | | 1.57/ 17 | 493 (M + H)+ | |
| 219 | 3-propoxy-benzoic acid | | 1.73/ 17 | 468 (M + H)+ | |
| 220 | benzo[1,3]di-oxole-4-carboxylic acid | | 1.54/ 17 | 454 (M + H)+ | |
| 221 | 8-chloro-2,3-dihydro-benzo[1,4]di-oxine-6-carboxylic acid | | 1.61/ 17 | 502 (M + H)+ | |

-continued

| Ex # | carboxylic acid | product | R$_t$ [min]/ HPLC method | ESI-MS m/z | yield |
|---|---|---|---|---|---|
| 222 | 1-methyl-1H-indole-6-carboxylic acid | | 1.62/ 17 | 463 (M + H)$^+$ | |
| 223 | 4-chloro-benzo[b]thiophene-2-carboxylic acid | | 1.83/ 17 | 500 (M + H)$^+$ | |
| 224 | 3,5-dimethoxy-benzoic acid | | 1.59/ 17 | 470 (M + H)$^+$ | |
| 225 | 3-(1-methyl-1H-pyrazol-3-yl)-benzoic acid | | 1.51/ 17 | 490 (M + H)$^+$ | |
| 226 | 3-chloro-ben-zo-[b]thio-phene-2-car-boxylic acid | | 1.79/ 17 | 500 (M + H)$^+$ | |

-continued

| Ex # | carboxylic acid | product | R_t [min]/ HPLC method | ESI-MS m/z | yield |
|---|---|---|---|---|---|
| 227 | 3,5-dimethyl-benzofuran-2-carboxylic acid | | 1.87/ 17 | 478 (M + H)+ | |
| 228 | 3-methyl-benzofuran-2-carboxylic acid | | 1.78/ 17 | 464 (M + H)+ | |
| 229 | 2-cyclopentyl methyl-1-methyl-1H-benzo-imidazole-5-carboxylic acid | | 1.69/ 17 | 546 (M + H)+ | |
| 230 | 1-methyl-1H-indole-3-carboxylic acid | | 1.64/ 17 | 463 (M + H)+ | |

-continued

| Ex # | carboxylic acid | product | R_t [min]/ HPLC method | ESI-MS m/z | yield |
|---|---|---|---|---|---|
| 231 | 5-chloro-thiophene-2-carboxylic acid | | 1.69/ 17 | 450 (M + H)+ | |
| 232 | 7-fluoro-3-methylbenzo-furan-2-carboxylic acid | | 1.80/ 17 | 482 (M + H)+ | |

By using the same synthesis strategy as for [1-(3-chloro-phenyl)-1H-[1,2,4]triazol-3-yl]-[4-(4,5-dibromo-furan-2-carbonyl)-3-methyl-piperazin-1-yl]-methanone the following compounds were prepared using [1-(3-fluoro-phenyl)-1H-[1,2,4]triazol-3-yl]-(3-methyl-piperazin-1-yl)-methanone as amine.

| Ex # | carboxylic acid | product | R_t [min]/ HPLC method | ESI-MS m/z |
|---|---|---|---|---|
| 233 | 3-methoxy-4-methyl-benzoic acid | | 1.60/ 17 | 438 (M + H)+ |
| 234 | 8-chloro-2,3-dihydro-benzo-[1,4]dioxine-6-carboxylic acid | | 1.52/ 17 | 486 (M + H)+ |

By using the same synthesis strategy as for [1-(3-chlorophenyl)-1H-[1,2,4]triazol-3-yl]-[4-(4,5-dibromo-furan-2-carbonyl)-3-methyl-piperazin-1-yl]-methanone the following compounds were prepared using (3-methyl-piperazin-1-yl)-(1-m-tolyl-1H-[1,2,4]triazol-3-yl)-methanone as amine.

| Ex # | carboxylic acid | product | $R_t$ [min]/ HPLC method | ESI-MS m/z |
|---|---|---|---|---|
| 235 | 3-methoxy-4-methyl-benzoic acid | | 1.66/ 17 | 434 (M + H)+ |
| 236 | 5-fluoro-3-methyl-benzo-furan-2-carboxylic acid | | 1.75/ 17 | 462 (M + H)+ |
| 237 | 5-methoxy-2-methyl-benzo-furan-3-carboxylic acid | | 1.68/ 17 | 474 (M + H)+ |
| 238 | 2-methyl-benzofuran-3-carboxylic acid | | 1.69/ 17 | 444 (M + H)+ |
| 239 | 8-chloro-2,3-dihydro-benzo-[1,4]dioxine-6-carboxylic acid | | 1.58/ 17 | 482 (M + H)+ |

By using the same synthesis strategy as for [1-(3-chlorophenyl)-1H-[1,2,4]triazol-3-yl]-[4-(4,5-dibromo-furan-2-carbonyl)-3-methyl-piperazin-1-yl]-methanone the following compounds were prepared using (3-methyl-piperazin-1-yl)-(1-phenyl-1H-[1,2,4]triazol-3-yl)-methanone as amine.

| Ex # | carboxylic acid | product | R$_t$ [min]/ HPLC method | ESI-MS m/z |
|---|---|---|---|---|
| 240 | 2-methyl-benzofuran-3-carboxylic acid | | 1.60/ 17 | 430 (M + H)$^+$ |
| 241 | 5-fluoro-3-methyl-benzofuran-2-carboxylic acid | | 1.68/ 17 | 448 (M + H)$^+$ |
| 242 | 5-methoxy-2-methyl-benzofuran-3-carboxylic acid | | 1.59/ 17 | 460 (M + H)$^+$ |

Example 243

(6-Methoxy-pyridin-2-yl)-[2-methyl-4-(2-m-tolyl-2H-tetrazole-5-carbonyl)-piperazin-1-yl]-methanone

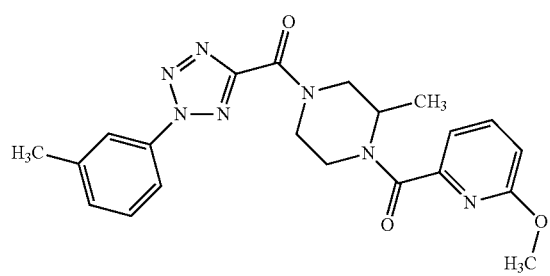 [SMILES: COc1cccc(C(=O)N2CCN(C(=O)c3nnn(-c4cccc(C)c4)n3)CC2C)n1]

A mixture of 20 mg (0.10 mmol) 2-m-tolyl-2H-tetrazole-5-carboxylic acid, 32 mg (0.10 mmol) TBTU and 17 μL (0.10 mmol) DIPEA in 0.5 mL DMF was stirred for 10 min A solution of 24 mg (0.10 mmol) (6-methoxy-pyridin-2-yl)-(2-methyl-piperazin-1-yl)-methanone and 17 μL (0.10 mmol) DIPEA in 0.5 mL DMF was added. The resulting mixture was stirred at RT for 5 h and purified using HPLC.

ESI-MS: m/z=422 (M+H)$^+$

R$_t$(HPLC): 0.75 min (method 19)

By using the same synthesis strategy as for (6-methoxy-pyridin-2-yl)-[2-methyl-4-(2-m-tolyl-2H-tetrazole-5-carbonyl)-piperazin-1-yl]-methanone the following compounds were prepared:

| Ex # | carboxylic acid | product | R_t [min]/ HPLC method | ESI- MS m/z |
|---|---|---|---|---|
| 244 | 1-m-tolyl-1H-[1,2,4]-triazol-3-car-boxylic acid | | 0.67/ 19 | 421 (M + H)+ |
| 245 | 1-(3-bromo-phenyl)-1H-[1,2,4]tri-azole-3-car-boxylic acid | | 0.69/ 19 | 485 (M + H)+ |
| 246 | 1-(3-fluoro-phenyl)-1H-[1,2,4]tri-azole-3-car-boxylic acid | | 0.64/ 19 | 425 (M + H)+ |
| 247 | 1-phenyl-1H-[1,2,4]tri-azole-3-car-boxylic acid | | 0.62/ 19 | 407 (M + H)+ |

Example 248

(R)-{4-[1-(3-Chloro-phenyl)-1H-[1,2,4]triazole-3-carbonyl]-2-methyl-piperazin-1-yl}-(6-methoxy-pyridin-2-yl)-methanone

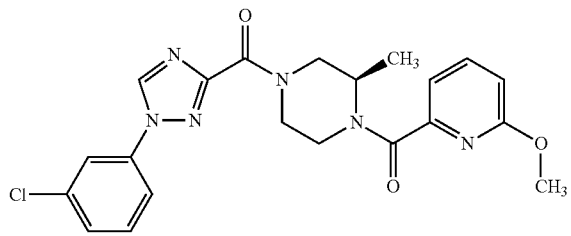 [SMILES: COc1cccc(C(=O)N2CCN(C(=O)c3ncn(-c4cccc(Cl)c4)n3)C[C@H]2C)n1]

A mixture of 92 mg (0.30 mmol) [1-(3-chloro-phenyl)-1H-[1,2,4]-triazol-3-yl]-((R)-3-methyl-piperazin-1-yl)-methanone, 46 mg (0.30 mmol) 6-methoxy-pyridine-2-carboxylic acid, 106 mg (0.330 mmol) TBTU and 77 μL (0.46 mmol) DIPEA in 3.0 mL DMF was stirred at RT for 12 h. The reaction mixture was purified by HPLC.

yield: 70 mg (53%)
ESI-MS: m/z=441 (M+H)$^+$
R$_t$(HPLC): 1.24 min (method 8)

By using the same synthesis strategy as for (R)-{4-1-(3-chloro-phenyl)-1H-[1,2,4]triazole-3-carbonyl]-2-methyl-piperazin-1-yl}-(6-methoxy-pyridin-2-yl)-methanone the following compounds were prepared:

Example 251

(R)-(6-Methoxy-pyridin-2-yl)-[2-methyl-4-(1-m-tolyl-1H-[1,2,4]-triazole-3-carbonyl)-piperazin-1-yl]-methanone

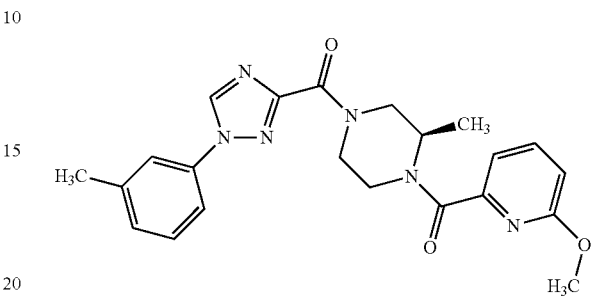

A mixture of 86 mg (0.30 mmol) ((R)-3-methyl-piperazin-1-yl)-(1-m-tolyl-1H-[1,2,4]-triazol-3-yl)-methanone, 46 mg (0.30 mmol) 6-methoxy-pyridine-2-carboxylic acid, 0.11 g (0.33 mmol) TBTU and 80 μL (0.45 mmol) DIPEA in 5.0 mL DMF was stirred at RT for 12 h. The reaction mixture was poured into ice water and extracted with EtOAc. The combined organic phases were dried over sodium sulfate, filtered and concentrated in vacuo.

yield: 108 mg (86%)
ESI-MS: m/z=421 (M+H)$^+$
R$_t$(HPLC): 1.29 min (method 8)

| Ex # | carboxylic acid | product | R$_t$ [min]/ HPLC method | ESI-MS m/z | yield |
|---|---|---|---|---|---|
| 249 | 4,5-dibromo-2-furoic acid | 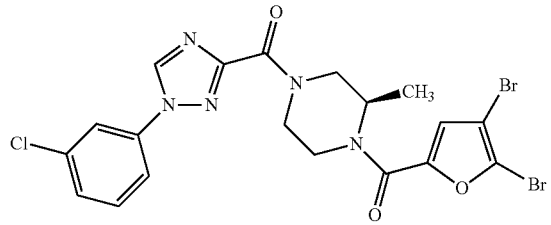 [SMILES: C[C@@H]1CN(C(=O)c2ncn(-c3cccc(Cl)c3)n2)CCN1C(=O)c1cc(Br)c(Br)o1] | 1.47/8 | 556 (M + H)$^+$ | 90 mg (54%) |
| 250 | 5-fluoro-3-methyl-benzo-furan-2-carboxylic acid | 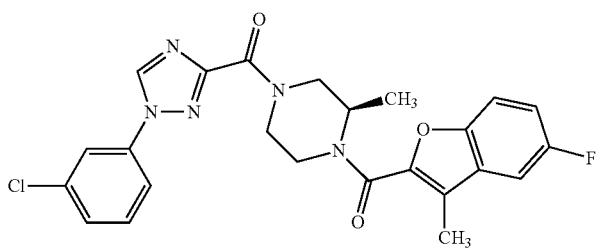 [SMILES: Cc1c(C(=O)N2CCN(C(=O)c3ncn(-c4cccc(Cl)c4)n3)C[C@H]2C)oc2ccc(F)cc12] | 1.49/8 | 482 (M + H)$^+$ | 82 mg (57%) |

Example 252

(S)-{4-[1-(3-Chloro-phenyl)-1H-[1,2,4]triazole-3-carbonyl]-2-methyl-piperazin-1-yl}-(6-methoxy-pyridin-2-yl)-methanone

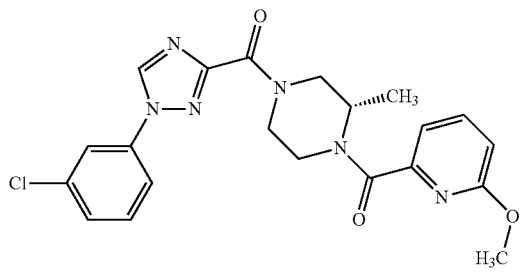 [SMILES: COc1cccc(C(=O)N2CCN(C(=O)c3ncn(-c4cccc(Cl)c4)n3)C[C@@H]2C)n1]

A mixture of 92 mg (0.30 mmol) [1-(3-chloro-phenyl)-1H-[1,2,4]-triazol-3-yl]-((S)-3-methyl-piperazin-1-yl)-methanone, 46 mg (0.30 mmol) 6-methoxy-pyridine-2-carboxylic acid, 0.11 g (0.33 mmol) TBTU and 80 µL (0.45 mmol) DIPEA in 3.0 mL DMF was stirred at RT for 12 h. The reaction mixture was purified by HPLC.

yield: 101 mg (76%)

ESI-MS: m/z=441 (M+H)$^+$

R$_t$(HPLC): 1.30 min (method 8)

By using the same synthesis strategy as for (S)-{4-[1-(3-chloro-phenyl)-1H-[1,2,4]-triazole-3-carbonyl]-2-methyl-piperazin-1-yl}-(6-methoxy-pyridin-2-yl)-methanone the following compounds were prepared:

Example 255

(S)-[4-(4,5-Dibromo-furan-2-carbonyl)-3-methyl-piperazin-1-yl]-(1-m-tolyl-1H-[1,2,4]triazol-3-yl)-methanone

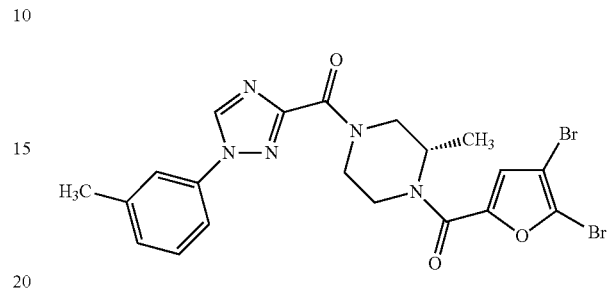

A mixture of 86 mg (0.30 mmol) ((S)-3-methyl-piperazin-1-yl)-(1-m-tolyl-1H-[1,2,4]triazol-3-yl)-methanone, 84 mg (0.30 mmol) 4,5-dibromo-2-furoic acid, 0.11 g (0.33 mmol) TBTU and 80 µL (0.45 mmol) DIPEA in 5.0 mL DMF was stirred at RT for 12 h. The reaction mixture was purified by HPLC.

yield: 70 mg (43%)

ESI-MS: m/z=536 (M+H)$^+$

R$_t$(HPLC): 1.48 min (method 8)

| | carboxylic acid | product | R$_t$ [min]/ HPLC method | ESI- MS m/z | yield |
|---|---|---|---|---|---|
| 253 | 5-fluoro-3-methyl-benzofuran-2-carboxylic acid | | 1.54/8 | 482 (M + H)$^+$ | 118 mg (82%) |
| 254 | 4,5-dibromo-2-furoic acid | | 1.50/8 | 556 (M + H)$^+$ | 131 mg (78%) |

Example 256

(S)-[4-(4,5-Dibromo-furan-2-carbonyl)-3-methyl-piperazin-1-yl]-[1-(3-fluoro-phenyl)-1H-[1,2,4]triazol-3-yl]-methanone

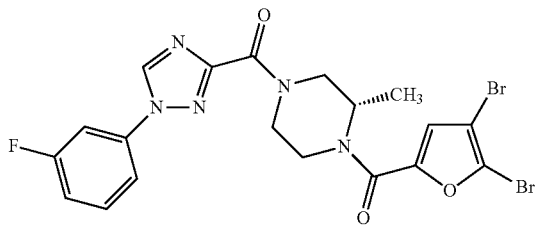 [SMILES: C[C@H]1CN(C(=O)c2ncn(-c3cccc(F)c3)n2)CCN1C(=O)c1cc(Br)c(Br)o1]

A mixture of 87 mg (0.30 mmol) [1-(3-fluoro-phenyl)-1H-[1,2,4]triazol-3-yl]-((S)-3-methyl-piperazin-1-yl)-methanone, 84 mg (0.30 mmol) 4,5-dibromo-2-furoic acid, 0.11 g (0.33 mmol) TBTU and 80 μL (0.45 mmol) DIPEA in 5.0 mL DMF was stirred at RT for 12 h. The reaction mixture was purified by HPLC.

yield: 80 mg (49%)
ESI-MS: m/z=540 (M+H)$^+$
R$_t$(HPLC): 1.44 min (method 8)

Example 257

{4-[1-(3-Chloro-phenyl)-1H-[1,2,4]triazole-3-carbonyl]-2,2-dimethyl-piperazin-1-yl}-(6-methoxy-pyridin-2-yl)-methanone

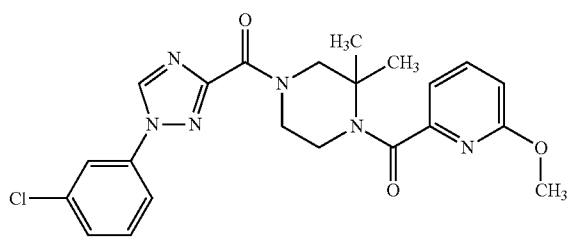 [SMILES: COc1cccc(C(=O)N2CCN(C(=O)c3ncn(-c4cccc(Cl)c4)n3)CC2(C)C)n1]

A mixture of 50 mg (0.22 mmol) 1-(3-chloro-phenyl)-1H-[1,2,4]-triazole-3-carboxylic acid, 80 mg (0.22 mmol) (2,2-dimethyl-piperazin-1-yl)-(6-methoxy-pyridin-2-yl)-methanone trifluoroacetate, 77 mg (0.24 mmol) TBTU and 0.10 mL (0.58 mmol) DIPEA in 1.5 mL DMF was stirred at RT for 12 h. The reaction mixture was purified by HPLC.

yield: 53 mg (53%)
ESI-MS: m/z=455 (M+H)$^+$
R$_t$(HPLC): 0.96 min (method 2)

Example 258

{4-[1-(3-Chloro-phenyl)-1H-[1,2,4]triazole-3-carbonyl]-2-ethyl-piperazin-1-yl}-(6-methoxy-pyridin-2-yl)-methanone

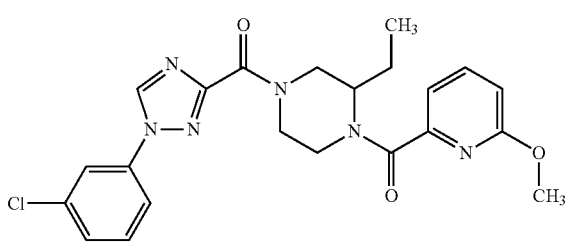 [SMILES: CCC1CN(C(=O)c2ncn(-c3cccc(Cl)c3)n2)CCN1C(=O)c1cccc(OC)n1]

420 mg (0.19 mmol) 1-(3-chloro-phenyl)-1H-[1,2,4]triazole-3-carboxylic acid was stirred with 67 mg (0.21 mmol) TBTU and 0.10 mL (0.57 mmol) DIPEA in 1.0 mL DMF at RT. After 5 min, 50 mg (0.19 mmol) (2-ethyl-piperazin-1-yl)-(6-methoxy-pyridin-2-yl)-methanone was added and the mixture was stirred at RT for 2 h. The reaction mixture was purified by HPLC.

yield: 20 mg (23%); ESI-MS: m/z=455 (M+H)$^+$; R$_t$(HPLC): 1.43 min (method 1)

By using the same synthesis strategy as for {4-[1-(3-chloro-phenyl)-1H-[1,2,4]-triazole-3-carbonyl]-2-ethyl-piperazin-1-yl}-(6-methoxy-pyridin-2-yl)-methanone the following compound was prepared:

| Ex # | carboxylic acid | product | R$_t$ [min]/ HPLC method | ESI-MS m/z | yield |
|---|---|---|---|---|---|
| 259 | 1-(3-fluoro-phenyl)-1H-[1,2,4]triazole-3-carboxylic acid | | 1.30/8 | 439 (M + H)$^+$ | 50 mg (57%) |

Example 260

[4-(4,5-Dibromo-furan-2-carbonyl)-3-ethyl-piperazin-1-yl]-[1-(3-(fluoro-phenyl)-1H-[1,2,4]-triazol-3-yl]-methanone

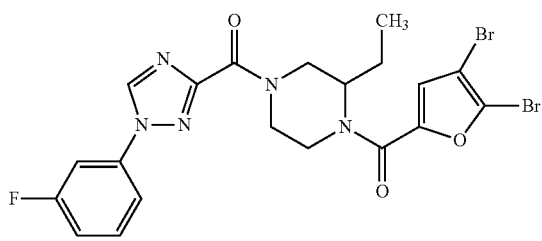 [SMILES: CCC1CN(C(=O)c2ncn(-c3cccc(F)c3)n2)CCN1C(=O)c1cc(Br)c(Br)o1]

50 mg (0.24 mmol) 1-(3-fluoro-phenyl)-1H-[1,2,4]-triazole-3-carboxylic acid was stirred with 85 mg (0.27 mmol) TBTU and 0.10 mL (0.57 mmol) DIPEA in 1.5 mL DMF at RT. After 10 min, 89 mg (0.24 mmol) (4,5-dibromo-furan-2-yl)-(2-ethyl-piperazin-1-yl)-methanone was added and the mixture was stirred at RT for 12 h. The reaction mixture was purified by HPLC.

yield: 85 mg (63%)

ESI-MS: m/z=554 (M+H)$^+$ $R_t$(HPLC): 1.53 min (method 8)

Example 261

(S)-{4-[1-(3-Fluoro-phenyl)-1H-[1,2,4]triazole-3-carbonyl]-2-propyl-piperazin-1-yl}-(6-methoxy-pyridin-2-yl)-methanone

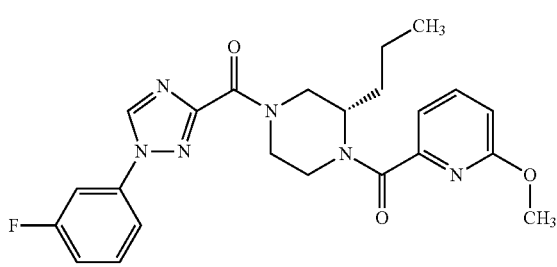 [SMILES: CCC[C@H]1CN(C(=O)c2ncn(-c3cccc(F)c3)n2)CCN1C(=O)c1cccc(OC)n1]

A mixture of 30 mg (90 μmol) [1-(3-fluoro-phenyl)-1H-[1,2,4]triazol-3-yl]-((S)-3-propyl-piperazin-1-yl)-methanone, 14 mg (91 μmol) 6-methoxy-pyridine-2-carboxylic acid, 30 mg (93 μmol) TBTU and 0.10 mL (0.59 mmol) DIPEA in 1.0 mL DMF was stirred at RT for 4 days. The reaction mixture was poured into ice water and extracted with EtOAc. The combined organic phases were dried over sodium sulfate, filtered, concentrated in vacuo and purified by HPLC.

yield: 26 mg (61%)

ESI-MS: m/z=453 (M+H)$^+$ $R_t$(HPLC): 1.37 min (method 8)

By using the same synthesis strategy as for (S)-{4-[1-(3-fluoro-phenyl)-1H-[1,2,4]triazole-3-carbonyl]-2-propyl-piperazin-1-yl}-(6-methoxy-pyridin-2-yl)-methanone the following compound was prepared:

| Ex # | carboxylic acid | product | $R_t$ [min]/ HPLC method | ESI- MS m/z | yield |
|---|---|---|---|---|---|
| 262 | 4,5-dibromo-2-furoic acid | 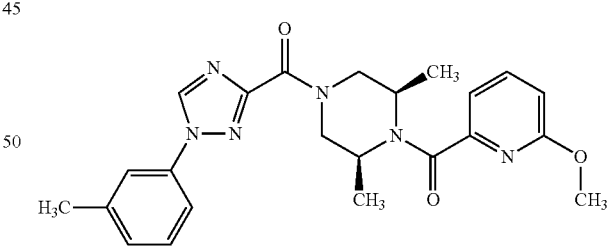 | 1.58/8 | 568 (M + H)$^+$ | 29 mg (54%) |

Example 263

(2R*,6S*)-1-[(6-Methoxypyridin-2-yl)carbonyl]-2,6-dimethyl-4-{[1-(3-methylphenyl)-1H-[1,2,4]-triazol-3-yl]carbonyl}piperazine A mixture of 99 mg (0.33 mmol) (3R*,5S*)-3,5-dimethyl-piperazin-1-yl)-(1-m-tolyl-1H-[1,2,4]-triazol-3-yl)-methanone, 51 mg (0.33 mmol) 6-methoxy-pyridine-2-carboxylic acid, 0.12 g (0.36 mmol) TBTU and 86 μL (0.50 mmol) DIPEA in 2.0 mL DMF was stirred at RT for 12 h. The reaction mixture was purified by HPLC.

yield: 85.0 mg (59%); ESI-MS: m/z=435 (M+H)$^+$; $R_t$(HPLC): 1.34 min (method 8)

By using the same synthesis strategy as for (2R*,6S*)-1-[(6-methoxypyridin-2-yl)carbonyl]-2,6-dimethyl-4-{[1-(3-methylphenyl)-1H-1,2,4-triazol-3-yl]carbonyl}piperazine the following compound was prepared:

| Ex # | carboxylic acid | product | R$_t$ [min]/ HPLC method | ESI- MS m/z | yield |
|---|---|---|---|---|---|
| 264 | 5-chloro-3-methyl-1-benzofuran-2-carboxylic acid | 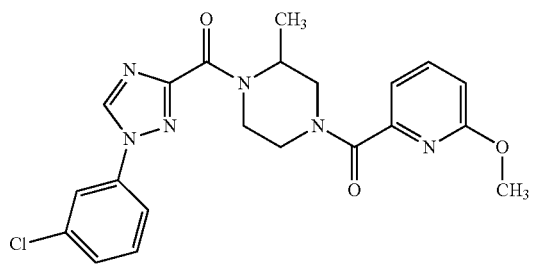 | 1.67/8 | 492 (M + H)$^+$ | 65 mg (44%) |

Example 265

{4-[1-(3-Chloro-phenyl)-1H-[1,2,4]-triazole-3-carbonyl]-3-methyl-piperazin-1-yl}-(6-methoxy-pyridin-2-yl)-methanone

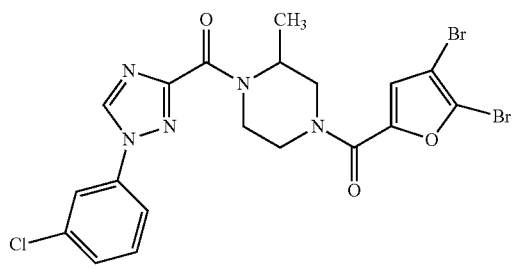 [SMILES: CC1CN(C(=O)c2cc(Br)c(Br)o2)CCN1C(=O)c1ncn(-c2cccc(Cl)c2)n1]

A mixture of 200 mg (0.654 mmol) [1-(3-chloro-phenyl)-1H-[1,2,4]-triazol-3-yl]-(2-methyl-piperazin-1-yl)-methanone, 100 mg (0.650 mmol) 6-methoxy-pyridine-2-carboxylic acid, 225 mg (0.700 mmol) TBTU and 170 μL (1.00 mmol) DIPEA in 3.0 mL DMF was stirred at RT for 12 h. The reaction mixture was poured into ice water and extracted with EtOAc. The combined organic phases were dried over sodium sulfate, filtered, concentrated in vacuo and purified by HPLC.

yield: 190 mg (66%)

ESI-MS: m/z=441 (M+H)$^+$

R$_t$(HPLC): 1.19 min (method 5)

By using the same synthesis strategy as for {4-[1-(3-chloro-phenyl)-1H-[1,2,4]-triazole-3-carbonyl]-3-methyl-piperazin-1-yl}-(6-methoxy-pyridin-2-yl)-methanone the following compounds were prepared:

| Ex # | carboxylic acid | product | R$_t$ [min]/ HPLC method | ESI- MS m/z | yield |
|---|---|---|---|---|---|
| 266 | 4,5-dibromo-2-furoic acid | 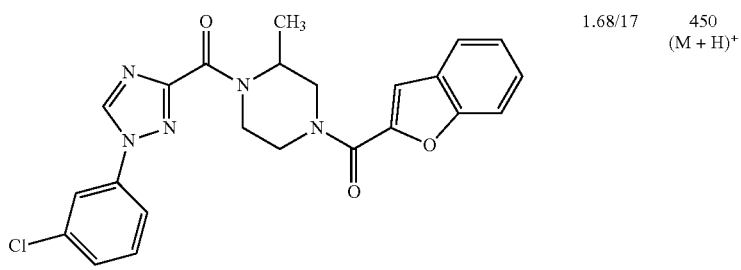 | 1.49/8 | 556 (M + H)$^+$ | 70 mg (33%) |
| 267 | benzofuran-2-carboxylic acid | | 1.68/17 | 450 (M + H)$^+$ | |

-continued

| Ex # | carboxylic acid | product | R$_t$ [min]/ HPLC method | ESI-MS m/z | yield |
|---|---|---|---|---|---|
| 268 | 4-chloro-benzo[b]thio-phene-2-car-boxylic acid | | 1.82/17 | 500 (M + H)$^+$ | |
| 269 | 3-(1-methyl-1H-pyrazol-3-yl)-benzoic acid | | 1.51/17 | 490 (M + H)$^+$ | |
| 270 | 3-thiazol-2-yl-benzoic acid | | 1.57/17 | 493 (M + H)$^+$ | |
| 271 | 3-chloro-benzo[b]thio-phene-2-car-boxylic acid | | 1.79/17 | 500 (M + H)$^+$ | |
| 272 | 1-methyl-1H-indole-6-car-boxylic acid | | 1.62/17 | 463 (M + H)$^+$ | |

| Ex # | carboxylic acid | product | R$_t$ [min]/ HPLC method | ESI- MS m/z | yield |
|---|---|---|---|---|---|
| 273 | 5-chloro-thiophene-2-carboxylic acid | | 1.68/17 | 450 (M + H)$^+$ | |
| 274 | 3-methoxy-methyl-benzofuran-2-carboxylic acid | | 1.74/17 | 494 (M + H)$^+$ | |
| 275 | 2-methyl-benzofuran-3-carboxylic acid | | 1.70/17 | 464 (M + H)$^+$ | |
| 276 | 1-methyl-1H-indole-3-carboxylic acid | | 1.61/17 | 463 (M + H)$^+$ | |
| 277 | 3-methoxy-4-methyl-benzoic acid | | 1.68/17 | 454 (M + H)$^+$ | |

-continued
| Ex # | carboxylic acid | product | R$_t$ [min]/ HPLC method | ESI- MS m/z | yield |
|---|---|---|---|---|---|
| 278 | 6-methoxy-3-methyl-benzofuran-2-carboxylic acid | 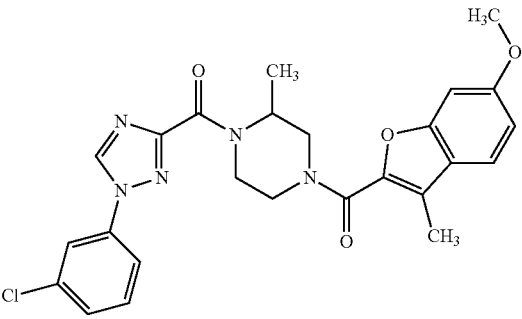 [SMILES: COc1ccc2c(C)c(C(=O)N3CCN(C(=O)c4ncn(-c5cccc(Cl)c5)n4)C(C)C3)oc2c1] | 1.78/17 | 494 (M + H)$^+$ | |
| 279 | 3-methyl-benzofuran-2-carboxylic acid | 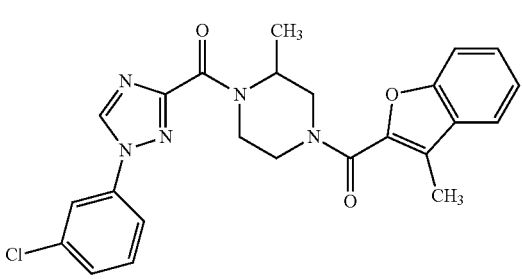 [SMILES: Cc1c(C(=O)N2CCN(C(=O)c3ncn(-c4cccc(Cl)c4)n3)C(C)C2)oc2ccccc12] | 1.78/17 | 464 (M + H)$^+$ | |
| 280 | 3,5-dimethoxy-benzoic acid | 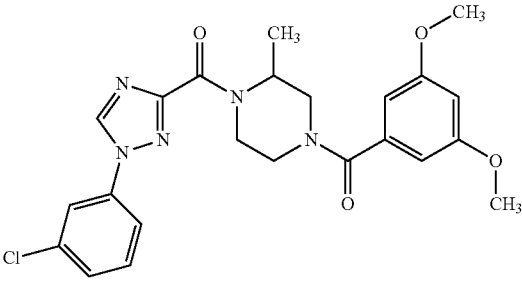 [SMILES: COc1cc(OC)cc(C(=O)N2CCN(C(=O)c3ncn(-c4cccc(Cl)c4)n3)C(C)C2)c1] | 1.59/17 | 470 (M + H)$^+$ | |
| 281 | 3,5-dimethyl-benzofuran-2-carboxylic acid | 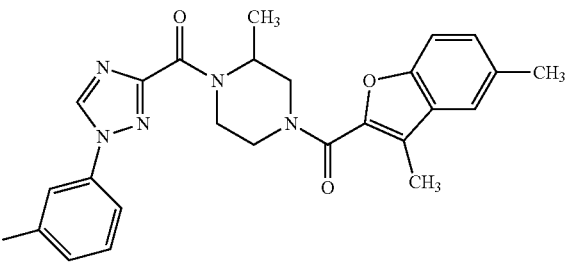 | 1.86/17 | 478 (M + H)$^+$ | |
| 282 | 3-isobutoxy-benzoic acid | 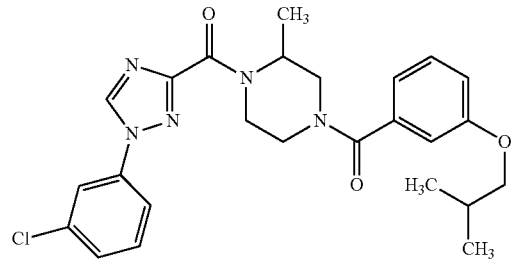 [SMILES: CC(C)COc1cccc(C(=O)N2CCN(C(=O)c3ncn(-c4cccc(Cl)c4)n3)C(C)C2)c1] | 1.82/17 | 482 (M + H)$^+$ | |

-continued

| Ex # | carboxylic acid | product | R<sub>f</sub> [min]/ HPLC method | ESI-MS m/z | yield |
|---|---|---|---|---|---|
| 283 | 8-chloro-2,3-dihydro-benzo[1,4]-dioxine-6-carboxylic acid | | 1.61/17 | 502 (M + H)⁺ | |
| 284 | 7-fluoro-3-methyl-benzofuran-2-carboxylic acid | | 1.79/17 | 482 (M + H)⁺ | |
| 285 | 3-propoxy-benzoic acid | | 1.74/17 | 468 (M + H)⁺ | |
| 286 | benzo[1,3]dioxole-4-carboxylic acid | | 1.52/17 | 454 (M + H)⁺ | |

By using the same synthesis strategy as for {4-[1-(3-chloro-phenyl)-1H-[1,2,4]-triazole-3-carbonyl]-3-methyl-piperazin-1-yl}-(6-methoxy-pyridin-2-yl)-methanone the following compound was prepared using [1-(3-fluoro-phenyl)-1H-[1,2,4]-triazol-3-yl]-(2-methyl-piperazin-1-yl)-methanone as amine:

| Ex # | carboxylic acid | product | $R_t$ [min]/ HPLC method | ESI- MS m/z | yield |
|---|---|---|---|---|---|
| 287 | 5-methoxy-2-methyl-benzofuran-3-carboxylic acid | 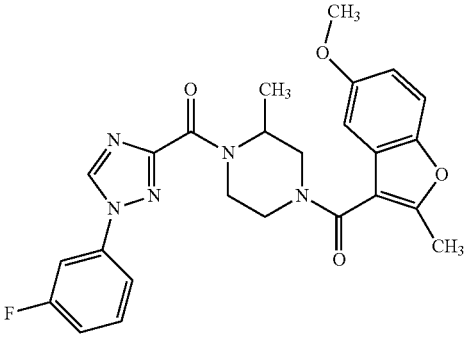 [SMILES: COc1ccc2oc(C)c(C(=O)N3CCN(C(=O)c4ncn(-c5cccc(F)c5)n4)C(C)C3)c2c1] | 1.62/17 | 478 (M + H)+ | |

By using the same synthesis strategy as for {4-[1-(3-chloro-phenyl)-1H-[1,2,4]-triazole-3-carbonyl]-3-methyl-piperazin-1-yl}-(6-methoxy-pyridin-2-yl)-methanone the following compounds were prepared using (2-methyl-piperazin-1-yl)-(1-m-tolyl-1H-[1,2,4]triazol-3-yl)-methanone as amine:

By using the same synthesis strategy as for {4-[1-(3-chloro-phenyl)-1H-[1,2,4]triazole-3-carbonyl]-3-methyl-piperazin-1-yl}-(6-methoxy-pyridin-2-yl)-methanone the following compounds were prepared using (2-methyl-piperazin-1-yl)-(1-phenyl-1H-[1,2,4]triazol-3-yl)-methanone as amine:

| Ex # | carboxylic acid | product | $R_t$ [min]/ HPLC method | ESI- MS m/z | yield |
|---|---|---|---|---|---|
| 288 | 3-methoxy-4-methyl-benzoic acid | 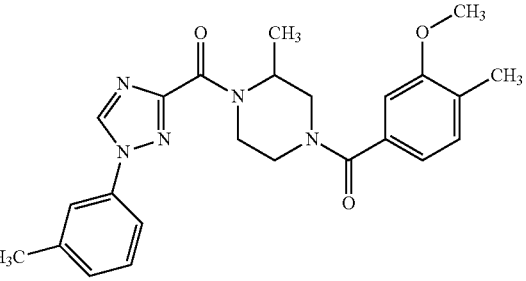 | 1.66/17 | 434 (M + H)+ | |
| 289 | 8-chloro-2,3-dihydro-benzo[1,4]dioxine-6-carboxylic acid | 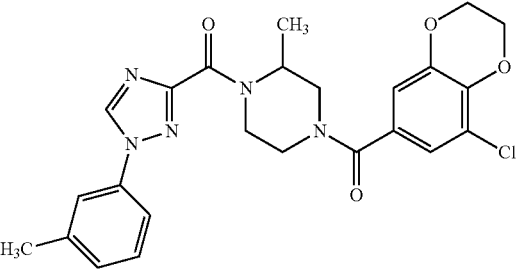 [SMILES: Cc1cccc(-n2cnc(C(=O)N3CCN(C(=O)c4cc(Cl)c5c(c4)OCCO5)CC3C)n2)c1] | 1.57/17 | 482 (M + H)+ | |
| 290 | 5-methoxy-2-methyl-benzofuran-3-carboxylic acid | 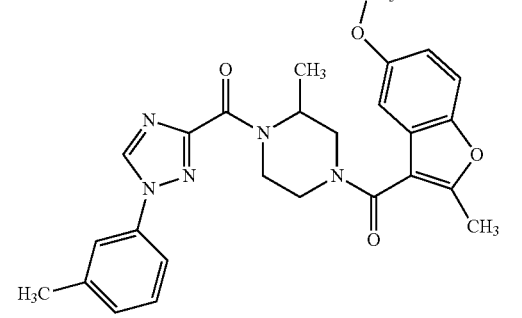 | 1.67/17 | 474 (M + H)+ | |

| Ex # | carboxylic acid | product | R$_t$ [min]/ HPLC method | ESI-MS m/z | yield |
|---|---|---|---|---|---|
| 291 | 5-methoxy-2-methyl-benzofuran-3-carboxylic acid | 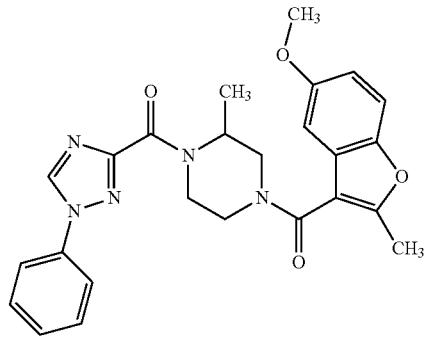 [SMILES: COc1ccc2oc(C)c(C(=O)N3CCN(C(=O)c4ncn(-c5ccccc5)n4)C(C)C3)c2c1] | 1.59/17 | 460 (M + H)$^+$ | |
| 292 | 3-methoxy-4-methyl-benzoic acid | 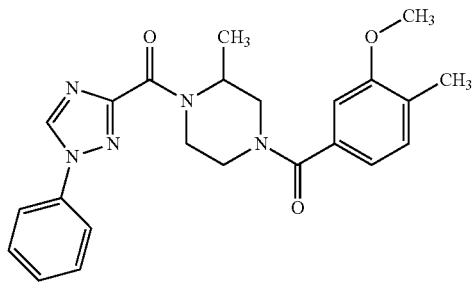 [SMILES: COc1cc(C(=O)N2CCN(C(=O)c3ncn(-c4ccccc4)n3)C(C)C2)ccc1C] | 1.55/17 | 420 (M + H)$^+$ | |
| 293 | 4-chloro-benzo[b]-thiophene-2-carboxylic acid | 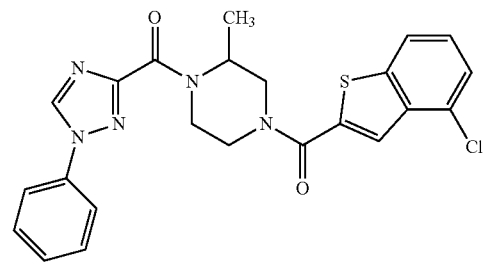 [SMILES: CC1CN(C(=O)c2cc3c(Cl)cccc3s2)CCN1C(=O)c1ncn(-c2ccccc2)n1] | 1.72/17 | 466 (M + H)$^+$ | |
| 294 | 5-fluoro-3-methyl-benzofuran-2-carboxylic acid | 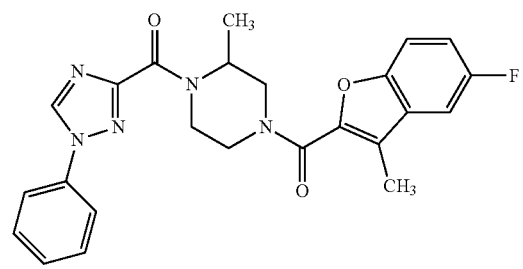 [SMILES: Cc1c(C(=O)N2CCN(C(=O)c3ncn(-c4ccccc4)n3)C(C)C2)oc2ccc(F)cc12] | 1.67/17 | 448 (M + H)$^+$ | |
| 295 | 2-methyl-benzofuran-3-carboxylic acid | 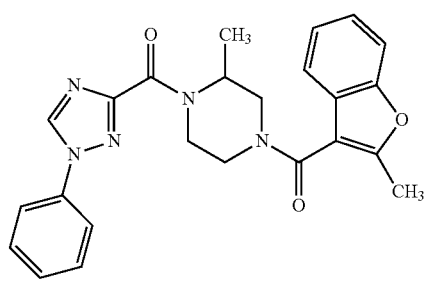 [SMILES: Cc1oc2ccccc2c1C(=O)N1CCN(C(=O)c2ncn(-c3ccccc3)n2)C(C)C1] | 1.58/17 | 430 (M + H)$^+$ | |

Example 296

[4-(6-Methoxy-pyridine-2-carbonyl)-2-methyl-piperazin-1-yl]-(1-m-tolyl-1H-[1,2,4]-triazol-3-yl)-methanone

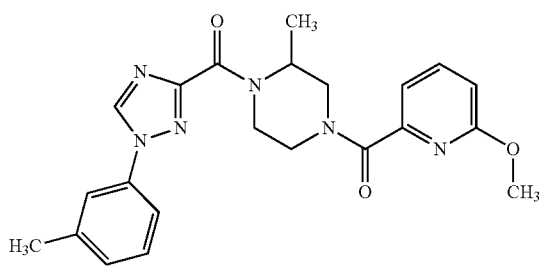

20 mg (0.10 mmol) 1-m-tolyl-1H-[1,2,4]-triazol-3-carboxylic acid was stirred with 32 mg (0.10 mmol) TBTU and 17 μL (0.10 mmol) DIPEA in 1.0 mL DMF at RT. After 5 min, a solution of 24 mg (0.10 mmol) (6-methoxy-pyridin-2-yl)-(3-methyl-piperazin-1-yl)-methanone and 17 μl (0.10 mmol) DIPEA in 1.0 mL DMF was added and the mixture was stirred at RT for 2 h. The reaction mixture was purified by HPLC.

ESI-MS: m/z=421 (M+H)$^+$ $R_t$(HPLC): 0.67 min (method 19)

By using the same synthesis strategy as for [4-(6-methoxy-pyridine-2-carbonyl)-2-methyl-piperazin-1-yl]-(1-m-tolyl-1H-[1,2,4]-triazol-3-yl)-methanone the following compounds were prepared:

| Ex # | carboxylic acid | product | $R_t$ [min]/ HPLC method | ESI-MS m/z |
|---|---|---|---|---|
| 297 | 1-(3-fluoro-phenyl)-1H-[1,2,4]triazole-3-carboxylic acid | | 0.64/19 | 425 (M + H)$^+$ |
| 298 | 1-phenyl-1H-[1,2,4]triazole-3-carboxylic acid | | 0.62/19 | 407 (M + H)$^+$ |
| 299 | 1-(3-bromo-phenyl)-1H [1,2,4]triazole-3-carboxylic acid | | 0.70/19 | 485 (M + H)$^+$ |

Example 300

(S)-{4-[1-(3-Chloro-phenyl)-1H-[1,2,4]triazole-3-carbonyl]-3-methyl-piperazin-1-yl}-(6-methoxy-pyridin-2-yl)-methanone

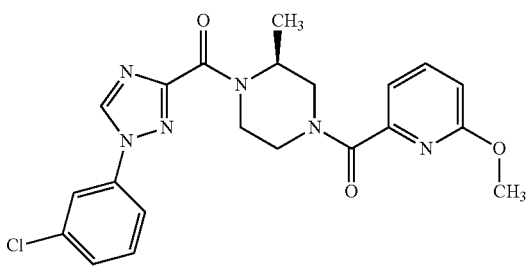 [SMILES: COc1cccc(C(=O)N2CCN(C(=O)c3ncn(-c4cccc(Cl)c4)n3)[C@@H](C)C2)n1]

A mixture of 71 mg (0.30 mmol) (6-methoxy-pyridin-2-yl)-((S)-3-methyl-piperazin-1-yl)-methanone, 67 mg (0.30 mmol) 1-(3-chloro-phenyl)-1H-[1,2,4]-triazole-3-carboxylic acid, 0.11 g (0.33 mmol) TBTU and 77 μL (0.450 mmol) DIPEA in 5.0 mL DMF was stirred at RT for 12 h. The reaction mixture was poured into ice water and extracted with EtOAc. The combined organic phases were dried over sodium sulfate, filtered and concentrated in vacuo.

yield: 70 mg (53%)
ESI-MS: m/z=441 (M+H)$^+$
$R_t$(HPLC): 1.31 min (method 8)

Example 301

(R)-{4-[1-(3-Chloro-phenyl)-1H-[1,2,4]triazole-3-carbonyl]-3-methyl-piperazin-1-yl}-(6-methoxy-pyridin-2-yl)-methanone

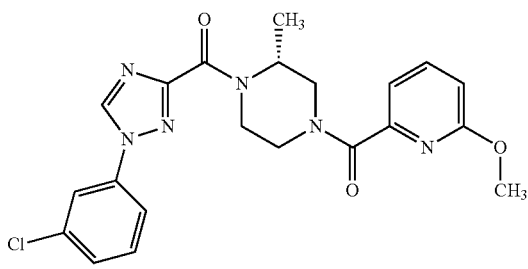 [SMILES: COc1cccc(C(=O)N2CCN(C(=O)c3ncn(-c4cccc(Cl)c4)n3)[C@H](C)C2)n1]

A mixture of 71 mg (0.30 mmol) (6-methoxy-pyridin-2-yl)-((R)-3-methyl-piperazin-1-yl)-methanone, 67 mg (0.30 mmol) 1-(3-chloro-phenyl)-1H-[1,2,4]-triazole-3-carboxylic acid, 0.11 g (0.33 mmol) TBTU and 77 μL (0.45 mmol) DIPEA in 1.5 mL DMF was stirred at RT for 12 h. The reaction mixture was purified by HPLC.

yield: 65 mg (49%)
ESI-MS: m/z=441 (M+H)$^+$
$R_t$(HPLC): 1.32 min (method 8)

Example 302

(2R*,6S*)-4-[(6-methoxypyridin-2-yl)carbonyl]-2,6-dimethyl-1-{[1-(3-methylphenyl)-1H-1,2,4-triazol-3-yl]carbonyl}piperazine

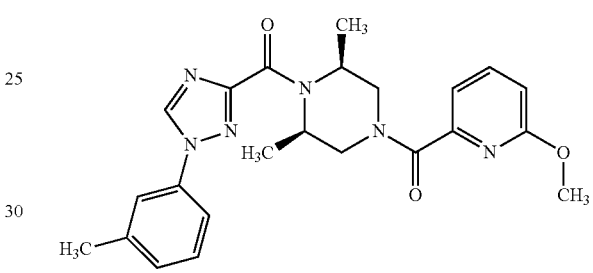

A mixture of 80 mg (0.32 mmol) (3S*,5R*)-3,5-dimethyl-piperazin-1-yl)-(6-methoxy-pyridin-2-yl)-methanone, 65 mg (0.32 mmol) 1-m-tolyl-1H-[1,2,4]triazol-3-carboxylic acid, 0.13 g (0.34 mmol) HATU and 0.10 mL (0.58 mmol) DIPEA in 1.5 mL DMF was stirred at RT for 12 h. The reaction mixture was purified by HPLC.

yield: 60 mg (41%)
ESI-MS: m/z=435 (M+H)$^+$
$R_t$(HPLC): 0.96 min (method 3)

By using the same synthesis strategy as for (2R*,6S*)-4-[(6-methoxypyridin-2-yl)carbonyl]-2,6-dimethyl-1-{[1-(3-methylphenyl)-1H-1,2,4-triazol-3-yl]carbonyl}piperazine the following compound was prepared:

| Ex # | carboxylic acid | product | $R_t$ [min]/ HPLC method | ESI-MS m/z | yield |
| --- | --- | --- | --- | --- | --- |
| 303 | 1-(3-fluoro-phenyl)-1H-[1,2,4]triazole-3-carboxylic acid | | 1.12/6 | 439 (M + H)$^+$ | 60 mg (41%) |

Example 304

{4-[1-(3-Fluoro-phenyl)-1H-[1,2,4]-triazole-3-carbonyl]-4,7-diaza-spiro[2.5]oct-7-yl}-(6-methoxy-pyridin-2-yl)-methanone

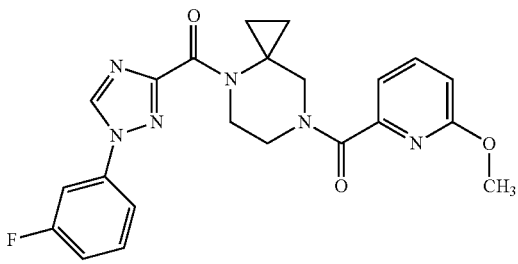 [SMILES: COc1cccc(C(=O)N2CCN(C(=O)c3ncn(-c4cccc(F)c4)n3)C3(CC3)C2)n1]

A mixture of 60 mg (0.23 mmol) (4,7-diaza-spiro[2.5]oct-7-yl)-(6-methoxy-pyridin-2-yl)-methanone, 48 mg (0.23 mmol) 1-(3-fluoro-phenyl)-1H-[1,2,4]triazole-3-carboxylic acid, 80 mg (0.25 mmol) TBTU and 58 μL (0.34 mmol) DIPEA in 1.5 mL DMF was stirred at RT for 2 h. The reaction mixture was purified by HPLC.

yield: 43 mg (43%)

ESI-MS: m/z=437 (M+H)$^+$

R$_t$(HPLC): 1.69 min (method 24 @ 60° C.)

By using the same synthesis strategy as for {4-[1-(3-fluoro-phenyl)-1H-[1,2,4]triazole-3-carbonyl]-4,7-diaza-spiro[2.5]oct-7-yl}-(6-methoxy-pyridin-2-yl)-methanone the following compounds were prepared from 1-(3-fluoro-phenyl)-1H-[1,2,4]triazole-3-carboxylic acid and the respective amine:

| Ex # | amine | product | R$_t$ [min]/ HPLC method | ESI-MS m/z | yield |
|---|---|---|---|---|---|
| 305 | (4,7-diaza-spiro[2.5]oct-7-yl)-(4,5-di-bromo-furan-2-yl)-methanone trifluoroacetate | | 1.25/10 | 552 (M + H)$^+$ | 62 mg (49%) |
| 306 | (5,8-diaza-spiro[3.5]non-8-yl)-(4,5-di-bromo-furan-2-yl)-methanone | | 1.31/4 | 566 (M + H)$^+$ | 10 mg (8%) |
| 307 | (5,8-diaza-spiro[3.5]non-8-yl)-(6-methoxy-pyridin-2-yl)-methanone | | 1.18/3 | 451 (M + H)$^+$ | 34 mg (36%) |

By using the same synthesis strategy as for {4-[1-(3-fluoro-phenyl)-1H-[1,2,4]triazole-3-carbonyl]-4,7-diaza-spiro[2.5]oct-7-yl}-(6-methoxy-pyridin-2-yl)-methanone the following compounds were prepared from (3-chloro-phenyl)-(6,9-diaza-spiro[4.5]dec-9-yl)-methanone trifluoroacetate and the respective carboxylic acid:

| Ex # | carboxylic acid | product | $R_t$ [min]/ HPLC method | ESI-MS m/z | yield |
|---|---|---|---|---|---|
| 308 | 1-(3-chloro-phenyl)-1H-[1,2,4]triazole-3-carboxylic acid | 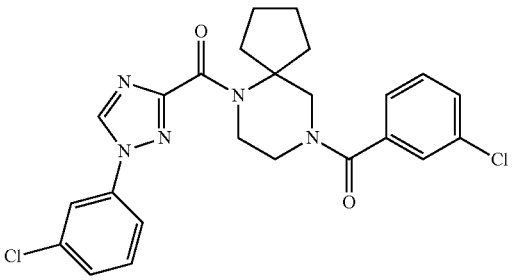 [SMILES: O=C(c1cccc(Cl)c1)N1CCN(C(=O)c2ncn(-c3cccc(Cl)c3)n2)C2(CCCC2)C1] | 1.33/5 | 484 (M + H)⁺ | 28 mg (57%) |
| 309 | 1-phenyl-1H-[1,2,4]triazole-3-carboxylic acid | 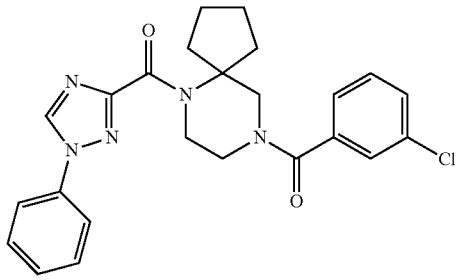 [SMILES: O=C(c1cccc(Cl)c1)N1CCN(C(=O)c2ncn(-c3ccccc3)n2)C2(CCCC2)C1] | 1.26/5 | 450 (M + H)⁺ | 28 mg (61%) |

By using the same synthesis strategy as for {4-[1-(3-fluoro-phenyl)-1H-[1,2,4]triazole-3-carbonyl]-4,7-diaza-spiro[2.5]oct-7-yl}-(6-methoxy-pyridin-2-yl)-methanone the following compounds were prepared from (3-methoxymethyl-3-methyl-piperazin-1-yl)-(6-methoxy-pyridin-2-yl)-methanone and the respective carboxylic acid:

| Ex # | carboxylic acid | product | $R_t$ [min]/ HPLC method | ESI-MS m/z | yield |
|---|---|---|---|---|---|
| 310 | 1-m-tolyl-1H-[1,2,4]-triazol-3-carboxylic acid | 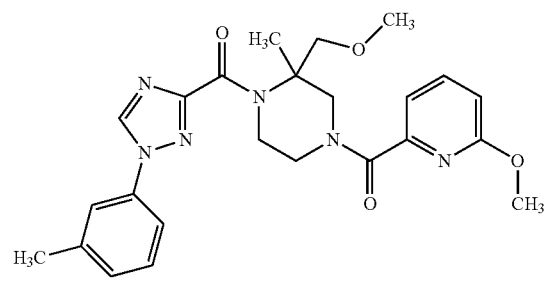 | 1.20/21 | 465 (M + H)⁺ | 19 mg (36%) |
| 311 | 1-(3-chloro-phenyl)-1H-[1,2,4]triazole-3-carboxylic acid | 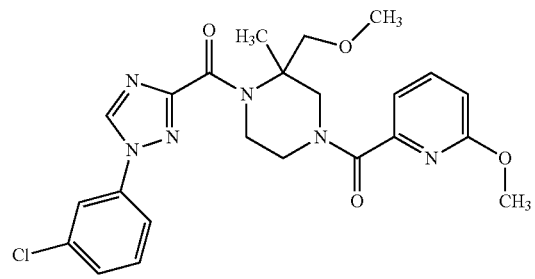 [SMILES: COCC1(C)CN(C(=O)c2cccc(OC)n2)CCN1C(=O)c1ncn(-c2cccc(Cl)c2)n1] | 0.99/21 | 485 (M + H)⁺ | 8 mg (15%) |

Example 312

(3-Chloro-phenyl)-{4-[1-(3-chloro-phenyl)-1H-[1,2,4]triazole-3-carbonyl]-3,3-diethyl-piperazin-1-yl}-methanone

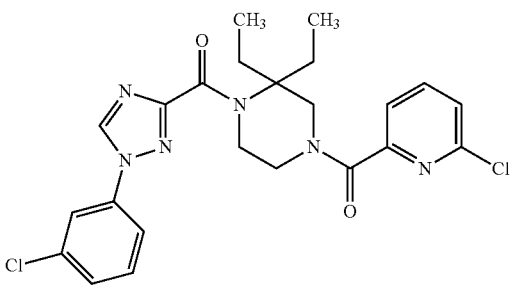 [SMILES: CCC1(CC)CN(C(=O)c2cccc(Cl)n2)CCN1C(=O)c1ncn(-c2cccc(Cl)c2)n1]

A mixture of 40 mg (0.18 mmol)-(3-chloro-phenyl)-1H-[1,2,4]-tri-azole-3-carboxylic acid and 30 µL (0.23 mmol) 1-chloro-N,N,2-trimethylpropylamine in 1.0 mL THF was stirred at RT for 2 h, 50 mg (0.18 mmol) (3-chloro-phenyl)-(1,4-diaza-spiro[5.5]undec-4-yl)-methanone trifluoroacetate and 0.10 mL (0.58 mmol) DIPEA were added and the mixture was stirred at RT for 45 min. The solvent was removed by distillation and the residue was purified by HPLC.

yield: 35 mg (73%)
ESI-MS: m/z=486 (M+H)$^+$
R$_t$(HPLC): 1.32 min (method 5)

By using the same synthesis strategy as for (3-chloro-phenyl)-[1-(1-phenyl-1H-[1,2,4]-triazole-3-carbonyl)-1,4-diaza-spiro[5.5]undec-4-yl]-methanone the following compounds were prepared from (3-chloro-phenyl)-(3,3-diethyl-piperazin-1-yl)-methanone trifluoroacetate as amine and the respective carboxylic acid:

| Ex # | carboxylic acid | product | R$_t$ [min]/ HPLC method | ESI-MS m/z | yield |
|---|---|---|---|---|---|
| 313 | 1-phenyl-1H-[1,2,4]triazole-3-carboxylic acid | 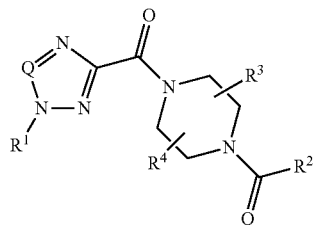 | 1.26/5 | 452 (M + H)$^+$ | 37 mg (46%) | nitro, amino, C$_{1-5}$alkyl, C$_{3-6}$cycloalkyl, —O—C$_{1-5}$alkyl, —N(R$^5$)(R$^6$) and —C(O)N(R$^5$)(R$^6$) which latter five groups are optionally substituted with one or more fluorine atoms;

R$^2$ represents a 6-14-membered aryl or 5-14-membered heteroaryl which latter two groups are optionally substituted with 1 to 4 groups selected from —OH, halogen, cyano, 4-9-membered heterocyclyl, C$_{6-10}$ aryl, 5-9 membered heteroaryl, C$_{1-5}$alkyl, —C$_{1-5}$alkyl-OH, —O—C$_{1-5}$-alkyl, —O—C$_{1-5}$alkyl-O—C$_{1-5}$-alkyl, C$_{3-5}$ alkynyl, —C$_{1-5}$alkyl-O—C$_{1-5}$alkyl, C$_{3-7}$cycloalkyl, —O—C$_{3-7}$cycloalkyl, —O—CH$_2$—C$_{3-7}$cycloalkyl, C$_{1-5}$alkyl-CO—, —C$_{1-5}$alkyl-N(R$^5$)(R$^6$), —N(R$^5$)(R$^6$) and —S(O)$_2$—C$_{1-5}$alkyl which latter sixteen groups are optionally substituted with one or more fluorine atoms;

R$^3$ and R$^4$ independently represent hydrogen, C$_{1-3}$alkyl and —C$_{1-3}$alkyl-O—C$_{1-3}$alkyl which latter three groups are optionally substituted with one or more fluorine atoms, with the proviso that R$^3$ and R$^4$ both are not hydrogen;

or

R$^3$ and R$^4$ if both are attached to the same carbon atom, they may together with the carbon atom to which they are attached form a ring selected from the group consisting of cyclopropyl, cyclobutyl, cyclopentyl, and cyclohexyl, which groups are optionally substituted with one or more fluorine atoms;

R$^5$ and R$^6$ independently represent hydrogen, C$_{1-5}$alkyl, benzyl, —C(O)—C$_{1-5}$alkyl, —C(S)—C$_{1-5}$alkyl and —S(O)$_2$—C$_{1-5}$alkyl which latter five groups are optionally substituted with one or more fluorine atoms, or R$^5$ and R$^6$ together with the nitrogen atom to which they are attached form a 4-6-membered heterocyclyl ring optionally substituted with one or more fluorine atoms;

Q represents CH or N;

or a physiologically acceptable salt thereof.

2. The compound according to claim 1, namely a compound of formula Ia

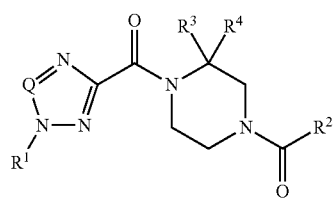

in which

R$^1$, R$^2$, R$^3$, R$^4$, Q have the same meaning as defined in claim 1;

The invention claimed is:
1. A compound of formula I

I in which

R$^1$ represents phenyl or pyridyl which latter two groups are optionally substituted with one to three groups selected independently of one another from halogen, cyano, or a salt thereof, particularly a physiologically acceptable salt thereof.

3. The compound according to claim 1, wherein R¹ represents phenyl,

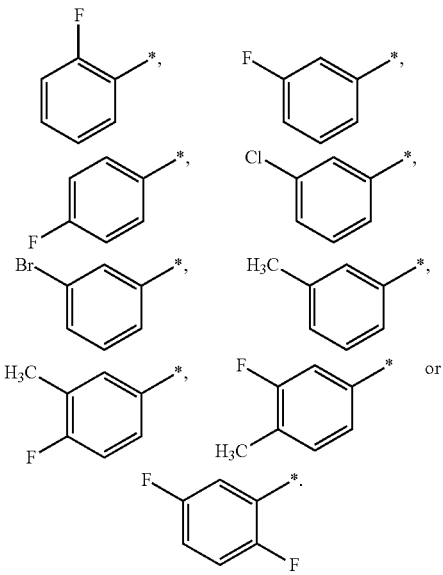

4. The compound according to claim 3, wherein
R³ and R⁴ independently represent hydrogen, methyl, ethyl, propyl or —CH₂—O—CH₃ which latter four groups are optionally substituted with one or more fluorine atoms with the proviso that R³ and R⁴ both are not hydrogen;
or
R³ and R⁴ if both are attached to the same carbon atom, they may together with the carbon atom to which they are attached form a ring selected from cyclopropyl, cyclobutyl and cyclopentyl which latter three groups are optionally substituted with one or more fluorine atoms.

5. The compound according to claim 4, wherein
R³ and R⁴ represent methyl.

6. The compound according to claim 1, namely a compound of formula Ib

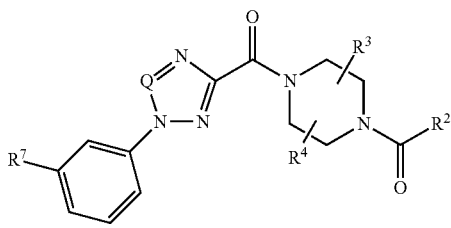

in which
R⁷ represents hydrogen, halogen, cyano, nitro, amino, $C_{1-5}$alkyl, $C_{3-6}$cycloalkyl, —O—$C_{1-5}$alkyl, —N(R⁵)(R⁶) or —C(O)N(R⁵)(R⁶) which latter five groups are optionally substituted with one or more fluorine atoms;
R⁵ and R⁶ independently represent hydrogen, $C_{1-3}$alkyl, benzyl or —C(O)—$C_{1-3}$alkyl, which latter three groups are optionally substituted with one or more fluorine atoms,
or
R⁵ and R⁶ together with the nitrogen atom to which they are attached form a group selected from azetidinyl, pyrrolidinyl, piperidinyl and morpholinyl which latter four groups are optionally substituted with one or more fluorine atoms.
or a physiologically acceptable salt thereof.

7. The compound according to claim 1, namely a compound of formula Ic

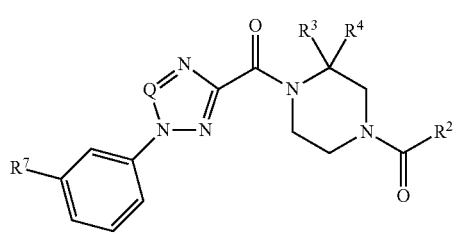

in which
R⁷ represents hydrogen, halogen, cyano, nitro, amino, $C_{1-5}$alkyl, $C_{3-6}$cycloalkyl, —O—$C_{1-5}$alkyl, —N(R⁵)(R⁶) or —C(O)N(R⁵)(R⁶) which latter five groups are optionally substituted with one or more fluorine atoms;
R⁵ and R⁶ independently represent hydrogen, $C_{1-3}$alkyl, benzyl or —C(O)—$C_{1-3}$alkyl, which latter three groups are optionally substituted with one or more fluorine atoms,
or
R⁵ and R⁶ together with the nitrogen atom to which they are attached form a group selected from azetidinyl, pyrrolidinyl, piperidinyl and morpholinyl which latter four groups are optionally substituted with one or more fluorine atoms.
or a physiologically acceptable salt thereof.

8. The compound according to claim 2, 6 or 7, wherein
R² represents phenyl, naphthyl, 3-isoquinolyl,

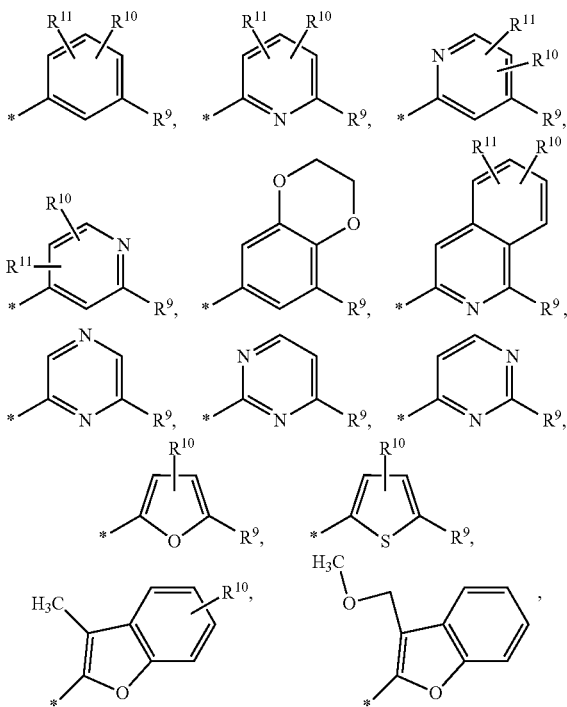

-continued

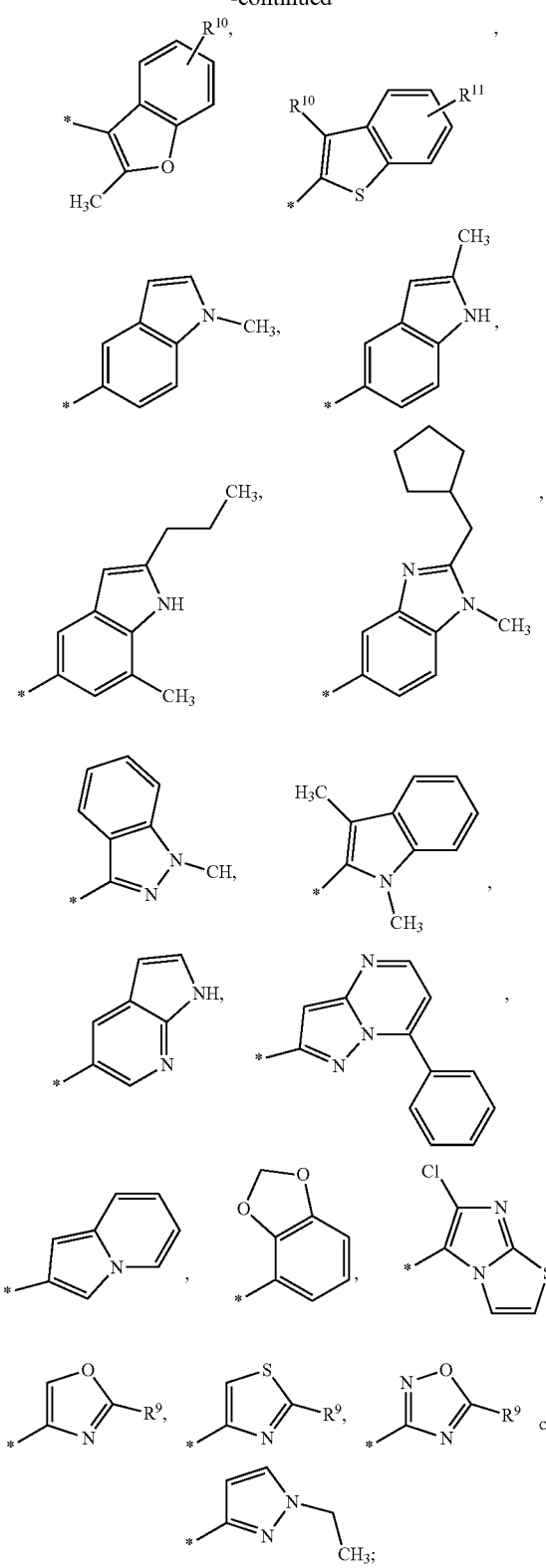

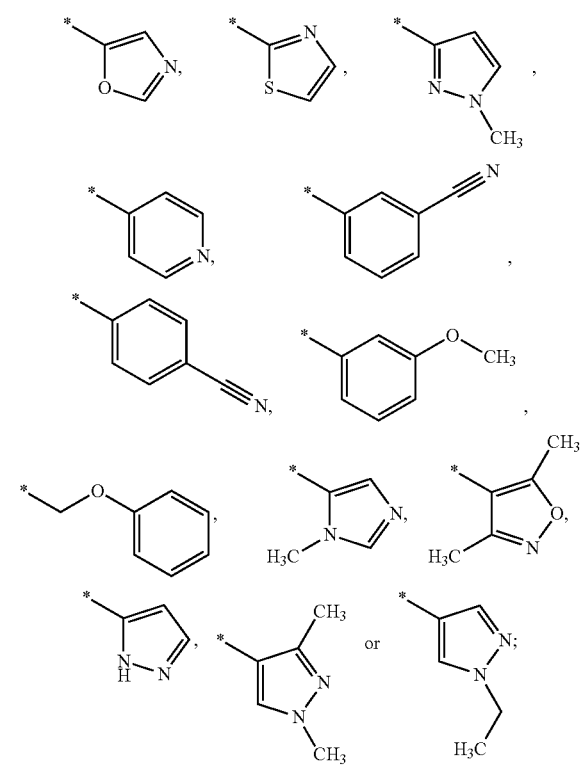

R⁹ represents fluoro, chloro, bromo, cyano, $C_{1-4}$-alkyl, $C_{3-6}$-cycloalkyl, —O—$C_{3-6}$cycloalkyl, —O—$CH_2$—$C_{3-6}$cycloalkyl, 4-6-membered heterocyclyl, —O—$C_{1-4}$-alkyl, —O—$CH_2$-ethynyl, —O—$C_{1-2}$alkyl-O—$C_{1-2}$alkyl, $CF_3$, —O—$CF_3$, $CF_2H$, —$NMe_2$, phenyl, $R^{10}$, $R^{11}$ independently represents hydrogen, chloro, fluoro, methyl, ethyl, propyl, iso-propyl, $CF_3$, —$CF_2H$, —$OCH_3$, —$OCF_3$ or —NH—$COCH_3$.

9. A compound of formula II

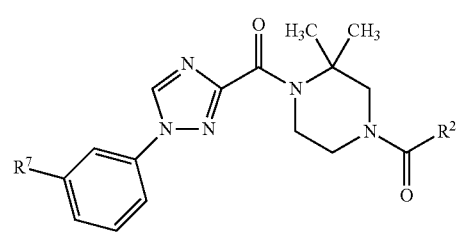

in which
R² represents phenyl, naphthyl, 3-isoquinolyl,

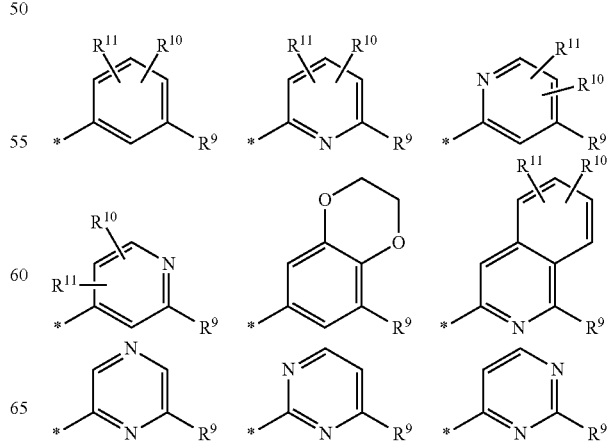

-continued

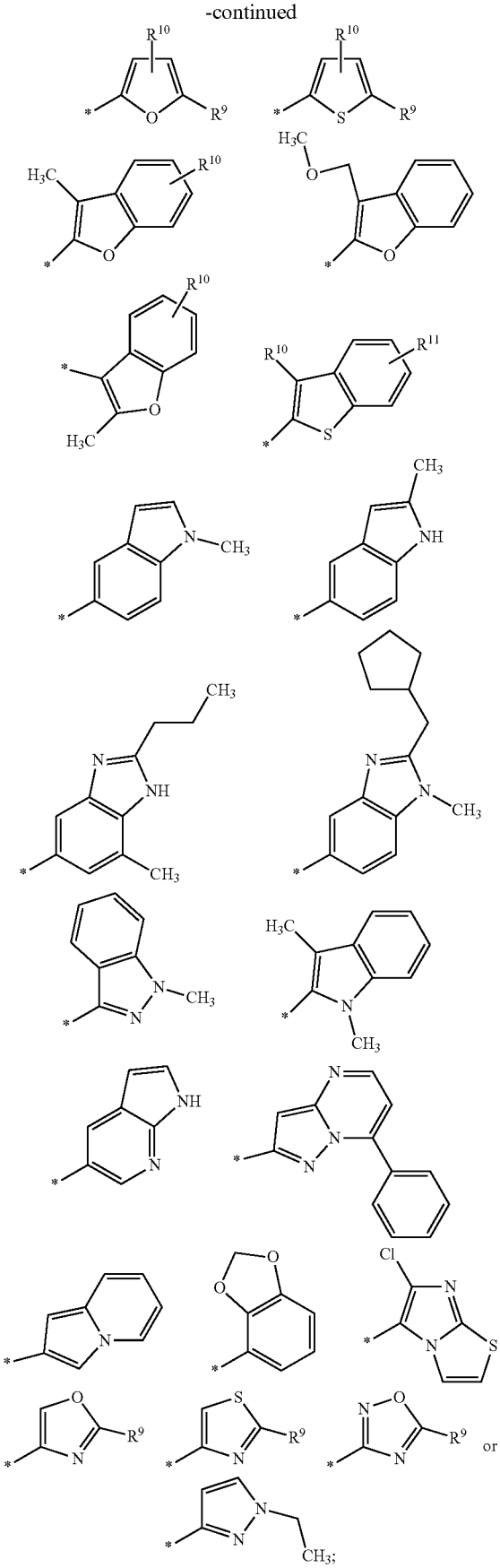

R[7] represents hydrogen, fluoro, bromo, chloro, cyano or methyl;

R[9] represents fluoro, chloro, bromo, cyano, $C_{1-4}$-alkyl, $C_{3-6}$-cycloalkyl, —O—$C_{3-6}$cycloalkyl, —O—$CH_2$—$C_{3-6}$cycloalkyl, 4-6-membered heterocyclyl, —O—$C_{1-4}$-alkyl, —O—$CH_2$-ethynyl, —O—$C_{1-2}$alkyl-O—$C_{1-2}$alkyl, $CF_3$, —O—$CF_3$, $CF_2H$, —$NMe_2$, phenyl,

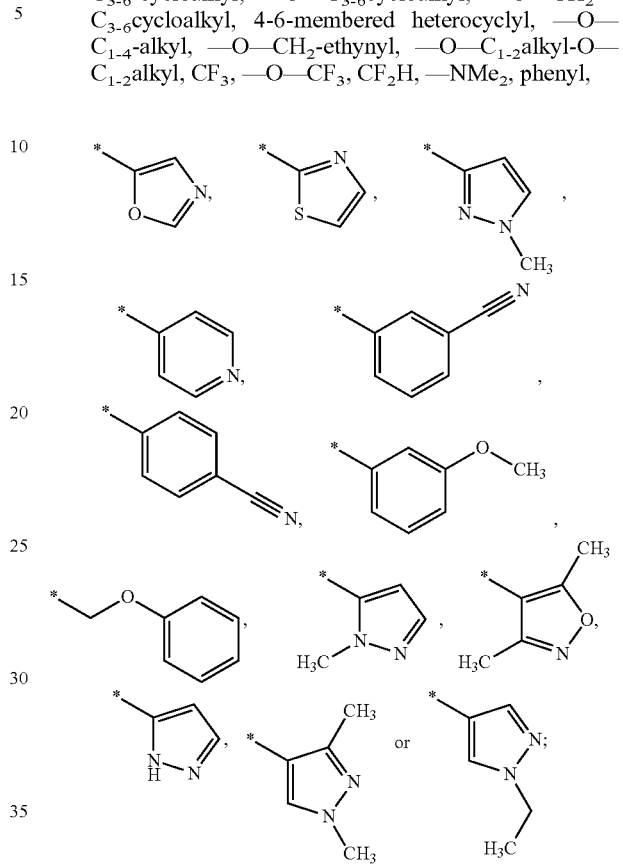

R[10], R[11] independently represents hydrogen, chloro, fluoro, methyl, ethyl, propyl, iso-propyl, $CF_3$, —$CF_2H$, —$OCH_3$, —$OCF_3$ or —NH—$COCH_3$;

or a physiologically acceptable salt thereof.

10. A compound according to formula III

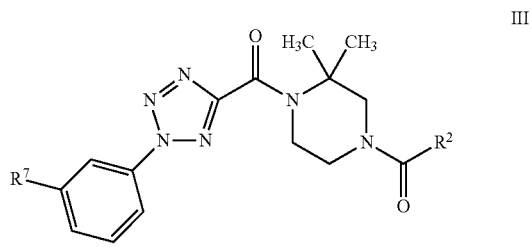

in which

R[2] represents phenyl, naphthyl, 3-isoquinolyl,

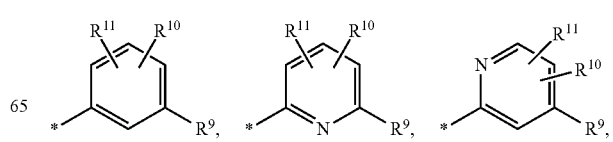

-continued

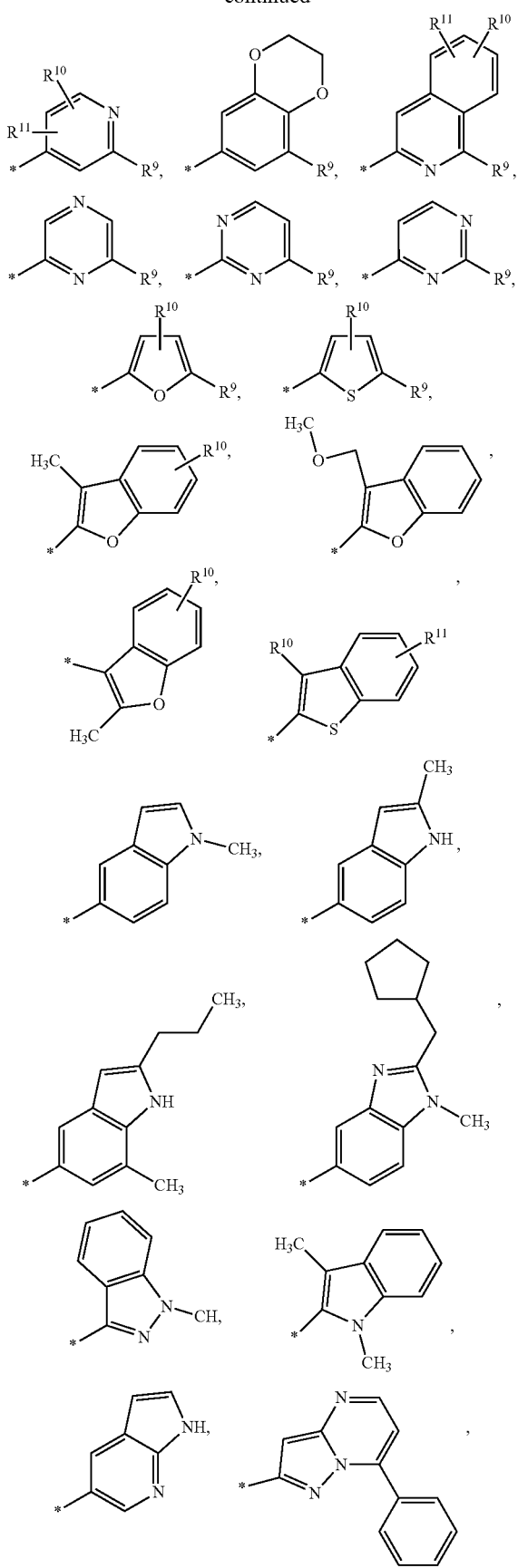

-continued

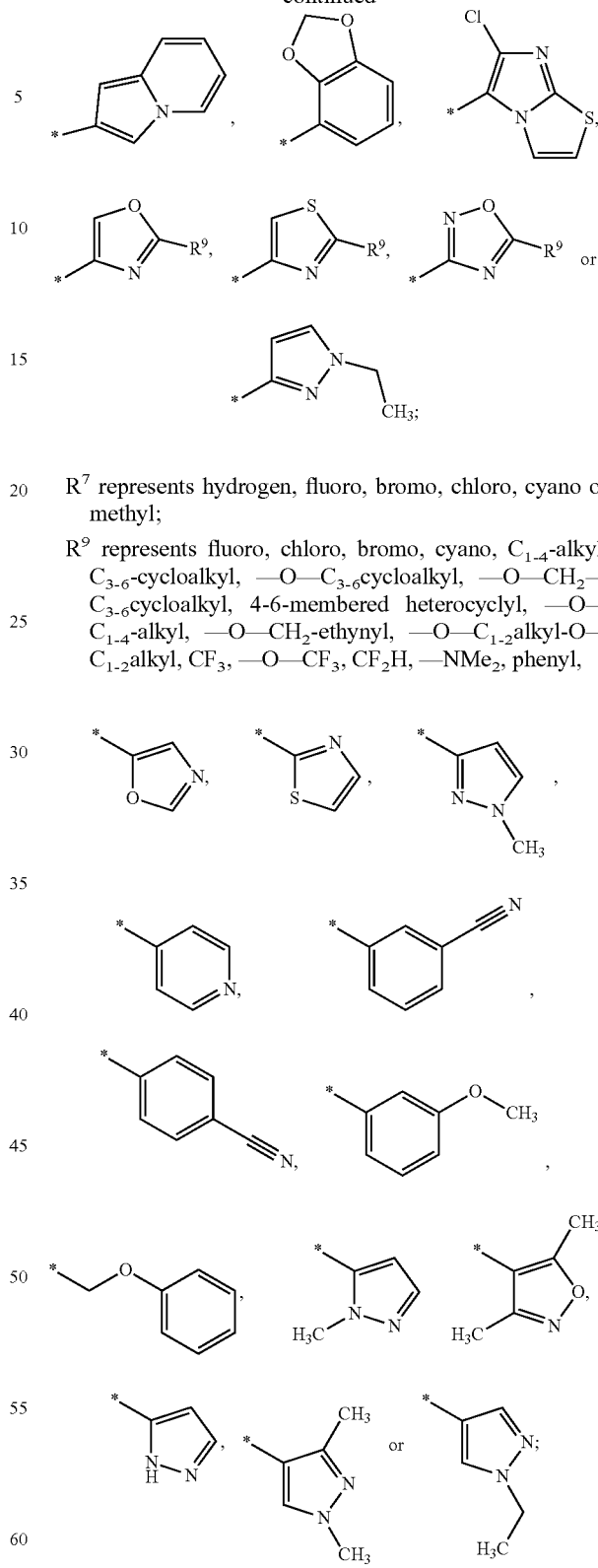

$R^7$ represents hydrogen, fluoro, bromo, chloro, cyano or methyl;

$R^9$ represents fluoro, chloro, bromo, cyano, $C_{1-4}$-alkyl, $C_{3-6}$-cycloalkyl, —O—$C_{3-6}$-cycloalkyl, —O—$CH_2$—$C_{3-6}$cycloalkyl, 4-6-membered heterocyclyl, —O—$C_{1-4}$-alkyl, —O—$CH_2$-ethynyl, —O—$C_{1-2}$alkyl-O—$C_{1-2}$alkyl, $CF_3$, —O—$CF_3$, $CF_2H$, —$NMe_2$, phenyl, $R^{10}$, $R^{11}$ independently represents hydrogen, chloro, fluoro, methyl, ethyl, propyl, iso-propyl, $CF_3$, —$CF_2H$, —$OCH_3$, —$OCF_3$ or —NH—$COCH_3$;

or a physiologically acceptable salt thereof.

11. The compound according to any one of claim 1, wherein
R[1] represents phenyl,
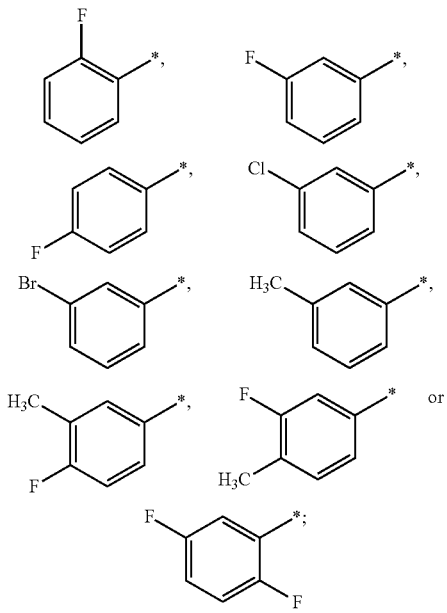
R[2] represents
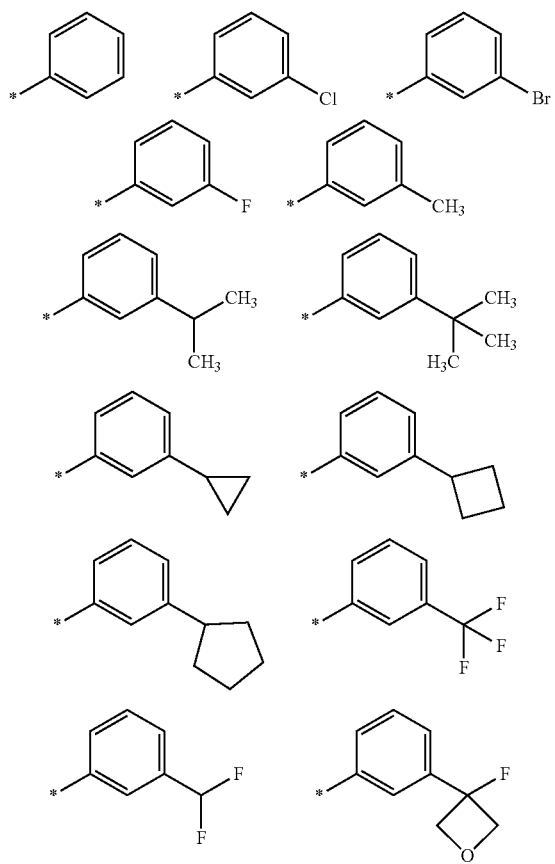
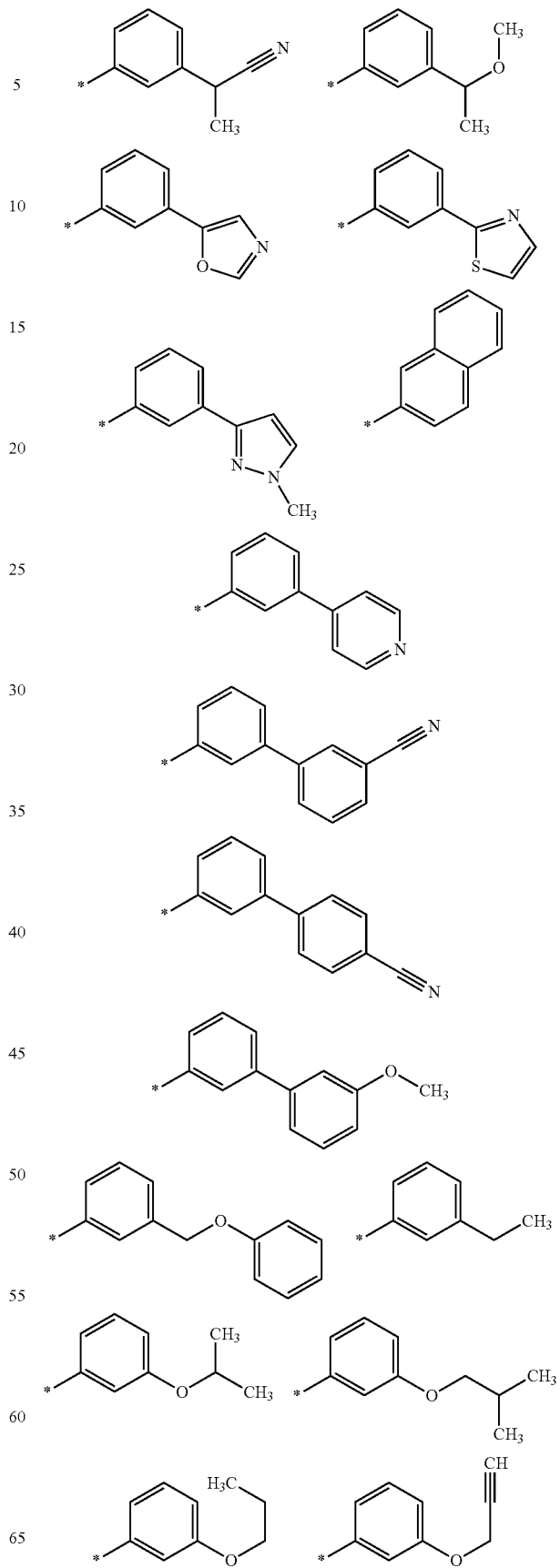

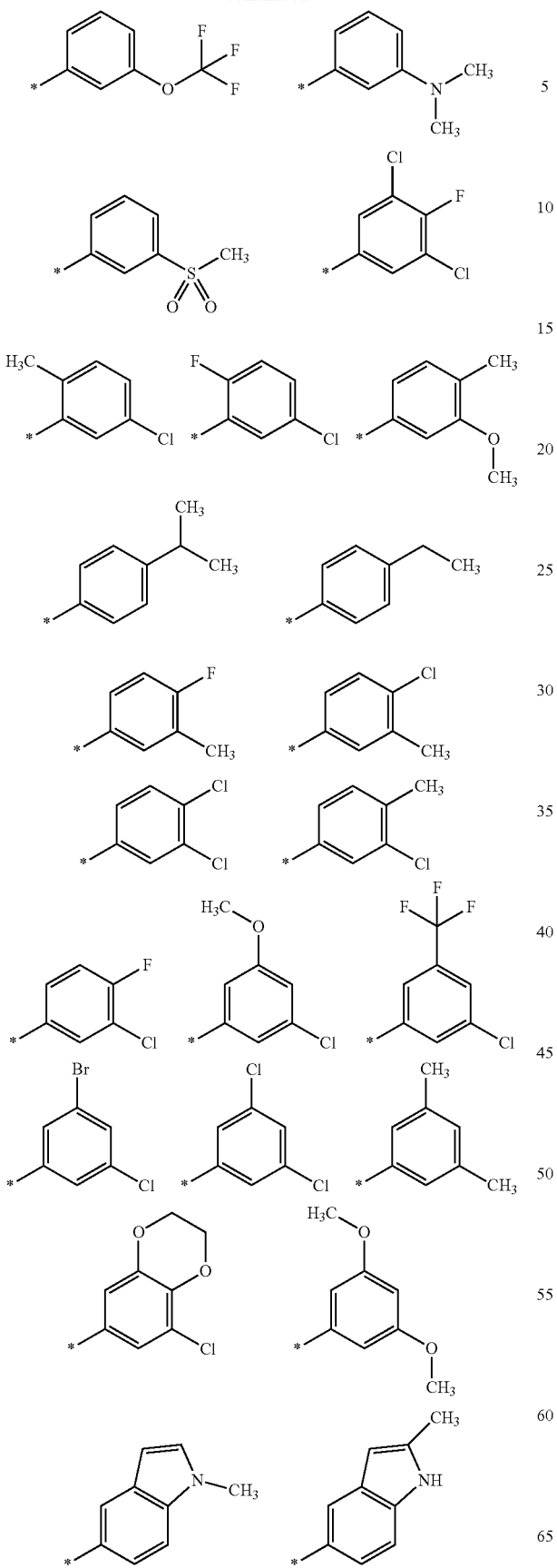
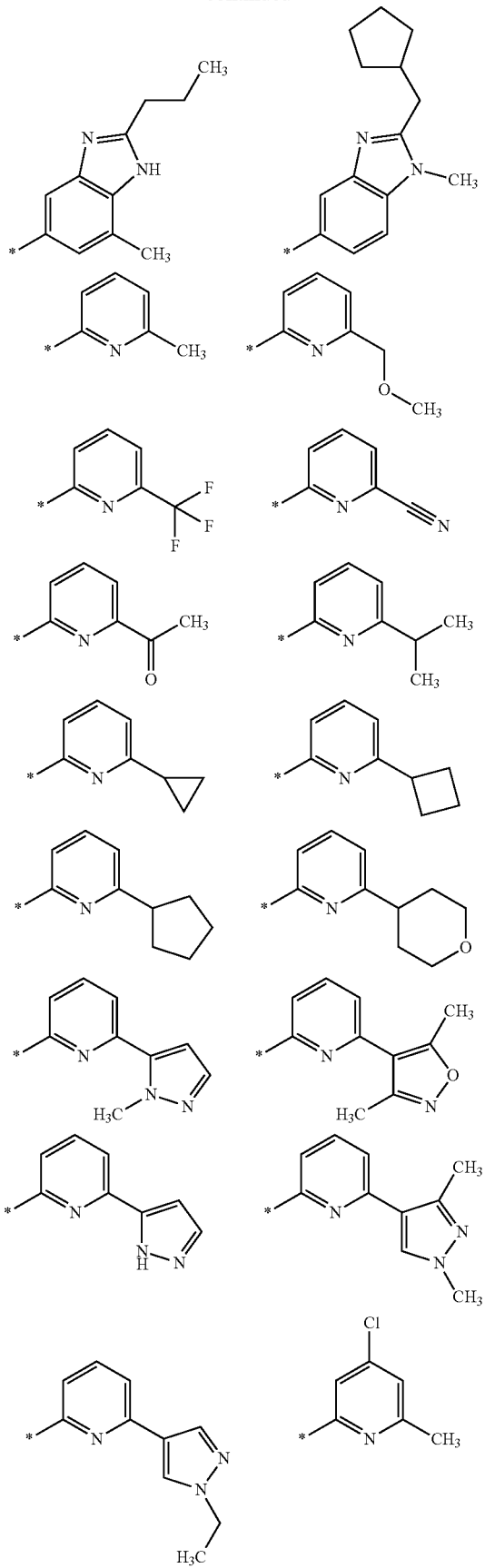

241
-continued
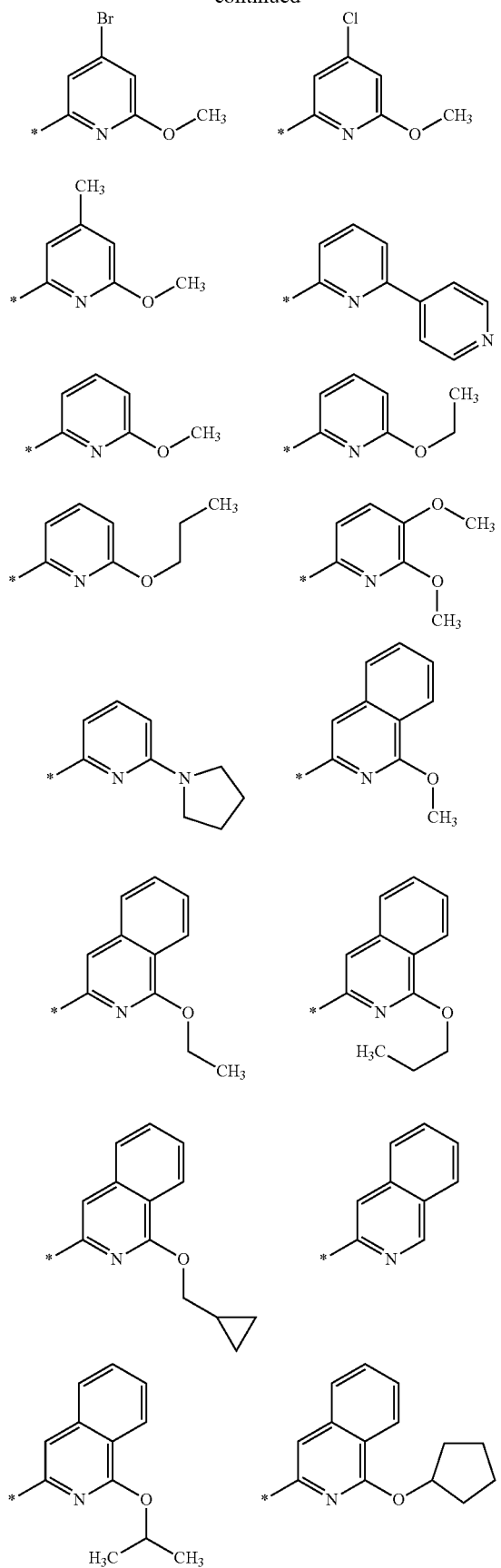
242
-continued
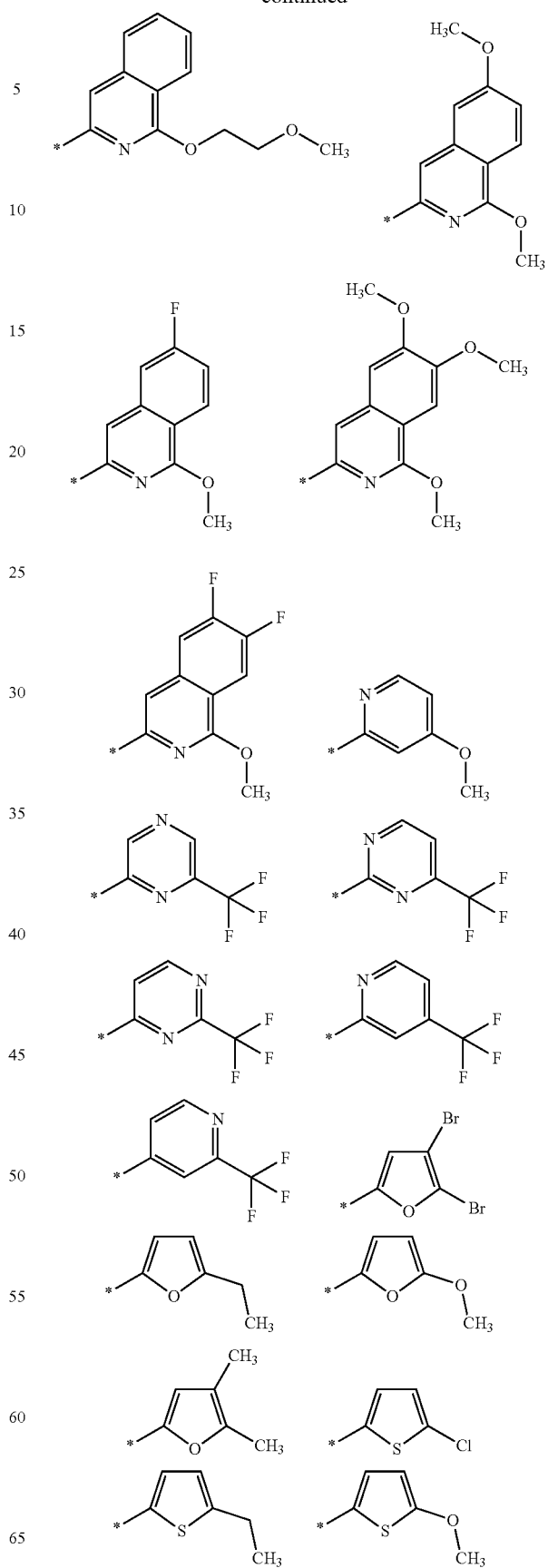

243
-continued

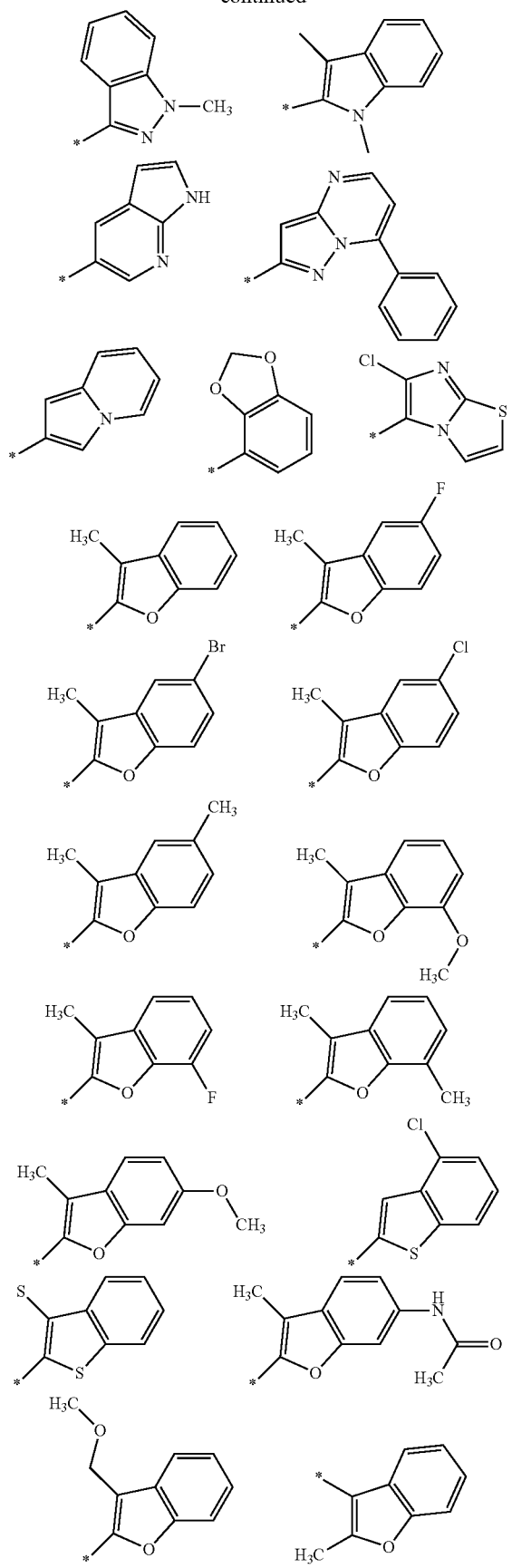

244
-continued

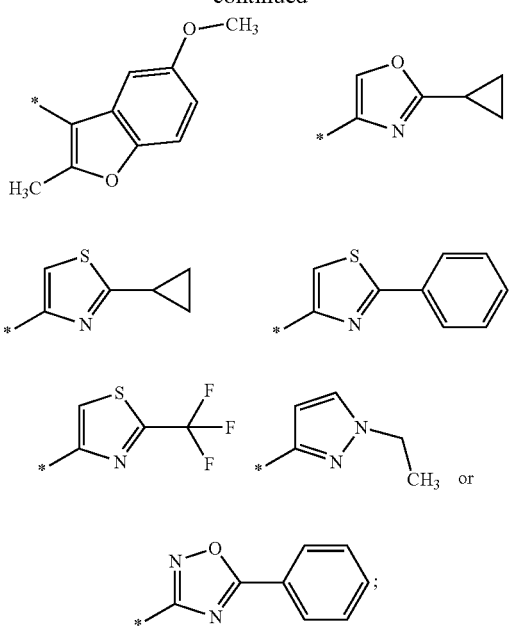

R³ and R⁴ independently represent hydrogen, methyl, ethyl, propyl or —CH₂—O—CH₃ which latter four groups are optionally substituted with one or more fluorine atoms with the proviso that R³ and R⁴ both are not hydrogen;

or

R³ and R⁴ if both are attached to the same carbon atom, they may together with the carbon atom to which they are attached form a ring selected from cyclopropyl, cyclobutyl and cyclopentyl which latter three groups are optionally substituted with one or more fluorine atoms;

or a physiologically acceptable salt thereof.

12. A compound selected from the group consisting of

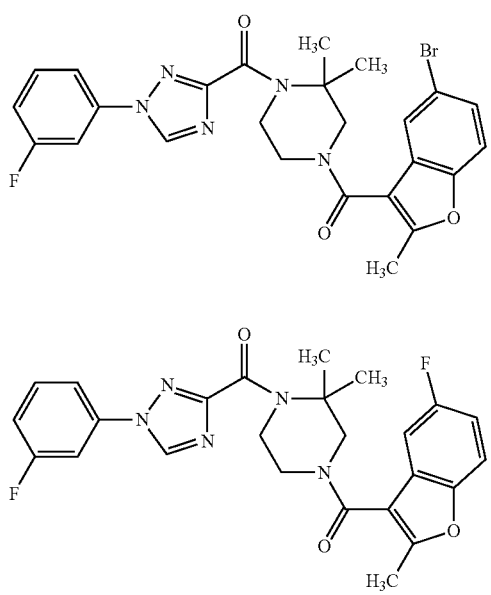

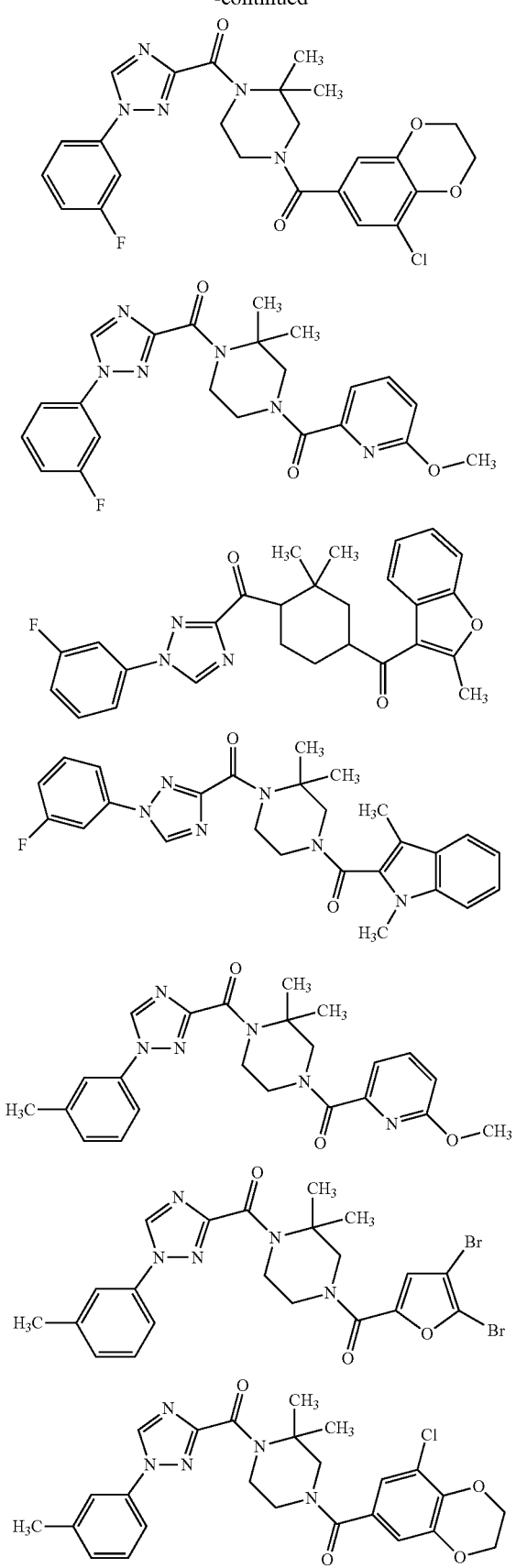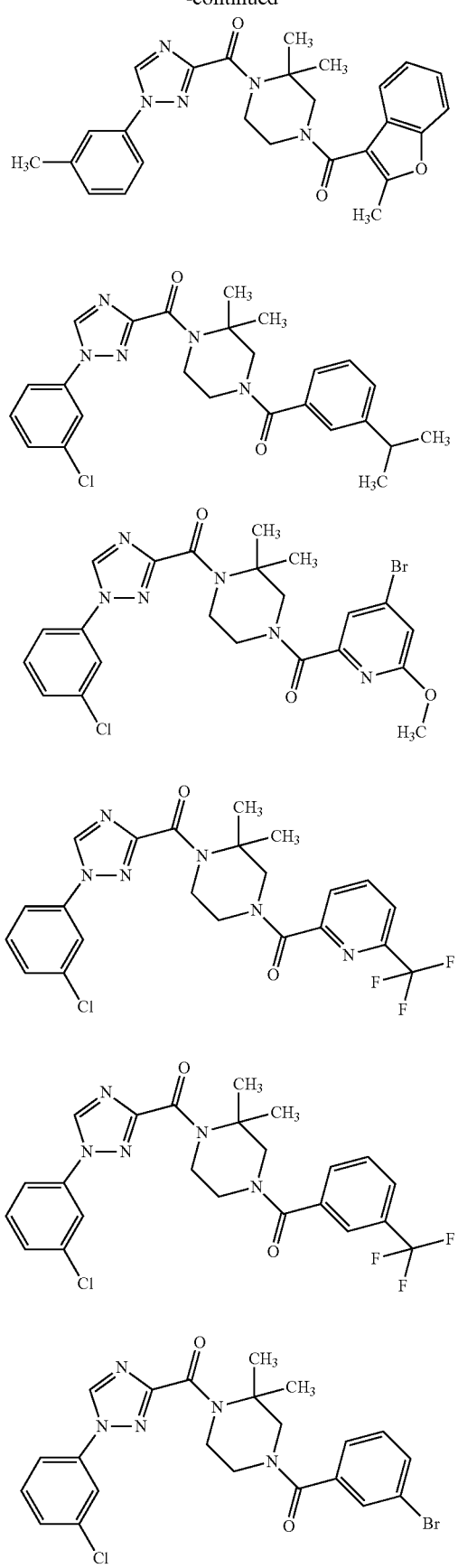

247
-continued
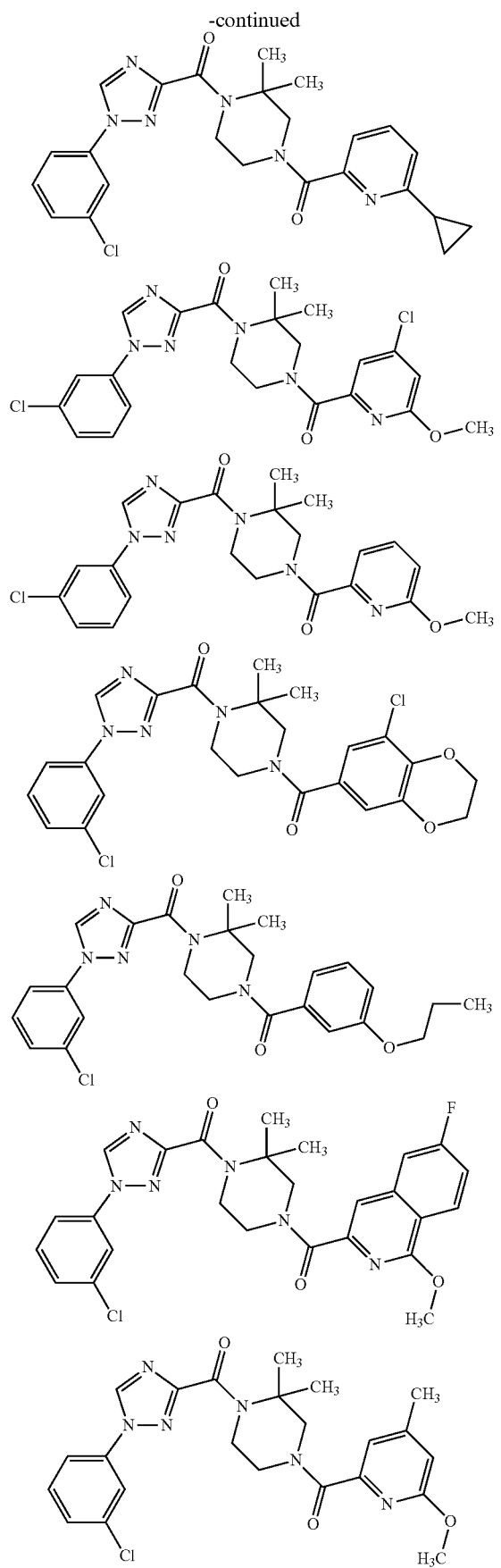
248
-continued
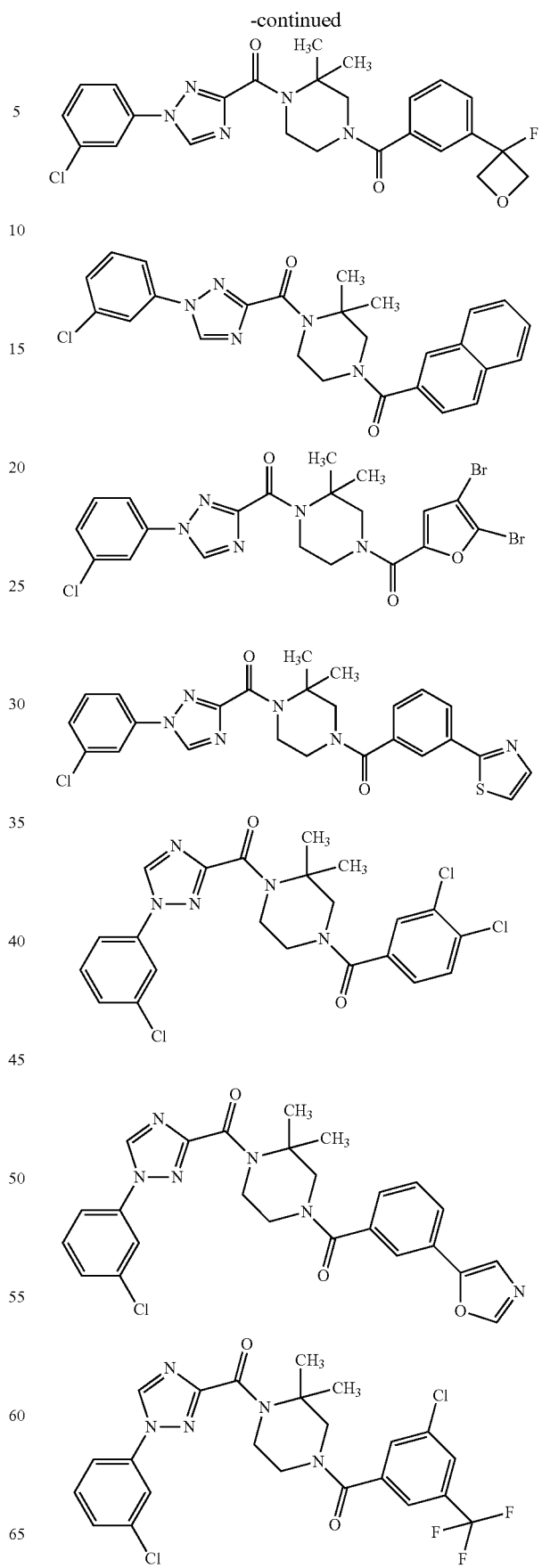

| 249 | 250 |
|---|---|
| -continued | -continued |
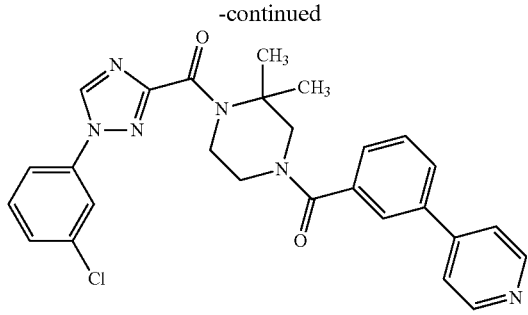
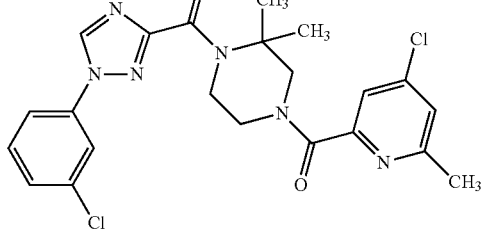
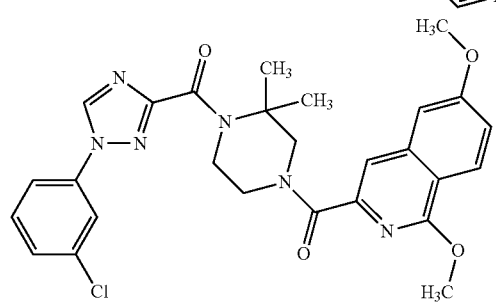
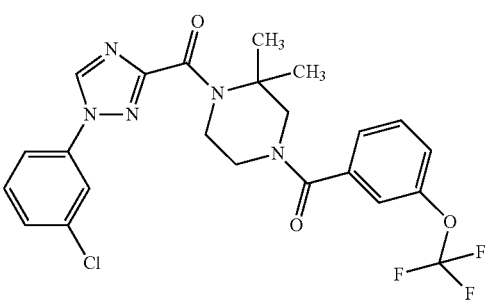
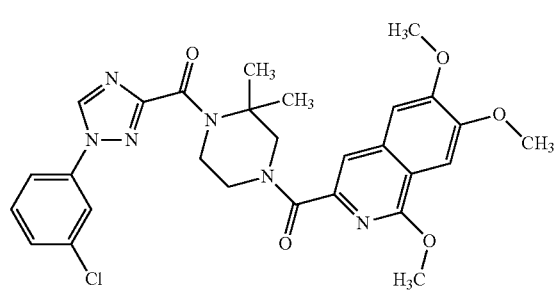
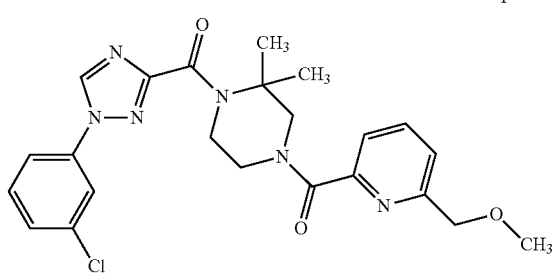
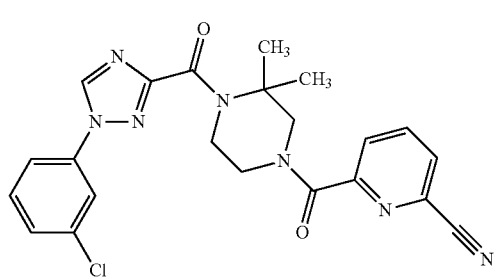
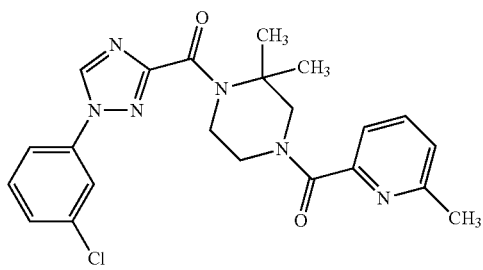
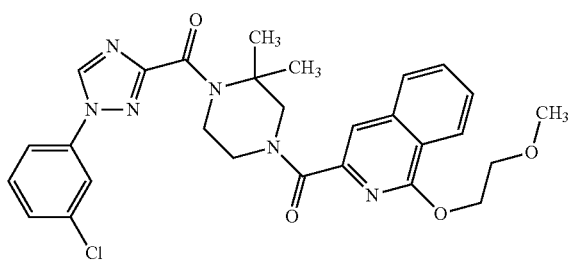
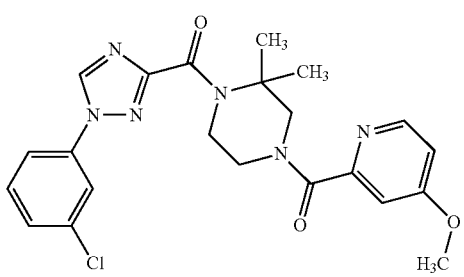
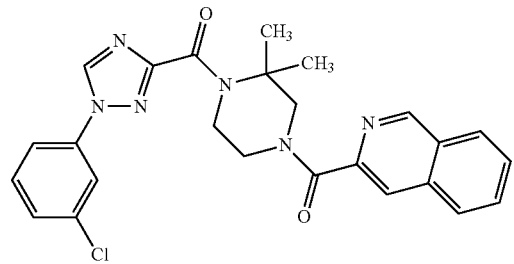
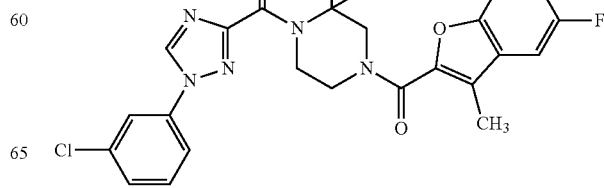

251
-continued
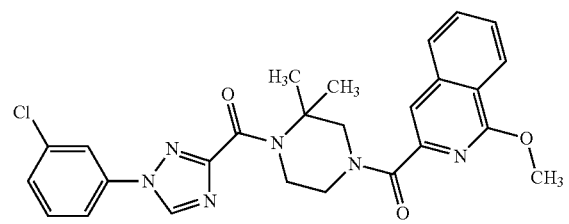
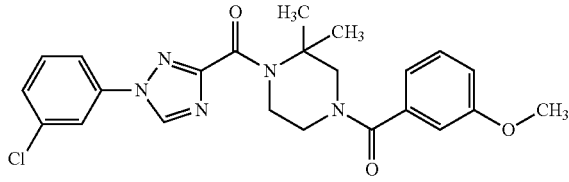
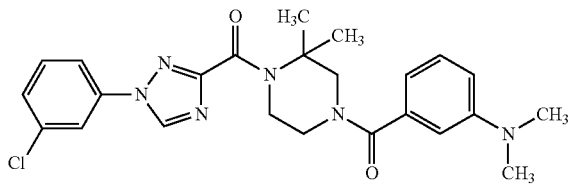
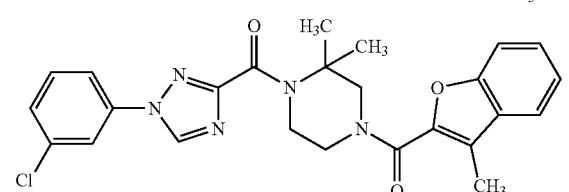
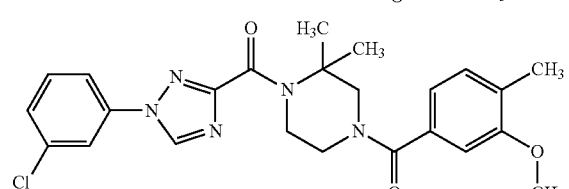
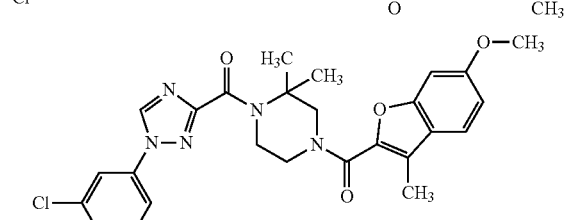
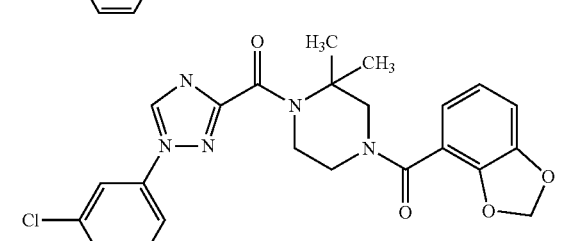
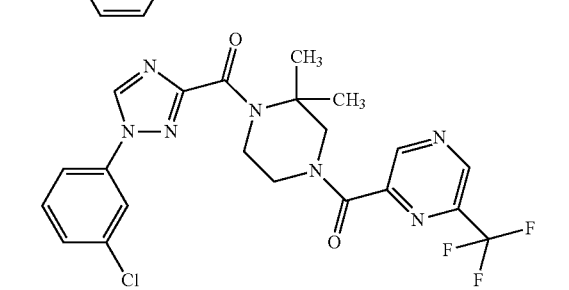
252
-continued
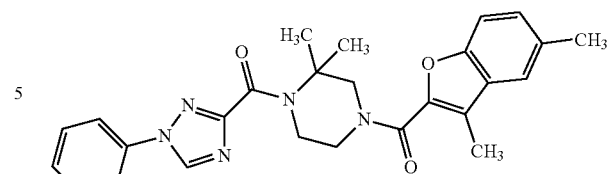
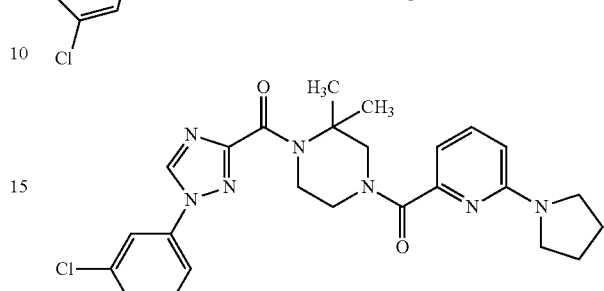
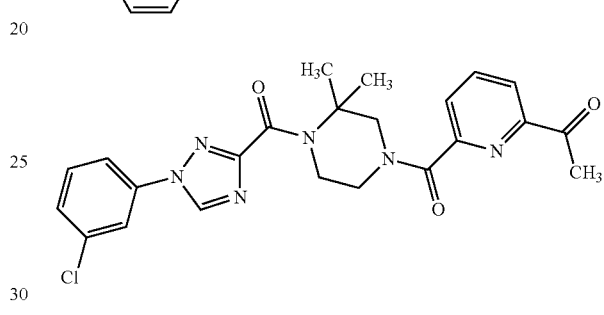
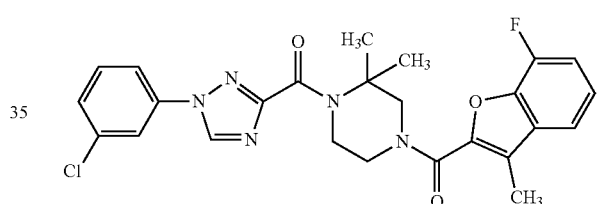
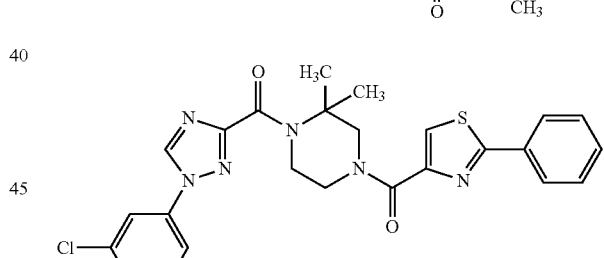
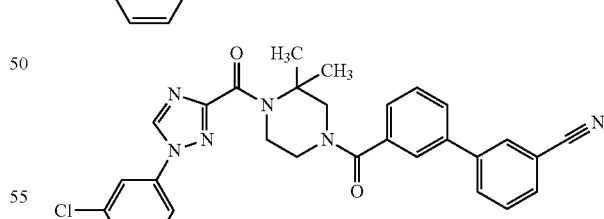
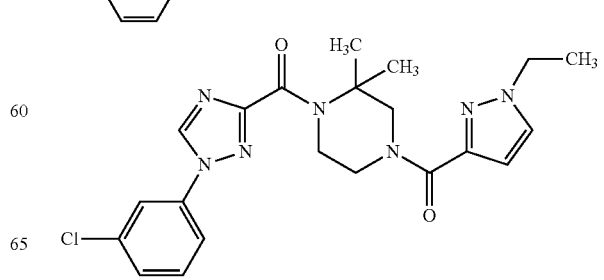

253
-continued
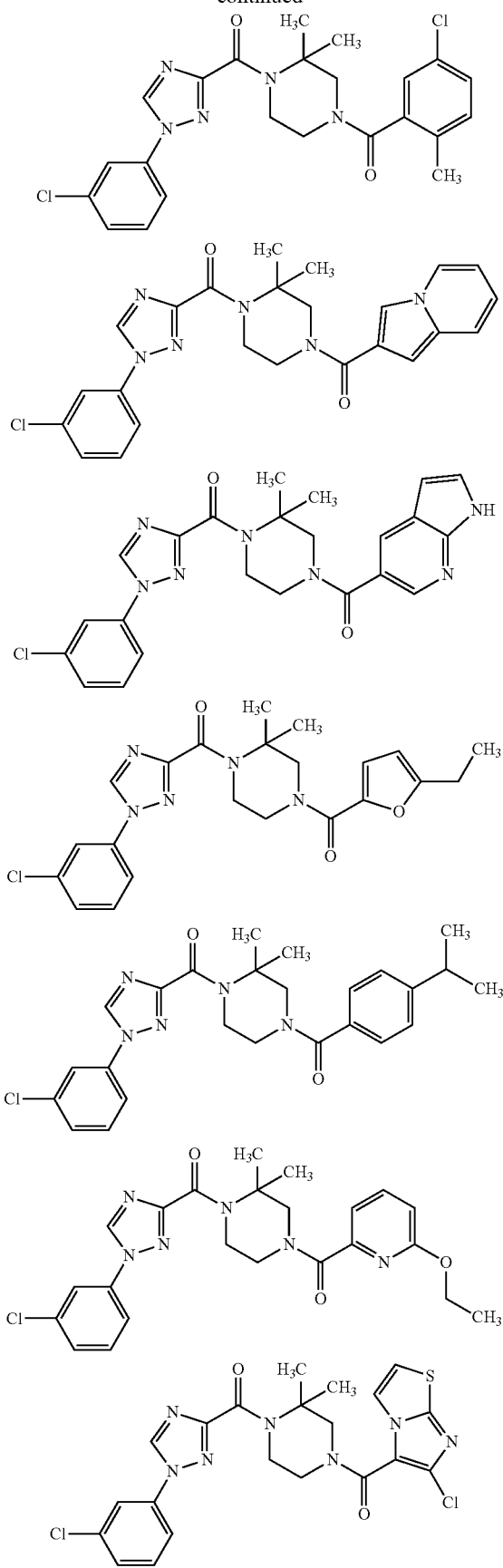
254
-continued
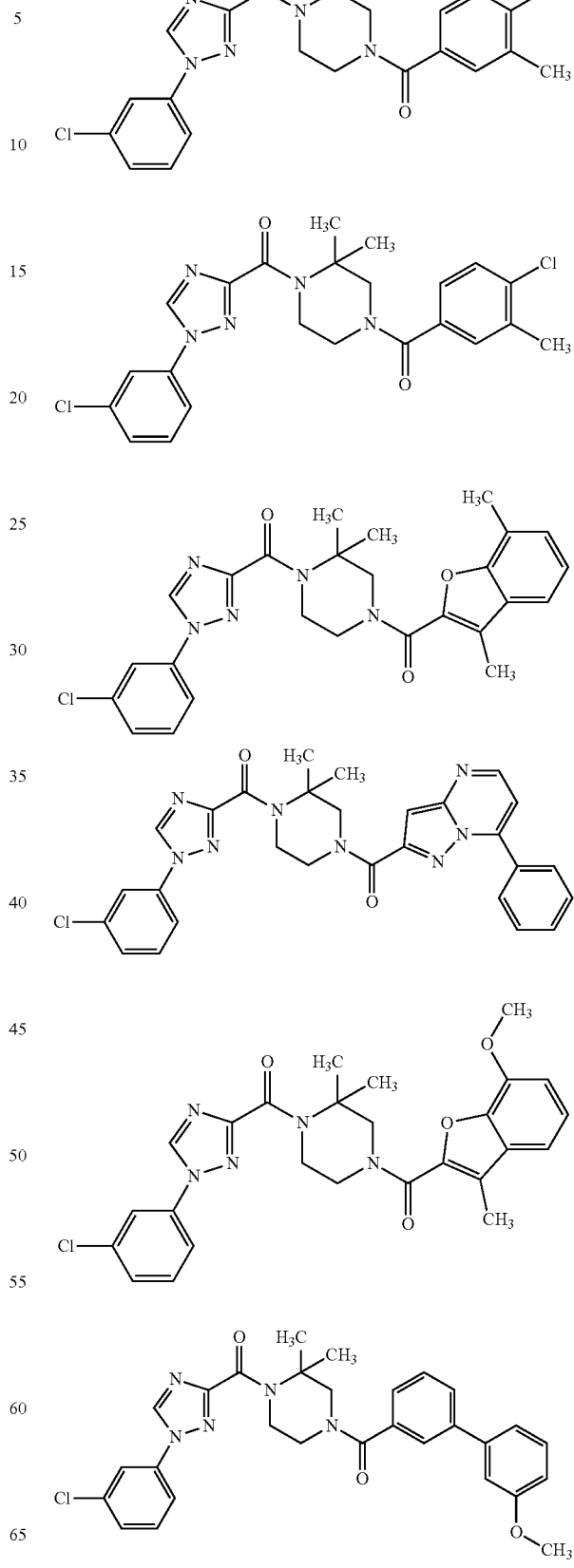

255
-continued
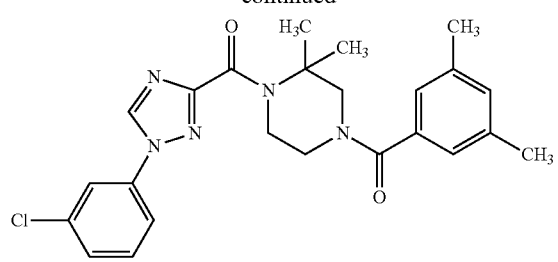
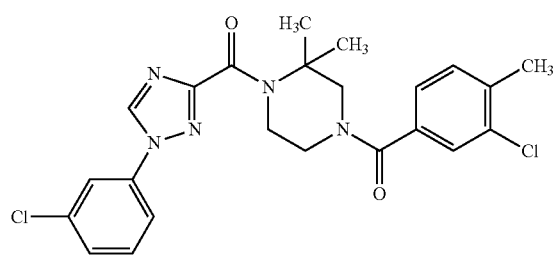
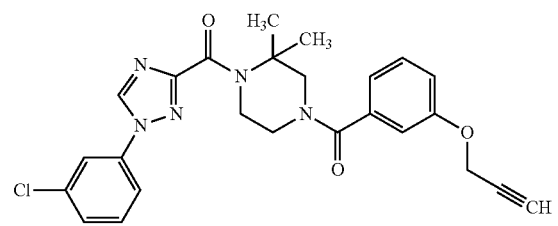
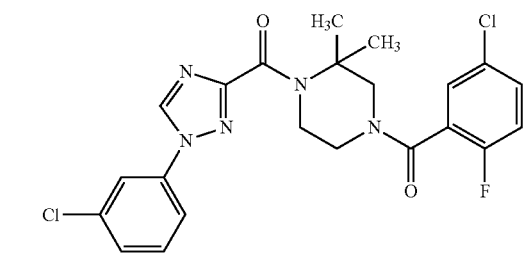
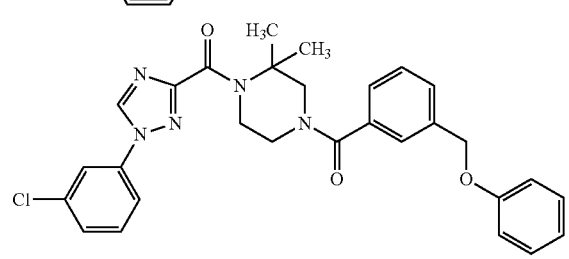
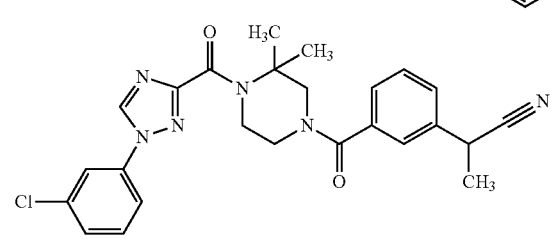
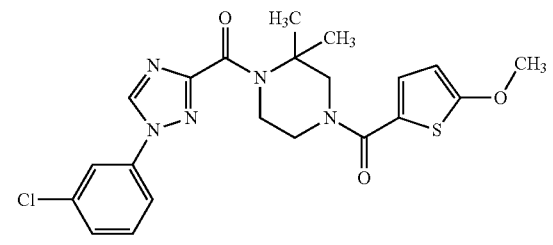
256
-continued
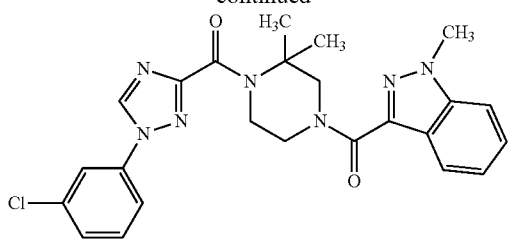
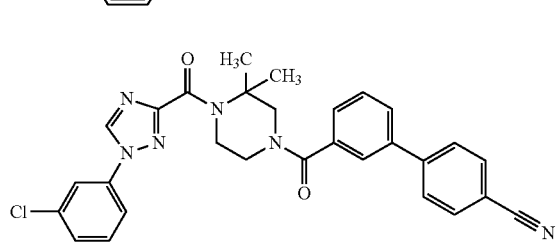
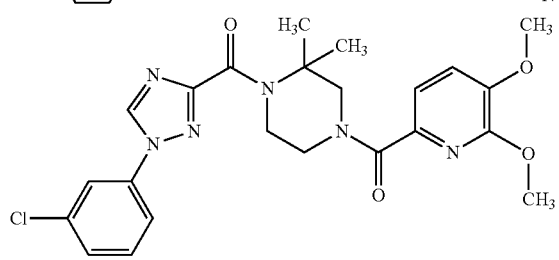
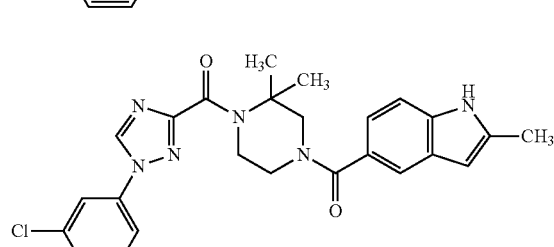
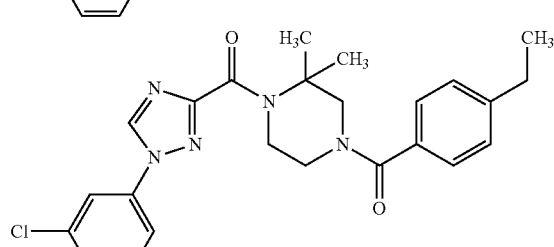
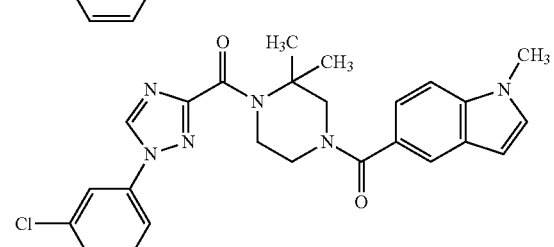
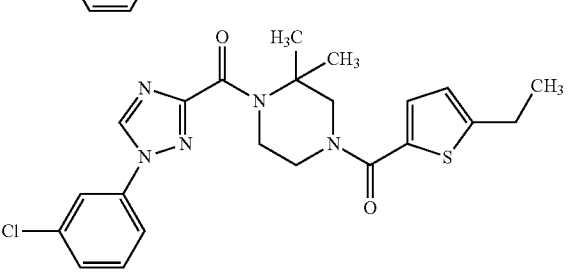

257
-continued
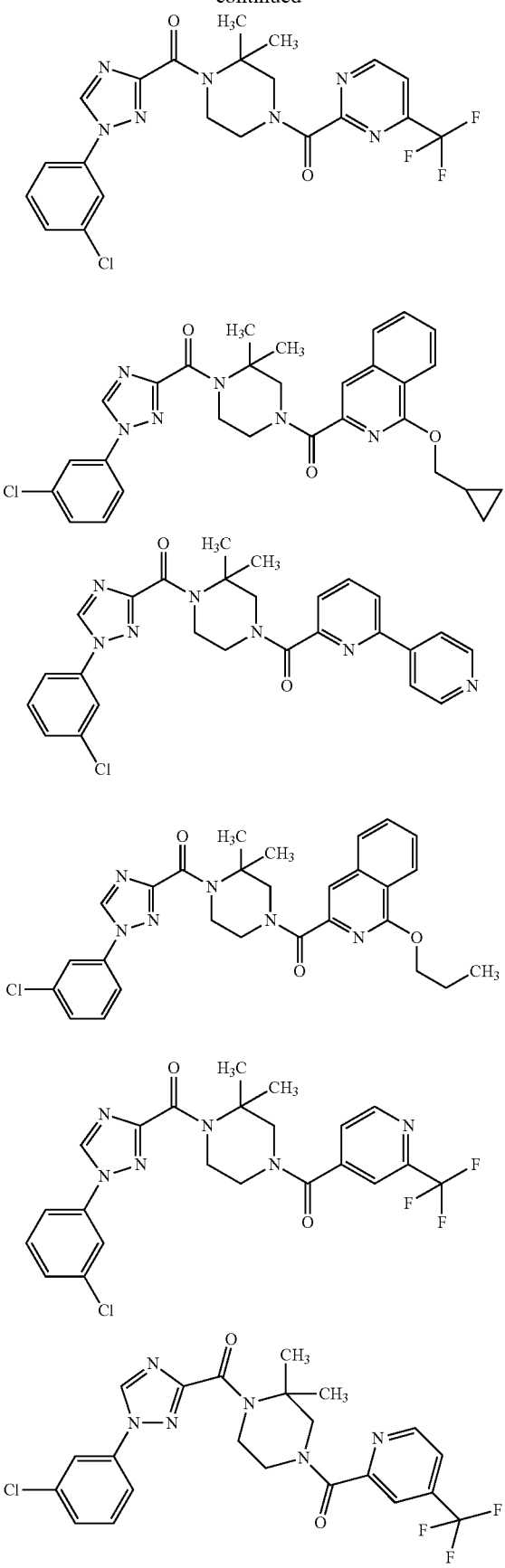
258
-continued
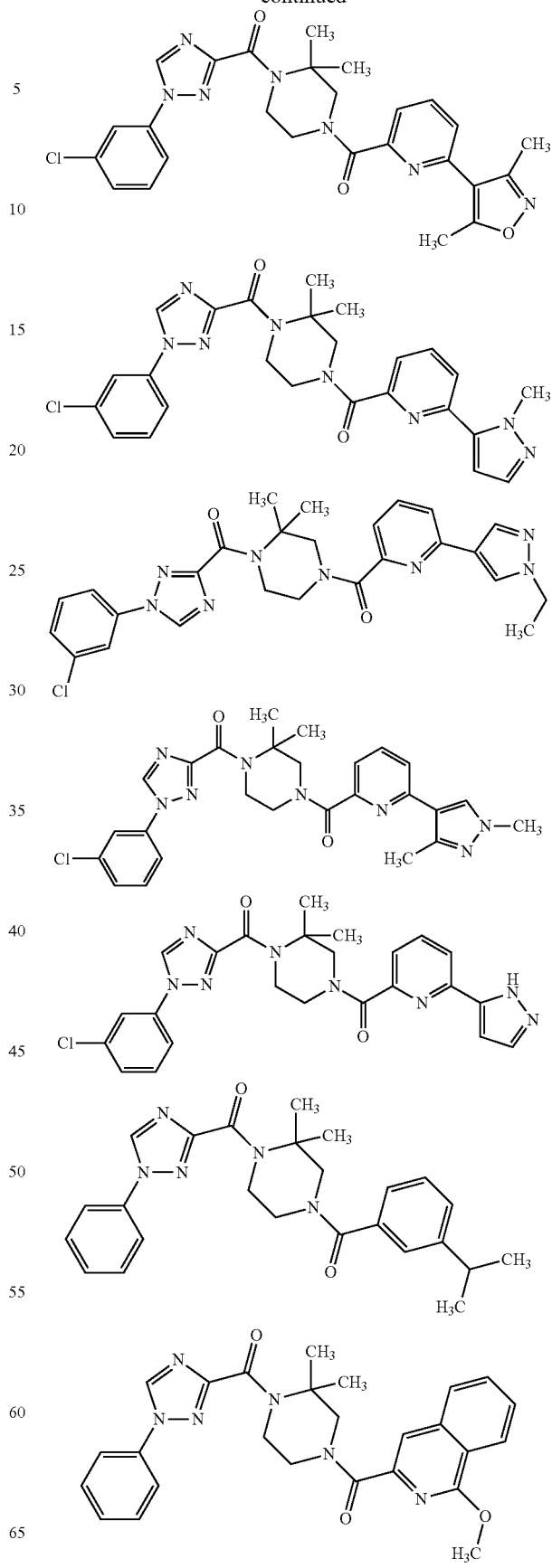

259
-continued
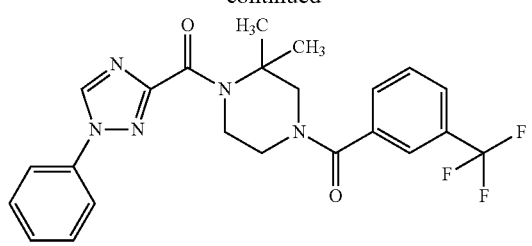
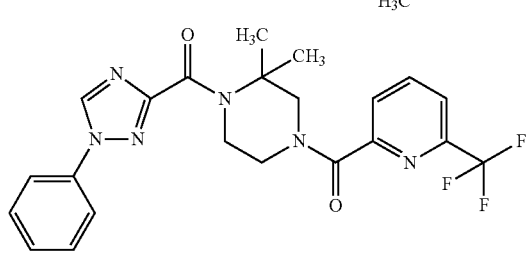
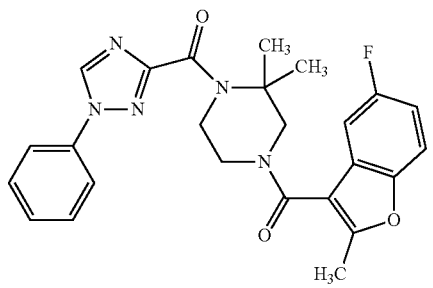
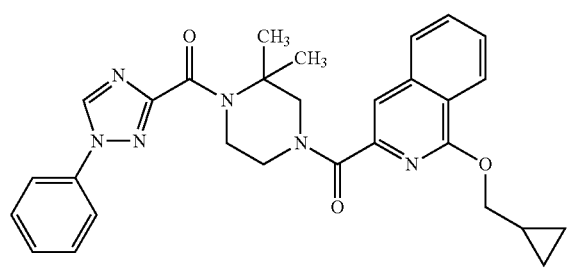
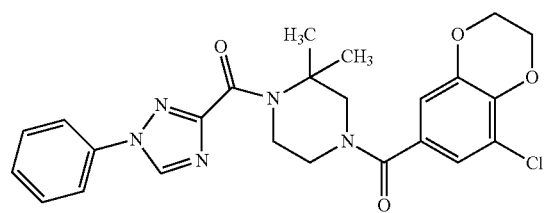
260
-continued
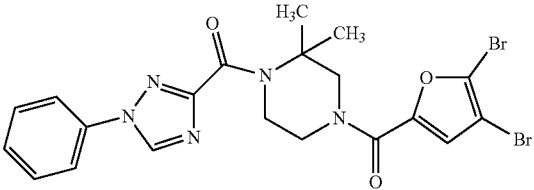
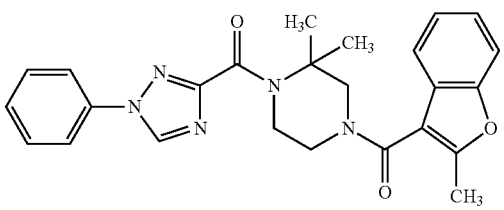
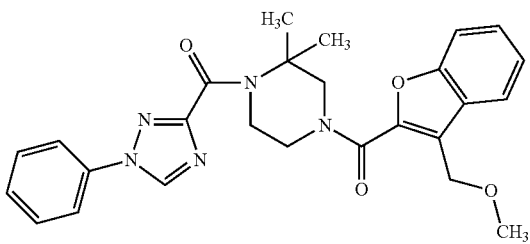
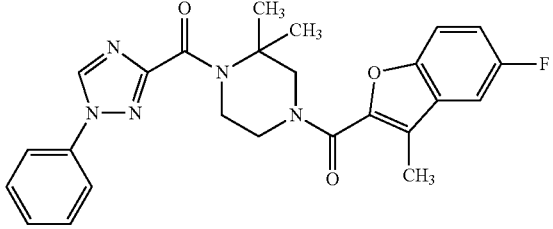
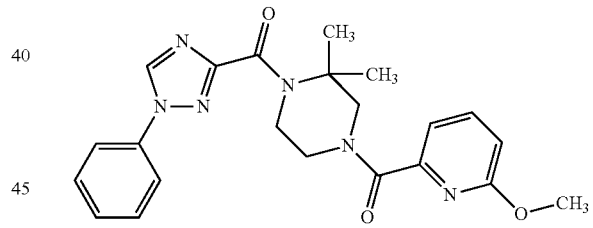
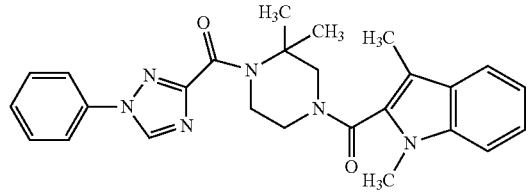
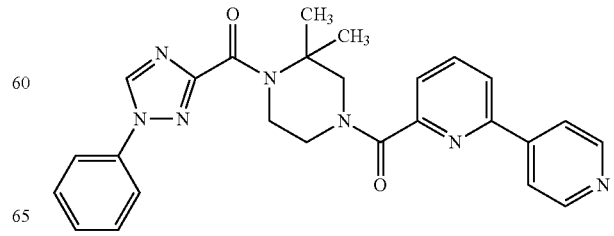

261
-continued
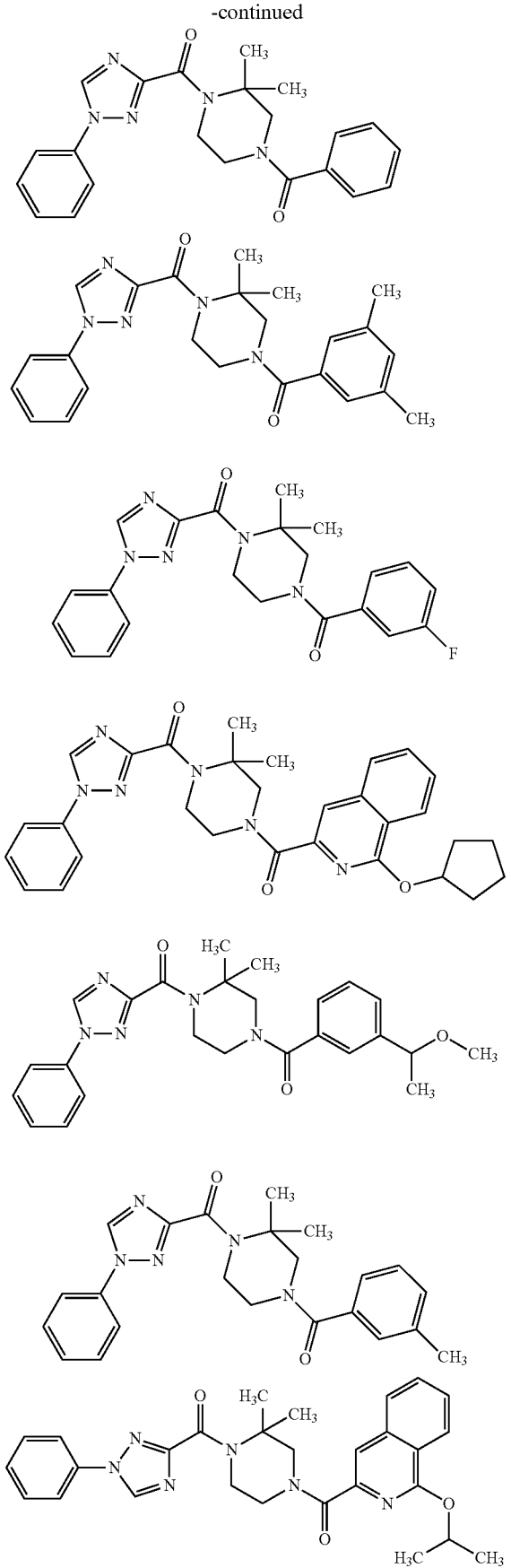
262
-continued
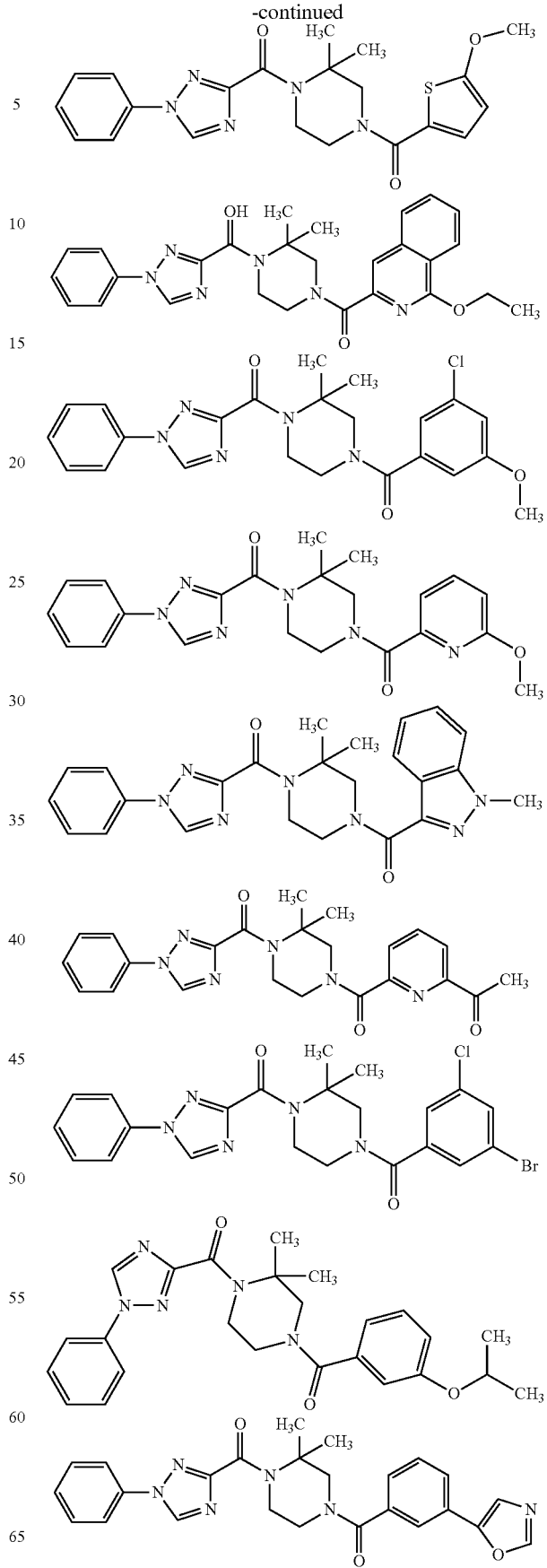

-continued
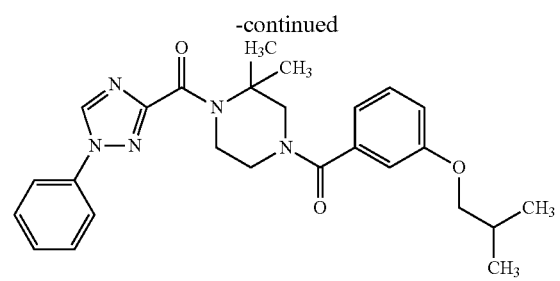
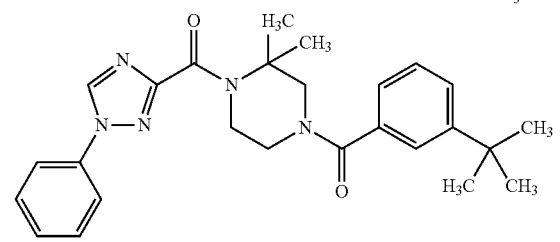
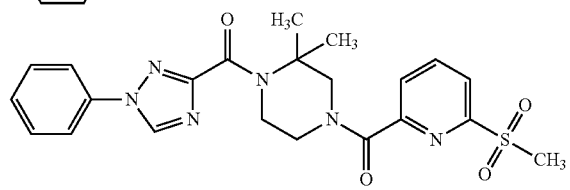
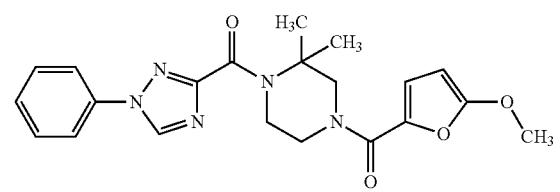
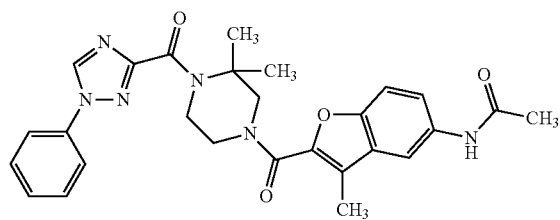
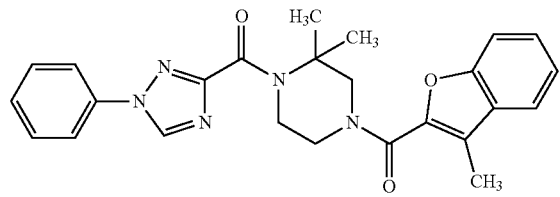
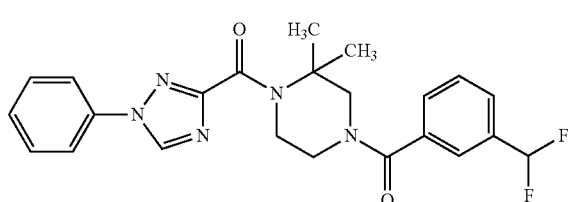
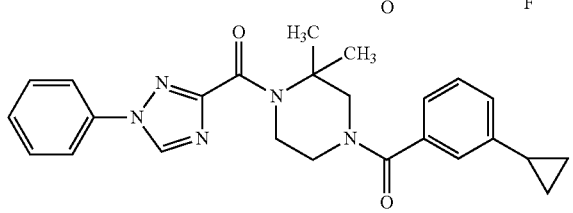
-continued
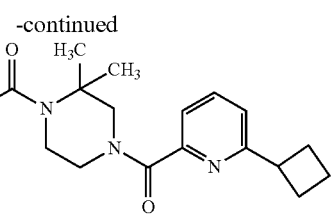
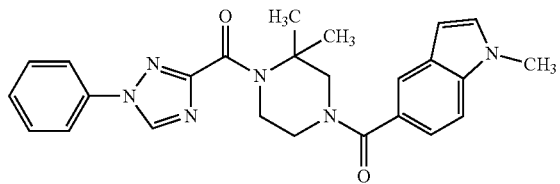
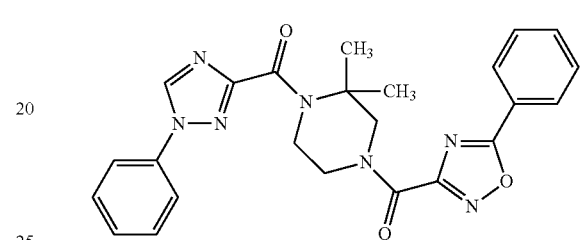
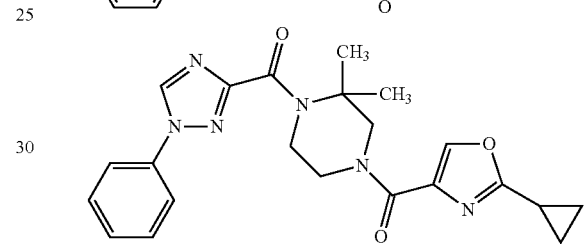
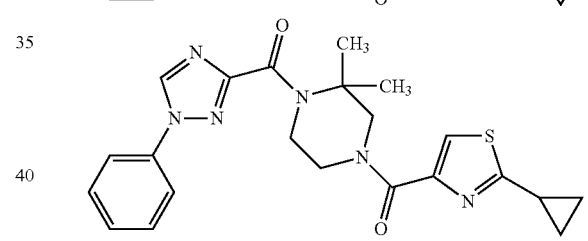
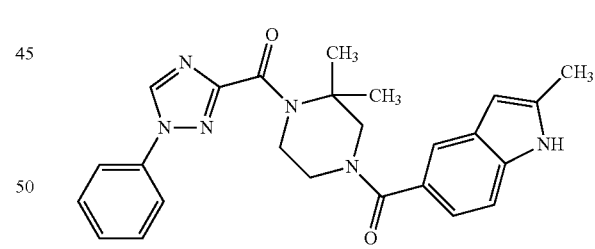
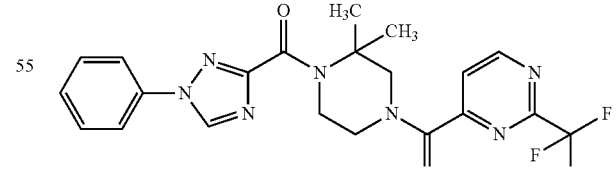
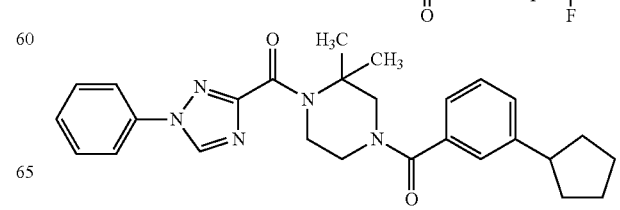

265
-continued
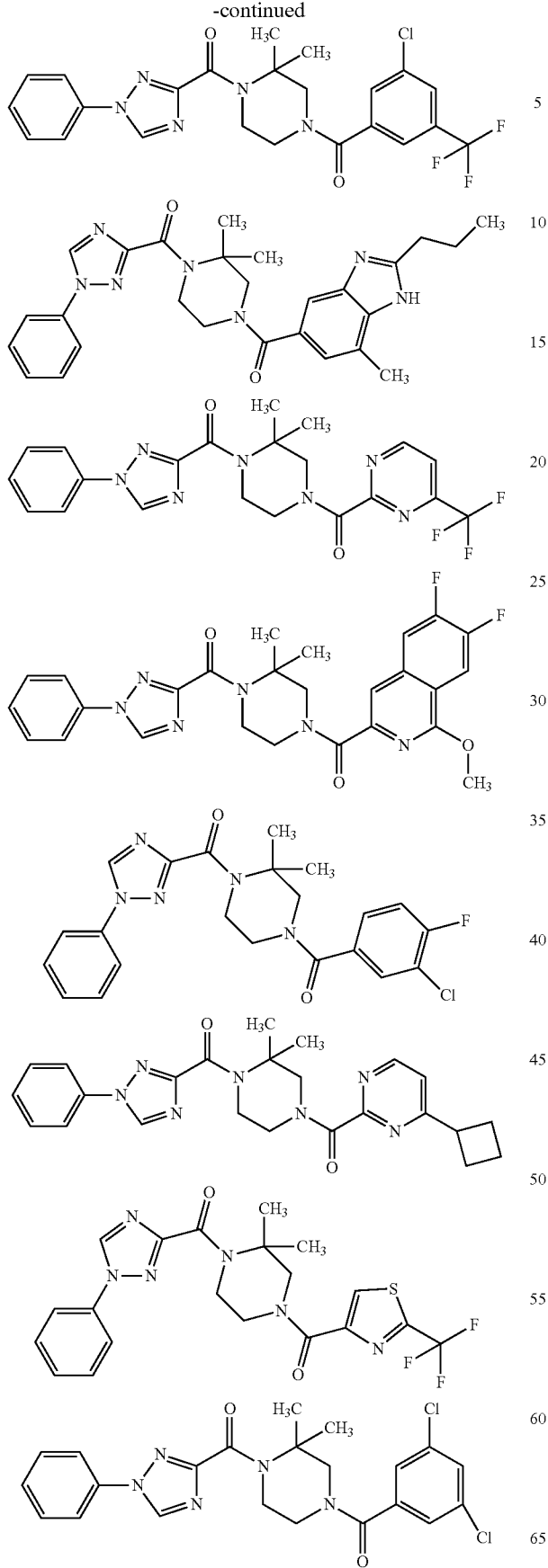
266
-continued
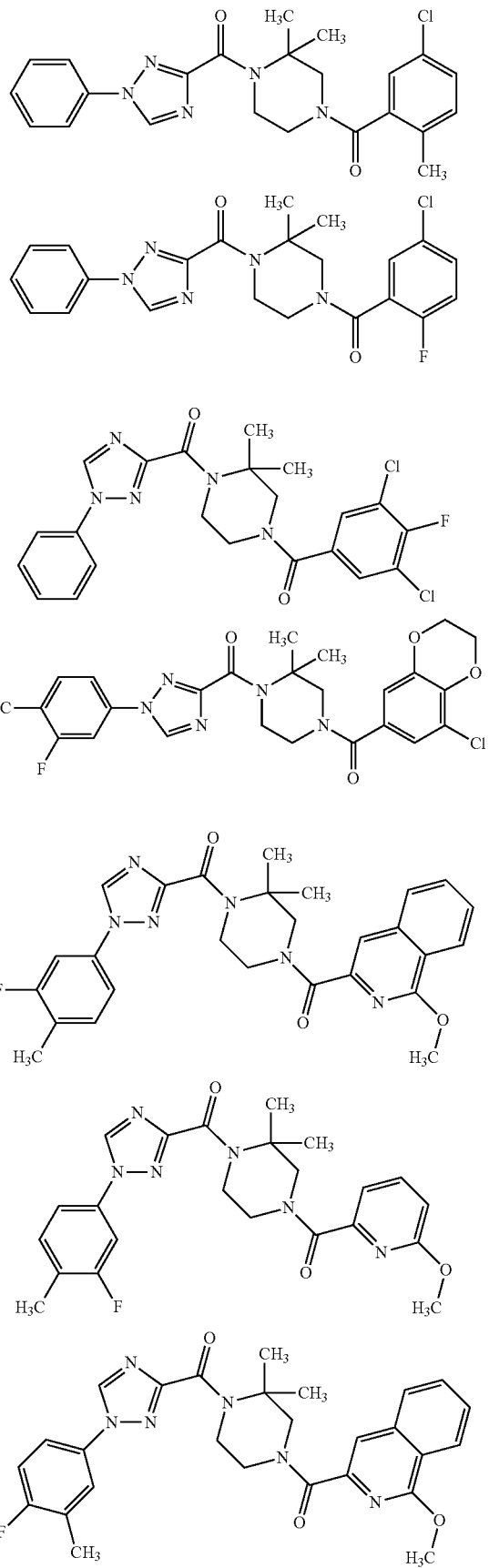

267
-continued
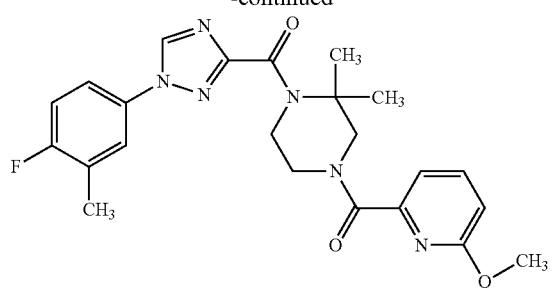
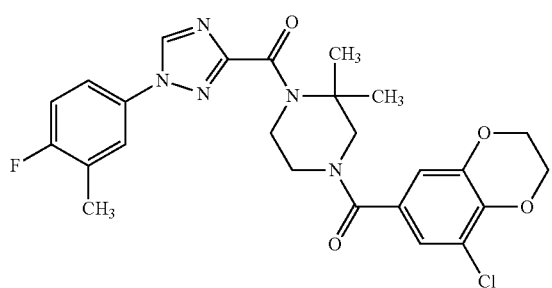
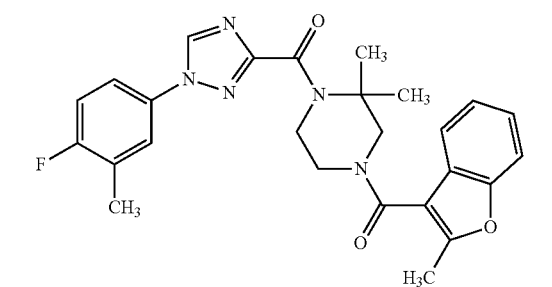
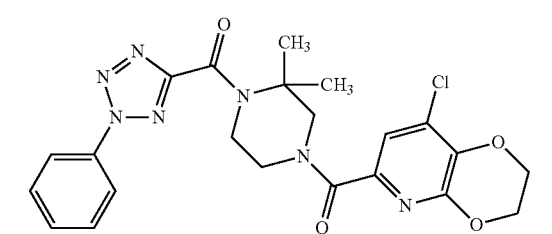
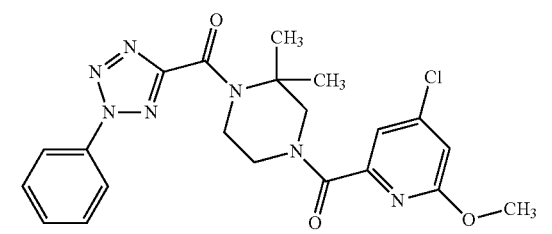
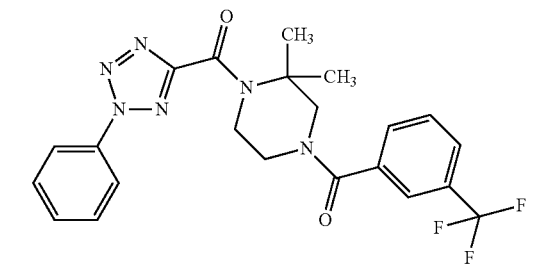
268
-continued
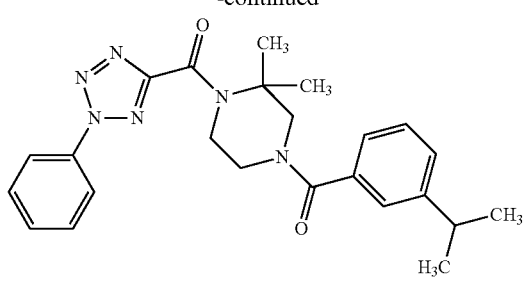
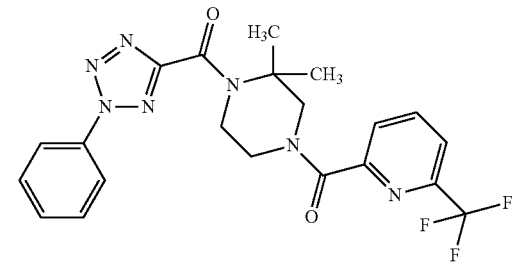
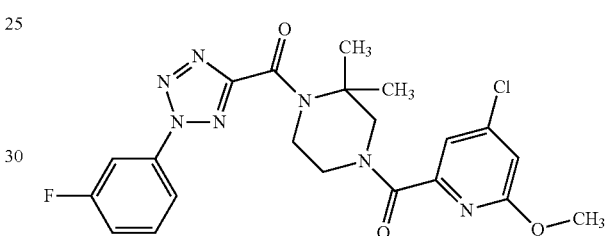
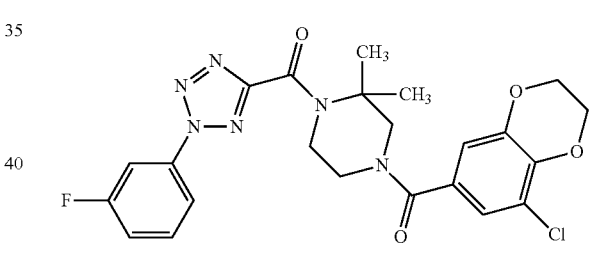
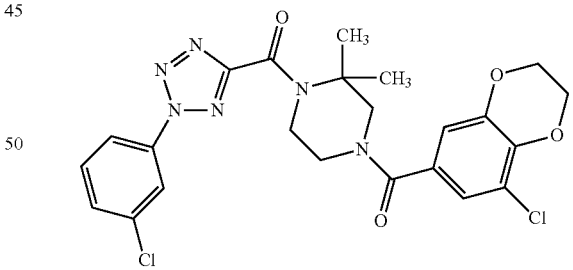
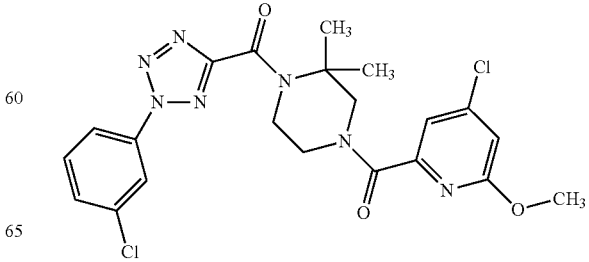

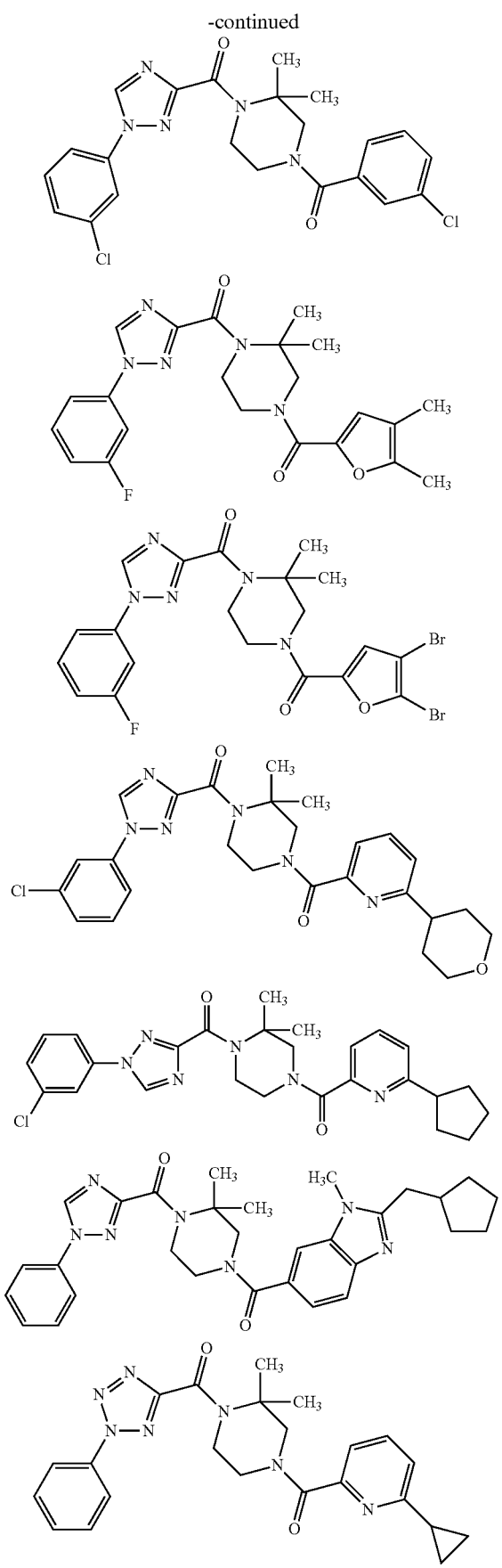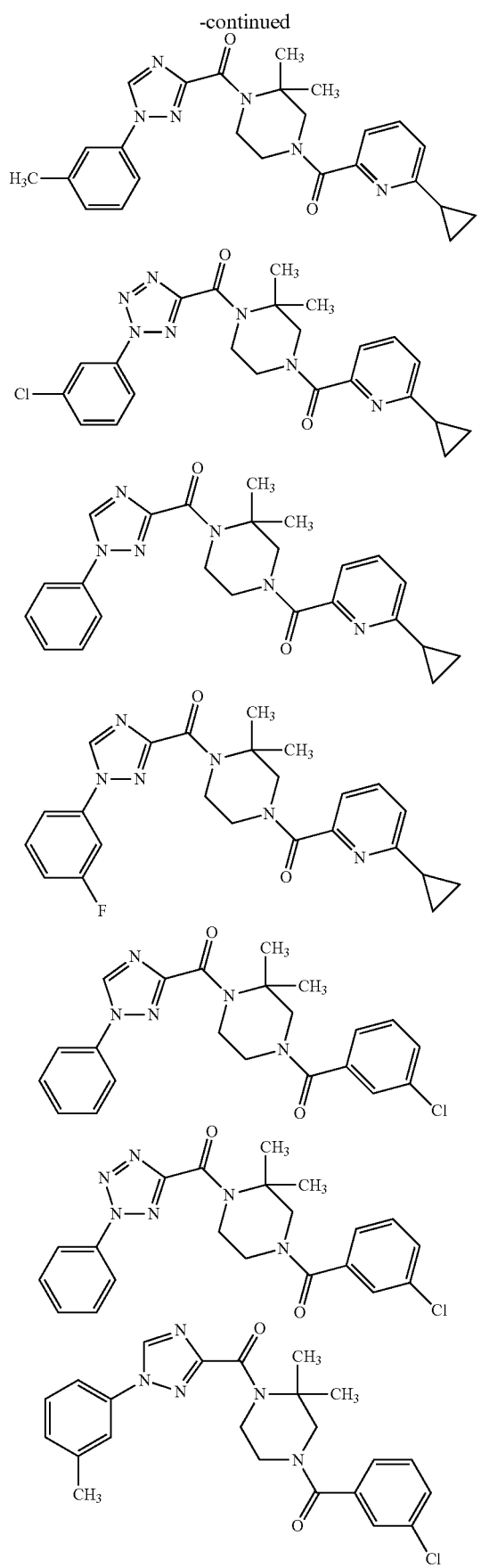

271
-continued
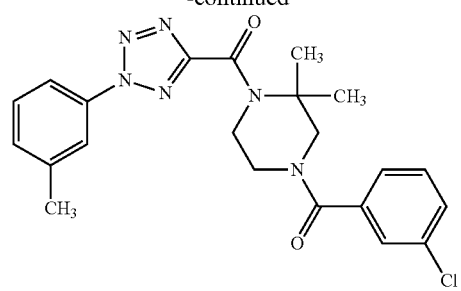
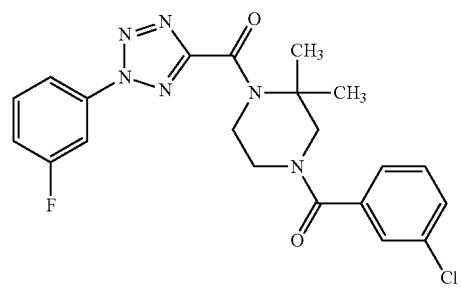
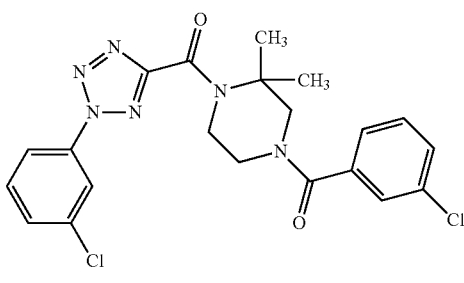
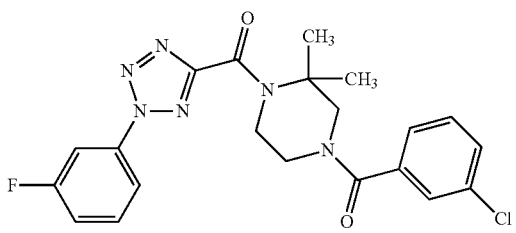
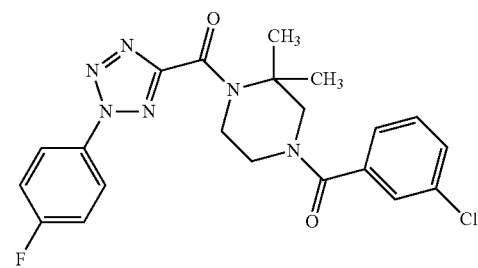
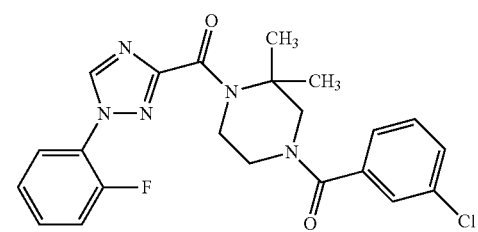
272
-continued
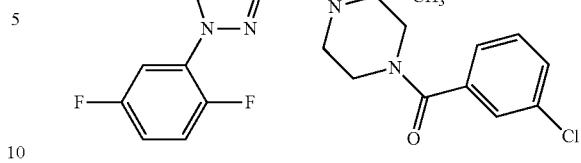
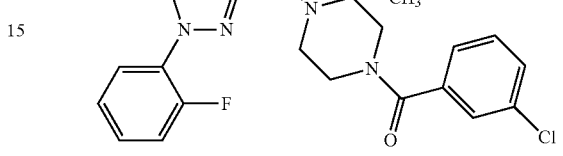
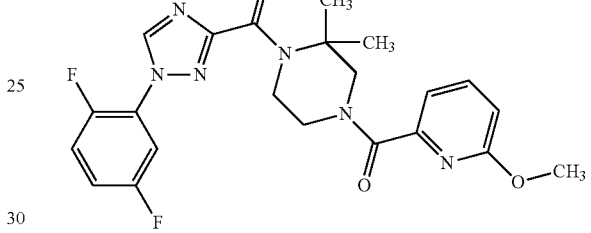
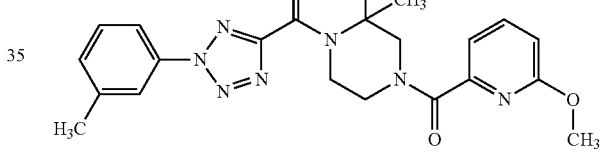
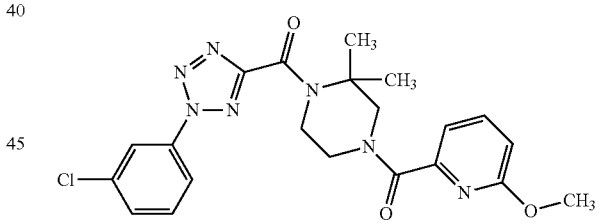
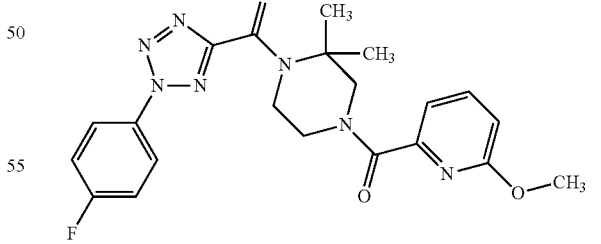
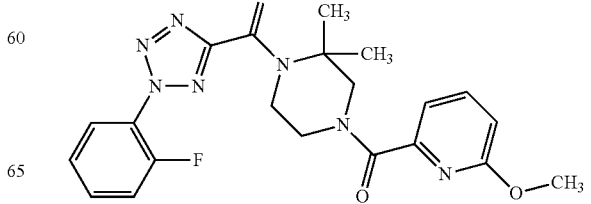

273
-continued
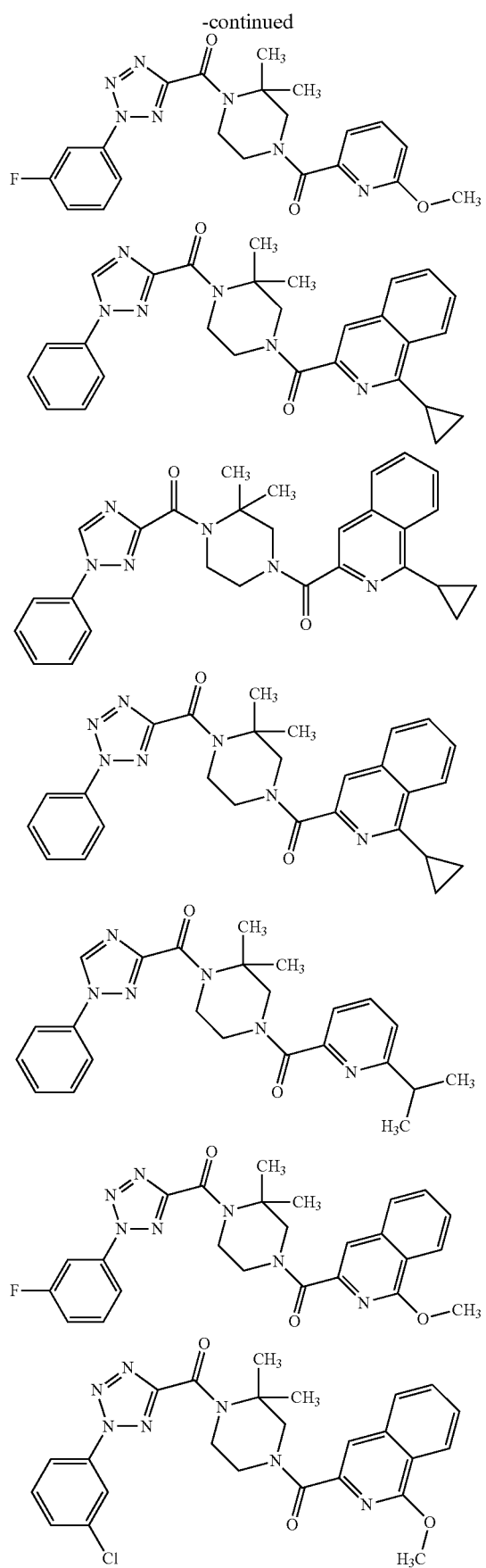
274
-continued
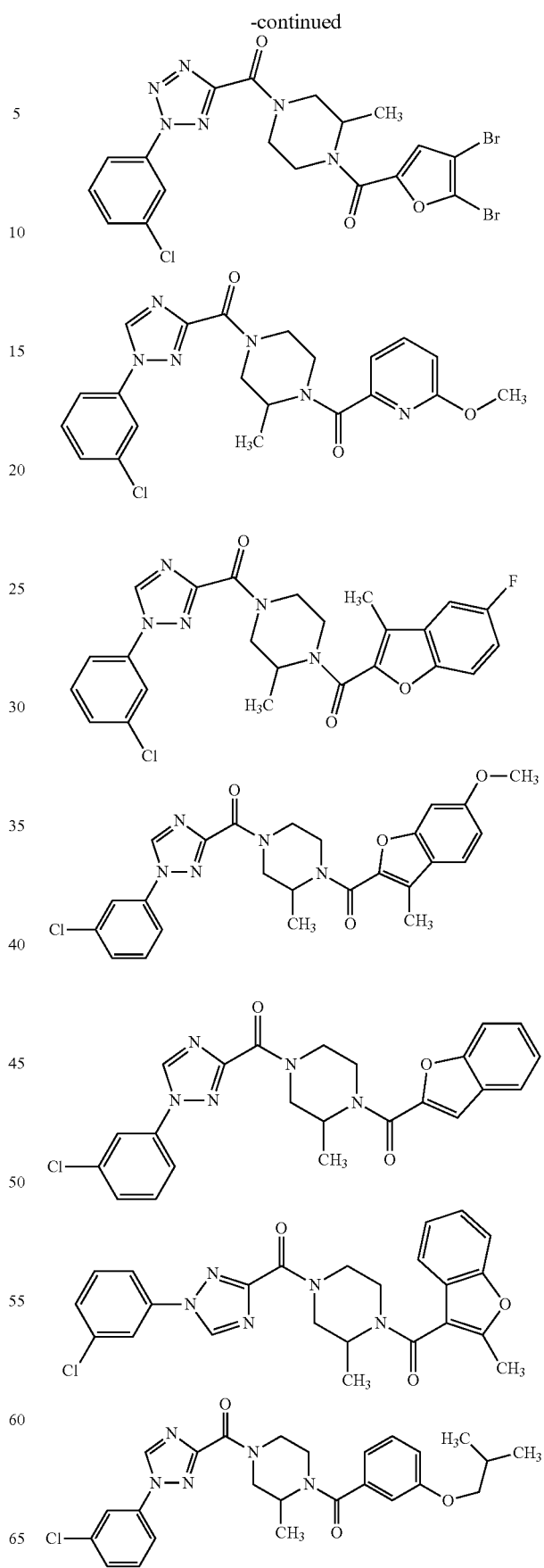

275
-continued
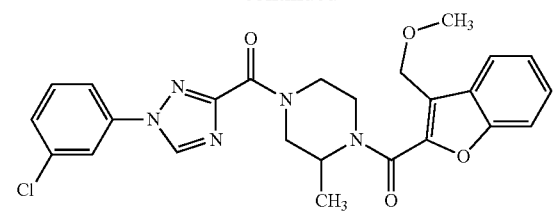
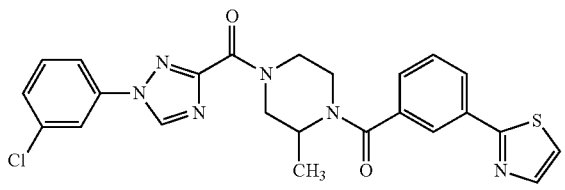
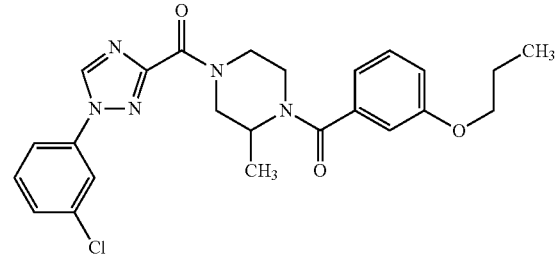
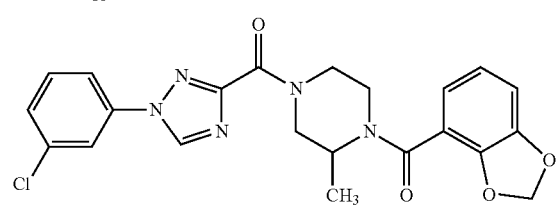
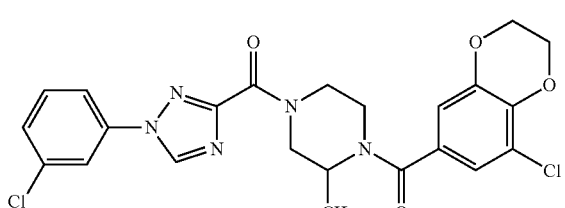
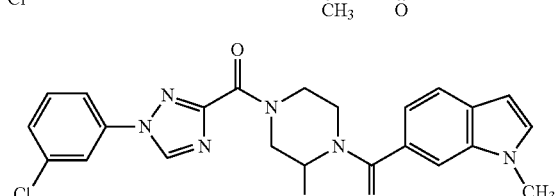
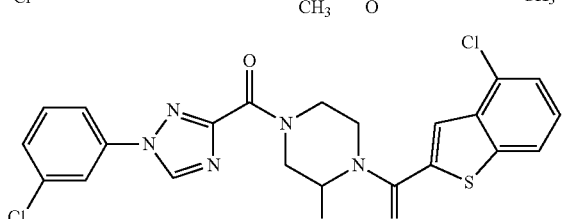
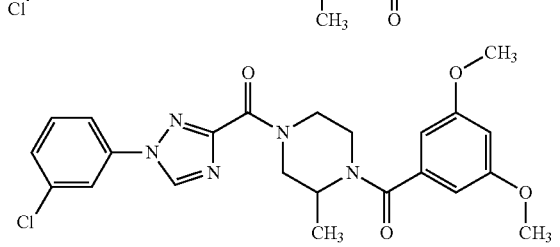
276
-continued
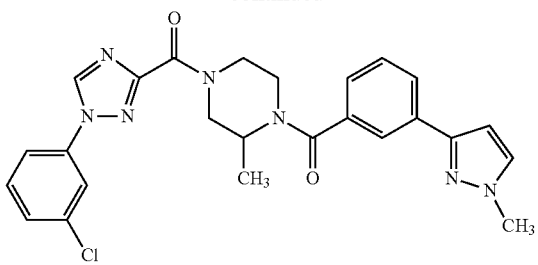
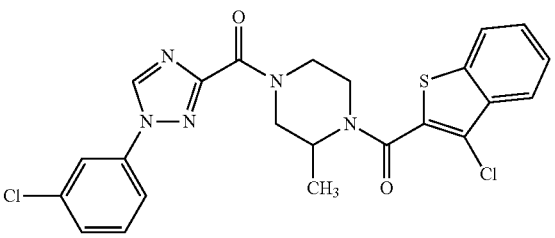
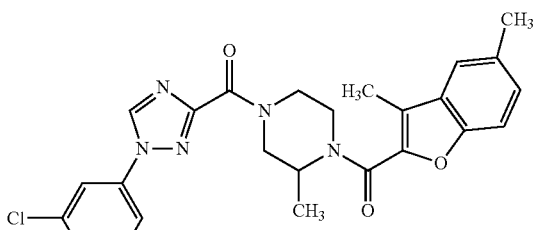
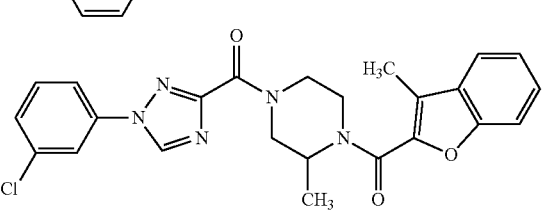
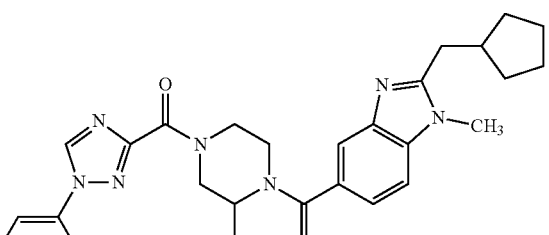
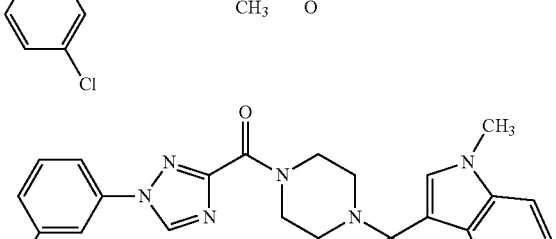
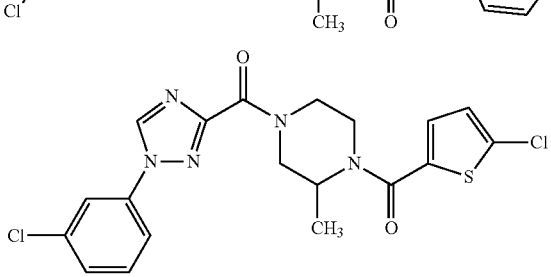

277
-continued
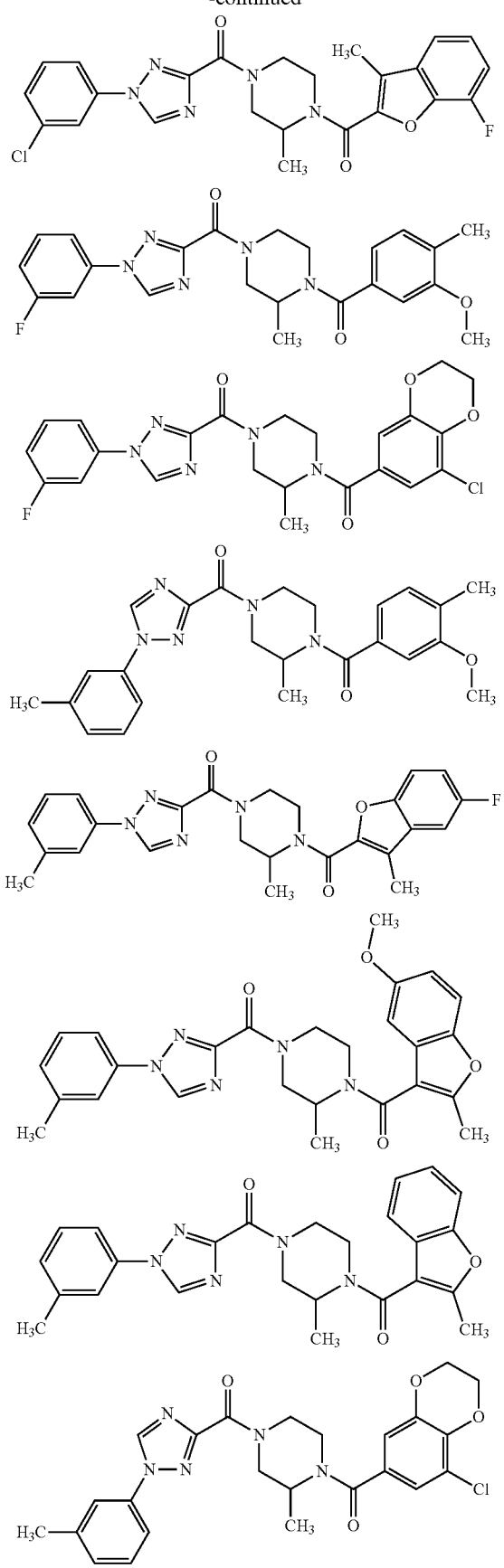
278
-continued
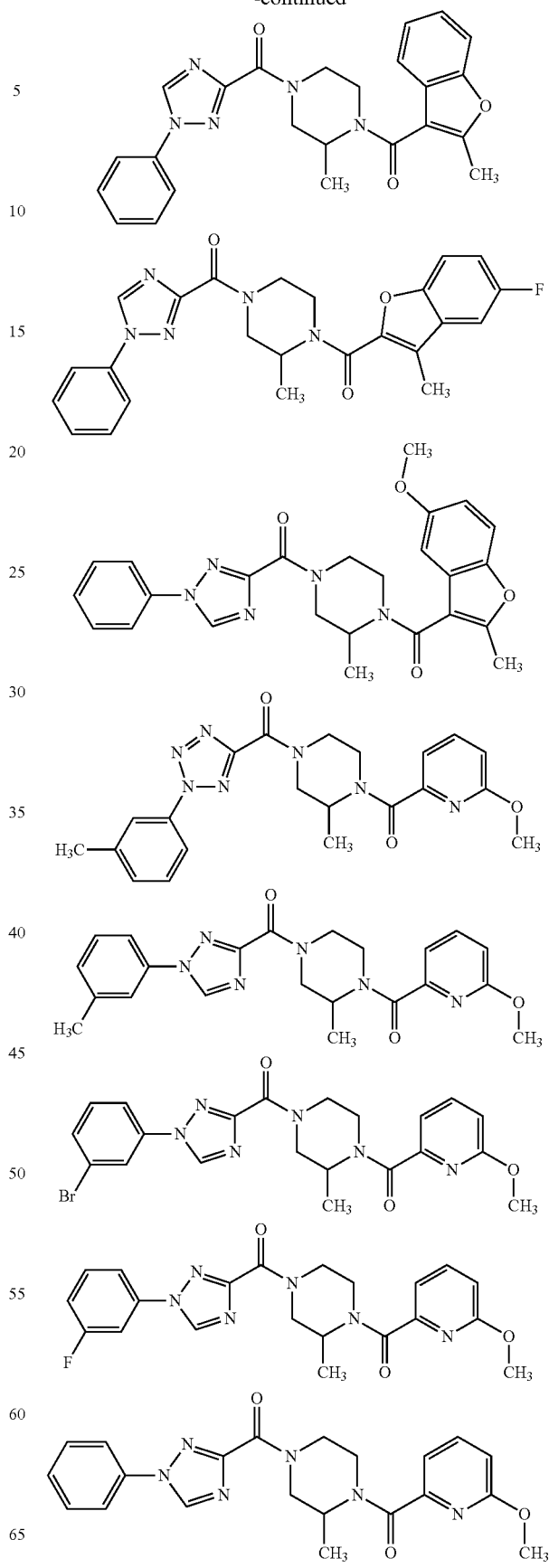

279
-continued
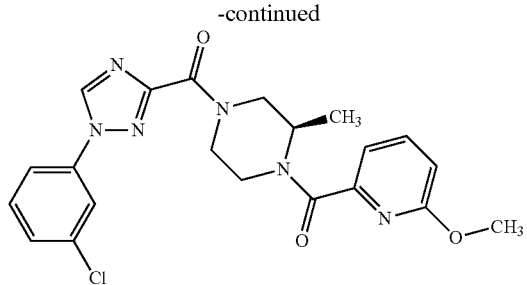
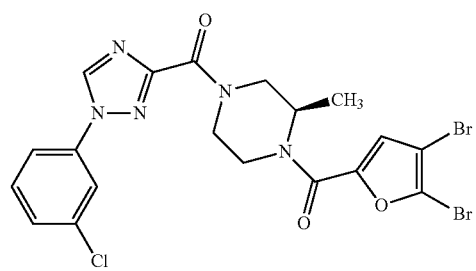
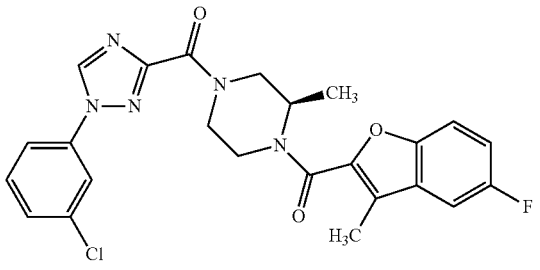
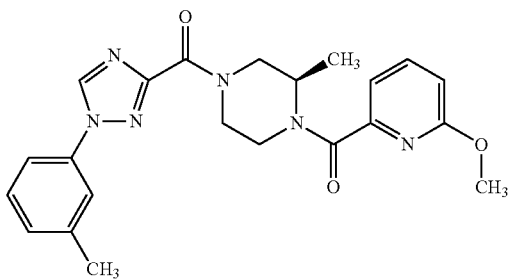
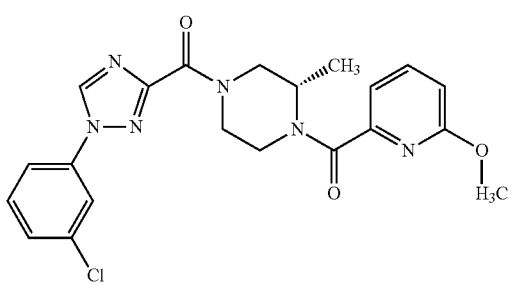
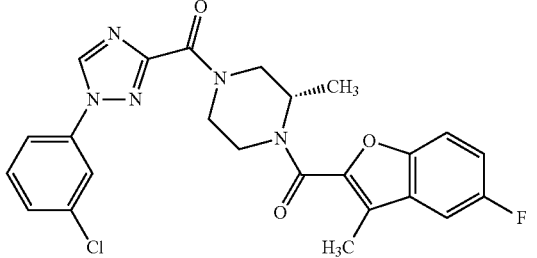
280
-continued
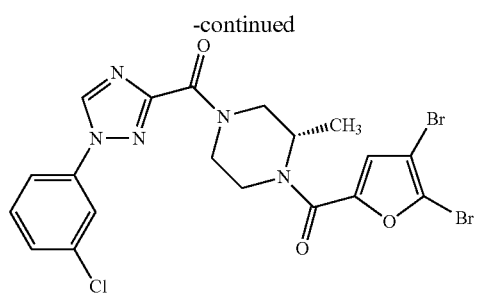
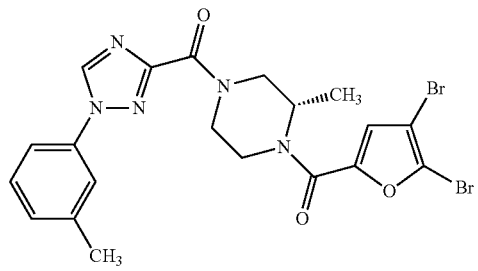
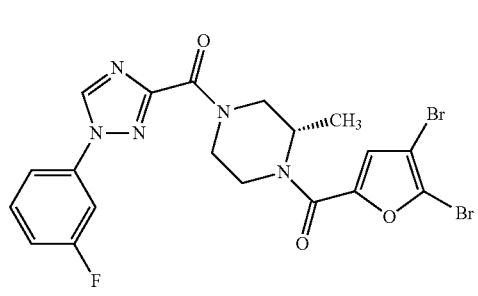
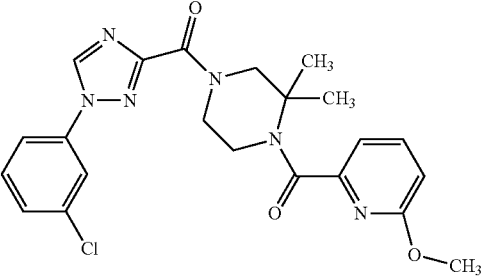
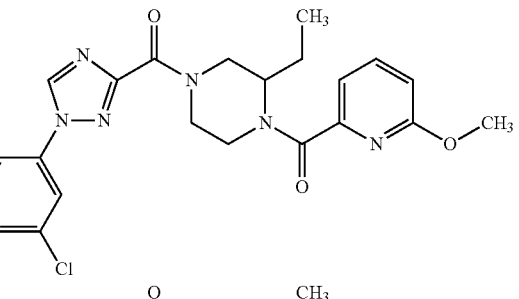
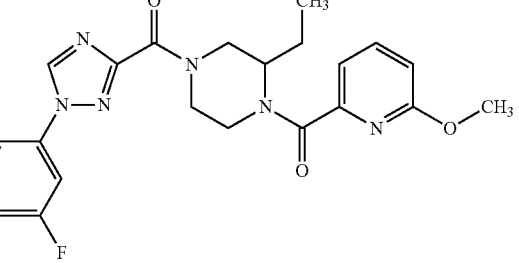

281
-continued
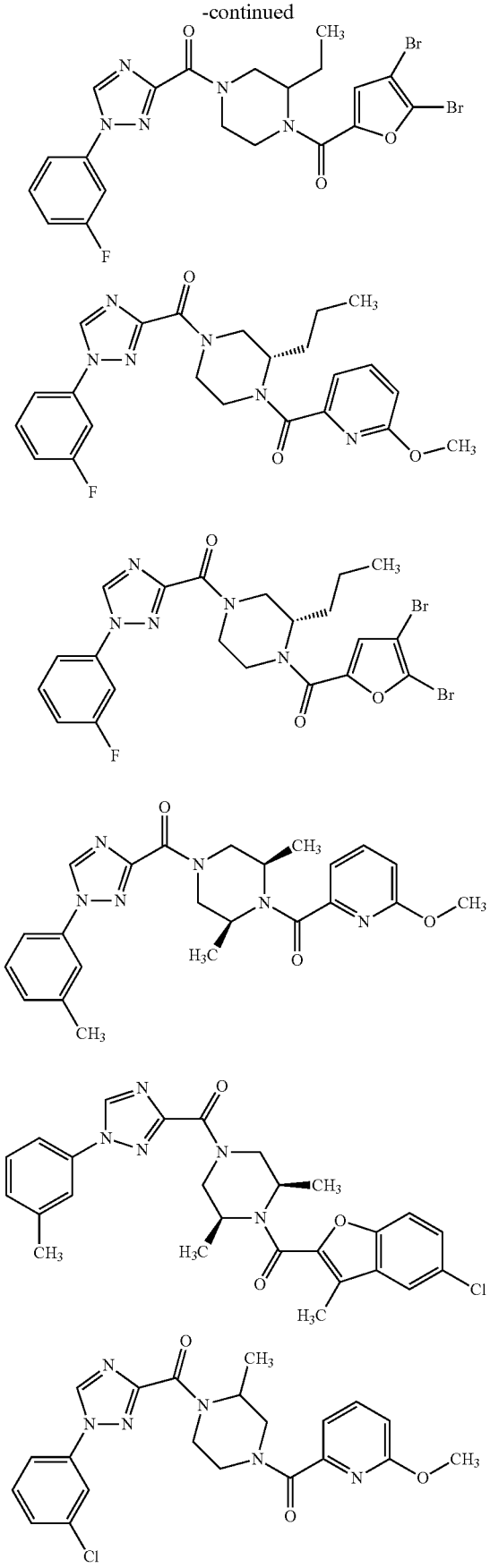
282
-continued
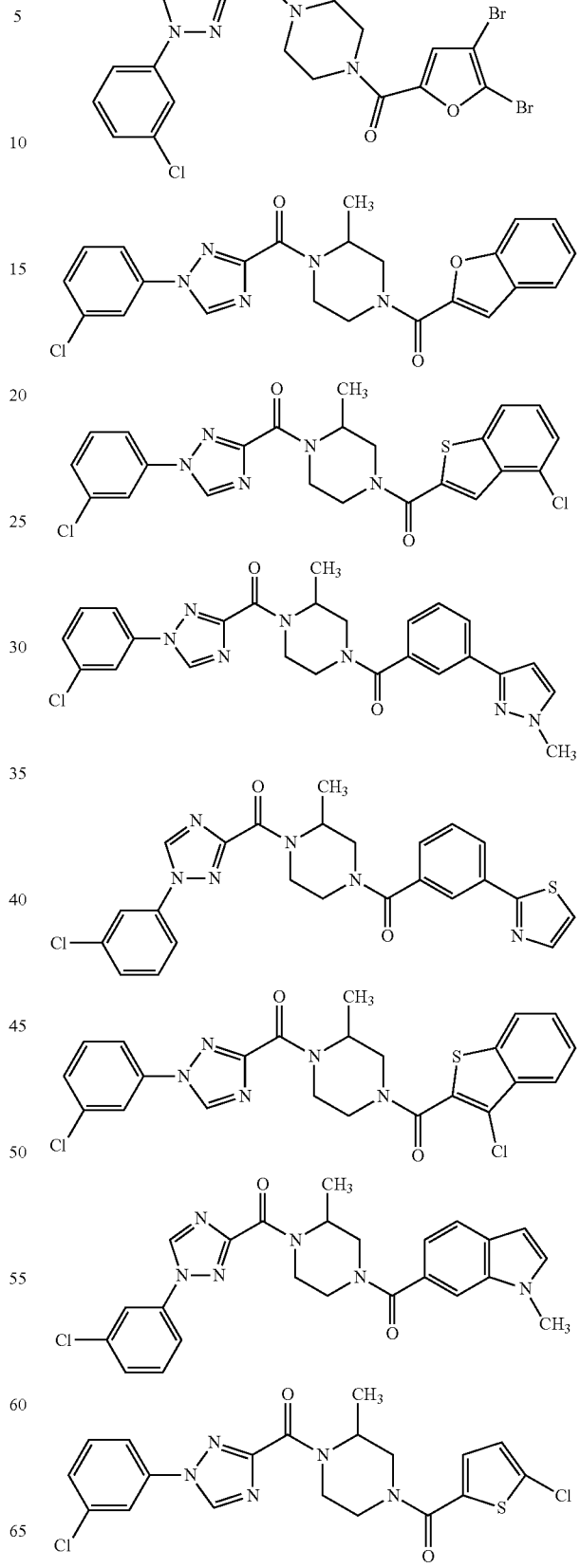

283
-continued
284
-continued
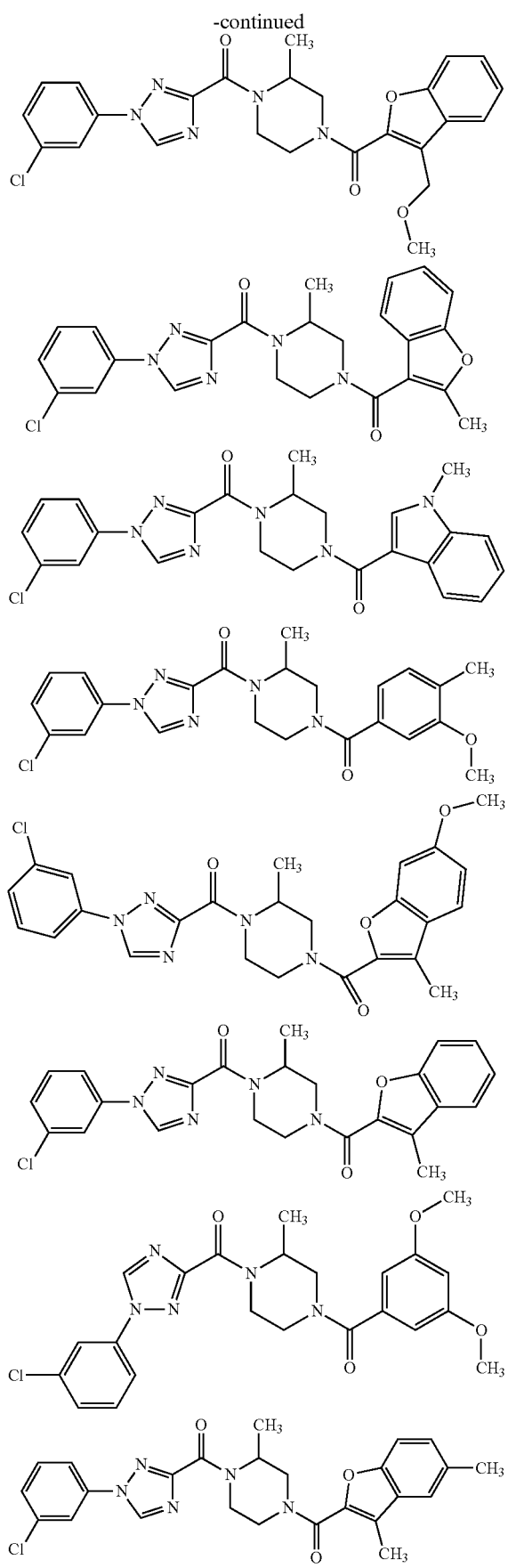
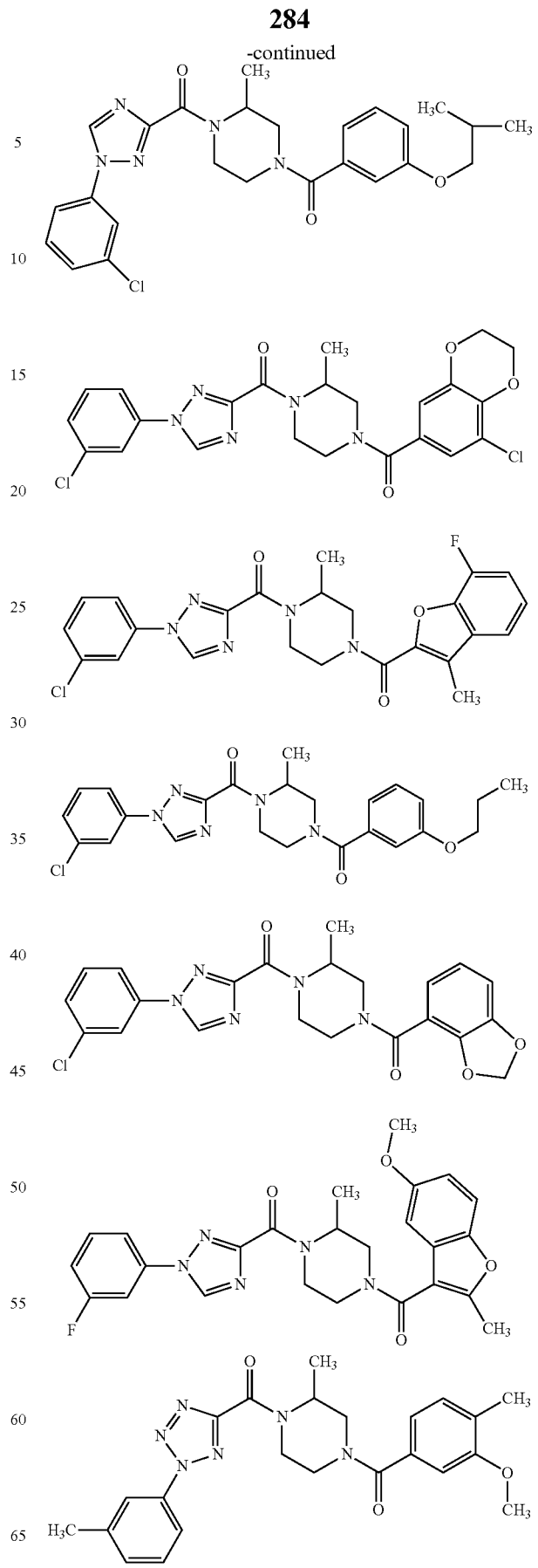

285
-continued
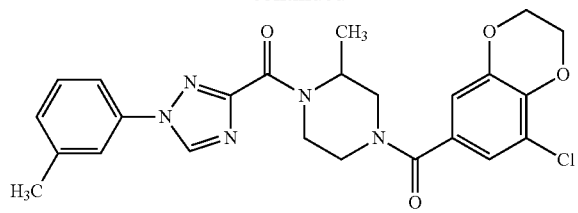
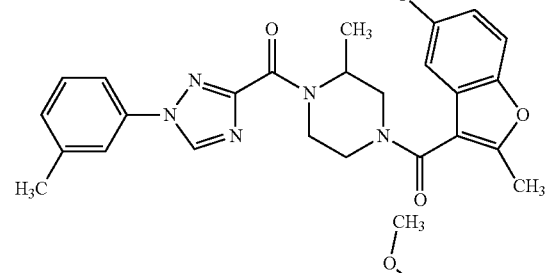
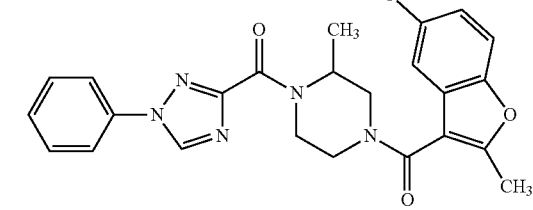
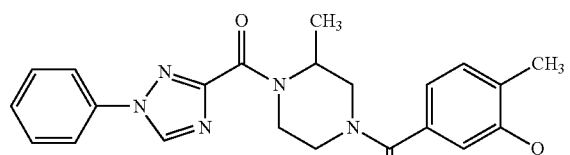
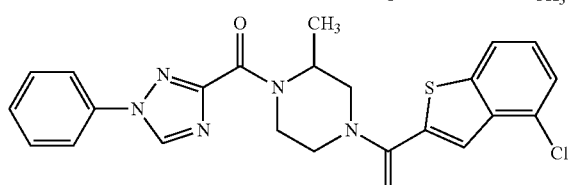
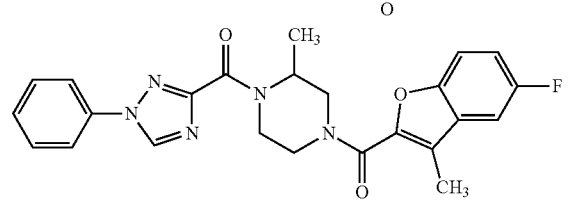
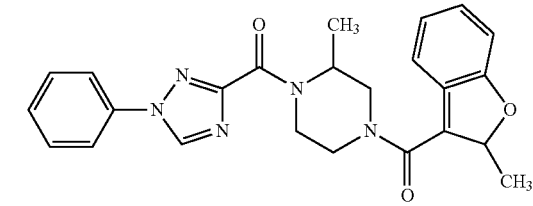
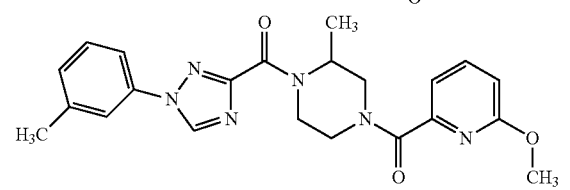
286
-continued
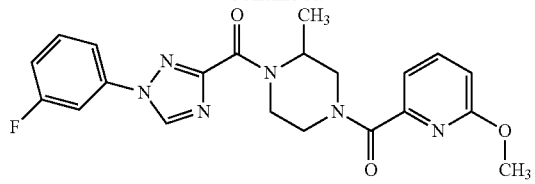
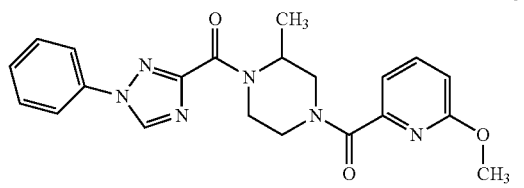
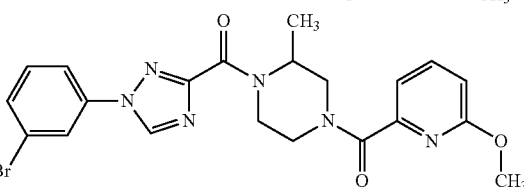
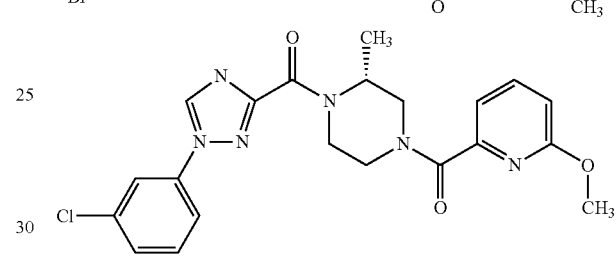
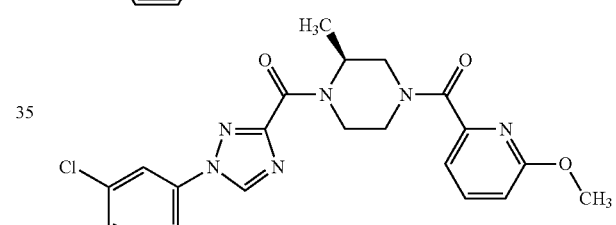
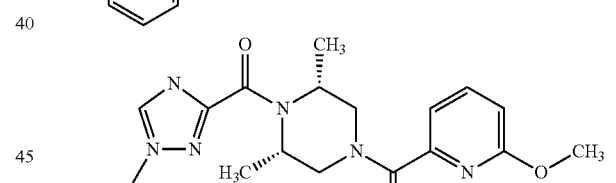
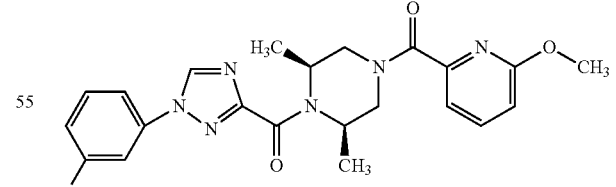
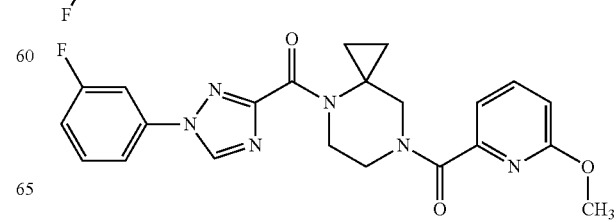

287
-continued
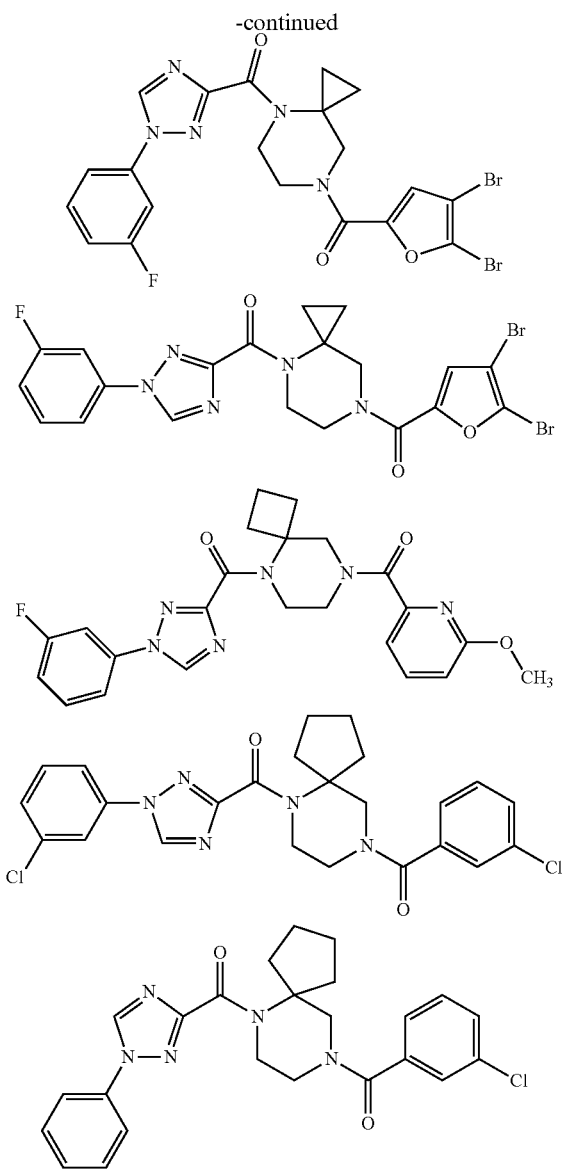
288
-continued
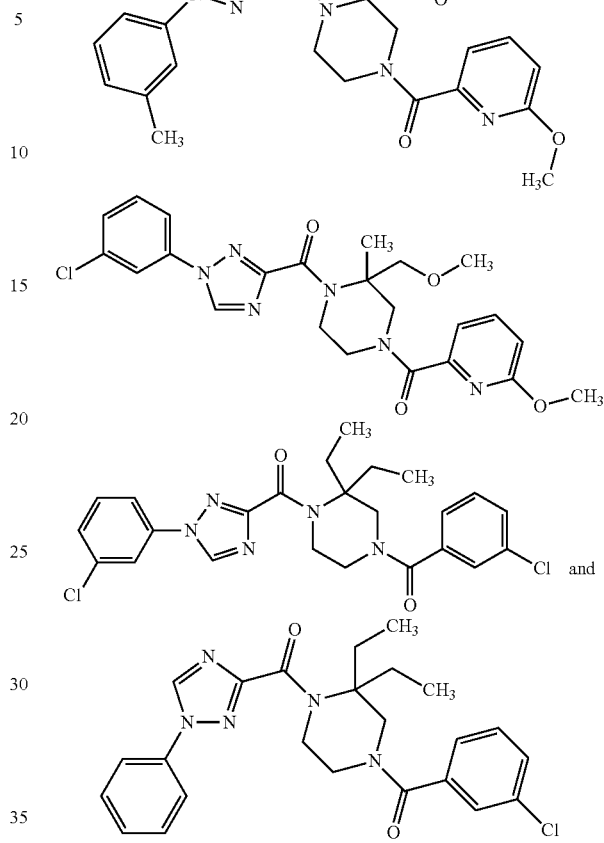
or a physiologically acceptable salt thereof.
13. A pharmaceutical composition comprising a therapeutically effective amount of a compound according to claim 1 or a pharmaceutically acceptable salt thereof in admixture with a pharmaceutically acceptable adjuvant, diluent and/or carrier.
* * * * *